(12) United States Patent
Merenick et al.

(10) Patent No.: US 9,724,430 B2
(45) Date of Patent: Aug. 8, 2017

(54) THERAPEUTIC GENE-SWITCH CONSTRUCTS AND BIOREACTORS FOR THE EXPRESSION OF BIOTHERAPEUTIC MOLECULES, AND USES THEREOF

(71) Applicant: Intrexon Corporation, Blacksburg, VA (US)

(72) Inventors: Bethany Lynn Merenick, Christiansburg, VA (US); Robert P. Beech, Cincinnati, OH (US); Thomas D. Reed, Blacksburg, VA (US); Anna P. Tretiakova, Royersford, PA (US); Richard E. Peterson, Blacksburg, VA (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 14/864,265

(22) Filed: Sep. 24, 2015

(65) Prior Publication Data

US 2016/0114059 A1  Apr. 28, 2016

Related U.S. Application Data

(63) Continuation of application No. 12/241,018, filed on Sep. 29, 2008, now abandoned.

(60) Provisional application No. 61/047,899, filed on Apr. 25, 2008, provisional application No. 60/975,986, filed on Sep. 28, 2007.

(51) Int. Cl.

| | |
|---|---|
| *C07H 21/04* | (2006.01) |
| *C12N 15/00* | (2006.01) |
| *C12N 15/63* | (2006.01) |
| *A61K 48/00* | (2006.01) |
| *A61K 31/7088* | (2006.01) |
| *C12N 15/85* | (2006.01) |
| *A01K 67/00* | (2006.01) |
| *A61K 35/12* | (2015.01) |

(52) U.S. Cl.
CPC ...... *A61K 48/0066* (2013.01); *A61K 31/7088* (2013.01); *C12N 15/635* (2013.01); *C12N 15/85* (2013.01); *A61K 35/12* (2013.01); *C12N 2510/02* (2013.01); *C12N 2830/002* (2013.01); *C12N 2830/15* (2013.01)

(58) Field of Classification Search
CPC .......... A61K 48/0066; A61K 31/7088; A61K 35/12; C12N 15/85; C12N 2510/02; C12N 2830/002; C12N 2830/15; C12N 15/635
USPC .............. 536/24.1; 435/320.1, 455
See application file for complete search history.

(56) References Cited

U.S. PATENT DOCUMENTS

| | | |
|---|---|---|
| 3,989,816 A | 11/1976 | Rajadhyaksha |
| 4,352,883 A | 10/1982 | Lim |
| 4,409,331 A | 10/1983 | Lim |
| 4,444,762 A | 4/1984 | Rajadhyaksha |
| 4,673,566 A | 6/1987 | Goosen et al. |
| 4,680,174 A | 7/1987 | Jarvis, Jr. et al. |
| 4,683,195 A | 7/1987 | Mullis et al. |
| 4,689,293 A | 8/1987 | Goosen et al. |
| 4,806,355 A | 2/1989 | Goosen et al. |
| 4,981,784 A | 1/1991 | Evans et al. |
| 4,985,461 A | 1/1991 | Hsu et al. |
| 5,082,779 A | 1/1992 | Rottman et al. |
| 5,117,057 A | 5/1992 | Hsu et al. |
| 5,151,508 A | 9/1992 | Salbaum et al. |
| 5,225,443 A | 7/1993 | Murphy et al. |
| 5,266,488 A | 11/1993 | Ordahl et al. |
| 5,288,846 A | 2/1994 | Quertermous et al. |
| 5,340,739 A | 8/1994 | Stevens et al. |
| 5,352,595 A | 10/1994 | Tapscott et al. |
| 5,374,544 A | 12/1994 | Schwartz et al. |
| 5,378,726 A | 1/1995 | Yanagi et al. |
| 5,459,127 A | 10/1995 | Felgner et al. |
| 5,464,758 A | 11/1995 | Gossen et al. |
| 5,518,885 A | 5/1996 | Raziuddin et al. |
| 5,530,028 A | 6/1996 | Lidert et al. |
| 5,530,101 A | 6/1996 | Queen et al. |
| 5,550,050 A | 8/1996 | Holland et al. |
| 5,550,178 A | 8/1996 | Desai et al. |
| 5,556,954 A | 9/1996 | Burn et al. |
| 5,580,859 A | 12/1996 | Felgner et al. |
| 5,589,466 A | 12/1996 | Felgner et al. |
| 5,627,023 A | 5/1997 | Bolognesi et al. |
| 5,643,726 A | 7/1997 | Tanzi et al. |
| 5,643,746 A | 7/1997 | Polakowska et al. |
| 5,648,099 A | 7/1997 | Batich et al. |

(Continued)

FOREIGN PATENT DOCUMENTS

| | | |
|---|---|---|
| AU | 765306 | 9/2003 |
| AU | 2002-306550 | 10/2007 |

(Continued)

OTHER PUBLICATIONS

Alam M et al. Lung surfactant protein B promoter function is dependent on the helical phasing, orientation and combinatorial actions of cis-DNA elements. Gene 282:103-111, 2002.*
Muller J et al. Repression of lac promoter as a function of distance, phase and quality of an auxiliary lac operator. J. Mol. Biol. 257:21-29, 1996.*
Xie W et al. Domains of the rat rDNA promoter must be aligned stereospecifically. Mol. & Cell. Biol. 12:1266-1275, 1992.*
Karzenowski D et al. Inducible control of transgene expression with ecdysone receptor. BioTechniques 39:191-200, 2005.*

(Continued)

*Primary Examiner* — Quang Nguyen
(74) *Attorney, Agent, or Firm* — Sterne, Kessler, Goldstein and Fox, P.L.L.C.

(57) ABSTRACT

The present invention relates to methods and compositions for treating, ameliorating or preventing a disease or disorder in a subject by introducing into cells of the subject a therapeutic gene switch construct that controls expression of one or more therapeutic products.

4 Claims, 17 Drawing Sheets

(56) References Cited

U.S. PATENT DOCUMENTS

| | | |
|---|---|---|
| 5,653,975 A | 8/1997 | Baetge et al. |
| 5,656,481 A | 8/1997 | Baetge et al. |
| 5,661,032 A | 8/1997 | Miller et al. |
| 5,668,012 A | 9/1997 | Newman et al. |
| 5,677,171 A | 10/1997 | Hudziak et al. |
| 5,681,706 A | 10/1997 | Anderson et al. |
| 5,693,622 A | 12/1997 | Wolff et al. |
| 5,698,389 A | 12/1997 | de la Brousse et al. |
| 5,698,413 A | 12/1997 | Hollingshead et al. |
| 5,700,848 A | 12/1997 | Soon-Shiong et al. |
| 5,736,137 A | 4/1998 | Anderson et al. |
| 5,744,304 A | 4/1998 | Munford |
| 5,744,310 A | 4/1998 | Reed |
| 5,753,502 A | 5/1998 | Kilgannon et al. |
| 5,759,578 A | 6/1998 | Soon-Shiong et al. |
| 5,763,591 A | 6/1998 | Toyoda et al. |
| 5,772,993 A | 6/1998 | Chung et al. |
| 5,773,215 A | 6/1998 | Hanausek-Walaszek et al. |
| 5,773,286 A | 6/1998 | Dionne et al. |
| 5,773,290 A | 6/1998 | Gould et al. |
| 5,786,216 A | 7/1998 | Dionne et al. |
| 5,788,988 A | 8/1998 | Soon-Shiong et al. |
| 5,798,113 A | 8/1998 | Dionne et al. |
| 5,800,828 A | 9/1998 | Dionne et al. |
| 5,800,829 A | 9/1998 | Dionne et al. |
| 5,801,033 A | 9/1998 | Hubbell et al. |
| 5,811,231 A | 9/1998 | Farr et al. |
| 5,824,794 A | 10/1998 | Borden et al. |
| 5,831,141 A | 11/1998 | Lubon et al. |
| 5,834,001 A | 11/1998 | Dionne et al. |
| 5,834,274 A | 11/1998 | Hubbell et al. |
| 5,837,234 A | 11/1998 | Gentile et al. |
| 5,837,534 A | 11/1998 | Olson et al. |
| 5,837,747 A | 11/1998 | Soon-Shiong et al. |
| 5,843,743 A | 12/1998 | Hubbell et al. |
| 5,846,530 A | 12/1998 | Soon-Shiong et al. |
| 5,851,822 A | 12/1998 | Munford |
| 5,853,985 A | 12/1998 | Salbaum et al. |
| 5,854,019 A | 12/1998 | Sedlacek et al. |
| 5,858,746 A | 1/1999 | Hubbell et al. |
| 5,866,329 A | 2/1999 | Demetriou et al. |
| 5,877,020 A | 3/1999 | Alitalo et al. |
| 5,888,764 A | 3/1999 | Mountz et al. |
| 5,888,765 A | 3/1999 | Patterson et al. |
| 5,892,019 A | 4/1999 | Schlom et al. |
| 5,902,745 A | 5/1999 | Butler et al. |
| 5,908,623 A | 6/1999 | Baetge et al. |
| 5,912,005 A | 6/1999 | Lanza et al. |
| 5,916,790 A | 6/1999 | Enevold |
| 5,919,652 A | 7/1999 | Pang et al. |
| 5,948,637 A | 9/1999 | Ikeda et al. |
| 5,959,094 A | 9/1999 | Wallach et al. |
| 5,965,790 A | 10/1999 | Acton |
| 5,972,609 A | 10/1999 | Tinsley et al. |
| 6,013,836 A | 1/2000 | Hsu et al. |
| 6,015,376 A | 1/2000 | Ain et al. |
| 6,015,709 A | 1/2000 | Natesan |
| 6,020,200 A | 2/2000 | Enevold |
| 6,060,273 A | 5/2000 | Dirks et al. |
| 6,066,726 A | 5/2000 | Farb et al. |
| 6,083,523 A | 7/2000 | Dionne et al. |
| 6,103,527 A | 8/2000 | Graulich et al. |
| 6,117,680 A | 9/2000 | Natesan et al. |
| 6,123,700 A | 9/2000 | Mills et al. |
| 6,126,936 A | 10/2000 | Lanza et al. |
| 6,147,282 A | 11/2000 | Goff et al. |
| 6,174,679 B1 | 1/2001 | Kaufmann |
| 6,177,242 B1 | 1/2001 | Changeux et al. |
| 6,180,007 B1 | 1/2001 | Gentile et al. |
| 6,187,757 B1 | 2/2001 | Clackson et al. |
| 6,217,866 B1 | 4/2001 | Schlessinger et al. |
| 6,225,459 B1 | 5/2001 | Mano et al. |
| 6,255,473 B1 | 7/2001 | Vitek et al. |
| 6,258,603 B1 | 7/2001 | Carlson et al. |
| 6,258,870 B1 | 7/2001 | Hubbell et al. |
| 6,264,941 B1 | 7/2001 | Baetge et al. |
| 6,267,985 B1 | 7/2001 | Chen et al. |
| 6,281,015 B1 | 8/2001 | Mooney et al. |
| 6,284,882 B1 | 9/2001 | Wu-Wong et al. |
| 6,287,558 B1 | 9/2001 | Lanza et al. |
| 6,303,355 B1 | 10/2001 | Opara |
| 6,303,361 B1 | 10/2001 | Vihko |
| 6,306,454 B1 | 10/2001 | Ung-Chhun et al. |
| 6,306,649 B1 | 10/2001 | Gilman et al. |
| 6,306,833 B1 | 10/2001 | Hochberg et al. |
| 6,320,038 B1 | 11/2001 | Panula et al. |
| 6,337,008 B1 | 1/2002 | Christensen et al. |
| 6,365,385 B1 | 4/2002 | Opara |
| 6,368,612 B1 | 4/2002 | Lanza et al. |
| 6,379,945 B1 | 4/2002 | Jepson et al. |
| 6,383,486 B1 | 5/2002 | Davis-Smyth et al. |
| 6,383,746 B1 | 5/2002 | Guignard et al. |
| 6,429,010 B1 | 8/2002 | Greengard et al. |
| 6,479,653 B1 | 11/2002 | Natesan et al. |
| 6,482,405 B1 | 11/2002 | Tahara et al. |
| 6,489,097 B2 | 12/2002 | Hirose et al. |
| 6,489,463 B1 | 12/2002 | Zetter et al. |
| 6,495,161 B1 | 12/2002 | Soon-Shiong et al. |
| 6,509,152 B1 | 1/2003 | Berlin et al. |
| 6,509,190 B2 | 1/2003 | Kandel et al. |
| RE38,027 E | 3/2003 | Jain et al. |
| 6,537,784 B1 | 3/2003 | Tatake et al. |
| 6,558,665 B1 | 5/2003 | Cohen et al. |
| 6,573,371 B2 | 6/2003 | Jung et al. |
| 6,589,745 B2 | 7/2003 | Kaufmann |
| 6,596,515 B2 | 7/2003 | Suh |
| 6,608,037 B2 | 8/2003 | Young et al. |
| 6,610,509 B1 | 8/2003 | Sandell et al. |
| 6,610,668 B2 | 8/2003 | Vournakis et al. |
| 6,630,326 B2 | 10/2003 | Markowitz et al. |
| 6,649,595 B2 | 11/2003 | Clackson et al. |
| 6,664,054 B2 | 12/2003 | Kennedy |
| 6,670,138 B2 | 12/2003 | Gonzalez-Zulueta et al. |
| 6,682,736 B1 | 1/2004 | Hanson et al. |
| 6,686,153 B1 | 2/2004 | Pahl |
| 6,699,971 B2 | 3/2004 | Birkenbach et al. |
| 6,716,824 B1 | 4/2004 | Brunicardi |
| 6,720,472 B2 | 4/2004 | Chada et al. |
| 6,723,531 B2 | 4/2004 | Evans et al. |
| 6,727,322 B2 | 4/2004 | Kennedy et al. |
| 6,737,523 B1 | 5/2004 | Fisher et al. |
| 6,740,523 B2 | 5/2004 | Hermeking et al. |
| 6,743,903 B1 | 6/2004 | Gordon et al. |
| 6,762,959 B2 | 7/2004 | Kim |
| 6,777,182 B2 | 8/2004 | Baban et al. |
| 6,777,203 B1 | 8/2004 | Morin et al. |
| 6,780,610 B1 | 8/2004 | Owens et al. |
| 6,783,758 B2 | 8/2004 | Wands et al. |
| 6,783,964 B2 | 8/2004 | Opara |
| 6,790,617 B1 | 9/2004 | Miyata |
| 6,794,131 B1 | 9/2004 | Lethe et al. |
| 6,800,604 B2 | 10/2004 | Gurney et al. |
| 6,808,705 B2 | 10/2004 | Asina et al. |
| 6,818,018 B1 | 11/2004 | Sawhney |
| 6,841,362 B1 | 1/2005 | Fisher et al. |
| 6,864,093 B1 | 3/2005 | Chai et al. |
| 6,870,044 B2 | 3/2005 | Massaad et al. |
| 6,881,834 B1 | 4/2005 | Noti |
| 6,884,616 B1 | 4/2005 | Negrier et al. |
| 6,884,619 B2 | 4/2005 | Hockfield et al. |
| 6,897,024 B2 | 5/2005 | Bussemakers et al. |
| 6,911,227 B2 | 6/2005 | Hubbell et al. |
| 6,916,640 B2 | 7/2005 | Yu et al. |
| 6,936,595 B2 | 8/2005 | Kupper et al. |
| 6,943,018 B2 | 9/2005 | Auernhammer et al. |
| 6,943,245 B2 | 9/2005 | Killary et al. |
| 6,951,923 B2 | 10/2005 | Fisher et al. |
| 6,960,351 B2 | 11/2005 | Dionne et al. |
| 7,030,099 B2 | 4/2006 | Tagawa |
| 7,033,746 B2 | 4/2006 | Band |
| 7,033,755 B2 | 4/2006 | Clark et al. |
| 7,037,647 B1 | 5/2006 | Israeli et al. |
| 7,038,028 B1 | 5/2006 | Sakai et al. |
| 7,045,294 B2 | 5/2006 | Abrahamsen et al. |

(56) References Cited

U.S. PATENT DOCUMENTS

| | | | |
|---|---|---|---|
| 7,045,315 B2 | 5/2006 | Evans et al. |
| 7,049,132 B1 | 5/2006 | Lee |
| 7,053,193 B2 | 5/2006 | Sun et al. |
| 7,063,960 B2 | 6/2006 | Choi et al. |
| 7,067,649 B2 | 6/2006 | Harats |
| 7,071,323 B2 | 7/2006 | Kalin et al. |
| 7,074,771 B2 | 7/2006 | Jessell et al. |
| 7,084,267 B1 | 8/2006 | Keith et al. |
| 7,087,385 B2 | 8/2006 | Kalin et al. |
| 7,091,038 B2 | 8/2006 | Palli et al. |
| 7,094,533 B1 | 8/2006 | Lin |
| 7,094,569 B2 | 8/2006 | Kim et al. |
| 7,094,878 B2 | 8/2006 | Lee et al. |
| 7,105,485 B2 | 9/2006 | Schipper |
| 7,129,328 B2 | 10/2006 | Farnham et al. |
| 7,138,118 B2 | 11/2006 | Le et al. |
| 7,138,235 B2 | 11/2006 | Bussemakers et al. |
| 7,138,511 B1 | 11/2006 | Nguyen et al. |
| 7,144,985 B2 | 12/2006 | Johnson et al. |
| 7,148,016 B1 | 12/2006 | Boman |
| 7,163,808 B2 | 1/2007 | Anderson et al. |
| 7,166,713 B2 | 1/2007 | Dass et al. |
| 7,176,294 B2 | 2/2007 | Berg |
| 7,183,051 B2 | 2/2007 | Androphy et al. |
| 7,193,075 B2 | 3/2007 | Benoit et al. |
| 7,195,910 B2 | 3/2007 | Iacovitti et al. |
| RE39,542 E | 4/2007 | Jain et al. |
| 7,202,024 B2 | 4/2007 | Han et al. |
| 7,211,646 B2 | 5/2007 | Terek |
| 7,217,795 B2 | 5/2007 | Steck et al. |
| 7,220,844 B2 | 5/2007 | Farnham et al. |
| 7,223,394 B2 | 5/2007 | Salfeld et al. |
| 7,226,978 B2 | 6/2007 | Tapsak et al. |
| 7,227,013 B1 | 6/2007 | Matzuk et al. |
| 7,247,297 B2 | 7/2007 | Weichselbaum et al. |
| 7,247,705 B2 | 7/2007 | Iwamoto et al. |
| 7,250,256 B2 | 7/2007 | Reinhard |
| 7,268,207 B2 | 9/2007 | Zauderer et al. |
| 7,273,874 B2 | 9/2007 | Graziani et al. |
| 7,276,477 B2 | 10/2007 | Osslund et al. |
| 7,276,498 B2 | 10/2007 | Graziani et al. |
| 7,276,595 B2 | 10/2007 | Ip et al. |
| 7,291,492 B2 | 11/2007 | Zelent et al. |
| 7,304,161 B2 | 12/2007 | Hormann et al. |
| 7,304,162 B2 | 12/2007 | Hormann et al. |
| 7,321,030 B2 | 1/2008 | Hamada |
| 7,332,282 B2 | 2/2008 | Fink et al. |
| 7,332,294 B2 | 2/2008 | Kelvin et al. |
| 7,348,156 B2 | 3/2008 | Westphal et al. |
| 7,357,931 B2 | 4/2008 | Clark et al. |
| 7,361,502 B2 | 4/2008 | Schneider et al. |
| 7,364,727 B2 | 4/2008 | Li et al. |
| 7,368,538 B2 | 5/2008 | Yeung et al. |
| 7,375,093 B2 | 5/2008 | Tice et al. |
| 7,393,657 B2 | 7/2008 | Diss et al. |
| 7,393,837 B2 | 7/2008 | Karaplis et al. |
| 7,405,289 B2 | 7/2008 | Johnson et al. |
| 7,413,873 B2 | 8/2008 | Waterman et al. |
| 7,432,349 B2 | 10/2008 | Harris et al. |
| 7,456,315 B2 | 11/2008 | Hormann et al. |
| 2001/0011128 A1 | 8/2001 | Batist et al. |
| 2001/0021771 A1 | 9/2001 | Prusiner et al. |
| 2001/0044151 A1 | 11/2001 | Carlson et al. |
| 2002/0009455 A1 | 1/2002 | Lau et al. |
| 2002/0015981 A1 | 2/2002 | Paszty et al. |
| 2002/0023277 A1 | 2/2002 | Stuhlmann et al. |
| 2002/0034741 A1 | 3/2002 | Werner et al. |
| 2002/0042057 A1 | 4/2002 | Knoell |
| 2002/0042062 A1 | 4/2002 | Stearns et al. |
| 2002/0045173 A1 | 4/2002 | Drucker et al. |
| 2002/0045577 A1 | 4/2002 | Stefansson et al. |
| 2002/0048792 A1 | 4/2002 | Natesan et al. |
| 2002/0052013 A1 | 5/2002 | Melvin et al. |
| 2002/0072066 A1 | 6/2002 | Styrkarsdottir et al. |
| 2002/0086014 A1 | 7/2002 | Korman et al. |
| 2002/0094954 A1 | 7/2002 | Stefansson et al. |
| 2002/0098559 A1 | 7/2002 | Opara |
| 2002/0106689 A1 | 8/2002 | Faustman et al. |
| 2002/0107219 A1 | 8/2002 | Curiel et al. |
| 2002/0110861 A1 | 8/2002 | Dhadialla et al. |
| 2002/0111325 A1 | 8/2002 | Li et al. |
| 2002/0115144 A1 | 8/2002 | Kaplan et al. |
| 2002/0119452 A1 | 8/2002 | Phippard et al. |
| 2002/0119521 A1 | 8/2002 | Palli et al. |
| 2002/0120120 A1 | 8/2002 | Bullerdiek |
| 2002/0127600 A1 | 9/2002 | Chen et al. |
| 2002/0132329 A1 | 9/2002 | Duan et al. |
| 2002/0142417 A1 | 10/2002 | Paigen et al. |
| 2002/0142442 A1 | 10/2002 | Vogelstein et al. |
| 2002/0142444 A1 | 10/2002 | Caras |
| 2002/0151018 A1 | 10/2002 | Prouty et al. |
| 2002/0159986 A1 | 10/2002 | Langenfeld |
| 2002/0160403 A1 | 10/2002 | Seeley |
| 2002/0161210 A1 | 10/2002 | Lazar |
| 2002/0161211 A1 | 10/2002 | Lindner et al. |
| 2002/0169127 A1 | 11/2002 | Charmley et al. |
| 2002/0169300 A1 | 11/2002 | Waterman et al. |
| 2002/0182676 A1 | 12/2002 | Tartaglia et al. |
| 2002/0193581 A1 | 12/2002 | Karayiorgou et al. |
| 2002/0198362 A1 | 12/2002 | Gaiger et al. |
| 2003/0017573 A1 | 1/2003 | Friedberg et al. |
| 2003/0022870 A1* | 1/2003 | Dzau .................. A61K 31/436 514/152 |
| 2003/0040476 A1 | 2/2003 | Stuhmer et al. |
| 2003/0044813 A1 | 3/2003 | Old et al. |
| 2003/0054531 A1 | 3/2003 | Gretarsdottir et al. |
| 2003/0072758 A1 | 4/2003 | Howe |
| 2003/0078224 A1 | 4/2003 | Chung et al. |
| 2003/0087243 A1 | 5/2003 | Nelkin et al. |
| 2003/0096781 A1 | 5/2003 | Masood et al. |
| 2003/0100033 A1 | 5/2003 | Stearns et al. |
| 2003/0108920 A1 | 6/2003 | Zhang et al. |
| 2003/0109443 A1 | 6/2003 | Rueda et al. |
| 2003/0109481 A1 | 6/2003 | Gallani et al. |
| 2003/0110522 A1 | 6/2003 | Xuan et al. |
| 2003/0129631 A1 | 7/2003 | Pasternack et al. |
| 2003/0134790 A1 | 7/2003 | Langenfeld |
| 2003/0138826 A1 | 7/2003 | Lazar et al. |
| 2003/0147887 A1 | 8/2003 | Wang et al. |
| 2003/0152963 A1 | 8/2003 | Duhl et al. |
| 2003/0157072 A1 | 8/2003 | Bouillon et al. |
| 2003/0157494 A1 | 8/2003 | van Eijs et al. |
| 2003/0157599 A1 | 8/2003 | Gudmundsson |
| 2003/0159159 A1 | 8/2003 | Linnik et al. |
| 2003/0166008 A1 | 9/2003 | Eishingdrelo et al. |
| 2003/0166150 A1 | 9/2003 | Renauld et al. |
| 2003/0166217 A1 | 9/2003 | Reinhard et al. |
| 2003/0166557 A1 | 9/2003 | Minna et al. |
| 2003/0166898 A1 | 9/2003 | Chopra et al. |
| 2003/0172388 A1 | 9/2003 | Fujise et al. |
| 2003/0180302 A1 | 9/2003 | Wolf et al. |
| 2003/0180728 A1 | 9/2003 | Kovacs et al. |
| 2003/0203380 A1 | 10/2003 | Stefansson |
| 2003/0207403 A1 | 11/2003 | Paszty et al. |
| 2003/0211065 A1 | 11/2003 | Pras et al. |
| 2003/0212264 A1 | 11/2003 | Kennedy |
| 2003/0224509 A1 | 12/2003 | Moon et al. |
| 2004/0002084 A1 | 1/2004 | Dotson et al. |
| 2004/0003420 A1 | 1/2004 | Kuhn et al. |
| 2004/0005294 A1 | 1/2004 | Lee |
| 2004/0005302 A1 | 1/2004 | Hortelano |
| 2004/0006210 A1 | 1/2004 | Randazzo |
| 2004/0010119 A1 | 1/2004 | Guo et al. |
| 2004/0014706 A1 | 1/2004 | Kluxen et al. |
| 2004/0029158 A1 | 2/2004 | Olson et al. |
| 2004/0029185 A1 | 2/2004 | Van Lohuizen et al. |
| 2004/0029198 A1 | 2/2004 | Gatti et al. |
| 2004/0033600 A1 | 2/2004 | Palli et al. |
| 2004/0038284 A1 | 2/2004 | Markowitz et al. |
| 2004/0049037 A1 | 3/2004 | Tice et al. |
| 2004/0049437 A1 | 3/2004 | Brikman et al. |
| 2004/0053325 A1 | 3/2004 | Breit et al. |
| 2004/0076965 A1 | 4/2004 | Bosserhoff et al. |
| 2004/0086494 A1 | 5/2004 | John |

(56) References Cited

U.S. PATENT DOCUMENTS

| | | |
|---|---|---|
| 2004/0086504 A1 | 5/2004 | Sampath et al. |
| 2004/0091928 A1 | 5/2004 | Vogeli et al. |
| 2004/0096942 A1 | 5/2004 | Kapitskaya et al. |
| 2004/0103448 A1 | 5/2004 | Bjorklund |
| 2004/0126824 A1 | 7/2004 | Liu et al. |
| 2004/0152112 A1 | 8/2004 | Croce et al. |
| 2004/0152871 A1 | 8/2004 | Nakajima et al. |
| 2004/0171108 A1 | 9/2004 | Fisher et al. |
| 2004/0171109 A1 | 9/2004 | Haudenschild et al. |
| 2004/0171651 A1 | 9/2004 | Hormann et al. |
| 2004/0175699 A1 | 9/2004 | Fiszman et al. |
| 2004/0177388 A1 | 9/2004 | Botas et al. |
| 2004/0180371 A1 | 9/2004 | Clayman et al. |
| 2004/0185556 A1 | 9/2004 | Reed |
| 2004/0197770 A1 | 10/2004 | Sperber et al. |
| 2004/0197861 A1 | 10/2004 | Palli et al. |
| 2004/0214214 A1 | 10/2004 | Friedman et al. |
| 2004/0229241 A1 | 11/2004 | Casero et al. |
| 2004/0229250 A1 | 11/2004 | Figura et al. |
| 2004/0235097 A1 | 11/2004 | Zhang et al. |
| 2004/0259777 A1 | 12/2004 | Thirstrup et al. |
| 2005/0003463 A1 | 1/2005 | Adorjan et al. |
| 2005/0031605 A1 | 2/2005 | Bunn et al. |
| 2005/0053592 A1 | 3/2005 | Pan |
| 2005/0053931 A1 | 3/2005 | Daniel et al. |
| 2005/0054826 A1 | 3/2005 | Mao |
| 2005/0064504 A1 | 3/2005 | Heston et al. |
| 2005/0069918 A1 | 3/2005 | Claret |
| 2005/0079496 A1 | 4/2005 | Serfling et al. |
| 2005/0107313 A1 | 5/2005 | Callen et al. |
| 2005/0107315 A1 | 5/2005 | McDonald et al. |
| 2005/0123538 A1 | 6/2005 | Shemesh et al. |
| 2005/0124068 A1 | 6/2005 | Arroyo et al. |
| 2005/0153287 A1 | 7/2005 | Hayashi |
| 2005/0153352 A1 | 7/2005 | Chang et al. |
| 2005/0156014 A1 | 7/2005 | Doh et al. |
| 2005/0181374 A1 | 8/2005 | Friedman et al. |
| 2005/0191659 A1* | 9/2005 | Voellmy .............. C07K 14/47 435/6.16 |
| 2005/0196784 A1 | 9/2005 | Reynisdottir et al. |
| 2005/0227233 A1 | 10/2005 | Buxton et al. |
| 2005/0228016 A1 | 10/2005 | Michelotti et al. |
| 2005/0265978 A1 | 12/2005 | Chancellor |
| 2005/0266443 A1 | 12/2005 | Croce et al. |
| 2005/0266457 A1 | 12/2005 | Palli et al. |
| 2006/0008455 A1 | 1/2006 | Shayman et al. |
| 2006/0014711 A1 | 1/2006 | Evans et al. |
| 2006/0014931 A1 | 1/2006 | Takeda et al. |
| 2006/0019362 A1 | 1/2006 | Yu et al. |
| 2006/0020146 A1* | 1/2006 | Hormann .............. C07C 243/24 564/123 |
| 2006/0041111 A1 | 2/2006 | Yajnik et al. |
| 2006/0052320 A1 | 3/2006 | Li |
| 2006/0067942 A1 | 3/2006 | Salama |
| 2006/0068411 A1 | 3/2006 | Chang et al. |
| 2006/0070134 A1 | 3/2006 | Su et al. |
| 2006/0079675 A1 | 4/2006 | Chen et al. |
| 2006/0088825 A1 | 4/2006 | Hayes et al. |
| 2006/0099676 A1 | 5/2006 | Li et al. |
| 2006/0100132 A1 | 5/2006 | Corneliussen et al. |
| 2006/0100416 A1 | 5/2006 | Palli et al. |
| 2006/0111290 A1 | 5/2006 | Itescu et al. |
| 2006/0134688 A1 | 6/2006 | Welsh et al. |
| 2006/0140945 A1 | 6/2006 | Inada et al. |
| 2006/0141462 A1 | 6/2006 | Reynisdottir et al. |
| 2006/0148032 A1 | 7/2006 | Olayioye et al. |
| 2006/0154331 A1 | 7/2006 | Avidan et al. |
| 2006/0154852 A1 | 7/2006 | Boden et al. |
| 2006/0155113 A1 | 7/2006 | Coverley |
| 2006/0160076 A1 | 7/2006 | Moodie et al. |
| 2006/0177418 A1 | 8/2006 | Braiman-Wiksman et al. |
| 2006/0188990 A1 | 8/2006 | Kretschmer et al. |
| 2006/0194235 A1 | 8/2006 | Chen et al. |
| 2006/0204957 A1 | 9/2006 | Kumar et al. |
| 2006/0210974 A1 | 9/2006 | Moodie et al. |
| 2006/0216231 A1 | 9/2006 | Shelley et al. |
| 2006/0216731 A1 | 9/2006 | Brodie |
| 2006/0222636 A1 | 10/2006 | Rambukkana |
| 2006/0228706 A1 | 10/2006 | Bernard et al. |
| 2006/0228776 A1 | 10/2006 | Kaplitt et al. |
| 2006/0239984 A1 | 10/2006 | Rubinstein et al. |
| 2006/0240021 A1 | 10/2006 | Li et al. |
| 2006/0252787 A1 | 11/2006 | Chin |
| 2006/0263405 A1 | 11/2006 | Bruce et al. |
| 2006/0275747 A1 | 12/2006 | Hardy et al. |
| 2006/0280725 A1 | 12/2006 | Bode |
| 2006/0292119 A1 | 12/2006 | Chen et al. |
| 2006/0292154 A1 | 12/2006 | Scanlan et al. |
| 2006/0292567 A1 | 12/2006 | Zimmermann et al. |
| 2006/0293240 A1 | 12/2006 | Ron |
| 2006/0294615 A1 | 12/2006 | Lin |
| 2007/0020275 A1 | 1/2007 | Bullerdiek et al. |
| 2007/0028314 A1 | 2/2007 | Komori et al. |
| 2007/0031830 A1 | 2/2007 | Camargo et al. |
| 2007/0032439 A1 | 2/2007 | Essand |
| 2007/0036771 A1 | 2/2007 | Wagner et al. |
| 2007/0036787 A1 | 2/2007 | Asfari et al. |
| 2007/0037194 A1 | 2/2007 | Sutcliffe et al. |
| 2007/0042420 A1 | 2/2007 | Farnham et al. |
| 2007/0053845 A1 | 3/2007 | Sengupta et al. |
| 2007/0054268 A1 | 3/2007 | Sutherland et al. |
| 2007/0059287 A1 | 3/2007 | Yun et al. |
| 2007/0072218 A1 | 3/2007 | Liang et al. |
| 2007/0116671 A1 | 5/2007 | Prakash et al. |
| 2007/0122802 A1 | 5/2007 | Allan |
| 2007/0128593 A1 | 6/2007 | Petroziello et al. |
| 2007/0134669 A1 | 6/2007 | Verjat |
| 2007/0154524 A1 | 7/2007 | Kauper et al. |
| 2007/0160996 A1 | 7/2007 | Leissner et al. |
| 2007/0161086 A1 | 7/2007 | Palli et al. |
| 2007/0166711 A1 | 7/2007 | Samuels et al. |
| 2007/0300313 A1 | 12/2007 | Palli et al. |
| 2008/0050808 A1 | 2/2008 | Reed et al. |
| 2008/0115237 A1 | 5/2008 | Palli et al. |
| 2008/0145935 A1 | 6/2008 | Palli et al. |
| 2008/0176280 A1 | 7/2008 | Kapitskaya et al. |
| 2008/0216184 A1 | 9/2008 | Palli et al. |
| 2008/0235816 A1 | 9/2008 | Dhadialla et al. |
| 2008/0263687 A1 | 10/2008 | Kapitskaya et al. |
| 2008/0301825 A1 | 12/2008 | Palli et al. |
| 2009/0123441 A1 | 5/2009 | Braughler et al. |
| 2009/0163592 A1 | 6/2009 | Hormann et al. |
| 2013/0266947 A1 | 10/2013 | Beech et al. |

FOREIGN PATENT DOCUMENTS

| | | |
|---|---|---|
| AU | 2002-248500 | 12/2007 |
| CA | 2012311 | 6/2003 |
| EP | 0 234 994 | 9/1987 |
| EP | 0 461 809 | 12/1991 |
| EP | 0 965 644 | 12/1999 |
| EP | 1 205 490 | 5/2002 |
| EP | 1 262 193 | 12/2002 |
| EP | 1 266 015 | 12/2002 |
| KR | 10-0563143 | 3/2006 |
| MX | 234 742 | 3/2006 |
| RU | 2004127439 A | 4/2005 |
| WO | WO 95/18863 | 7/1995 |
| WO | WO 95/21931 | 8/1995 |
| WO | WO 96/17823 | 6/1996 |
| WO | WO 96/25508 | 8/1996 |
| WO | WO 00/37504 | 6/2000 |
| WO | WO 00/56861 A1 | 9/2000 |
| WO | WO 01/70816 | 9/2001 |
| WO | WO 02/29075 | 4/2002 |
| WO | WO 02/066612 | 8/2002 |
| WO | WO 02/066613 | 8/2002 |
| WO | WO 02/066614 | 8/2002 |
| WO | WO 02/066615 | 8/2002 |
| WO | WO 2004/005478 A2 | 1/2004 |
| WO | WO 2004/078924 | 9/2004 |
| WO | WO 2005/017126 A2 | 2/2005 |
| WO | WO 2005/017165 A1 | 2/2005 |
| WO | WO 2005/040336 | 5/2005 |

(56) References Cited

FOREIGN PATENT DOCUMENTS

| | | |
|---|---|---|
| WO | WO 2005/108617 | 11/2005 |
| WO | WO 2005/116231 | 12/2005 |
| WO | WO 2006/083253 | 8/2006 |
| WO | WO 2007/038276 | 4/2007 |
| WO | WO 2008/153801 | 12/2008 |
| WO | WO 2009/025866 A1 | 2/2009 |
| WO | WO 2009/048560 A1 | 4/2009 |
| WO | WO 2009/045370 A3 | 4/2010 |
| WO | WO 2010/042189 A2 | 4/2010 |

OTHER PUBLICATIONS

"FGF-4 Gene Therapy GENERX—Collateral Therapeutics," *BioDrugs* 16:75-76, Adis International (2002).
Altschul, S.F., et al., "Basic Local Alignment Search Tool," *J. Mol. Biol.* 215:403-410, Academic Press (1990).
Antoniewski, C., et al., "The Ecdysone Response Enhancer of the Fbp1 Gene of *Drosophila melanogaster* Is a Direct Target for the EcR/USP Nuclear Receptor," *Mol. Cell Biol.* 14:4465-4474, American Society for Microbiology (1994).
Arsic, N., et al., "Induction of Functional Neovascularization by Combined VEGF and Angiopoietin-1 Gene Transfer Using AAV Vectors," *Mol. Ther.* 7:450-459, Academic Press (2003).
Asahi, M., et al., "Cardiac-specific overexpression of sarcolipin inhibits sarco(endo)plasmic reticulum $Ca^{2+}$ ATPase (SERCA2a) activity and impairs cardiac function in mice," *Proc. Natl. Acad. Sci. U.S.A.* 101:9199-9204, National Academy of Sciences (2004).
Austin, S., et al., "A Novel Role for Site-Specific Recombination in Maintenance of Bacterial Replicons," *Cell* 25:729-736, Cell Press (1981).
Bani, D., et al., "Relaxin Protects Against Myocardial Injury Caused by Ischemia and Reperfusion in Rat Heart," 152:1367-1376, American Society for Investigative Pathology (1998).
Barton, P.J., et al., "Myocardial Insulin-Like Growth Factor-I Gene Expression During Recovery From Heart Failure After Combined Left Ventricular Assist Device and Clenbuterol Therapy," *Circulation* 112:146-150, Lippincott Williams & Wilkins (2005).
Basile, A., et al., "Characterization of the Promoter for the Human Long Pentraxin PTX3. Role of NF-κβ in Tumor Necrosis Factor-α and Interleukin-1β regulation," *J. Biol. Chem.* 272:8172-8178, American Society for Biochemistry and Molecular Biology (1997).
Bathgate, R..A., et al., "Adenovirus-mediated delivery of relaxin reverses cardiac fibrosis," *Mol. Cell Endocrinol.* 280:30-38, North Holland Publishing (Jan. 2008).
Becker, C., et al., "Skeletal muscle cells expressing VEGF induce capillary formation and reduce cardiac injury in rats," *Int. J. Cardiol.* 113:348-354, Elsevier (Nov. 2006).
Ben-Dor, I., et al., "Repeated Low-dose of Erythropoietin is Associated with Improved Left Ventricular Function in Rat Acute Myocardial Infarction Model," *Cardiovasc. Drugs Ther.* 21:339-346, Kluwer Academic (Oct. 2007).
Benest, A.V., et al., "VEGF and Angiopoietin-1 Stimulate Different Angiogenic Phenotypes That Combine to Enhance Functional Neovascularization in Adult Tissue," *Microcirculation* 13:423-437, Taylor & Francis (Sep. 2006).
Benoist, C., and Chambon, P., "In vivo sequence requirements of the SV40 early promotor region," *Nature* 290:304-310, Nature Publishing Group (1981).
Bhavsar, P.K., et al., "Identification of cis-acting DNA Elements Required for Expression of the Human Cardiac Troponin I Gene Promoter," *J. Mol. Cell Cardiol.* 32:95-108, Academic Press (2000).
Blasi, P., et al., "Preparation and in vitro and in vivo characterization of composite microcapsules for cell encapsulation," *Int. J. Pharm.* 324:27-36, Elsevier B.V. (2006).
Bonaros, N., et al., "Neoangiogenesis after combined transplantation of skeletal myoblasts and angiopoietic progenitors leads to increased cell engraftment and lower apoptosis rates in ischemic heart failure," *Interact. Cardiovasc. Thorac. Surg.* 7:249-255, European Association for Cardio-Thoracic Surgery (Apr. 2008).

Brent, R., and Ptashne, M., "A Eukaryotic Transcriptional Activator Bearing the DNA Specificity of a Prokaryotic Repressor," *Cell* 43:729-736, Cell Press (1985).
Buchholz, F., et al., "Improved properties of FLP recombinase evolved by cycling mutagenesis," *Nat. Biotechnol.* 16:657-662, Nature America Publishing (1998).
Burnett Jr., J.C., "Novel therapeutic directions for the natriuretic peptides in cardiovascular diseases: what's on the horizon," *J. Cardiol.* 48:235-241, Japanese College of Cardiology (Nov. 2006).
Cavagna, M., et al., "Exogenous $Ca^{2+}$-ATPase isoform effects on $Ca^{2+}$ transients of embryonic chicken and neonatal rat cardiac myocytes," *J. Physiol.* 528:53-63, Cambridge University Press (2000).
Chae, J.K., et al., "Coadministration of Angiopoietin-1 and Vascular Endothelial Growth Factor Enhances Collateral Vascularization," *Arterioscler. Thromb. Vasc. Biol.* 20:2573-2578, Lippincott Williams & Wilkins (2000).
Chae, J.K., et al., "Coadministration of Angiopoietin-1 and Vascular Endothelial Growth Factor Enhances Collateral Vascularization," *Arterioscler. Thromb. Vasc. Biol.* 20:2573-2578, Lippincott Williams & Wilkins (2000) (Supplementary Materials and Methods).
Chao, W., et al., "Strategic advantages of insulin-like growth factor-I expression for cardioprotection," *J. Gene Med.* 5:277-286, John Wiley & Sons (2003).
Chaudhri, B., et al., "Contractile effects of adenovirally-mediated increases in SERCA2a activity: a comparison between adult rat and rabbit ventricular myocytes," *Mol. Cell Biochem.* 251:103-109, Kluwer Academic (2003).
Chen, H.K., et al., "Combined cord blood stem cells and gene therapy enhances angiogenesis and improves cardiac performance in mouse after acute myocardial infarction," *Eur. J. Clin. Invest.* 35:677-686, Blackwell Scientific Publications (2005).
Chen, Y., et al., "Risk factors for bronchopulmonary dysplasia in neonates with respiratory distress syndrome," *Zhongguo. Dang. Dai. Er. Ke. Za. Zhi.* 9:15-18. Zhongguo dang dai. er ke za zhi she (Feb. 2007).
Chen, F., et al., "Adeno-associated virus vectors simultaneously encoding VEGF and angiopoietin-1 enhances neovascularization in ischemic rabbit hind-limbs," *Acta. Pharmacol. Sin.* 28:493-502, Shanghai Institute of Materia Medica (Apr. 2007).
Chen, F., et al., "Combination of $VEGF_{165}$/Angiopoietin-1 gene and endothelial progenitor cells for therapeutic neovascularization," *Eur. J. Pharmacol.* 568:222-23, , Elsevier Science (Jul. 2007).
Cherbas, L., et al., "Identification of ecdysone response elements by analysis of the *Drosophila* Eip28/29 gene," *Genes Dev.* 5:120-131, Cold Spring Harbor Laboratory Press (1991).
Ciavatta, D., et al., "A DNA insulator prevents repression of a targeted X-linked transgene but not its random or imprinted X inactivation," *Proc. Natl. Acad Sci. U.S.A.* 103:9958-9963, National Academy of Sciences (Jun. 2006).
Climent, V., et al., "Pharmacologic Therapy in Growth Hormone Disorders and the Heart," *Curr. Med. Chem.* 14:1399-1407, Bentham Science Publishers (Jan. 2007).
Curiel, D.T., et al., "High-Efficiency Gene Transfer Mediated by Adenovirus Coupled to DNA-Polylysine Complexes," *Hum. Gene Ther.* 3:147-154, M.A. Liebert (1992).
Darrabie, M.D., et al., "Characteristics of Poly-$_L$-Ornithine-coated alginate microcapsules," *Biomaterials* 26:6846-6852, Elsevier B. V. (2005).
Davia, K., et al., "SERCA2A Overexpression Decreases the Incidence of Aftercontractions in Adult Rabbit Ventricular Myocytes," *J. Mol. Cell Cardiol.* 33:1005-1015, Academic Press (2001).
D'Avino, P.P., et al., "The moulting hormone ecdysone is able to recognize target elements composed of direct repeats," *Mol. Cell Endocrinol.* 113:1-9, North Holland Publishing (1995).
Del Monte, F., et al., "Improvement in Survival and Cardiac Metabolism After Gene Transfer of Sarcoplasmic Reticulum $Ca(^{2+})$-ATPase in a Rat Model of Heart Failure," *Circulation* 104:1424-1429, Lippincott Williams & Wilkins (2001).
Del Monte., F., et al., "Restoration of Contractile Function in Isolated Cardiomyocytes From Failing Human Hearts by Gene Transfer of SERCA2a," *Circulation* 100:2308-2311, Lippincott Williams & Wilkins (1999).

(56) References Cited

OTHER PUBLICATIONS

Díaz, V., et ai., "The Prokaryotic β-Recombinase Catalyzes Site-specific Recombination in Mammalian Cells," *J. Biol. Chem.* 274:6634-6640, American Society for Biochemistry and Molecular Biology (1999).
Ding, W., et al., "Genomic structure and promoter characterization of the human Sprouty4 gene, a novel regulator of lung morphogenesis," *Am. J. Physiol. Lung Cell Mol. Physiol.* 287:L52-L59, American Physiological Society (2004).
Doi, K., et al., "Enhanced angiogenesis by gelatin hydrogels incorporating basic fibroblast growth factor in rabbit model of hind limb ischemia," *Heart Vessels* 22:104-108, Springer Verlag (Mar. 2007).
Dschietzig, T., et al., "The pregnancy hormone relaxin is a player in human heart failure," *FASEB J.* 15:2187-2195, The Federation (2001).
Du, X.J., "Re-modelling 'hostile' milieu of diseased myocardium via paracrine function of transplanted cells or relaxin," *J. Cell Mol. Med.* 11:1101-1104, Carol Davila University Press (Sep.-Oct. 2007).
Duncan, B., and Zhao, K., "HMGA1 Mediates the Activation of the CRYAB Promoter by BRG1," *DNA Cell Biol.* 26:745-752, Mary Ann Liebert (Oct. 2007).
Dunn, P.F., et al., "Seeding of Vascular Grafts With Genetically Modified Endothelial Cells. Secretion of Recombinant TPA Results in Decreased Seeded Cell Retention in vitro and in vivo," *Circulation* 93:1439-1446, Lippincott Williams & Wilkins (1996).
Elmadbouh, I., et al., "Ex vivo delivered stromal cell-derived factor-1α promotes stem cell homing and induces angiomyogenesis in the infarcted myocardium," *J. Mol. Cell Cardiol.* 42:792-803, Academic Press (Apr. 2007).
Evans, R.M., "The Steroid and Thyroid Hormone Receptor Superfamily," *Science* 240:889-895, American Association for the Advancement of Science (1988).
Fazio, S., et al., "Effects of Growth Hormone on Exercise Capacity and Cardiopulmonary Performance in Patients with Chronic Head Failure," *J. Clin. Endocrinol. Metab.* 92:4218-4223, Endocrine Society (Nov. 2007).
Felgner, P.L., et al., "Lipofection: A highly efficient, lipid-mediated DNA-transfection procedure," *Proc. Natl. Acad. Sci. U.S.A.* 84:7413-7417, National Academy of Sciences (1987).
Felgner, P.L., and Ringold, G.M., "Cationic liposome-mediated transfection," *Nature* 337:387-388, Nature Publishing Group (1989).
Formigli, L., et al., "Paracrine effects of transplanted myoblasts and relaxin on post-infarction heart remodelling," *J. Cell Mol. Med.* 11:1087-1100, Carol Davila University Press (Sep.-Oct. 2007).
Fujita, M., et al., "Efficacy of Photocrosslinkable Chitosan Hydrogel Containing Fibroblast Growth Factor-2 in a Rabbit Model of Chronic Myocardial Infarction," *J. Surg. Res.* 126:27-33, Academic Press (2005).
Fujita, M., et al., "Therapeutic angiogenesis induced by controlled release of fibroblast growth factor-2 from injectable chitosan/non-anticoagulant heparin hydrogel in a rat hindlimb ischemia model," *Wound Repair Regen.* 15:58-65, Blackwell Science (Jan.-Feb. 2007).
Furth, P.A., et al., "Temporal control of gene expression in transgenic mice by a tetracycline-responsive promoter," *Proc. Natl. Acad. Sci. U.S.A.* 91:9302-9306, National Academy of Sciences (1994).
Gao, M., et al., "Increased expression of adenylyleyclase type VI proportionately increases β-adrenergic receptor-stimulated production of cAMP in neonatal rat cardiac myocytes," *Proc. Natl. Acad. Sci. U.S.A.* 95:1038-1043, National Academy of Sciences (1998).
Gao, M.H., et al.,"Controlled expression of cardiac-directed adenylylcyclase type VI provides increased contractile function," *Cardiovasc. Res.* 56:197-204, Oxford Journals (2002).
Gao, M.H., et al., "Adenylyl Cyclase Type VI Gene Transfer Reduces Phospholamban Expression in Cardiac Myocytes via Activating Transcription Factor 3," *J. Biol. Chem.* 279:38797-38802, American Society for Biochemistry and Molecular Biology (2004).

Gao, F., et al., "A promising strategy for the treatment of ischemic heart disease: Mesenchymal stem cell-mediated vascular endothelial growth factor gene transfer in rats," *Can. J. Cardiol.* 23:891-898, Pulsus Group, Inc. (Sep. 2007).
García-Martin, C., et al., "Therapeutic levels of human factor VIII in mice implanted with encapsulated cells: potential for gene therapy of haemophilia A," *J. Gene Med.* 4:215-223, John Wiley & Sons (2002).
Glass, C.K., et al., "Nuclear receptor coactivators," *Curr. Opin Cell Biol.* 9:222-232, Current Science (1997).
Gong, Y.S., et al., "Retroviral gene transfer of tissue-type plasminogen activator targets thrombolysis in vitro and in vivo," *Gene Ther.* 14:1537-1542, Nature Publishing Group (Nov. 2007).
Gopal-Srivastava, R., "Regulation of the Murine αB-Crystallin/ Small Heat Shock Protein Gene in Cardiac Muscle," *Mol. Cell Biol.* 15:7081-7090, American Society for Microbiology (1995).
Gossen, M., and Bujard, H., "Tight control of gene expression in mammalian cells by tetracycline-responsive promoters," *Proc. Natl. Acad. Sci. U.S.A.* 89:5547-5551, National Academy of Sciences (1992).
Gossen, M., el. al., "Control of gene activity in higher eukaryotic cells by prokaryotic regulatory eletmnts," *Trends Biochem. Sci.* 18:471-475, Elsevier Trends Journals (1993).
Grines, C., et al., "Angiogenic Gene Therapy with Adenovinis 5 Fibroblast Growth Factor-4 (Ad5FGF-4): A New Option for the Treatment of Coronary Artery Disease," *Am. J. Cardiol.* 92:24N-31N, Excerpta Medica (2003).
Groth, A.C., et al., "A phage integrase directs efficient site-specific integration in human cells," *Proc. Natl. Acad. Sci. U.S.A.* 97:5995-6000, National Academy of Sciences (2000).
Guo, Y., et al., "Locally Overexpressing Hepatocyte Growth Factor Prevents Post-ischemic Heart Failure by Inhibition of Apoptosis via Calcineurin-mediated Pathway and Angiogenesis," *Arch. Med. Res.* 39:179-188, Elsevier Science (Feb. 2008).
Gupta, R.C., et al., "Cardiac SR-coupled PP1 activity and expression are increased and inhibitor 1 protein expression is decreased in failing hearts," *Am. J. Physiol. Heart Circ. Physiol.* 285:H2373-H2381, American Physiological Society (2003).
Gupta, R.C., et al., "Reduced inhibitor 1 and 2 activity is associated with increased protein phosphatase type 1 activity in left ventricular myocardium of one-kidney, one-clip hypertensive rats," *Mol. Cell Biochem.* 269:49-57, Kluwer Academic (2005).
Haider, H.K.H., et al., "Angiomyogenesis for cardiac repair using human myoblasts as carriers of human vascular endothelial growth factor," *J. Mol. Med.* 82:539-549, Elsevier Scientific Publishing Company (2004).
Hajjar, R.J., et al., "Adenoviral Gene Transfer of Phospholamban in Isolated Rat Cardionlyocytes. Rescue Effects by Concomitant Gene Transfer of Sarcoplasmic Reticulum $Ca^{2+}$-ATPase," *Circ. Res.* 81:145-153, Lippincott Williams & Wilkins (1997).
Hamer, D.H., and Walling, M., "Regulation In Vivo of a Cloned Mammalian Gene: Cadmium Induces the Transcription of a Mouse Metallothionein Gene in SV40 Vectors," *J. Mol. Appl. Genet.* 1:273-288, Raven Press (1982).
Hammond, H.K., et al, "Adenylyl Cyclase Gene Transfer in Heart Failure," *Ann. NY Acad. Sci.* 1080:426-436, New York Academy of Sciences (Oct. 2006).
Henry, T.D., et al., "Effects of Ad5FGF-4 in Patients with Angina: An Analysis of Pooled Data From the AGENT-3 and AGENT-4 Trials," *J. Am. Coll. Cardiol.* 50:1038-1046, Elsevier Biomedical (Sep. 2007).
Higgins, D.G., and Sharp, P.M., "Fast and sensitive multiple sequence alignments on a microcomputer," *Comput. Appl. Biosci.* 5:151-153, Oxford University Press (1989).
Hirsch, J.C., et al., "Comparative analysis of parvalbumin and SERCA2a cardiac myocyte gene transfer in a large animal model of diastolic dysfunction," *Am. J. Physiol Heart Circ. Physiol.* 286:H2314-H2321, American Physiological Society (2004).
Horwitz, K.B., et al., "Nuclear Receptor Coactivators and Corepressors," *Mol. Endocrinol.* 10:1167-1177, Endocrine Society (1996).
Hosaka, A., et al., "Gelatin Hydrogel Microspheres Enable Pinpoint Delivery of Basic Fibroblast Growth Factor for the Development of

(56) References Cited

OTHER PUBLICATIONS

Functional Collateral Vessels," *Circulation* 110:3322-3328, Lippincott Williams & Wilkins (2004).

Hutchinson III, C.A., et al., "A complete library of point substitution mutations in the glucocorticoid response element of mouse mammary tumor virus," *Proc. Natl. Acad. Sci. U.S.A.* 83:710-714, National Academy of Sciences (1986).

Hutchinson III, C.A., et al., "Mutagenesis at a Specific Position in a DNA Sequence," *J. Biol. Chem.* 253:6551-6560, American Society for Biochemistry and Molecular Biology (1978).

Inoue, A., et al., "The Therapeutic Effects of Basic Fibroblast Growth Factor Contained in Gelatin Hydrogel Microspheres on Experimental Osteoarthritis in the Rabbit Knee," *Arthritis Rheum.* 54:264-270, Wiley-Liss, Inc. (Jan. 2006).

Isgaard, J., and Bergh, C.H., "Clinical Potential of Growth Hormone in the Treatment of Congestive Heart Failure," *BioDrugs* 12:245-250, Adis International (1999).

Iwakura, A., et al., "Intramyocardial sustained delivery of basic fibroblast growth factor improves angiogenesis and ventricular function in a rat infarct model," *Heart Vessels* 18:93-99, Springer Verlag (2003).

Jiang, J., et al., "Augmentation of revascularization and prevention of plasma leakage by angiopoietin-1 and vascular endothelial growth factor co-transfection in rats with experimental limb ischaemia," *Acta. Cardiol.* 61:145-153, Acta Medica Belgica (Apr. 2006).

Kapur, N.K., and Rade, J.J., et al., "Fibroblast Growth Factor 4 Gene Therapy for Chronic Ischemic Heart Disease," *Trends Cardiovasc. Med.* 18:133-141, Elsevier Science Publishing (May 2008).

Kawase, Y., et al.,"Reversal of Cardiac Dysfunction After Long-Term Expression of SERCA2a by Gene Transfer in a Pre-Clinical Model of Heart Failure," *J. Am. Coll. Cardiol.* 51:1112-1119, Elsevier Biomedical (Mar. 2008).

Kelly, R., et al., "Myosin Light Chain 3F Regulatory Sequences Confer Regionalized Cardiac and Skeletal Muscle Expression in Transgenic Mice," *J. Cell Biol.* 129:383-396, Rockefeller University Press (1995).

Kim, J.S., et al., "Design of TATA box-binding protein/zinc finger fusions for targeted regulation of gene expression," *Proc. Natl. Acad. Sci. U.S.A.* 94:3616-3620, National Academy of Sciences (1997).

Kim, et al., "Effects of Cell-Based Angiogenic Gene Therapy at 6 Months: Persistent Angiogenesis and Absence of Oncogenicity," *Ann. Thorac. Surg.* 83:640-646, Elsevier (Feb. 2007).

Kirchhefer, U., et al., "Enhanced cardiac function in mice overexpressing protein phosphatase Inhibitor-2," *Cardiovasc. Res.* 68:98-108, Oxford Journals (2005).

Kolot, M., et al., "Site-specific recombination in mammalian cells expressing the Int recombinase of bacteriophage HK022," *Mol. Biol. Rep.* 26:207-213, Reidel (1999).

Kumon, Y., et al., "Transcriptional Regulation of Serum Amyloid A1 Gene Expression in Human Aortic Smooth Muscle Cells Involves CCAAT/Enhancer Binding Proteins (C/EBP) and is Distinct From HepG2 Cells," *Scand. J. Immunol.* 56:504-511, Blackwell Scientific Publications (2002).

Lai, N.C., et al., "Intracoronary Delivery of Adenovirus Encoding Adenylyl Cyclase VI Increases Left Ventricular Function and cAMP-Generating Capacity," *Circulation* 102:2396-2401, Lippincott Williams & Wilkins (2000).

Lai, N.C., et al., "Intracoronary Adenovirus Encoding Adenylyl Cyclase VI Increases Left Ventricular Function in Heart Failure," *Circulation* 110:330-336, Lippincott Williams & Wilkins (2004).

Lai, P.H., et al., "Acellular Biological Tissues Containing Inherent Glycosaminoglycans for Loading Basic Fibroblast Growth Factor Promote Angiogenesis and Tissue Regeneration," *Tissue Eng.* 12:2499-2508, Mary Ann Liebert, Inc. (Sep. 2006).

Lai, N.C., et al., "Activation of Cardiac Adenylyl Cyclase Expression Increases Function of the Failing Ischemic Heart in Mice," *J. Am. Coll. Cardiol.* 51:1490-1497, Elsevier Biomedical (Apr. 2008).

Le Corvoisier, P., et al., "Cardiac Effects of Growth Hormone Treatment in Chronic Heart Failure: A Meta-Analysis," *J. Clin. Encdocrinol. Metab.* 92:180-185, Endocrine Society (Jan. 2007).

Lee, K.J., et al., "Positive Regulatory Elements (HF-1a and HF-1b) and a Novel Negative Regulatory Element (HF-3) Mediate Ventricular Muscle-Specific Expression of Myosin Light-Chain 2-Luciferase Fusion Genes in Transgenic Mice," *Mol. Cell. Biol.* 14:1220-1229, American Society for Microbiology (1994).

Lekgabe, E.D., et al., "The Effects of Relaxin and Estrogen Deficiency on Collagen Deposition and Hypertrophy of Nonreproductive Organs," 147:5575-5583, Endocrine Society (Dec. 2006).

Li, Y., et al., "Fabrication of dual-layer polyethersulfone (PES) hollow fiber membranes with an ultrathin dense-selective layer for gas separation," *J. Membrane Sci.* 245:53-60, Elsevier B.V. (2004).

Li, Z., et al., "Hepatocyte growth factor combined with insulin like growth factor-1 improves expression of GATA-4 in mesenchymal stem cells cocultured with cardiomyocytes," *Chin. Med. J. (Engl).* 121:336-340, Chinese Medical Association and Pergamon Press (Feb. 2008).

Lin, X., et al., "Sustained-Release Erythropoietin ameliorates Cardiac Function in Infarcted Rat-Heart Without Inducing Polycythemia," *Circ. J.* 71:132-137, Japanese Circulation Society (Jan. 2007).

Liu, X., et al., "Synergistically therapeutic effects of VEGF165 and angiopoietin-1 on ischemic rat myocardium," *Scand. Cardiovasc. J.* 41:95-101, Taylor & Francis (Apr. 2007).

Lorbach, E., et al., "Site-specific Recombination in Human Cells Catalyzed by Phage λ Integrase Mutants," *J. Mol. Biol.* 296:1175-1181, Academic Press (2000).

Lubiatowski, P., et al., "Gene Therapy by Adenovirus-Mediated Vascular Endothelial Growth Factor and Angiopoietin-1 Promotes Perfusion of Muscle Flaps," *Plast. Reoncstr. Surg.* 110:149-159, Lippincott Williams & Wilkins (2002).

Luo, el al., "A Constitutively Active Hypoxia-Inducible Factor-1α/VP16 Hybrid Factor Activates Expression of the Human B-Type Natriuretic Peptide Gene," *Mol. Pharmacol.* 69:1953-1962, American Society for Pharmacology and Experimental Therapeutics (Jun. 2006).

Ma, J., et al., "Time course of myocardial stromal cell-derived factor 1 expression and beneficial effects of intravenously administered bone marrow stem cells in rats with experimental myocardial infarction," *Basic Res. Cardiol.* 100:217-223, Dr. Dietrich Steinkopff Verlag (2005).

Machy, P., et al., "Gene transfer from targeted liposomes to specific lymphoid cells by electroporation," *Proc. Natl. Acad. Sci. U.S.A.* 85:8027-8031, National Academy of Sciences (1988).

Mahony, D., et al., "Plasminogen activator ininbitor type-2 (PAI-2) gene transcription requires a novel NF-κB-like transcriptional regulatory motif," *Eur. J. Biochem.* 263:795-772, Blackwell Science Ltd. (1999).

Maier, L.S., et al., "Increased SR $Ca^{2+}$ cycling contributes to improved contractile performance in SERCA2a-overexpressing transgenic rats," *Cardiovasc. Res.* 67:636-646, Oxford Journals (2005).

Masini, E., et al., "The effect of relaxin on myocardial ischaemia-reperfusion injury and histamine release in vitro and in vivo," *Inflamm. Res.* 45:S27-S28, Birkhäuser (1996).

Masini, E., et al., "Protective effect of relaxin in cardiac anaphylaxis: involvement of the nitric oxide pathway," *Br. J. Pharmacol.* 137:337-344, Wiley (2002).

Matsuo, S., et al., "Crucial roles of binding sites for NF-κB and C/EBPs in IκB-ξ-mediated transcriptional activation," *Biochem. J.* 405:605-615, Portland Press (Aug. 2007).

McKnight, S.L., "Functional Relationships between Transcriptional Control Signals of the Thymidine Kinase Gene of Herpes Simplex Virus," *Cell* 31:355-365, Cell Press (1982).

Mercurial, F., et al., "Use of erythropoietin to increase the volume of autologous blood donated by orthopedic patients," *Transfusion* 33:55-60, Libraire Arnette (1993).

Meyer, M., and Dillman, W.H., "Sarcoplasmic reticulum $Ca^{2+}$-ATPase overexpression by adenovirus mediated gene transfer and in transgenic mice," *Cardiovasc. Res.* 37:360-366, Oxford Journals (1998).

(56) References Cited

OTHER PUBLICATIONS

Michele, D.E., et al., "Parvalbumin Gene Delivery: Improves Diastolic Function in the Aged Myocardium in Vivo," *Mol. Ther.* 10:399-403, Academic Press (2004).

Miyamoto, M.I., et al., "Adenoviral gene transfer of SERCA2a improves left-ventricular function in aortic-banded rats in transition to heart failure," *Proc. Natl. Acad. Sci. U.S.A.* 97:793-798, National Academy of Sciences (2000).

Moore, X.L., et al., "Relaxin Antagonizes Hypertrophy and Apoptosis in Neonatal Rat Cardiomyocytes," *Endocrinology* 148:1582-1589, Endocrine Society (Apr. 2007).

Most, P., et al., "Transgenic Overexpression of the $Ca^{2+}$-binding Protein S100A1 in the Heart Leads to Increased in Vivo Myocardial Contractile Performance," *J. Biol. Chem.* 278:33809-33817, American Society for Biochemistry and Molecular Biology (2003).

Most, P., et al., "Cardiac adenoviral S100A1 gene delivery rescues failing myocardium," *J. Clin. Invest.* 114:1550-1563, American Society for Clinical Investigation (2004).

Most, P., et al, "Cardiac S100A1 Protein Levels Determine Contractile Performance and Propensity Toward Heart Failure after Myocardial Infarction," *Circulation* 114:1258-1268, Lippincott Williams & Wilkins (Sep. 2006).

Most, P., et al., "S100A1: a novel inotropic regulator of cardiac performance. Transition from molecular physiology to pathophysiological relevance," *Am. J. Physiol. Regul. Integr. Comp. Physiol.* 293:R568-R577, American Physiological Society (Aug. 2007).

Müller, O.J., et al., "Transgenic rat hearts overexpressing SERCA2a show improved contractility under baseline conditions and pressure overload," *Cardiovasc. Res.* 59:380-389, Oxford Journals (2003).

Nakajima, H., et al., "Therapeutic angiogenesis by the controlled release of basic fibroblast growth factor for ischemic limb and heart injury: toward safety and minimal invasiveness," *J. Artif. Organs* 7:58-61, Springer Verlag (2004).

Ndisang, J.F., et al., "Relaxin generates nitric oxide and provides protection against cardiac anaphylaxis," *Inflamm. Res.* 50:S122-S123, Birkhäuser (2001).

Nelson, T.J., et al., "SRF-dependent gene expression in isolated cardiomyocytes: regulation of genes involved in cardiac hypertrophy," *J. Mol. Cell Cardiol.* 39:479-489, Academic Press (Sep. 2005).

Nistri, S., et al., "Relaxin as a Cardiovascular Hormone: Physiology, Pathophysiology and Therapeutic Promises," *Cardiovasc. Hematol. Agents Med. Chem.* 5:101-108, Bentham Science Publishers (Apr. 2007).

Nistri, S., et al., "Relaxin induces mast cell inhibition and reduces ventricular arrhythmias in a swine model of acute myocardial infarction," *Pharmacol. Res.* 57:43-48; Academic Press (Jan. 2008).

Oliphant, A.R., et al., "Cloning of random-sequence oligodeoxynucleotides," *Gene* 44:177-183, Elsevier/North-Holland (1986).

Ozawa, C.R., et al., "Microenvironmental VEGF concentration, not total dose, determines a threshold between normal and aberrant angiogenesis," *J. Clin. Invest.* 113:516-527, American Society for Clinical Investigation (2004).

Perets, A., et al., "Enhancing the vascularization of three-dimensional porous alginate, scaffolds by incorporating controlled release basic fibroblast growth factor microspheres," *J. Biomed. Mater. Res. A* 65:489-497, John Wiley & Sons (2003).

Pérez-Berbel, P., et al., "Short- and long-tetm effects of growth hormone on the heart," *Int. J. Cardiol.* 124:393-394, Elsevier (Mar. 2008).

Perna, A.M., et al., "Human Recombinant Relaxin Reduces Heart Injury and Improves Ventricular Performance in a Swine Model of Acute Myocardial Infarction," *Ann. NY Acad. Sci.* 1041:431-433, New York Academy of Sciences (2005).

Perna, A.M., et al., "Novel drug development opportunity for relaxin in acute myocardial infarction: evidences from a swine model," *FASEB J.* 19:1525-1527, The Federation (2005).

Phan, H.M., et al., "New Signaling Pathways Associated with Increased Cardiac Adenyly1 Cyclase 6 Expression: Implications for Possible Congestive Heart Failure Therapy," *Trends Cardiovasc. Med.* 17:215-221, Elsevier Science Publishing (Oct. 2007).

Pike, D.B., et al., "Heparin-regulated release of growth factors in vitro and angiogenic response in vivo to implanted hyaluronan hydrogels containing VEGF and bFGF," *Biomateriais* 27:5242-5251, Butterworth-Heinemann in Association With the Biological Engineering Society (Oct. 2006).

Pipe, S.W., et al., "The promise and challenges of bioengineered recombinant clotting factors," *J. Thromb. Haemost.* 3:1692-1701, Blackwell Publishing (2005).

Pleger, S.T., et al., "S100A1 Gene Therapy Presetves in Vivo Cardiac Function after Myocardial Infarction," *Mol. Ther.* 12:1120-1129, Academic Press (2005).

Pleger, S.T., et al., "S100A1 Gene Transfer in Myocardium," *Eur. J. Med. Res.* 11:418-422, I. Holzapfel Publishers (Oct. 2006).

Pleger, S.T., et al., "Stable Myocardial-Specific AAV6-S100A1 Gene Therapy Results in Chronic Functional Heart Failure Rescue," *Circulation* 115:2506-2515, Lippincott Williams & Wilkins (May 2007).

Prunier, F., et al., "Delayed erythropoietin therapy reduces post-MI cardiac remodeling only at a dose that mobilizes endothelial progenitor cells," *Am. J. Physiol. Heart Circ. Physiol.* 292:H522-H529, American Physiological Society (Jan. 2007).

Rabinovsky, E.D., and Draghia-Akli, R., "Insulin-like Growth Factor I Plasmid Therapy Promotes in vivo Angiogenesis," *Mol. Ther.* 9:46-55, Academic Press (2004).

Rajagopalan, S., et al., "Use of a Constitutively Active Hypoxia-Inducible Factor-1α Transgene as a Therapeutic Strategy in No-Option Critical Limb Ischemia Patients: Phase 1 Dose-Escalation Experience," *Circulation* 115:1234-1243, Lippincott Williams & Wilkins (Mar. 2007).

Rebolledo, B., et al., "Adenylylcyclase Gene Transfer Increases Function of the Failing Heart," *Hum. Gene Ther.* 17:1043-1048, M.A. Liebert (Oct. 2006).

Reeck, G.R., et al., "'Homology' in Proteins and Nucleic Acids: A Terminology Muddle and a Way out of It," *Cell* 50:667, Cell Press (1987).

Remppis, A., et al., "The small EF-hand $Ca^{2+}$ binding protein S100A1 increases contractility and $Ca^{2+}$ cycling in rat cardiac myocytes," *Basic Res. Cardiol.* 87:I56-I62, Dr. Dietrich Steinkopff Verlag (2002).

Remppis, A., et al., "S100A1 gene transfer: a strategy to strengthen engineered cardiac grafts," *J. Gene Med.* 6:387-394, John Wiley & Sons (2004).

Riley, C.M., et al., "Stimulation of in vivo angiogenesis using dual growth factor-loaded crosslinked glycosaminoglycan hydrogels," *Biomaterials* 27:5935-5943, Butterworth-Heinemann (Dec. 2006).

Ringrose, L., et al., "The Kw recombinase, an integrase from *Kluyveromyces waltii*," *Eur. J. Biochem.* 248:903-912, Blackwell Science Ltd. (1997).

Rong, S.L., et al., "Effects of transplanted myoblasts transfected with human growth hormone gene on improvement of ventricular function of rats," *Chin. Med. J. (Engl).* 121:347-354, (Feb. 2008).

Ross, R.S., et al., "An HF-1a/HF-1b/MEF-2 combinatorial element confers cardiac ventricular specificity and established an anterior-posterior gradient of expression," *Development* 122:1799-1809, Company of Biologists Limited (1996).

Roth, D.M., et al., "Cardiac-Directed Adenylyl Cyclase Expression Improves Heart Function in Murine Cardiomyopathy," *Circulation* 99:3099-3102, Lippincott Williams & Wilkins (1999).

Roth, D.M., et al., "Adenylyl Cyclase Increases Survival in Cardiomyopathy," *Circulation* 105:1989-1994, Lippincott Williams & Wilkins (2002).

Roth, D.M., et al., "Cardiac-directed expression of adenytyl cyclase and heart rate regulation," *Basic Res. Cardiol.* 98:380-387, Dr. Dietrich Steinkopff Verlag (2003).

Roth, D,M., et al., "Indirect intracoronary delivery of adenovirus encoding adenylyl cyclase increases left ventricular contractile function in mice," *Am. J. Physiol. Heart Circ. Physiol.* 287:H172-H177, American Physiological Society (2004).

Roth, D.M., et al., "Nitroprusside Increases Gene Transfer Associated with Intracoronary Delivery of Adenovirus," *Hum. Gene Ther.* 15:989-994, M.A. Liebert (2004).

(56) References Cited

OTHER PUBLICATIONS

Ryu, J.K., et al., "Combined Angiopoietin-1 and Vascular Endothelial Growth Factor Gene Transfer Restores Cavernous Angiogenesis and Erectile Function in a Rat Model of Hypercholesterolemia," *Mol. Ther.* 13:705-715, Academic Press (Apr. 2006).
Sadowski, I., et al., "GAL4-VP16 is an unusually potent transcriptional activator," *Nature* 335:563-564, Nature Publishing Group (1988).
Saetrum Opgaard, O., and Wang, P.H., "IGF-1 is a matter of heart," *Growth Horm. IGF Res.* 15:89-94, Churchill Livingstone (2005).
Sakaguchi, G., et al., "Control-Released Hepatocyte Growth Factor Prevents the Progression of Heart Failure in Stroke-Prone Spontaneously Hypertensive Rats," *Ann. Thorac. Surg.* 79:1627-1634, Elsevier (2005).
Sakakibara, Y., et al., "Prevascularization with gelatin microspheres containing basic fibroblast growth factor enhances the benefits of cardiomyocyte transplantation," *J. Thorac. Cardiovasc. Surg.* 124:50-56, Mosby (2002).
Sakakibara, Y., et al., "Toward surgical angiogenesis using slow-released basic fibroblast growth factor," *Eur. J. Cardiothorac. Surg.* 24:105-111, Elsevier Science (2003).
Sakata, S., et al., "Restoration of mechanical and energetic function in failing aortic-banded rat hearts by gene transfer of calcium cycling proteins," *J. Mol. Cell Cardiol.* 42:852-861, Academic Press (Apr. 2007).
Sakata, S., et al., "Transcoronary gene transfer of SERCA2a increases coronary blood flow and decreases cardiomyocyte size in a type 2 diabetic rat model," *Am. J. Physiol. Heart Circ. Physiol.* 292:H12044-H1207, American Physiological Society (Feb. 2007).
Samuel, C.S., et al., "Relaxin Modulates Cardiac Fibroblast Proliferation, Differentiation, and Collagen Production and Reverses Cardiac Fibrosis in Vivo," *Endocrinology* 145:4125-4133, Endocrine Society (2004).
Sameul, C.S., et al., "Relaxin' the stiffened heart and arteries: The therapeutic potential for relaxin in the treatment of cardiovascular disease," *Pharmcol. Ther.* 112:529-552, Pergamon Press (Nov. 2006).
Samuel, C.S., et al., "The Effects of Relaxin on Extracellular Matrix Remodeling in Health and Fibrotic Disease," *Adv. Exp. Med. Biol.* 612:88-103, (Jan. 2007).
Santini. M.P., et al., "Signalling pathways in cardiac regeneration," *Novartis Found Symp.* 274:228-238, Wiley (Jan. 2006).
Sastry, A., et al., "Cardiac-Directed Expression of Adenytyl Cyclase VI Facilitates Atrioventricular Nodal Conduction," *J. Am. Coll. Cardiol.* 48:559-565, Elsevier Biomedical (Aug. 2006).
Schmidt, U., et al., "Restoration of Diastolic Function in Senescent Rat Hearts Through Adenoviral Gene Transfer of Sarcoplasmic Reticulum $Ca^{2+}$-ATPase," *Circulation* 101:790-796, Lippincott Williams & Wilkins (2000).
Scholl, F.G., et al., "Effects of Human Tissue Plasminogen Gene Transfer on Allograft Coronary Atherosclerosis," *J. Heart Lung Transplant.* 20:322-329, Elsevier (2001).
Schwikardi, M., and Dröge, P., "Site-specific recombination in mammalian cells catalyzed by γδ resolvase mutants: implications for the topology of episomal DNA," *FEBS Lett.* 471:147-150, Elsevier Science B.V. (2000).
Shao, Z.Q., et al., "Effects of Intramyocardial Administration of Slow-Release Basic Fibroblast Growth Factor on Angiogenesis and Ventricular Remodeling in a Rat Infarct Model," *Circ. J.* 70:471-477, Japanese Circulation Society (Apr. 2006).
Shockett, P., et al., "A modified tetracycline-regulated system provides autoregulatory, inducible gene expression in cultured cells and transgenic mice," *Proc. Natl. Acad. Sci. U.S.A.* 92:6522-6526, National Academy of Sciences (1995).
Shoichet, M.S., and Winn, S.R., "Cell delivery to the central nervous system," *Adv. Drug Deliv. Rev.* 42:81-102, Elsevier Science Publishers, B.V. (2000).

Shyu, K.G., et al., "Intramyocardial injection of naked DNA encoding HIF-1α/VP16 hybrid to enhance angiogenesis in an acute myocardial infarction model in the rat," *Cardiovasc. Res.* 54:576-583, Oxford Journals (2002).
Shyu, K.G., et al., "Synergistic effect of angiopoietin-1 and vascular endothelial growth factor on neoangiogenesis in hypercholesterolemic rabbit model with acute hindlimb ischemia," *Life Sci.* 73:563-579, Pergamon Press (2003).
Shyu, K.G., et al., "Mesenchymal stem cells are superior to angiogenic growth factor genes for improving myocardial performance in the mouse model of acute myocardial infarction," *J. Biomed. Sci.* 13:47-58, Springer (Jan. 2006).
Su, H., et al., "Adeno-associated viral vector-mediated hypoxia response element-regulated gene expression in mouse ischemic heart model" *Proc. Natl. Acad. Sci. U.S.A.* 99:9480-9485, National Academy of Sciences (2002).
Su, H., et al., "Adeno-associated viral vector delivers cardiac-specific and hypoxia-inducible VEGF expression in ischemic mouse hearts," *Proc. Natl. Acad. Sci. U.S.A.* 101:16280-16285, National Academy of Sciences (2004).
Su, E.J., et al., "Gene therapy vector-mediated expression of insulin-like growth factors protects cardiomyocytes from apoptosis and enhances neovascularization," *Am. J. Physiol. Heart Circ. Physiol.* 284:H1429-H1440, American Physiological Society (2003).
Suarez, J., et al., "Doxycycline inducible expression of SERCA2a improves calcium handling and reverts cardiac dysfunction in pressure overload-induced cardiac hypertrophy," *Am. J. Physiol. Heart Circ. Physiol.* 287:H2164-H2172, American Physiological Society (2004).
Sugimoto, T., et al., "Gene Therapy for Myocardial Angiogenesis: With Direct Intramuscular Gene Transfer of Naked Deoxyribonucleic Acid Encoding Vascular Endothelial Growth Factor and Cell Transplantation of Vascular Endothelial Growth Factor Transfected H9c2 Myoblast," *Jpn. J. Thorac. Cardiovasc. Surg.* 51:192-197, Nihon Kyōbu Geka Gakkai (2003).
Suzuki, K., et al., "Cell Transplantation for the Treatment of Acute Myocardial Infarction Using Vascular Endothelial Growth Factor-Expressing Skeletal Myoblasts," *Circulation* 104:I207-I212, Lippincott Williams & Wilkins (2001).
Tabata, Y., and Ikada, Y., "Vascularization effect of basic fibroblast growth factor released from gelatin hydrogels with different biodegradabilities," *Biomaterials* 20:2169-2175, Butterworth-Heinemann in Association With the Biological Engineering Society (1999).
Takahashi, T., et al., "Increased Cardiac Adenylyl Cyclase Expression is Associated With Increased Survival After Myocardial Infarction," *Circulation* 114:388-396, Lippincott Williams & Wilkins (Aug. 2006).
Tambara, K., "Administration of Control-Released Hepatocyte Growth Factor Enhances the Efficacy of Skeletal Myoblast Transplantation in Rat infarcted Hearts by Greatly Increasing Both Quantity and Quality of the Graft," *Circulation* 112:1129-1134, Lippincott Williams & Wilkins (2005).
Tang, T., et al., "Adenylyl Cyclase Type 6 Deletion Decreases Left Ventricular Function via Impaired Calcium Handling," *Circulation* 117:61-69, Lippincott Williams & Wilkins (Jan. 2008).
Tang, T., et al., "Adenylyl cyclase type VI corrects cardiac sarcoplasmic reticulum calcium uptake defects in cardiomyopathy," *Am. J. Physiol. Heart Circ. Physiol.* 287:H1906-H1912, American Physiological Society (2004).
Terracciano, C.M., et al., "Overexpression of SERCA2a accelerates repolarisation in rahbit ventricular myocytes," *Cell Calcium* 31:299-305, Elsevier (2002).
Thurston, G., et al., "Complementary actions of VEGF and Angiopoietin-1 on blood vessel growth and leakage," *J. Anat.* 200:575-580, Blackwell Publishing (2002).
Thyagarajan, B., et al., "Site-Specific Genomic Integration in Mammalian Cells Mediated by Phage φC31 Integrase," *Mol Cell Biol.* 21:3926-3934, American Society for Microbiology (2001).
Timofeyev, V., et al., "Cardiac-directed expression of adertylyl cyclase reverses electrical remodeling in cardiomyopathy," *J. Mol. Cell Cardiol.* 41:170-181, Academic Press (Jul. 2006).

(56) References Cited

OTHER PUBLICATIONS

Trost, S.U., et al., "Overexpression of the Sarcoplasmic Reticulum $Ca^{2+}$-ATPase Improves Myocardial Contractility in Diabetic Cardiomyopathy," *Diabetes* 51:1166-1171, American Diabetes Association (2002).

Tsoporis, J.N., et al., "Expression of S100A6 in Cardiac Myocytes Limits Apoptosis Induced by Tumor Necrosis Factor-α," *J. Biol. Chem.* 283:30174-30183, American Society for Biochemistry and Molecular Biology (Oct. 2008).

Ulmer, J.B., et al., "Heterologous Protection Against Influenza by Injection of DNA Encoding a Viral Protein," *Science* 259:1745-1749, American Association for the Advancement of Science (1993).

Ventura. C., et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts," *J. Biol. Chem.* 282:14243-14252, American Society for Biochemistry and Molecular Biology (May 2007).

Vetter, R., et al., "Transgenic overexpression of the sarcoplasmic reticulum $Ca^{2+}$ ATPase improves reticular $Ca^{2+}$ handling in normal and diabetic rat hearts," *FASEB J.* 16:1657-1659, The Federation (2002).

Vincent, K.A., et al., "Angiogenesis Is induced in a Rabbit Model of Hindlimb Ischemia by Naked DNA Encoding an HIF-1α/VP16 Hybrid Transcription Factor," *Circulation* 102:2255-2261, Lippincott Williams & Wilkins (2000).

Wang, Y., et al., "Combining pharmacological mobilization with intramyocardial delivery of bone marrow cells over-expressing VEGF is more effective for cardiac repair," *J. Mol. Cell Cardiol.* 40:736-745, Academic Press (May 2006).

Wilhide, M.E., el al., "Potential Therapeutic Gene for the Treatment of Ischemic Disease: Ad2/Hypoxia-Inducible Factor-1α (HIF-1)/VP16 Enhances B-Type Natriuretic Peptide Gene Expression via a HIF-1-Responsive Element," *Mol. Pharmacol.* 69:1773-1778, American Society for Pharmacology and Experimental Therapeutics (Jun. 2006).

Wilson, J.M., et al., "Hepatocyte-directed Gene Transfer in Vivo Leads to Transient Improvement of Hypercholesterolemia in Low Density Lipoprotein Receptor-deficient Rabbits," *J . Biol. Chem.* 267:963-967, American Society for Biochemistry and Molecular Biology (1992).

Wu, G.Y., and Wu, C.H., "Receptor-mediated in Vitro Gene Transformation by a Soluble DNA Carrier System," *J. Biol. Chem.* 262:4429-4432, American Society for Biochemistry and Molecular Biology (1987).

Wu, G.Y., and Wu, C.H., "Receptor-mediated Gene Delivery and Expression in Vivo," *J. Biol. Chem.* 263:14621-14624, American Society for Biochemistry and Molecular Biology (1988).

Xu, H.X., et al., "Implantation of BM cells transfected with $phVEGF_{165}$ enhances functional improvement of the infarcted heart," *Cytotherapy* 6:204-211, Taylor & Francis (2004).

Xu, L., et al.,"Regulation of Ncx1 Expression. Identification of Regulatory Elements Mediating Cardiac-Specific Expression and Up-Regulation," *J. Biol. Chem.* 281:34430-34440, American Society for Biochemistry and Molecular Biology (Nov. 2006).

Yamada, M., et al., "Inhibition of protein phosphatase 1 by inhibitor-2 gene delivery ameliorates heart failure progression in genetic cardiomyopathy," *FASEB J.* 20:1197-1199, The Federation (Jun. 2006).

Yamamoto, T., et al., "Intramyocardial Delivery of Basic Fibroblast Growth Factor-Impregnated Gelatin Hydrogel Microspheres Enhances Collateral Circulation to Infarcted Canine Myocardium," *Jpn. Circ. J.* 65:439-444, Japanese Circulation Society (2001).

Yamamoto, M., et al., "Improved Therapeutic Efficacy in Cardiomyocyte Transplantation for Myocardial Infarction with Release System of Basic Fibroblast Growth Factor," *Artif. Organs* 27:181-184, Blackwell Science (2003).

Yamauchi, A., et al., "Pre-administration of angiopoietin-1 followed by VEGF induces functional and mature vascular formation in a rabbit ischemic model," *J. Gene Med.* 5:994-1004, John Wiley & Sons (2003).

Yang, C.F., et al., "Experimental Corneal Neovascularization by Basic Fibroblast Growth Factor Incorporated into Gelatin Hydrogel," *Ophthalmic Res.* 32:19-24, Karger (2000).

Yang, Z.J., et al., "Experimental study of bone marrow-derived mesenchymal stem cells combined with hepatocyte growth factor transplantation via noninfarct-relative artery in acute myocardial infarction," *Gene Ther.* 13:1564-1568, Nature Publishing Group (Nov. 2006).

Yang, J., et al., "Effects of Myocardial Transplantation of Marrow Mesenchymal Stem Cells Transfected with Vascular Endothelial Growth Factor the the Improvement of Heart Function and Angiogenesis after Myocardial Infarction," *Cardiology* 107:17-29, Karger (Jan. 2007).

Yao, T.P., et al., "*Drosophila* ultraspiracle Modulates Ecdysone Receptor Function via Heterodimer Formation," *Cell* 71:63-72, Cell Press (1992).

Yao, T.P., et al., "Functional ecdysone receptor is the product of EcR and Ultraspiracle genes," *Nature* 366:476-479, Nature Publishing Group (1993).

Yau, T.M., et al., "Enhanced Angiogenesis With Multimodal Cell-Based Gene Therapy," *Ann. Thorac. Surg.* 83:1110-1119, Elsevier (Mar. 2007).

Ye, L., et al., "Angiomyogenesis using Human Myoblast Carrying Human $VEGF_{165}$ for Injured Heart," *Ann. Acad. Med. Singapore* 32:S21-523, Academy of Medicine, Singapore (2003).

Ye, L., et al.,"In Vitro Functional Assessment of Human Skeletal Myoblasts After Transduction With Adenoviral Bicistronic Vector Carrying Human $VEGF_{165}$ and Angiopoietin-1," *J. Heart Lung Transplant.* 24:1393-1402, Elsevier (2005).

Ye, L., et al., "Reversal of myocardial injury using genetically modulated human skeletal myoblasts in a rodent cryoinjured heart model," *Eur. J. Heart Fail.* 7:945-952, Elsevier Science (2005).

Ye, L., et al., "Improved angiogenic response in pig heart following ischaemic injury using human skeletal myoblast simultaneously expressing $VEGF_{165}$ and angiopoietin-1," *Eur. J. Heart. Fail.* 9:15-22, Elsevier Science (Jan. 2007).

Ye, L., et al., "Transplantation of Nanoparticle Transfected Skeletal Myoblasts Overexpressing Vascular Endothelial Growth Factor-165 for Cardiac Repair," *Circulation* 116:1113-1120, Lippincott Williams & Wilkins (Sep. 2007).

Ylä-Herttuala, S., et al., "Vascular Endothelial Growth Factors: Biology and Current Status of Clinical Applications in Cardiovascular Medicine," *J. Am. Coll. Cardiol.* 49:1015-1026, Elsevier Biomedical (Mar. 2007).

Zacchinga, et al., "In Vivo Imaging Shows Abnormal Function of Vascular Endothelial Growth Factor-Induced Vasculature," *Hum. Gene. Ther.* 18:515-524, M.A. Liebert (Jun. 2007).

Zhang, D., et al., "Over-expression of CXCR4 on mesenehymal stem cells augments myoangiogenesis in the infarcted myocardium," *J. Mol. Cell Cardiol.* 44 :281-292, Academic Press (Feb. 2008).

Zhang, G., et al., "Controlled Release of Stromal Cell-Derived Factor-1 α In Situ Increases C-kit+ Cell Homing to the Infarcted Heart," *Tissue Eng.* 13:2063-2071, Mary Ann Liebert, Inc. (Aug. 2007).

Zhang, G., et al., "Enhancing Efficacy of Stem Cell Transplantation to the Heart with a PEGylated Fibrin Biomatrix," *Tissue Eng. Part A* 14:1025-1036, Mary Ann Liebert, Inc. (Jun. 2008).

Zhang, J., et al., "Effect of relaxin on myocardial ischemia injury induced by isoproterenol," *Peptides* 26:1632-1639, Elsevier Science Inc. (2005).

Zhang, S., et al., "Purified Human Bone Marrow Multipotent Mesenchymal Stem Cells Regenerate Infarcted Myocardium in Experimental Rats," *Cell Transplant.* 14:787-798, Cognizant Communication (2005).

Zhou, L., et al., "$VEGF_{165}$ and Angiopoietin-1 decreased myocardium infarct size through phosphatidylinositol-3 kinase and Bcl-2 pathways," *Gene Ther.* 12:196-202, Nature Publishing Group (2005).

(56) References Cited

OTHER PUBLICATIONS

Zhu, H., et al.,"The effect of basic fibroblast growth factor slow-release microcapsules on angiogenesis in infarcted rabbit myocardium," *Chin. Med. Sci. J.* 15:210-213, Chinese Academy of Medical Sciences (2000).
Zimmermann, U., et al., "A Novel Class of Amitogenic Alginate Microcapsules for Long-Term Immunoisolated Transplantation," *Ann. N Y Acad. Sci.* 944:199-215, New York Academy of Sciences (2001).
Zinn, K.R. et al., "Noninvasive Monitoring of Gene Transfer Using a Reporter Receptor imaged with a High-Affinity Peptide Radiolabeled with $^{99m}$T or $^{188}$Re," *J. Nucl. Med.* 41:887-895, Society of Nuclear Medicine (2000).
Zoller, M.J., and Smith, M., "Oligonucleotide-Directed Mutagenesis: A Simple Method using Two Oligonucleotide Primers and a Single-Stranded DNA Template," *DNA* 3:479-488, Mary Aim Liebert (1984).
NCBI Entrez, GenBank Report, Accession No. 28274638 (Entry date 1993).
NCBI Entrez, GenBank Report, Accession No. AAA37385 (Entry date 1993).
NCBI Entrez, GenBank Report, Accession No. AAA40788 (Entry date 1993).
NCBI Entrez, GenBank Report, Accession No. AAA52122 (Entry date 1993).
NCBI Entrez, GenBank Report, Accession No. AAA52485 (Entry date 1993).
NCBI Entrez, GenBank Report, Accession No. AAA98618 (Entry date 1993).
NCBI Entrez, GenBank Report, Accession No. AAB59375 (Entry date 1993).
NCBI Entrez, GenBank Report, Accession No. AAC28869 (Entry date 1993).
NCBI Entrez, GenBank Report, Accession No, CAA26095.1 (Entry date 1993).
NCBI Entrez, GenBank Report, Accession No. D10763 (Entry date 1993).
NCBI Entrez, GenBank Report, Accession No. K01396 (Entry date 1993).
NCBI Entrez, GenBank Report, Accession No. L05573 (Entry date 1993).
NCBI Entrez, GenBank Report, Accession No. M11734 (Entry date 1993).
NCBI Entrez, GenBank Report, Accession No. M13438 (Entry date 1993).
NCBI Entrez, GenBank Report, Accession No. M14113 (Entry date 1993).
NCBI Entrez, GenBank Report, Accession No. M25296 (Entry date 1993).
NCBI Entrez, GenBank Report, Accession No. M29145 (Entry date 1993).
NCBI Entrez, GenBank Report, Accession No. M32247 (Entry date 1993).
NCBI Entrez, GenBank Report, Accession No. M75721 (Entry date 1993).
NCBI Entrez, GenBank Report, Accession No. NM 000930 (Entry date 1999).
NCBI Entrez, GenBank Report, Accession No. NM 008117 (Entry date 1993).
Ncbi En(rez, GenBank Report, Accession No. P10845 (Entry date 1993).
NCBI Entrez, GenBank Report, Accession No. P20333 (Entry date 1993).
NCBI Entrez, GenBank Repott Accession No. U16752 (Entry date 1993).
NCBI Entrez, GenBank Report, Accession No. P34021 (Entry date 1994).
NCBI Entrez, GenBank Report, Accession No. NM 002521 (Entry date 1999).
NCBI Entrez, GenBank Report, Accession No. NM 033011 (Entry date 1999)
NCBI Entrez, GenBank Report, Accession No. NP 000921 (Entry date 1999).
NCBI Entrez, GenBank Report, Accession No. NP 001997 (Ently date 1999).
NCBI Entrez, GenBank Report Accession No. NP 002512 (Entry date 1999).
NCBI Entrez, GenBank Report, Accession No. NP 006172 (Entry date 1999).
NCBI Entrez, GenBank Report, Accession No. NP 032143 (Entry date 2000).
NCBI Entrez, GenBank Report, Accession No. NP 047974 (Entry date 2000).
NCBI Entrez, GenBank Report, Accession No. AAH05255 (Entry date 2001).
NCBI Entrez, GenBank Report, Accession No. BAA01593 (Entry date 1993).
NCBI Entrez, GenBank Report, Accession No. NP 127509 (Entry date 2001).
NCBI Entrez, GenBank Report, Accession No. NM 009969 (Entry date 2002).
NCBI Entrez, GenBank Report, Accession No. NM 133555 (Entry date 2002).
NCBI Entrez, GenBank Report, Accession No. NP 006163 (Ently date 2002).
NCBI Entrez, GenBank Report, Accession No. NP 034099 (Entry date 2002).
NCBI Entrez, GenBank Report, Accession No. NP 598239 (Entry date 2002).
NCBI Entrez, GenBank Report, Accession No. NP 604390.1 (Entry date 2002).
NCBI Entrez, GenBank Report, Accession No. AAO34406 (Entry date 2003).
NCBI Entrez, GenBank Report, Accession No. NP 000592.3 (Entry date 2003).
NCBI Entrez, GenBank Report, Accession No. NP 954637(Entry date 2003).
NCBI Entrez, GenBank Report, Accession No. AAH93628 (Entry date 2005).
NCBI Entrez, GenBank Report, Accession No. BC005255 (Entry date 2001).
NCBI Entrez, GenBank Report, Accession No. NM 001034848 (Entry date 2005).
NCBI Entrez GenBank Report, Accession No. NM 001037660 (Entry date 2005).
NCBI Entrez, GenBank Report, Accession No. NP 001030020 (Entry date 2005).
NCBI Entrez, GenBank Report, Accession No. NP 001032749 (Entry date 2005).
NCBI Entrez, GenBank Report, Accession No. AAI19266 (Entry date 2006).
NCBI Entrez, GenBank Report, Accession No. BC093628 (Entry date 2005).
NCBI Entrez, GenBank Report, Accession No. BC119265 (Entry date 2006).
NCBI Entrez, GenBank Report, Accession No. DD292498 (Entry date 2006).
NCBI Entrez, GenBank Report, Accession No. DD292499 (Entry date 2006).
NCBI Entrez, GenBank Report, Accession No. NP 001104753.1 (Entry date 2007).
Dialog File 351, Accession No. 2000-064453, Derwent WPI English language abstract of MX 234 742 (Document FP24).
Dialog File 351, Accession No. 2000-064453, Derwent WPI English language abstract of KR 10-0563413 (Document FP25).
Office Action mailed Mar. 9, 2010 in U.S. Appl. No. 12/247,738, inventors Braughler et al., filed Oct. 8, 2008.
Written Opinion of the International Searching Authority for Application No. PCT/US08/11270, filed Sep. 29, 2008, published as WO 2009/045370 A2 (date of completion of opinion Dec. 24, 2009).

(56) References Cited

OTHER PUBLICATIONS

Leeser, D.B. et al., "Pulsatile Pump Perfusion of Pancreata Before Human Islet Cell Isolation," *Transplantation Proceedings 36*: 1050-1051, Elsevier, Inc. New York, NY (2004).

Weber, M. et al., "Formation of cartilage matrix proteins by BMP-transfected murine mesenchymal stem cells encapsulated in a novel class of alginates," *Biomateriais 23*: 2003-2013, Elsevier Science Ltd. (2002).

Communication from the European Patent Office mailed Nov. 18, 2010 in European Application No. 08834828.9, regarding the extended European Search Report, including the Supplementary European Search Report dated Nov. 11, 2010, and the European Search Opinion.

\* cited by examiner

THERAPEUTIC GENE-SWITCH CONSTRUCTS AND BIOREACTORS FOR THE EXPRESSION OF BIOTHERAPEUTIC MOLECULES, AND USES THEREOF

CROSS-REFERENCE TO RELATED APPLICATIONS

The present application claims the benefit of the filing date of U.S. Provisional Application No. 61/047,899, files Apr. 25, 2008 and U.S. Provisional Application No. 60/975,986, filed Sep. 28, 2007, both of which are incorporated herein by reference in their entireties.

REFERENCE TO SEQUENCE LISTING SUBMITTED ELECTRONICALLY VIA EFS-WEB

The content of the electronically submitted sequence listing (Name: Sequence Listing.ST25.txt; Size: 243,000 bytes; and Date of Creation: Sep. 29, 2008) filed herewith with the application is incorporated herein by reference in its entirety:

BACKGROUND OF THE INVENTION

Field of the Invention

The present invention relates to methods and compositions for treating, ameliorating, or preventing a disease, disorder, or condition in a subject by introducing into the subject a therapeutic gene switch construct that controls expression of one or more therapeutic products. In a further embodiment, the present invention relates to methods and compositions for treating, ameliorating, or preventing a disease, disorder, or condition in a subject by introducing into the subject a "bioreactor," a therapeutic implant composed of a cell or cells that secrete a therapeutic protein. A bioreactor may be immuno-isolated by encapsulation or non-immunoisolated. In particular embodiments, the bioreactor comprises a therapeutic gene switch construct.

Background of the Invention

The concept of treating or preventing a disease in a subject through introduction of a polynucleotide encoding a therapeutic molecule, e.g., a therapeutic polypeptide or therapeutic polynucleotide into cells of the subject, or introducing into the subject modified cells engineered to secrete the therapeutic molecule has been in existence for many years. Several difficulties in the practical aspects of the concept have hindered progress towards successful therapies. Direct introduction of genetic material into a subject to be treated presents difficulties such as: safety of delivery, obtaining sufficient expression levels of the therapeutic product for a sufficient period of time, limiting expression of the therapeutic product to desired cells, and maintaining the ability to modulate or pulse the expression of the therapeutic product, including the ability to turn off expression of the therapeutic product if it is no longer needed. Cell based therapies are subject to rejection via the subject's immune response, therefore immuno-isolation strategies such as cell encapsulation methods have been developed to increase the longevity of implanted cells and allow use of xenogeneic cells, i.e., cells from a different species. Current encapsulated and non-encapsulated cell therapies are engineered to secrete the therapeutic protein constitutively. Once implanted, protein secretion can not be regulated. To improve the safety and clinical application of direct or cell-mediated bioreactor therapeutic protein delivery it would be advantageous to be able to turn off the protein production or regulate the rate at which protein production occurs.

Thus, there is a need in the art for new therapeutic methods and compositions that provide these desired characteristics.

SUMMARY OF THE INVENTION

The present invention relates to methods and compositions for treating, ameliorating, or preventing a disease, disorder, or condition in a subject.

In one embodiment, the present invention provides a method for treating, ameliorating, or preventing a disease, disorder, or condition in a subject, comprising:
  (a) introducing into a subject (1) a first polynucleotide encoding a gene switch, where the gene switch comprises at least one transcription factor sequence encoding a ligand-dependent transcription factor through operable association with a therapeutic switch promoter, where the therapeutic switch promoter is constitutively active and (2) a second polynucleotide encoding a therapeutic polypeptide or therapeutic polynucleotide in operable association with a factor-regulated promoter which is activated by said ligand-dependent transcription factor, where the first and second polynucleotides are introduced so as to permit their expression in the presence of ligand; and
  (b) administering ligand to the subject to induce expression of the therapeutic polypeptide or therapeutic polynucleotide.

A further embodiment of the invention provides a method for expressing a therapeutic polypeptide or therapeutic polynucleotide in a subject, comprising:
  (a) introducing into a subject (1) a first polynucleotide encoding a gene switch, where the gene switch comprises at least one transcription factor sequence encoding a ligand-dependent transcription factor through operable association with a therapeutic switch promoter, where the therapeutic switch promoter is activated under conditions associated with the disease, disorder, or condition to be treated, and (2) a second polynucleotide encoding a therapeutic polypeptide or therapeutic polynucleotide in operable association with a factor-regulated promoter which is activated by said ligand-dependent transcription factor, where the first and second polynucleotides are introduced so as to permit their expression in the subject under conditions associated with the disease, disorder, or condition; and
  (b) administering ligand to the subject to induce expression of the therapeutic polypeptide or therapeutic polynucleotide.

A further embodiment of the invention provides a method for expressing a therapeutic polypeptide or therapeutic polynucleotide in a subject, comprising:
  (a) introducing into a subject (1) a first polynucleotide encoding a gene switch, where the gene switch comprises at least one transcription factor sequence encoding a ligand-dependent transcription factor through operable association with a therapeutic switch promoter, where the therapeutic switch promoter is activated under conditions associated with a disease, disorder, or condition treatable by the therapeutic polypeptide or therapeutic polynucleotide, and (2) a second polynucleotide encoding the therapeutic polypeptide or therapeutic polynucleotide in operable association with a factor-regulated promoter which is activated by the ligand-dependent transcription factor, wherein said the and second polynucleotides are introduced so as to permit expression of the first polynucleotide under conditions associated with the disease, disorder, or condition; and (b) administering ligand to the subject to induce expression of the therapeutic polypeptide or therapeutic polynucleotide.

In the methods described above, in one embodiment, the first polynucleotide encoding the therapeutic gene switch and the second polynucleotide encoding the therapeutic polypeptide or polynucleotide linked to a factor-regulated promoter are part of one larger polynucleotide, e.g., a vector. In another embodiment, the first polynucleotide encoding the therapeutic gene switch and the second polynucleotide encoding the therapeutic polypeptide or polynucleotide linked to a factor-regulated promoter are separate polynucleotides which may be administered as a nucleic acid composition.

The invention further relates to therapeutic gene switch constructs that are useful in the disclosed methods.

The invention additionally relates to vectors comprising the therapeutic gene switch constructs of the invention.

The invention further provides a method for expressing a therapeutic polypeptide or therapeutic polynucleotide in one or more modified cells, comprising:

(a) introducing into a cell (1) a first polynucleotide encoding a gene switch, where the gene switch comprises at least one transcription factor sequence encoding a ligand-dependent transcription factor through operable association with a therapeutic switch promoter which is activated under conditions associated with a disease, disorder, or condition, and (2) a second polynucleotide encoding a therapeutic polypeptide or therapeutic polynucleotide through operable association with a factor-regulated promoter which is activated by the ligand-dependent transcription factor, thereby producing a modified cell; and (b) administering ligand to the modified cell to induce expression of said therapeutic polypeptide or therapeutic polynucleotide.

The invention further relates to modified cells comprising the therapeutic gene switch constructs of the invention.

The invention also relates to bioreactor devices comprising modified cells of the invention either non-encapsulated, or encapsulated in such a way to shield the cells from the subject's immune system. Such bioreactors may take the form, for example, of coated cells, micro-encapsulated cells, or macro-encapsulated cells.

The invention also relates to kits for carrying out the methods of the invention, comprising, e.g., gene switch constructs, vectors, ligands, etc.

DETAILED DESCRIPTION OF THE INVENTION

Figure 1:
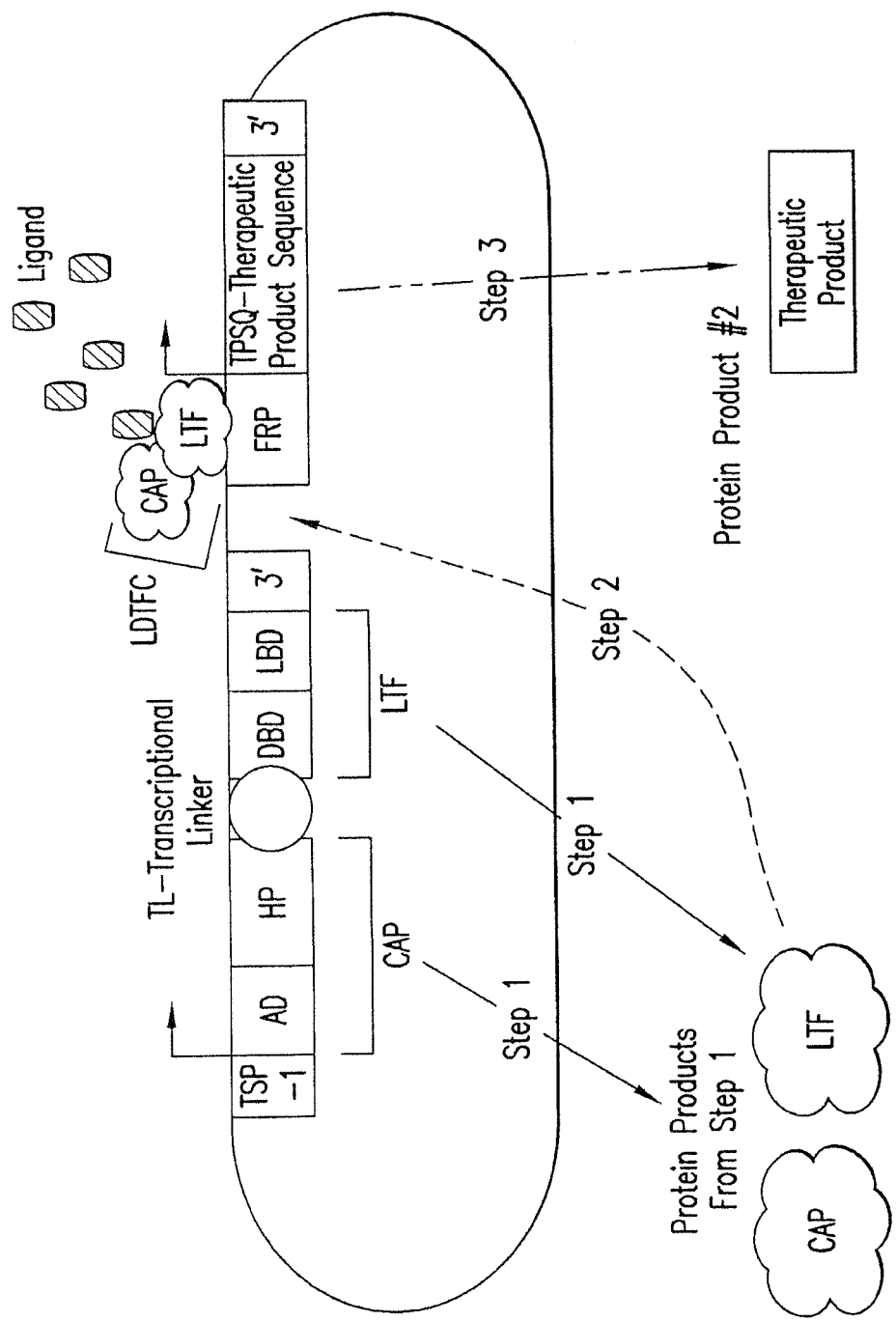
FIG. 1 shows an embodiment of the therapeutic gene switch of the invention in which two transcription factor sequences encoding two separate portions of a ligand-dependent transcription factor complex are under the control of a single promoter. "AD" represents a transactivation domain; "HP" represents a heterodimerization partner domain. The AD and HP domains are expressed as a fusion protein termed a "coactivation protein" or "CAP." "DBD" represents a DNA binding domain; "LBD" represents a ligand binding domain. The DBD and LBD domains are expressed as a fusion protein termed a "ligand-dependent transcription factor," or "LTF." "Transcriptional Linker" represents an IRES (Internal ribosomal entry site) or means of generating two separate protein products from a single open reading frame. "Therapeutic Product Sequence" represents a polynucleotide encoding a therapeutic polypeptide or therapeutic polynucleotide; "Therapeutic Product" represents a therapeutic polypeptide or therapeutic polynucleotide; and "TSP-1," represents either a constitutive therapeutic switch promoter, or a therapeutic switch promoter activated under conditions associated with a disease, disorder, or condition. CAP and LTF combine to form a ligand-dependent transcription factor complex (LDTFC) which in combination with ligand activates a factor-regulated promoter (FRP).

The invention relates to methods and compositions for using a gene switch to express a therapeutic polypeptide or therapeutic polynucleotide in a cell. The methods and compositions may be used in vitro, ex vivo or in vivo. The invention further relates to methods and compositions for using a gene switch controlling expression of a therapeutic polypeptide or therapeutic polynucleotide for the treatment, amelioration, or prevention of diseases, disorders, or conditions in a subject. The methods of the invention can be carried out either ex vivo (by introducing the gene switch into isolated cells of a subject or non-autologous cells, and introducing the modified cells to the subject or into a different subject) or in vivo (by introducing the gene switch directly into cells of the subject). The methods of the invention involve the use of a gene switch in which expression of a ligand-dependent transcription factor is under the control of one or more therapeutic switch promoters. The methods also include, without limitation, applications of the gene switch technology in direct introduction into the subject to be treated, non-encapsulated and encapsulated cell therapies. The methods and compositions described herein provide a highly specific and tightly regulated therapeutic technique in which the level and timing of expression of a therapeutic product is controlled by administration of ligand to cells comprising the gene switch.

The following definitions are provided and should be helpful in understanding the scope and practice of the present invention.

The term "isolated" for the purposes of the present invention designates a biological material (cell, nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated."

The term "purified," as applied to biological materials does not require the material to be present in a form exhibiting absolute purity, exclusive of the presence of other compounds. It is rather a relative definition.

"Nucleic acid," "nucleic acid molecule," "oligonucleotide," and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes, but is not limited to, cDNA, genomic DNA, plasmid DNA, synthetic DNA, and semi-synthetic DNA. A "nucleic acid composition" of the invention comprises one or more nucleic acids as described herein.

The term "fragment," as applied to polynucleotide sequences, refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000, 1500, 2000, 3000, 4000, 5000, or more consecutive nucleotides of a nucleic acid according to the invention.

As used herein, an "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to a polynucleotide comprising nucleotides that encode a functional molecule, including functional molecules produced by transcription only (e.g., a bioactive RNA species) or by transcription and translation (e.g., a polypeptide). The term "gene" encompasses cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous DNA" refers to DNA not naturally located in the cell, or in a chromosomal site of the cell. The heterologous DNA may include a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook et al. in *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS. Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the present invention also includes isolated nucleic acid fragments that are complementary to the complete sequences as disclosed or used herein as well as those substantially similar nucleic acid sequences.

In one embodiment of the invention, polynucleotides are detected by employing hybridization conditions comprising a hybridization step at $T_m$ of 55° C., and utilizing conditions as set forth above. In other embodiments, the $T_m$ is 60° C., 63° C., or 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 min, and then repeated twice with 0.2×SSC, 0.5% SDS at 50° C. for 30 min. A preferred set of stringent conditions uses higher temperatures in which the washes are identical to those above except for the temperature of the final two 30 min washes in 0.2×SSC, 0.5% SDS is increased to 60° C. Another preferred set of highly stringent conditions uses two final washes in 0.1×SSC, 0.1% SDS at 65° C.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment of the invention, polynucleotides are detected by employing hybridization conditions comprising a hybridization step in less than 500 mM salt and at least 37° C., and a washing step in 2×SSPE at a temperature of at least 63° C. In another embodiment, the hybridization conditions comprise less than 200 mM salt and at least 37° C. for the hybridization step. In a further embodiment, the hybridization conditions comprise 2×SSPE and 63° C. for both the hybridization and washing steps.

In another embodiment, the length for a hybridizable nucleic acid is at least about 10 nucleotides. Preferably a minimum length for a hybridizable nucleic acid is at least about 15 nucleotides; e.g., at least about 20 nucleotides; e.g., at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a short nucleic acid that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, for DNA sequencing, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" refers to an oligonucleotide that hybridizes to a target nucleic acid sequence to create a double stranded nucleic acid region that can serve as an initiation point for DNA synthesis under suitable conditions. Such primers may be used in a polymerase chain reaction or for DNA sequencing.

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and refers to an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" refers to a double-stranded DNA sequence that encodes a polypeptide and can be transcribed and translated into a polypeptide in a cell in vitro or in vivo when placed under the control of suitable regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" are used interchangeably and refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. Another example of vectors that are useful in the present invention is the UltraVector™ Production System (Intrexon Corp., Blacksburg, Va.) as described in WO 2007/038276, incorporated herein by reference. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include, but are not limited to, retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector"). Cloning vectors may comprise one or more sequences that can be used for selection of cells comprising the vector and/or one or more multiple cloning sites for insertion of sequences of interest.

The term "expression vector" refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving expression of these genes can be used in an expression vector, including but not limited to, viral promoters, bacterial promoters, animal promoters, mammalian promoters, synthetic promoters, constitutive promoters, tissue specific promoters, pathogenesis or disease related promoters, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art including, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., *Proc. Natl. Acad. Sci. USA.* 84:7413 (1987); Mackey et al., *Proc. Natl. Acad. Sci. USA* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in WO95/18863, WO96/17823 and U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., *Hum. Gene Ther.* 3:147 (1992); and Wu et al., *J. Biol. Chem.* 262:4429 (1987)).

The term "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

In addition, the recombinant vector comprising a polynucleotide according to the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter and "promoter sequence" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

"Therapeutic switch promoter" ("TSP") refers to a promoter that controls expression of a gene switch component. Gene switches and their various components are described in detail elsewhere herein. In certain embodiments a TSP is constitutive, i.e., continuously active. A constitutive TSP may be either constitutive-ubiquitous (i.e., generally functions, without the need for additional factors or regulators, in any tissue or cell) or constitutive-tissue or cell specific (i.e., generally functions, without the need for additional factors or regulators, in a specific tissue type or cell type). In certain embodiments a TSP of the invention is activated under conditions associated with a disease, disorder, or condition. In certain embodiments of the invention where two or more TSPs are involved the promoters may be a combination of constitutive and activatable promoters. As used herein, a "promoter activated under conditions associated with a disease, disorder, or condition" includes, without limitation, disease-specific promoters, promoters responsive to particular physiological, developmental, differentiation, or pathological conditions, promoters responsive to specific biological molecules, and promoters specific for a particular tissue or cell type associated with the disease, disorder, or condition, e.g. tumor tissue or malignant cells. TSPs can comprise the sequence of naturally occurring promoters, modified sequences derived from naturally occurring promoters, or synthetic sequences (e.g., insertion of a response element into a minimal promoter sequence to alter the responsiveness of the promoter).

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" ("RE") refers to one or more cis-acting DNA elements which confer responsiveness on a promoter mediated through interaction with the DNA-binding domains of a transcription factor. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the transcription factor binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANT-GAC/ACYY (SEQ ID NO: 1) (see Cherbas et. al., *Genes Dev.* 5:120 (1991)); AGGTCAN$_{(n)}$AGGTCA, where N$_{(n)}$ can be one or more spacer nucleotides (SEQ ID NO: 2) (see D'Avino et al., *Mol. Cell. Endocrinol.* 113:1 (1995)); and GGGTTGAATGAATTT (SEQ ID NO: 3) (see Antoniewski et al., *Mol. Cell Biol.* 14:4465 (1994)).

"Factor-regulated promoter" ("FRP") refers to a promoter comprising at least one response element that is recognized by the DNA binding domain of a ligand-dependent transcription factor encoded by a gene switch of the invention.

The terms "operably linked," "operably associated," "through operable association," and the like refer to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein refers to the transcription and stable accumulation of sense (mRNA) or antisense RNA derived from a nucleic acid or polynucleotide. Expression may also refer to translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and a ligand-dependent transcription factor-based system which, in the presence of one or more ligands, modulates the expression of a gene into which the response element and promoter are incorporated.

The term "ecdysone receptor-based," with respect to a gene switch, refers to a gene switch comprising at least a functional part of a naturally occurring or synthetic ecdysone receptor ligand binding domain and which regulates gene expression in response to a ligand that binds to the ecdysone receptor ligand binding domain.

As used herein, the terms "bioreactor" or "bioreactor device" includes a cell or cells intended to secrete a therapeutic protein or therapeutic polynucleotide. In certain non-limiting embodiments, the bioreactor comprises modified cells as described elsewhere herein. In certain, but not all embodiments, bioreactor cells may be "immunoisolated." Bioreactor cells are considered "immunoisolated" from a subject when the cells are treated such that the cells, upon introduction or implantation into the subject, are protected from the subject's immune system. For example, immunoisolated bioreactor cells may be contained within a barrier system which allows dissemination of said therapeutic protein or therapeutic polynucleotide, but which prevents direct contact of bioreactor cells with cells of the subject's immune system. Immunoisolated cells may be, for example, coated or encapsulated. Immunoisolation methods include but are not limited to conformal coating of cells, microencapsulation where cells are suspended in a biocompatible material and separated into spherical masses, or macroencapsulation, where the cells are enclosed in devices composed of natural or synthetic polymers that are used to enclose cells.

The terms "modulate" and "modulates" mean to induce, reduce or inhibit nucleic acid or gene expression, resulting in the respective induction, reduction or inhibition of protein or polypeptide production.

The polynucleotides or vectors according to the invention may further comprise at least one promoter suitable for driving expression of a gene in a modified cell.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

A "3' reg" as defined herein, is an expression modulating element situated 3' to a coding region of a gene or transcript. Such elements include, without limitation: primary transcript-encoded Splicing elements, UTR from processed transcript, a polyadenylation signal or a DNA-encoded Transcription termination domain.

Termination control regions, i.e., terminator or polyadenylation nucleotide sequences, may also be derived from various genes native to the preferred hosts. Optionally, a termination site may be unnecessary, however, it is most preferred if included. In a one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" refers to a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

"Polypeptide," "peptide" and "protein" are used interchangeably and refer to a polymeric compound comprised of covalently linked amino acid residues.

An "isolated polypeptide," "isolated peptide" or "isolated protein" refer to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one wild-type or naturally occurring amino acid with a different amino acid relative to the wild-type or naturally occurring polypeptide. A substitution mutant polypeptide may comprise only one wild-type or naturally occurring amino acid substitution and may be referred to as a "point mutant" or a "single point mutant" polypeptide. Alternatively, a substitution mutant polypeptide may comprise a substitution of two or more wild-type or naturally occurring amino acids with two or more amino acids relative to the wild-type or naturally occurring polypeptide. According to the invention, a Group H nuclear receptor ligand binding domain polypeptide comprising a substitution mutation comprises a substitution of at least one wild-type or naturally occurring amino acid with a different amino acid relative to the wild-type or naturally occurring Group H nuclear receptor ligand binding domain polypeptide.

When the substitution mutant polypeptide comprises a substitution of two or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson et al., *J. Biol. Chem.* 253:6551 (1978); Zoller et al., *DNA* 3:479 (1984); Oliphant et al., *Gene* 44:177 (1986); Hutchinson et al., *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

The term "fragment," as applied to a polypeptide, refers to a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 or more amino acids.

A "variant" of a polypeptide or protein refers to any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. In one embodiment, a variant polypeptide comprises at least about 14 amino acids.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., *Cell* 50:667 (1987)). Such proteins (and their encoding genes) have sequence homology, as reflected by their high degree of sequence similarity. However, in common usage and in the present application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., *Cell* 50:667 (1987)). In one embodiment, two DNA sequences are "substantially homologous" or "substantially similar" when at least about 50% (e.g., at least about 75%, 90%, or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the present invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the present invention are those nucleic acid fragments whose DNA sequences are at least about 70%, 80%, 90% or 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403 (1993)); available at ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using sequence analysis software such as the Megalign program of the LASERGENE bioinformatics computing suite (DNASTAR Inc., Madison, Wis.). Multiple alignment of the sequences may be performed using the Clustal method of alignment (Higgins et al., *CABIOS.* 5:151 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software includes, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism, e.g., at least 5-fold, 10-fold, 100-fold, or 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal." The present invention is useful to search for orthogonal ligands and orthogonal receptor-based gene expression systems such as those described in US 2002/0110861 A1, which is incorporated herein by reference in its entirety.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. Exogenous genes can be either natural or synthetic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells into the subject.

The terms "therapeutic product" and "therapeutic molecule" as used herein refer to a therapeutic polypeptide ("TP", encoded by a "therapeutic proteins sequence" ("TPSQ")) or therapeutic polynucleotide which imparts a beneficial function to the subject to be treated. Therapeutic polypeptides may include, without limitation, peptides as small as three amino acids in length, single- or multiple-chain proteins, and fusion proteins. Therapeutic polynucleotides may include, without limitation, antisense oligonucleotides, small interfering RNAs, ribozymes, and RNA external guide sequences. Non-limiting examples of therapeutic products are disclosed elsewhere herein. The therapeutic product may comprise a naturally occurring sequence, a synthetic sequence or a combination of natural and synthetic sequences.

The term "ligand-dependent transcription factor complex" or "LDTFC" refers to a transcription factor comprising one or more protein subunits, which complex can regulate gene expression driven by a "factor-regulated promoter" as defined herein. A model LDTFC is an "ecdysone receptor complex" generally refers to a heterodimeric protein complex having at least two members of the nuclear receptor family, ecdysone receptor ("EcR") and ultraspiracle ("USP") proteins (see Yao et al., *Nature* 366:476 (1993)); Yao et al., *Cell* 71:63 (1992)). A functional LDTFC such as an EcR complex may also include additional protein(s) such as immunophilins. Additional members of the nuclear receptor family of proteins, known as transcriptional factors (such as DHR38, betaFTZ-1 or other insect homologs), may also be ligand dependent or independent partners for EcR and/or USP. A LDTFC such as an EcR complex can also be a heterodimer of EcR protein and the vertebrate homolog of ultraspiracle protein, retinoic acid-X-receptor ("RXR") protein or a chimera of USP and RXR. The terms "LDTFC" and "EcR complex" also encompass homodimer complexes of the EcR protein or USP, as well as single polypeptides or trimers, tetramer, and other multimers serving the same function.

A LDTFC such as an EcR complex can be activated by an active ecdysteroid or non-steroidal ligand bound to one of the proteins of the complex, inclusive of EcR, but not excluding other proteins of the complex. As used herein, the term "ligand," as applied to LDTFC-based gene switches e.g., EcD complex based gene switches, describes small and soluble molecules having the capability of activating a gene switch to stimulate expression of a polypeptide encoded therein. Examples of ligands include, without limitation, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117, 057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N, N'-diaroylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; amidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, farnesol, bile acids, 1,1-biphosphonate esters, juvenile hormone III, and the like. Examples of diacylhydrazine ligands useful in the present invention include RG-115819 (3,5-Dimethyl-benzoic acid N-(1-ethyl-2,2-dimethyl-propyl)-N'-(2-methyl-3-methoxy-benzoyl)-hydrazide), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

A LDTFC such as an EcR complex includes proteins which are members of the nuclear receptor superfamily wherein all members are characterized by the presence of one or more polypeptide subunits comprising an amino-terminal transactivation domain ("AD," "TD," or "TA," used interchangeably herein), a DNA binding domain ("DBD"), and a ligand binding domain ("LBD"). The AD may be present as a fusion with a "heterodimerization partner" or "HP." A fusion protein comprising an AD and HP of the invention is referred to herein as a "coactivation protein" or "CAP." The DBD and LBD may be expressed as a fusion protein, referred to herein as a "ligand-inducible transcription factor ("LTF"). The fusion partners may be separated by a linker, e.g., a hinge region. Some members of the LTF family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the LDTFC, e.g., EcR complex, may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the EcR. As a result, they are "substantially insensitive" to the ligands of this invention. Thus, the ligands useful in this invention will have negligible physiological or other effects on transformed cells, or the whole organism. Therefore, cells can grow and express the desired product, substantially unaffected by the presence of the ligand itself.

The term "subject" means an intact insect, plant or animal. It is also anticipated that the ligands will work equally well when the subject is a fungus or yeast. When the subject is an intact animal, preferably the animal is a vertebrate, most preferably a mammal.

EcR ligands, when used with a LDTFC, e.g., an EcR complex, which in turn is bound to the response element linked to an exogenous gene (e.g., a reporter gene), provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of a LDTFC, e.g., an EcR complex, to a specific control, or regulatory, DNA element. The EcR protein, like other members of the nuclear receptor family, possesses at least three domains, an AD, a DBD, and a LBD. This receptor, like a subset of the nuclear receptor family, also possesses less well-defined regions responsible for heterodimerization properties (referred to herein as a "heterodimerization partner" or "HP"). Binding of the ligand to the ligand binding domain of a LTF, e.g., an EcR protein, after heterodimerization with a CAP including, e.g., an AD and/or an HP, e.g., a USP or RXR protein, enables the DNA binding domains of the heterodimeric proteins to bind to the response element in an activated form, thus resulting in expression or suppression of the exogenous gene. This mechanism does not exclude the potential for ligand binding to individual subunits, e.g., LTF or CAP, e.g., an EcR or USP, and the resulting formation of active homodimer complexes (e.g. EcR+EcR or USP+USP). In one embodiment, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988) or LexA protein from *E. coli* (see Brent et al., *Cell* 43:729 (1985)) to accommodate chimeric LDTFCs, e.g., EcR complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

Numerous genomic and cDNA nucleic acid sequences coding for a variety of polypeptides, such as transcription factors and reporter genes, are well known in the art. Those skilled in the art have access to nucleic acid sequence information for virtually all known genes and can either obtain the nucleic acid molecule directly from a public depository, the institution that published the sequence, or employ routine methods to prepare the molecule.

For in vivo use, the ligands described herein may be taken up in pharmaceutically acceptable carriers, such as, for example, solutions, suspensions, tablets, capsules, ointments, elixirs, and injectable compositions. Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression.

Suitable routes of administering the pharmaceutical preparations include oral, rectal, topical (including dermal, buccal and sublingual), vaginal, parenteral (including subcutaneous, intramuscular, intravenous, intradermal, intrathecal and epidural) and by naso-gastric tube. It will be understood by those skilled in the art that the preferred route of administration will depend upon the condition being treated and may vary with factors such as the condition of the recipient.

One embodiment of the invention comprises methods for treating, ameliorating, or preventing a disease, disorder, or condition in a subject, comprising:

(a) introducing into cells of said subject (1) a polynucleotide encoding a gene switch, said gene switch comprising at least one transcription factor sequence, wherein said at least one transcription factor sequence encodes a ligand-dependent transcription factor complex, operably linked to a therapeutic switch promoter, wherein the promoter is activated during said disease, disorder, or condition, and (2) a polynucleotide encoding a therapeutic polypeptide or therapeutic polynucleotide linked to a promoter which is activated by said ligand-dependent transcription factor complex; and (b) administering ligand to said subject to induce expression of said therapeutic polypeptide or therapeutic polynucleotide;

wherein said therapeutic polypeptide or therapeutic polynucleotide is expressed at a level sufficient to treat, ameliorate, or prevent said disease, disorder, or condition.

One embodiment of the invention comprises methods for treating, ameliorating, or preventing a disease, disorder, or condition in a subject, comprising:

(a) introducing into a subject (1) a first polynucleotide encoding a gene switch, said gene switch comprising at least one transcription factor sequence, wherein said at least one transcription factor sequence encodes a ligand-dependent transcription factor complex through operable association with a therapeutic switch promoter, and (2) a second polynucleotide encoding a therapeutic polypeptide or therapeutic polynucleotide operably associated with a factor-regulated promoter which is activated by said ligand-dependent transcription factor complex, wherein said first and second polynucleotides are introduced so as to permit expression of said ligand-dependent transcription factor complex; and (b) administering ligand to said subject to induce expression of said therapeutic polypeptide or therapeutic polynucleotide.

One embodiment of the invention comprises methods for expressing a therapeutic polypeptide or therapeutic polynucleotide in a subject, comprising:

(a) introducing into a subject (1) a first polynucleotide encoding a gene switch, said gene switch comprising at least one transcription factor sequence, wherein said at least one transcription factor sequence encodes a ligand-dependent transcription factor complex through operable association with a therapeutic switch promoter, and (2) a second polynucleotide encoding said therapeutic polypeptide or therapeutic polynucleotide operably associated with a factor-regulated promoter which is activated by said ligand-dependent transcription factor complex, wherein said first and second polynucleotides are introduced so as to permit expression of said ligand-dependent transcription factor complex; and (b) administering ligand to said subject to induce expression of said therapeutic polypeptide or therapeutic polynucleotide.

In certain embodiments, the therapeutic switch promoter described in the methods is consititutive. In certain embodiments, the therapeutic switch promoter is activated under conditions associated with a disease, disorder, or condition, e.g., the promoter is activated in response to a disease, in response to a particular physiological, developmental, differentiation, or pathological condition, and/or in response to one or more specific biological molecules; and/or the promoter is activated in particular tissue or cell types. In certain embodiments, the disease, disorder, or condition is responsive to the therapeutic polypeptide or polynucleotide. For example in certain non-limiting embodiments the therapeutic polynucleotide or polypeptide is useful to treat, prevent, ameliorate, reduce symptoms, prevent progression, or cure the disease, disorder or condition, but need not accomplish any one or all of these things. In certain embodiments, the first and second polynucleotides are introduced so as to permit expression of the ligand-dependent transcription factor complex under conditions associated with a disease, disorder or condition. In one embodiment, the therapeutic methods are carried out such that the therapeutic polypeptide or therapeutic polynucleotide is expressed and disseminated through the subject at a level sufficient to treat, ameliorate, or prevent said disease, disorder, or condition. As used herein, "disseminated" means that the polypeptide is expressed and released from the modified cell sufficiently to have an effect or activity in the subject. Dissemination may be systemic, local or anything in between. For example, the therapeutic polypeptide or therapeutic polynucleotide might be systemically disseminated through the bloodstream or lymph system. Alternatively, the therapeutic polypeptide or therapeutic polynucleotide might be disseminated locally in a tissue or organ to be treated.

In one embodiment, the therapeutic methods are carried out by administering compositions of the invention, such as the first and second polynucleotides described above, directly to the subject to be treated, such that the polynucleotides are taken up, in vivo, by cells of the subject to be treated, and one or more therapeutic polypeptides or polynucleotides will be expressed by those cells under appropriate conditions, as described in detail elsewhere herein. Polynucleotides may be directly delivered to a subject to be treated by a variety of methods including, without limitation, viral vectors, e.g., retroviral vectors, adeno-associated virus vectors, pox virus vectors, e.g., vaccinia virus vectors, baculovirus vectors, herpes virus vectors, e.g., herpes simplex vectors or Epstein-Barr virus vectors, adenovirus vectors, geminivirus vectors, or caulimovirus vectors; non-viral vectors such as plasmids, which may be delivered, for example complexed with liposomes, electrically charged lipids (cytofectins), biopolymers or as DNA-protein complexes.

In another embodiment, the therapeutic methods are carried out by introducing the compositions of the invention, such as the first and second polynucleotides described above, into the subject to be treated contained in one or more modified cells. Following administration of the modified cells the one or more therapeutic polypeptides or polynucleotides are expressed by the modified cells under appropriate conditions, as described in detail elsewhere herein. The term "modified cell" refers to a cell or cells into which at least a first and second polynucleotide as described above have been inserted. As such, "a modified cell" refers to the cell harboring the first and second polynucleotides, which may or may not be a cell from, or related to, the subject to be treated. Such cells are included in the definition of "bioreactors" or "bioreactor devices" as described herein. As defined herein, however, a "bioreactor" or "bioreactor device" need not be not a modified cell, rather, a bioreactor or bioreactor device as defined herein is any cell or cells intended to secrete a therapeutic protein or therapeutic polynucleotide, whether or not the cell(s) are "modified cells."

In one embodiment, the therapeutic methods are carried out by introducing the compositions of the invention, such as the first and second polynucleotides described above, into cells that have been isolated from said subject, i.e., autologous cells, to produce modified cells, and the modified cells are re-introduced into said subject.

Alternatively, modified cells may be prepared by introducing the compositions of the invention, such as the first and second polynucleotides described above, into cells which are not isolated from the subject, i.e., they are non-autologous relative to the subject, to produce modified non-autologous (MNA) cells. Such MNA cells may be allogeneic relative to the subject to be treated, i.e., they are derived from a genetically non-identical member of the same species as the subject. For example, in treating a human subject, the cells would be human cells, but not directly derived from the subject to be treated. Alternatively, MNA cells may be xenogeneic relative to the subject to be treated. i.e., they are derived from a different species than the subject to be treated. For example, in treating a human subject the cells might be mouse cells, monkey cells, or pig cells.

MNA cells suitable for use in the present invention may be generated from any number of cells types, including, but not limited to immortalized cells, primary cells, and cells capable of terminal differentiation. Non-limiting examples of cells suitable for generating MNA modified cells for the present invention include C2C12 mouse myoblast cells, HEK293 human embryonic kidney cells, ARPE-19 cells, hMSC cells, pancreatic islet cells, MDCK cell, BHK cell, hybridoma cell CHO cell, an astrocyte derived cell, an oligodendrocyte derived cell, a myoblast derived cell, a parathyroid derived cell. In a specific embodiment where pancreatic islet cells are used to generate modified cells to treat a human subject, the pancreatic islet cells may be xenogeneic, e.g., porcine islet cells, or allogeneic, e.g., human islet cells derived from cadavers.

In one embodiment, the therapeutic methods are carried out in vivo.

In one embodiment, the polynucleotide encoding the gene switch and the polynucleotide encoding the therapeutic polypeptide or therapeutic polynucleotide linked to a promoter are part of one larger polynucleotide, e.g., a vector. In another embodiment, the polynucleotide encoding the gene switch and the polynucleotide encoding the therapeutic polypeptide or therapeutic polynucleotide linked to a promoter are separate polynucleotides, which may be combined to form a "nucleic acid composition.".

In certain embodiments, a bioreactor of the invention comprises modified or non-modified cells surrounded by a barrier (e.g., encapsulated) prior to being introduced into the subject. Such a bioreactor may be used with any subject instead of having to modify autologous cells from each individual. Cellular encapsulation methods have been used to immunoisolate cells while allowing, either selectively or unselectively, the release of desired biological materials. It may be desirable to provide encapsulation compositions and methods for making them, which are capable of providing improved structural characteristics and/or immune protection. Such compositions and methods may find use, where encapsulated cells can withstand mechanical, chemical or immune destruction within the subject to be treated, and would additionally provide for free permeability to nutrients, ions, oxygen, and other materials needed to both maintain the tissue and support normal metabolic functions, but impermeable to bacteria, lymphocytes, and large proteins of the type responsible for immunochemical reactions. Barriers suitable for use in the present invention allow dissemination of a therapeutic protein or therapeutic polynucleotide expressed by modified or non-modified cells contained within the barrier, but prevent direct contact of the cells with cells of the subject's immune system. The barrier may also function to prevent non-autologous or autologous modified or non-modified cells from escaping from the site of introduction, e.g., rogue cells that might cause harm to the subject if allowed to circulate. In one embodiment the barrier is a selectively permeable barrier, e.g., a barrier that is permeable to small molecules such as hormones and small peptides but impermeable to larger polypeptides such as antibodies. For example, the barrier may be impermeable to molecules with a molecular weight greater than about 100,000, about 50,000, about 25,000, about 10,000, about 5,000 or about 1,000 daltons.

Any number of barrier systems are suitable for use in the present invention. In one embodiment, for example, the barrier comprises a conformal coating which encases one or more cells. Typically a conformal coating is made of a polymer material, e.g., polyethylene glycol or hydroxyethyl methacrylate-methyl methacrylate (HEMA-MMA). Conformal coatings typically enclose a small number of modified cells, e.g., 1-10 cells, 1-20 cells, 1-30 cells 1-50 cells 1-70 cells or 1-90 cells. See, e.g., Shoichet M S, Winn S R., *Adv Drug Delivery Rev.* 42:81-102 (2000), which is incorporated herein by reference in its entirety.

In other embodiments, a barrier system suitable for use in the present invention comprises a bioreactor, which comprises encapsulated cells. Two non-limiting encapsulation methods, microencapsulation and macroencapsulation, are known in the art. Typically, in microencapsulation, the cells are suspended in a biologically compatible encapsulation material which is then shaped into bead-like structures, whereas in macroencapsulation the device is generally manufactured prior to the addition of cells and can be composed of one or more synthetic membranes. As compared to conformal coatings, barrier systems comprising encapsulated cells tend to be more uniform in size, and tend to have uniform pore size allowing better control of protein dissemination. For encapsulation, living cells and other sensitive materials may be treated under sufficiently mild conditions allowing the cells or biomaterial to remain substantially unaffected by the encapsulation process, yet permitting the formation of a capsule of sufficient strength to exist over long periods of time.

Living cell(s) can be encapsulated and the resulting encapsulated cell(s) maintain long term in vivo activity by encapsulating the cells within a biocompatible semi-permeable membrane. One way to increase biocompatibility is to add an outer surface of biocompatible negatively-charged material. The term "biocompatible" as used herein refers collectively to both the intact capsule and its contents. Specifically, it refers to the capability of the implanted intact encapsulated cell to avoid detrimental effects of the body's various protective systems, such as immune system or foreign body fibrotic response, and remain functional for a significant period of time.

Bioreactors comprising encapsulated cells which are suitable for use in the present invention are especially useful for the administration of cells to an animal, wherein the immune response of the animal towards the cell is to be minimized. Cells which produce antibodies, enzymes, and other bioactive materials can also be administered. The small size of the resulting encapsulated cells within the subject of the invention facilitate administration of the microcapsules by injection, implantation or transplantation into a subject.

Living cells can be encapsulated in a variety of gels, e.g., alginate, to form implantable bead-like structures, e.g., microbeads or microspheres to physically isolate the cells once implanted into a subject to be treated. To prevent entry of smaller molecular weight substances such as antibodies and complement (with a molecular weight of about 150 kDa) into these bead-like structures, they can be coated with a material such as poly-L-lysine, chitosan, or PAN-PVC, which provides an outer shell with a controlled pore size or they can be treated by e.g., cross-linking, to control their internal porosity. Additional examples of useful materials include conventional biocompatible materials made up of natural or synthetic polymers or co-polymers, such as poly-L-lysine-alginate, collagen, gelatin, laminin, methyl methacrylate, hydroxyethyl methacrylate, MATRIGEL, VIRTOGEN, polyvinylalcohol, agarose, polyethylene glycol, hydrogels, polylactic acid, polyglycolic acid, poly(lactide-co-glycolide), polyhydroxybutyrate-polyhydroxyvalerate, copolymer, poly(lactide-co-caprolactone), polyesteramides, polyorthoesters, poly 13-hydroxybutyric acid, polyanhydrides, polyethylene terephthalate, polytetrafluoroethylene, polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, and poly(acrylonitrile/covinyl chloride).

One form of encapsulation is microencapsulation, which involves suspension of the cells in a liquid or gelatinous encapsulation material, which is then formed into a supporting particulate matrix, e.g., a hydrogel matrix to form a bead-like structure, which serves as a core of an implantable device. The core maintains a proper cell distribution, provides strength, and enhances cell viability, longevity, and function. The core can also contribute to immunoisolation. It also protects the internal cells contained in the bead-like structures from direct cell-cell interactions that can elicit an undesirable immune response in the subject to be treated.

A barrier system may contain multiple layers, e.g., where each layer serves a different purpose (e.g., support, control of permeability). Barriers may comprise contrast agents or other properties that render the barrier imageable (e.g., by x-ray, sonography, etc.) to ensure proper positioning of the implanted cells. Examples of barrier systems useful for cell implantation are described in U.S. Pat. No. 7,226,978, RE39,542 (agarose), U.S. Pat. Nos. 6,960,351, 6,916,640, 6,911,227 (polyethylene glycol), U.S. Pat. Nos. 6,818,018, 6,808,705, 6,783,964, 6,762,959, 6,727,322, 6,610,668 (poly-14-N-acetylglucosamine (p-GlcNAc) polysaccharide), U.S. Pat. No. 6,558,665, RE38,027, U.S. Pat. Nos.

6,495,161, 6,368,612, 6,365,385, 6,337,008, 6,306,454 (polyalkylene), U.S. Pat. Nos. 6,303,355, 6,287,558 (gel super matrix), U.S. Pat. Nos. 6,281,015, 6,264,941, 6,258,870, 6,180,007, 6,126,936 (polyamine acid), U.S. Pat. Nos. 6,123,700, 6,083,523, 6,020,200, 5,916,790, 5,912,005, 5,908,623, 5,902,745, 5,858,746, 5,846,530 (polysaccharides), U.S. Pat. Nos. 5,843,743, 5,837,747, 5,837,234, 5,834,274, 5,834,001, 5,801,033, 5,800,829, 5,800,828, 5,798,113, 5,788,988, 5,786,216, 5,773,286, 5,759,578, 5,700,848, 5,656,481, 5,653,975, 5,648,099, 5,550,178, 5,550,050, 4,806,355, 4,689,293, 4,680,174, 4,673,566, 4,409,331, 4,352,883, and U.S. Patent Application Publications 2006/0263405 (alginate/polymer) and 2004/0005302 (alignate-poly-L-lysine), each incorporated herein by references in its entirety.

In certain embodiments, a barrier system suitable for use in the present invention comprises microencapsulated cells. Microencapsulation generates approximately spherical and relatively uniform bead-like structures comprising encapsulated cells, where the bead-like structures are about 100-700 μm in diameter, e.g., about 100, 200, 300, 400, 500, 600 or 700 μm in diameter. Microencapsulated cells of the invention may be produced using a variety of encapsulation materials as described above. In one embodiment, the encapsulation material comprises a hydrogel. In another embodiment the encapsulation material comprises a polymer. Suitable polymers include, without limitation, cellulose, e.g., cellulose sulfate, and alginate. For example, one microcapsule of the invention comprises polyanionic alginate and a poly-cationic polymer to interact and form a physical perm-selective membrane barrier. An alternative method of microencapsulation comprises the formation of poly (L-lactide) acid (PLLA) or a poly-L-ornithine (PLO) alginate microspheres. See, e.g., Darrabic, M. D. et al. *Biomaterials* 26:6846-6852 (2005) and Blasi, P. et al. *Int J Pharm.* 324:27-36 (2006). Alginate based microencapsulation materials may further contain ultra high viscosity (UHV) polymers, which may also be biodegradable. See, e.g., Zimmermann, U. et al. *Ann N Y Acad Sci.* 944:199-215 (2001).

Bioreactors of the present invention comprising microencapsulated cells typically comprise at least one up to about 1000 cells per "bead," e.g., modified or non-modified cells intended to secrete a desired therapeutic polypeptide or polynucleotide as described herein. For example, a bioreactor of the invention which comprises microencapsulated cells may result in at least 50, at least 100, at least 200, at least 400, at least 500, at least 800 to about 1000 or more cells per "bead."

In certain embodiments, a bioreactor suitable for use in the present invention comprises cells enclosed in a macroencapsulation device. As compared to bioreactors comprising microencapsulated cells, bioreactors comprising macroencapsulation devices are typically larger and often non-spherical encapsulated cell entities, and may be composed of one or more synthetic membranes, e.g., one, two, three, four, 8, 10, or more membranes, which may be the same composition of different compositions. As denoted by the name, macrocapsulated cell devices are of a size such that individual entities may be easily manipulated. For example, a typical macroencapsulation device may be an oblong shape, about 3 mm, 4 mm, 5 mm, 6 mm, 7 mm, 8 mm, 9 mm, 10 mm or more long and about 1 mm, 2 mm, 3 mm, 4 mm, or 5 mm or more in diameter. An exemplary but non-limiting macroencapsulation device of the invention is about 6 mm long and about 1 mm in diameter.

In certain embodiments a macroencapsulation device suitable for use in the present invention comprises two or more synthetic membranes, where the synthetic membranes have different pore sizes so as to regulate transit of therapeutic molecules through the device and their dissemination into the environment. In certain embodiments, a macroencapsulation device of the invention comprises a semi-permeable polymer outer membrane and an internal scaffold to support the cells. In non-limiting examples, the outer membrane comprises pores of about 15 nm to allow exchange of nutrients of therapeutic molecules. The internal scaffold may comprise any number of materials. In one non-limiting example the scaffold comprises poly(ethylene terephthalate) yarn (available from Neurotech (www.neurotechusa.com)).

In another non-limiting example, a macroencapsulaton device suitable for use in the invention comprises a polymeric membrane bilayer, where the bilayer comprises an outer layer of 5 μm poly(tetrafluoroethylene) (PTFE) membrane laminated onto an inner tighter pore 0.45 uM PTFE immunobarrier layer (available from Theracyte (www.theracyte.com)). Such a macroencapsulation device may further comprise a non-woven poly mesh layer exterior to said polymeric membrane bilayer. In yet another non-limiting example, a macroencapsulation device suitable for use in the invention is composed of polyethersulfone (PES) hollow fibers. See, e.g., Li, Y., et al. *J. Membrane Sci.* 245:53-60 (2004).

Macroencapsulation devices suitable for use in the present invention may optionally have additional structures to allow convenient implantation into and retrieval from a subject to be treated. For example, a macroencapsulation device may comprise, without limitation, a suture clip, a loading port, a tether, or other structure for ease of use.

The interior space of macroencapsulation devices of the invention is typically suitable to comprise at least one up to about $10^5$ cells, e.g., modified or non-modified cells intended to secrete a desired therapeutic polypeptide or polynucleotide. For example, a macroencapsulation device of the invention may comprise at least 500, at least 1,000, at least 2,000, at least 4,000, at least 5,000, at least 8,000 to about 10,000 or more cells.

Some bioreactor devices, e.g., encapsulated or coated modified or non-modified cells of the present invention intended to secrete a desired therapeutic polypeptide or polynucleotide, may further comprise protective cells, e.g., within the barrier or capsule, where the protective cells are capable of providing protection to the modified or non-modified cells intended to secrete a desired therapeutic polypeptide or polynucleotide. Non-limiting examples of such protective cells include modified or non-modified sertoli cells and erythrocytes. Additionally, some bioreactor devices, e.g., encapsulated or coated modified or non-modified cells of the present invention intended to secrete a desired therapeutic polypeptide or polynucleotide, may further comprise an outer coating capable of creating a more compatible or protective micro-environment. Exemplary, non-limiting micro-environments which may be created include an anti-inflammatory micro-environment and a pro-angiogenic micro-environment.

In still other embodiments, bioreactor devices of the present invention may include modified cells with a "safety-shutoff" mechanism. For example, modified cells contained in a bioreactor device may comprise a regulated suicide gene which encodes a lethal polypeptide where the gene, upon activation, would induce destruction of the modified cell itself. For example, a modified cell might be programmed to die if it escapes from a barrier system, or if it undergoes oncogenic conversion. Non-limiting examples of lethal polypeptides suitable for use in the present invention are described in more detail below.

The subject on which the therapeutic methods are carried out may be any subject for which treatment or prevention is desired. For example, the subject may be one that is exhibiting one or more symptoms of a disease, disorder, or condition. The subject may also be one that is predisposed to a disease, disorder, or condition, e.g., due to genetics, family history, or environmental exposure. The subject may be a member of the general public, e.g., as part of a preventative immunization against a disease, disorder, or condition in a population.

The disease, disorder, or condition to be treated or prevented by the methods of the invention may be any disease, disorder, or condition for which one or more therapeutic switch promoters is available. Examples of diseases or disorders which may be treated or prevented by the methods of the invention include, without limitation, hyperproliferative diseases, disorders, or conditions (e.g., cancer), cardiovascular diseases, disorders, or conditions, neural diseases, disorders, or conditions, autoimmune diseases, disorders, or conditions, bone diseases, disorders, or conditions, gastrointestinal diseases, disorders, or conditions, blood diseases, disorders, or conditions, metabolic diseases, disorders, or conditions, inflammatory diseases, disorders, or conditions, and infectious diseases, disorders, or conditions.

The therapeutic switch promoters of the invention may be any promoter that is useful for treating, ameliorating, or preventing a specific disease, disorder, or condition. Examples include, without limitation, promoters of genes that exhibit increased expression only during a specific disease, disorder, or condition and promoters of genes that exhibit increased expression under specific cell conditions (e.g., proliferation, apoptosis, change in pH, oxidation state, oxygen level). In some embodiments where the gene switch comprises more than one transcription factor sequence, the specificity of the therapeutic methods can be increased by combining a disease- or condition-specific promoter with a tissue- or cell type-specific promoter to limit the tissues in which the therapeutic product is expressed. Thus, tissue- or cell type-specific promoters are encompassed within the definition of therapeutic switch promoter.

As an example of disease-specific promoters, useful promoters for treating cancer include the promoters of oncogenes. Examples of classes of oncogenes include, but are not limited to, growth factors, growth factor receptors, protein kinases, programmed cell death regulators and transcription factors. Specific examples of oncogenes include, but are not limited to, sis, erb B, erb B-2, ras, abl, myc and bcl-2 and TERT. Examples of other cancer-related genes include tumor associated antigen genes and other genes that are overexpressed in neoplastic cells (e.g., MAGE-1, carcinoembryonic antigen, tyrosinase, prostate specific antigen, prostate specific membrane antigen, p53, MUC-1, MUC-2, MUC-4, HER-2/neu, T/Tn, MART-1, gp100, GM2, Tn, sTn, and Thompson-Friedenreich antigen (TF)).

Examples of promoter sequences and other regulatory elements (e.g., enhancers) that are known in the art and are useful as therapeutic switch promoters in the present invention are disclosed in the references listed in Tables 1 and 2, along with the disease/disorder (Table 1) or tissue specificity (Table 2) associated with each promoter. The promoter sequences disclosed in these references are herein incorporated by reference in their entirety.

TABLE 1

| Promoter Sequence | Disease/Disorder | Patent/Published Application No. |
|---|---|---|
| Her-2/neu (ERBB2/c-erbB-2) | cancer | 5,518,885 |
| osteocalcin | calcified tumors | 5,772,993 |
| stromelysin-1 | cancer | 5,824,794 |
| prostate specific antigen | prostate cancer | 5,919,652 |
| human sodium-iodide symporter | thyroid carcinoma | 6,015,376 |
| H19, IF-1, IGF-2 | cancer | 6,306,833 |
| thymosin β15 | breast, pancreatic, prostate cancer | 6,489,463 |
| T cell factor | cancer | 6,608,037 |
| cartilage-derived retinoic acid-sensitive protein | chondrosarcoma, mammary tumor | 6,610,509 |
| insulin | pancreatic cancer | 6,716,824 |
| PEG-3 | cancer | 6,737,523 |
| telomerase reverse transcriptase | cancer | 6,777,203 |
| melanoma differentiation associated gene-7 | cancer | 6,841,362 |
| prostasin | cancer | 6,864,093 |
| telomerase catalytic subunit; cyclin-A | cancer | 6,936,595 |
| midkine; c-erbB-2 | cancer | 7,030,099 |
| prostate-specific membrane antigen | prostate cancer | 7,037,647 |
| p51 | cancer | 7,038,028 |
| telomerase RNA | cancer | 7,084,267 |
| prostatic acid phosphatase | prostate cancer | 7,094,533 |
| PCA3$_{dd3}$ | prostate cancer | 7,138,235 |
| DF3/MUC1 | cancer | 7,247,297 |
| hex II | cancer | 2001/0011128 |
| cyclooxygenase-2 | cancer | 2002/0107219 |
| super PSA | prostate cancer | 2003/0078224 |
| skp2 | cancer | 2003/0109481 |
| PRL-3 | metastatic colon cancer | 2004/0126785 |
| CA125/M17S2 | ovarian cancer | 2004/0126824 |
| IAI.3B | ovarian cancer | 2005/0031591 |
| CRG-L2 | liver cancer | 2005/0124068 |
| TRPM4 | prostate cancer | 2006/0188990 |
| RTVP | glioma | 2006/0216731 |

TABLE 1-continued

| Promoter Sequence | Disease/Disorder | Patent/Published Application No. |
|---|---|---|
| TARP | prostate cancer, breast cancer | 2007/0032439 |
| telomere reverse transcriptase | cancer | 2007/0059287 |
| A4 amyloid protein | Alzheimer's disease | 5,151,508 |
| amyloid β-protein precursor | Alzheimer's disease | 5,643,726 |
| precursor of the Alzheimer's Disease A4 amyloid protein | Alzheimer's disease | 5,853,985 |
| neuropeptide FF | CNS disorders | 6,320,038 |
| endoplasmic reticulum stress elements | stress | 7,049,132 |
| urocortin II | psychopathologies | 7,087,385 |
| tyrosine hydroxylase | neurological disorders | 7,195,910 |
| complement factor 3; serum amyloid A3 | inflammation | 5,851,822 |
| tissue inhibitor of metalloproteinase-3 (TIMP-3) | rheumatism, cancer, autoimmune disease, inflammation | 5,854,019 |
| p75 tumor necrosis factor receptor | autoimmune disease | 5,959,094 |
| tumor necrosis factor-α | inflammation | 6,537,784 |
| peroxisome proliferator activated receptor/IIA-1 nonpancreatic secreted phospholipase A2 | inflammation | 6,870,044 |
| SOCS-3 | growth disorders, autoimmune disease, inflammation | 2002/0174448 |
| SR-BI | lipid disorders | 5,965,790 |
| Ob | obesity | 5,698,389 |
| site-1 protease | obesity, diabetes | 7,045,294 |
| TIGR | glaucoma | 7,138,511 |
| VL30 | anoxia | 5,681,706 |
| excitatory amino acid transporter-2 | nervous system ischemia | 2004/0171108 |
| MDTS9 | renal failure | 2006/0014931 |
| LIM, pyrroline 5-carboxylate reductase, SIM2 | prostate disorders | 2006/0134688 |
| Bax | apoptosis | 5,744,310 |
| fas | apoptosis | 5,888,764 |
| bbc3 | apoptosis | 7,202,024 |
| PINK-1 | PI-3 kinase/Akt pathway disorders | 2006/0228776 |

TABLE 2

| Promoter Sequence | Tissue Specificity | Patent/Published Application No. |
|---|---|---|
| troponin T | skeletal muscle | 5,266,488 |
| myoD | muscle | 5,352,595 |
| actin | muscle | 5,374,544 |
| smooth muscle 22α | arterial smooth muscle | 5,837,534 |
| utrophin | muscle | 5,972,609 |
| myostatin | muscle | 6,284,882 |
| smooth muscle myosin heavy chain | smooth muscle | 6,780,610 |
| cardiac ankyrin repeat protein | cardiac muscle | 7,193,075 |
| MLP | muscle | 2002/0042057 |
| smoothelin | smooth muscle | 2003/0157494 |
| MYBPC3 | cardiomyocytes | 2004/0175699 |
| Tα1 α-tubulin | neurons | 5,661,032 |
| intercellular adhesion molecule-4 (ICAM-4) | neurons | 5,753,502 |
| γ-aminobutyric acid type A receptor β1 subunit | hippocampus | 6,066,726 |
| neuronal nicotinic acetylcholine receptor β2-subunit | neurons | 6,177,242 |
| presenilin-1 | neurons | 6,255,473 |
| calcium-calmodulin-dependent kinase IIα | forebrain | 6,509,190 |
| CRF$_{2α}$ receptor | brain | 7,071,323 |
| nerve growth factor | neurons | 2003/159159 |
| GLP-2 receptor | gut, brain | 2002/0045173 |
| type I transglutaminase | keratinocytes | 5,643,746 |
| K14 | keratinocytes | 6,596,515 |
| stearoyl-CoA desaturase | skin | 2002/0151018 |
| megsin | renal cells | 6,790,617 |

TABLE 2-continued

| Promoter Sequence | Tissue Specificity | Patent/Published Application No. |
|---|---|---|
| prolactin | pituitary | 5,082,779 |
| GDF-9 | ovary, testes, hypothalamus, pituitary, placenta | 7,227,013 |
| PSP94 | prostate | 2003/0110522 |
| NRL; NGAL | mammary gland | 5,773,290 |
| long whey acidic protein | mammary gland | 5,831,141 |
| mammary associated amyloid A | mammary ductal epithelial cells | 2005/0107315 |
| endothelin-1 | endothelial cells | 5,288,846 |
| serglycin | hematopoietic cells | 5,340,739 |
| platelet-endothelial cell adhesion molecule-1 (PECAM-1) | platelets, leukocytes, endothelial cells | 5,668,012 |
| Tie receptor tyrosine kinase | endothelial cells, bone marrow | 5,877,020 |
| KDR/flk-1 | endothelial cells | 5,888,765 |
| endoglin | endothelial cells | 6,103,527 |
| CCR5 | myeloid and lymphoid cells | 6,383,746 |
| CD11d | myeloid cells | 6,881,834 |
| platelet glycoprotein IIb | hematopoietic cells | 6,884,616 |
| preproendothelin-1 | endothelial cells | 7,067,649 |
| interleukin-18 binding protein | mononuclear cells | 2006/0239984 |
| CD34 | hematopoietic stem cells | 5,556,954 |
| Tec tyrosine kinase | hematopoietic stem cells, liver | 6,225,459 |

Other genes that exhibit changes in expression levels during specific diseases or disorders and therefore may provide promoters that are useful in the present invention include, without limitation, the genes (along with the associated disease/disorder) listed in Table 3.

TABLE 3

| Gene | Disease/Disorder | Patent/Published Application No. |
|---|---|---|
| MLH1, MSH2, MSH6, PMS1, APC | Colorectal cancer | 7,148,016 |
| LEF-1 | Colon cancer | 2002/0169300 |
| $F_2$ receptor | Colon cancer | 2002/0187502 |
| TGF-β type II receptor | Colon cancer | 2004/0038284 |
| EYA4 | Colon cancer | 2005/0003463 |
| PCA3 | Prostate cancer | 7,138,235 |
| K2 | Prostate cancer | 6,303,361 |
| PROST 03 | Prostate cancer metastases | 2002/0009455 |
| PCAM-1 | Prostate cancer | 2002/0042062 |
| PCADM-1 | Prostate cancer | 2003/0100033 |
| $PCA3_{dd3}$ | Prostate cancer | 2003/0165850 |
| PCAV | Prostate cancer | 2006/0275747 |
| PAcP | Androgen-insensitive prostate cancer | 2006/0294615 |
| SEQ ID NO: 1 of the Pat. 5,866,329, incorporated by reference herein | Liver cancer | 5,866,329 |
| SEQ ID NOS: 1, 3 of the U.S. patent application publication 2002/0115094, incorporated by reference herein | Hepatocellular cancer | 2002/0115094 |
| SEQ ID NO: 1 of the patent U.S. application publication 2005/0037372, incorporated by reference herein | Hepatocellular carcinoma | 2005/0037372 |
| $ATB_0$ | Hepatocellular carcinoma | 2006/0280725 |
| SEQ ID NOS: 1, 3 of the U.S. patent application publication 2007/0042420, incorporated by reference herein | Liver cancer | 2007/0042420 |
| CSA-1 | Chondrosarcoma | 2001/0016649 |
| SEQ ID NOS: 1-15 of the U.S. patent application publication 2001/0016651, incorporated by reference herein | Pancreatic cancer | 2001/0016651 |

TABLE 3-continued

| Gene | Disease/Disorder | Patent/Published Application No. |
|---|---|---|
| SEQ ID NOS: 1-15 of the U.S. patent application publication 2003/0212264, incorporated by reference herein | Pancreatic cancer | 2003/0212264 |
| SYG972 | Breast cancer | 2002/0055107 |
| Urb-ctf | Breast cancer | 2003/0143546 |
| BCU399 | Breast cancer | 2003/0180728 |
| TBX2 | Breast cancer | 2004/0029185 |
| Cyr61 | Breast cancer | 2004/0086504 |
| DIAPH3 | Breast cancer | 2005/0054826 |
| SEQ ID NOS: 1-24 of the U.S. patent application publication 2007/0134669, incorporated by reference herein | Breast cancer | 2007/0134669 |
| Human aspartyl (asparaginyl) beta-hydroxylase | CNS cancer | 2002/0102263 |
| BEHAB | CNS cancer | 2003/0068661 |
| IL-8 | Kaposi's Sarcoma | 2003/0096781 |
| SEQ ID NOS: 1-278 of the U.S. patent application publication 2002/0198362, incorporated by reference herein | Hematological cancers | 2002/0198362 |
| BLSA | B-cell cancer | 2003/0147887 |
| BP1 | Leukemia | 2003/0171273 |
| DAP-kinase, HOXA9 | Non-small cell lung cancer | 2003/0224509 |
| ARP | Clear cell renal carcinoma, inflammatory disorders | 2004/0010119 |
| Nbk | Renal cancer | 2005/0053931 |
| CD43 | Ovarian cancer | 2006/0216231 |
| SEQ ID NOS: 1-84 of the U.S. patent application publication 2007/0054268, incorporated by reference herein | Ovarian cancer | 2007/0054268 |
| β7-hcG, β6-hCG, β6e-hCG, β5-hCG, β8-hcG, β3-hCG | Uterine tumors | 2006/0292567 |
| MTA1s | Hormone insensitive cancer | 2006/0204957 |
| Old-35, Old-64 | Tumor proliferation | 2003/0099660 |
| LAGE-1 | Cancer | 6,794,131 |
| CIF150/hTAF$_{II}$150 | Cancer | 6,174,679 |
| P65 oncofetal protein | Cancer | 5,773,215 |
| Telomerase | Cancer | 2002/0025518 |
| CYP1B1 | Cancer | 2002/0052013 |
| 14-3-3σ | Cancer | 2002/0102245 |
| NES1 | Cancer | 2002/0106367 |
| CAR-1 | Cancer | 2002/0119541 |
| HMGI, MAG | Cancer | 2002/0120120 |
| ELL2 | Cancer | 2002/0132329 |
| Ephrin B2 | Cancer | 2002/0136726 |
| WAF1 | Cancer | 2002/0142442 |
| CIF130 | Cancer | 2002/0143154 |
| C35 | Cancer | 2002/0155447 |
| BMP2 | Cancer | 2002/0159986 |
| BUB3 | Cancer | 2002/0160403 |
| Polymerase kappa | Cancer | 2003/0017573 |
| EAG1, EAG2 | Cancer | 2003/0040476 |
| SEQ ID NOS: 18, 20, 22 of the U.S. patent application publication 2003/0044813, incorporated by reference herein | Cancer | 2003/0044813 |
| HMG I | Cancer | 2003/0051260 |
| HLTF | Cancer | 2003/0082526 |
| Barx2 | Cancer | 2003/0087243 |
| SEQ ID NOS: 18, 20, 22, 32, 34, 36 of the U.S. patent application publication 2003/0108920, incorporated by reference herein | Cancer | 2003/0108920 |
| Cables | Cancer | 2003/0109443 |
| Pp 32r1 | Cancer | 2003/0129631 |
| BMP4 | Cancer | 2003/0134790 |
| TS10q23.3 | Cancer | 2003/0139324 |
| Nuclear spindle-associating protein | Cancer | 2003/0157072 |
| PFTAIRE | Cancer | 2003/0166217 |
| SEMA3B | Cancer | 2003/0166557 |
| MOGp | Cancer, multiple sclerosis, inflammatory disease | 2003/0166898 |
| Fortilin | Cancer | 2003/0172388 |

TABLE 3-continued

| Gene | Disease/Disorder | Patent/Published Application No. |
|---|---|---|
| SEQ ID NO: 1 of the U.S. patent application publication 2003/0215833, incorporated by reference herein | Cancer | 2003/0215833 |
| IGFBP-3 | Cancer | 2004/0005294 |
| Polyhomeotic 2 | Cancer | 2004/0006210 |
| PNQALRE | Cancer | 2004/0077009 |
| SEQ ID NOS: 1, 3 of the U.S. patent application publication 2004/0086916, incorporated by reference herein | Cancer | 2004/0086916 |
| SCN5A | Cancer | 2004/0146877 |
| miR15, miR16 | Cancer | 2004/0152112 |
| Headpin | Cancer | 2004/0180371 |
| PAOh1/SMO | Cancer | 2004/0229241 |
| Hippo, Mst2 | Cancer | 2005/0053592 |
| PSMA-like | Cancer, neurological disorders | 2005/0064504 |
| JAB1 | Cancer | 2005/0069918 |
| NF-AT | Cancer | 2005/0079496 |
| P28ING5 | Cancer | 2005/0097626 |
| MTG16 | Cancer | 2005/0107313 |
| ErbB-2 | Cancer | 2005/0123538 |
| HDAC9 | Cancer | 2005/0130146 |
| GPBP | Cancer | 2005/0130227 |
| MG20 | Cancer | 2005/0153352 |
| KLF6 | Cancer | 2005/0181374 |
| ARTS1 | Cancer | 2005/0266443 |
| Dock 3 | Cancer | 2006/0041111 |
| Annexin 8 | Cancer | 2006/0052320 |
| MH15 | Cancer | 2006/0068411 |
| DELTA-N p73 | Cancer | 2006/0088825 |
| RapR6 | Cancer | 2006/099676 |
| StarD10 | Cancer | 2006/0148032 |
| Ciz1 | Cancer | 2006/0155113 |
| HLJ1 | Cancer | 2006/0194235 |
| RapR7 | Cancer | 2006/0240021 |
| A34 | Cancer | 2006/0292154 |
| Sef | Cancer | 2006/0293240 |
| Killin | Cancer | 2007/0072218 |
| SGA-1M | Cancer | 2007/0128593 |
| TGFβ Type II receptor | Cancer | 2002/0064786 |
| GCA-associated genes | Giant cell arteritis | 6,743,903 |
| PRV-1 | Polycythemia vera | 6,686,153 |
| SEQ ID NOS: 2, 4 of the U.S. Pat. No. 5,948,637, incorporated by reference herein | Ischemia | 5,948,637 |
| Vezf1 | Vascular disorders | 2002/0023277 |
| MLP | Dilatative cardiomyopathy | 2002/0042057 |
| VEGI | Pathological angiogenesis | 2002/0111325 |
| PRO256 | Cardiovascular disorders | 2002/0123091 |
| AOP2 | Atherosclerosis | 2002/0142417 |
| Remodelin | Arterial restenosis, fibrosis | 2002/0161211 |
| Phosphodiesterase 4D | Stroke | 2003/0054531 |
| Prostaglandin receptor subtype EP3 | Peripheral arterial occlusive disease | 2003/0157599 |
| CARP | Heart disorders | 2004/0014706 |
| HOP | Congenital heart disease | 2004/0029158 |
| SEQ ID NOS: 1-4 of the U.S. patent application publication 2004/0087784, incorporated by reference herein | Apoplexy | 2004/0087784 |
| PLTP | Atherosclerosis, vascular disease, hypercholesterolemia, Tangier's disease, familial HDL deficiency disease | 2006/0252787 |
| SEQ ID NOS: 1, 3-8, 15, 16 of the U.S. patent application publication 2007/0160996, incorporated by reference herein | Thrombosis | 2007/0160996 |
| UCP-2 | Stroke | 2002/0172958 |
| FLJ11011 | Fanconi's Anemia | 2006/0070134 |
| Codanin-1 | Anemia | 2006/0154331 |
| SEQ ID NOS: 1, 6, 8 of the U.S. Pat. No. 5,763,591, incorporated by reference herein | Insulin-dependent diabetes mellitus | 5,763,591 |

TABLE 3-continued

| Gene | Disease/Disorder | Patent/Published Application No. |
|---|---|---|
| Resistin | Type II diabetes | 2002/0161210 |
| Archipelin | Diabetes | 2003/0202976 |
| SEQ ID NOS: 2, 7, 16, 27 of the U.S. patent application publication 2004/0053397, incorporated by reference herein | Diabetes, hyperlipidemia | 2004/0053397 |
| Neuronatin | Metabolic disorders | 2004/0259777 |
| Ncb5or | Diabetes | 2005/0031605 |
| 7B2 | Endocrine disorders | 2005/0086709 |
| PTHrP, PEX | Metabolic bone diseases | 2005/0113303 |
| KChIPl | Type II diabetes | 2005/0196784 |
| SLIT-3 | Type II diabetes | 2006/0141462 |
| CX3CR1 | Type II diabetes | 2006/0160076 |
| SMAP-2 | Diabetes | 2006/0210974 |
| SEQ ID NOS: 2, 8, 12, 16, 22, 26, 28, 32 of the U.S. patent application publication 2006/0228706, incorporated by reference herein | Type II diabetes | 2006/0228706 |
| IC-RFX | Diabetes | 2006/0264611 |
| E2IG4 | Diabetes, insulin resistance, obesity | 2007/0036787 |
| SEQ ID NOS: 2, 8, 10, 14, 18, 24, 26, 30, 34, 38, 44, 50, 54, 60, 62, 68, 74, 80, 86, 92, 98, 104, 110 of the U.S. patent application publication 2007/0122802, incorporated by reference herein | Diabetes | 2007/0122802 |
| UCP2 | Body weight disorders | 2002/0127600 |
| Ob receptor | Body weight disorders | 2002/0182676 |
| Ob | Body weight disorders | 2004/0214214 |
| Dp1 | Neurodegenerative disorders | 2001/0021771 |
| NRG-1 | Schizophrenia | 2002/0045577 |
| Synapsin III | Schizophrenia | 2002/0064811 |
| NRG1AG1 | Schizophrenia | 2002/0094954 |
| AL-2 | Neuronal disorders | 2002/0142444 |
| Proline dehydrogenase | Bipolar disorder, major depressive disorder, schizophrenia, obsessive compulsive disorder | 2002/0193581 |
| MNR2 | Chronic neurodegenerative disease | 2002/0197678 |
| ATM | Ataxia-telangiectasia | 2004/0029198 |
| Ho-1 | Dementing diseases | 2004/0033563 |
| CON202 | Schizophrenia | 2004/0091928 |
| Ataxin-1 | Neurodegenerative disorders | 2004/0177388 |
| NR3B | Motor neuron disorders | 2005/0153287 |
| NIPA-1 | Hereditary spastic paraplegia | 2005/0164228 |
| DEPP, adrenomedullin, csdA | Schizophrenia | 2005/0227233 |
| Inf-20 | Neurodegenerative diseases | 2006/0079675 |
| EOPA | Brain development and degeneration disorders | 2007/0031830 |
| SERT | Autism | 2007/0037194 |
| FRP-1 | Glaucoma | 2002/0049177 |
| Serum amyloid A | Glaucoma | 2005/0153927 |
| BMP2 | Osteoporosis | 2002/0072066 |
| BMPR1A | Juvenile polyposis | 2003/0072758 |
| ACLP | Gastroschisis | 2003/0084464 |
| Resistin-like molecule β | Familial adenomatous polyposis, diabetes, insulin resistance, colon cancer, inflammatory bowel disorder | 2003/0138826 |
| Dlg5 | Inflammatory bowel disease | 2006/0100132 |
| SEQ ID NOS: 1-82 of the U.S. patent application publication 2002/0119452, incorporated by reference herein | Osteoarthritis | 2002/0119452 |
| TRANCE | Immune system disorders | 2003/0185820 |
| Matrilin-3 | Osteoarthritis | 2003/0203380 |
| Synoviolin | Rheumatoid arthritis | 2004/0152871 |

TABLE 3-continued

| Gene | Disease/Disorder | Patent/Published Application No. |
| --- | --- | --- |
| SEQ ID NOS: 9, 35 of the U.S. patent application publication 2007/0028314, incorporated by reference herein | Osteoarthritis | 2007/0028314 |
| HIV LTR | HIV infection | 5,627,023 |
| SHIVA | HIV infection | 2004/0197770 |
| EBI 1, EBI 2, EBI 3 | Epstein Barr virus infection | 2002/0040133 |
| NM23 family | Skin/intestinal disorders | 2002/0034741 |
| SEQ ID NO: 1 of the U.S. patent application publication 2002/0169127, incorporated by reference herein | Psoriasis | 2002/0169127 |
| Eps8 | Skin disorders, wound healing | 2003/0180302 |
| Beta-10 | Thyroid gland pathology | 2002/0015981 |
| SEQ ID NO: 2 of the U.S. patent application publication 2003/0207403, incorporated by reference herein | Thyroid conditions | 2003/0207403 |
| SEQ ID NO: 3 of the U.S. patent application publication 2007/0020275, incorporated by reference herein | Thyroid disorders | 2007/0020275 |
| Hair follicle growth factor | Alopecia | 2003/0036174 |
| Corneodesmosin | Alopecia | 2003/0211065 |
| GCR9 | Asthma, lymphoma, leukemia | 2003/0166150 |
| SEQ ID NO: 1-71 of the U.S. patent application publication 2004/0002084, incorporated by reference herein | Asthma | 2004/0002084 |
| Bg | Chediak-Higashi syndrome | 2002/0115144 |
| SEQ ID NOS: 1-16 of the U.S. patent application publication 2002/0127555, incorporated by reference herein | Endometriosis | 2002/0127555 |
| FGF23 | Hypophosphatemic disorders | 2005/0156014 |
| BBSR | Bardet-Biedl syndrome | 2003/0152963 |
| MIC-1 | Fetal abnormalities, cancer, inflammatory disorders, miscarriage, premature birth | 2004/0053325 |
| MIA-2 | Liver damage | 2004/0076965 |
| IL-17B | Cartilage degenerative disorders | 2004/0171109 |
| Formylglycine generating enzyme | Multiple sulfatase deficiency | 2004/0229250 |
| LPLA2 | Pulmonary alveolar proteinosis | 2006/0008455 |
| CXCL1O | Respiratory illnesses | 2006/0040329 |
| SEQ ID NOS: 1, 2 of the U.S. patent application publication 2006/0140945, incorporated by reference herein | Nephropathy | 2006/0140945 |
| HFE2A | Iron metabolism disease | 2007/0166711 |

Once a gene with an expression pattern that is modulated during a disease, disorder, or condition is identified, the promoter of the gene may be used in the gene switch of the invention. The sequence of many genes, including the promoter region, is known in the art and available in public databases, e.g., GenBank. Thus, once an appropriate gene is identified, the promoter sequence can be readily identified and obtained. Another aspect of the present invention is directed towards identifying suitable genes whose promoter can be isolated and placed into a gene switch. The identity of the gene, therefore, may not be critical to specific embodiments of the present invention, provided the promoter can be isolated and used in subsequent settings or environments. The current invention thus includes the use of promoters from genes that are yet to be identified. Once suitable genes are identified, it is a matter of routine skill or experimentation to determine the genetic sequences needed for promoter function. Indeed, several commercial protocols exist to aid in the determination of the promoter region of genes of interest. By way of example, Ding et al. recently elucidated the promoter sequence of the novel Sprouty4 gene (*Am. J. Physiol. Lung Cell. Mol. Physiol.* 287: L52 (2004), which is incorporated by reference) by progressively deleting the 5'-flanking sequence of the human Sprouty4 gene. Briefly, once the transcription initiation site was determined, PCR fragments were generated using common PCR primers to clone segments of the 5'-flanking segment in a unidirectional manner. The generated segments were cloned into a luciferase reporter vector and luciferase activity was measured to determine the promoter region of the human Sprouty4 gene.

Another example of a protocol for acquiring and validating gene promoters includes the following steps: (1) acquire diseased and non-diseased cell/tissue samples of similar/same tissue type; (2) isolate total RNA or mRNA from the samples; (3) perform differential microarray analysis of diseased and non-diseased RNA; (4) identify candidate disease-specific transcripts; (5) identify genomic sequences associated with the disease-specific transcripts; (6) acquire or synthesize DNA sequence upstream and downstream of the predicted transcription start site of the disease-specific transcript; (7) design and produce promoter reporter vectors using different lengths of DNA from step 6; and (8) test promoter reporter vectors in diseased and non-diseased cells/tissues, as well as in unrelated cells/tissues.

The source of the promoter that is inserted into the gene switch can be natural or synthetic, and the source of the promoter should not limit the scope of the invention described herein. In other words, the promoter may be directly cloned from cells, or the promoter may have been previously cloned from a different source, or the promoter may have been synthesized.

Gene Switch Systems

The gene switch may be any gene switch that regulates gene expression by addition or removal of a specific ligand. In one embodiment, the gene switch is one in which the level of gene expression is dependent on the level of ligand that is present. Examples of ligand-dependent transcription factor complexes that may be used in the gene switches of the invention include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. In one aspect of the invention, the gene switch is an EcR-based gene switch. Examples of such systems include, without limitation, the systems described in U.S. Pat. Nos. 6,258,603, 7,045,315, U.S. Published Patent Application Nos. 2006/0014711, 2007/0161086, and International Published Application No. WO 01/70816. Examples of chimeric ecdysone receptor systems are described in U.S. Pat. No. 7,091,038, U.S. Published Patent Application Nos. 2002/0110861, 2004/0033600, 2004/0096942, 2005/0266457, and 2006/0100416, and International Published Application Nos. WO 01/70816, WO 02/066612, WO 02/066613, WO 02/066614, WO 02/066615, WO 02/29075, and WO 2005/108617, each of which is incorporated by reference in its entirety. An example of a non-steroidal ecdysone agonist-regulated system is the RheoSwitch® Mammalian Inducible Expression System (New England Biolabs, Ipswich, Mass.). In another aspect of the invention, the gene switch is based on heterodimerization of FK506 binding protein (FKBP) with FKBP rapamycin associated protein (FRAP) and is regulated through rapamycin or its non-immunosuppressive analogs. Examples of such systems, include, without limitation, the ARGENT™ Transcriptional Technology (ARIAD Pharmaceuticals, Cambridge, Mass.) and the systems described in U.S. Pat. Nos. 6,015,709, 6,117,680, 6,479,653, 6,187,757, and 6,649,595.

In one embodiment, the gene switch comprises a single transcription factor sequence encoding a ligand-dependent transcription factor complex under the control of a therapeutic switch promoter. The transcription factor sequence may encode a ligand-dependent transcription factor complex that is a naturally occurring or an artificial ligand-dependent transcription factor complex. An artificial transcription factor is one in which the natural sequence of the transcription factor has been altered, e.g., by mutation of the sequence or by the combining of domains from different transcription factors. In one embodiment, the transcription factor comprises a Group H nuclear receptor ligand binding domain. In one embodiment, the Group H nuclear receptor ligand binding domain is from an ecdysone receptor, a ubiquitous receptor (UR), an orphan receptor 1 (OR-1), a steroid hormone nuclear receptor 1 (NER-1), a retinoid X receptor interacting protein-15 (RIP-15), a liver X receptor β (LXRβ), a steroid hormone receptor like protein (RLD-1), a liver X receptor (LXR), a liver X receptor α (LXRα), a farnesoid X receptor (FXR), a receptor interacting protein 14 (RIP-14), or a farnesol receptor (HRR-1). In another embodiment, the Group H nuclear receptor LBD is from an ecdysone receptor.

A. Ecdysone-Based Gene Switch

The EcR and the other Group H nuclear receptors are members of the nuclear receptor superfamily wherein all members are generally characterized by the presence of an amino-terminal transactivation domain (AD, also referred to interchangeably as "TA" or "TD"), optionally fused to a heterodimerization partner (HP) to form a coactivation protein (CAP), a DNA binding domain (DBD), and a LBD fused to the DBD via a hinge region to form a ligand-dependent transcription factor (LTF). As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (sec U.S. Pat. No. 4,981,784 and Evans, *Science* 240:889 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The following polypeptide sequence was reported as a polypeptide sequence of Ecdysone receptor (Ecdysteroid receptor) (20-hydroxy-ecdysone receptor) (20E receptor) (EcRH) (Nuclear receptor subfamily 1 group H member 1) and has the accession number P34021 in Genbank.

```
Ecdysone receptor (878aa) from Drosophila melanogaster (Fruit fly)
                                                              (SEQ ID NO: 5)
  1 mkrrwsnngg fmrlpeesss evtsssnglv lpsgvnmsps sldshdycdq dlwlcgnesg 61 sfggsnghgl sqqqqsvitl amhgcsstlp aqttiiping nangnggstn gqyvpgatnl 121 galangmlng gfngmqqqiq nghglinstt pstpttplhl qqnlggaggg giggmgilhh 181 angtpnglig vvggggvgl gvggggvggl gmqhtprsds vnsissgrdd lspssslngy 241 sanescdakk skkgpaprvq eelclvcgdr asgyhynalt cegckgffrr svtksavycc
```

-continued

```
301 kfgracemdm ymrrkcqecr lkkclavgmr pecvvpenqc amkrrekkaq kekdkmttsp 361 ssqhggngsl asgggqdfvk keildlmtce ppghatipll pdeilakcqa rnipsltynq 421 laviykliwy qdgyeqpsee dlrrimsqpd enesqtdvsf rhiteitilt vglivefakg 481 lpaftkipqe dqitllkacs sevmmlrmar rydhssdsif fannrsytrd sykmagmadn 541 iedllhfcrq mfsmkvdnve yalltaivif sdrpglekaq lveaiqsyyi dtlriyilnr 601 hcgdsmslvf yakllsilte lrtlgnqnae mcfslklknr klpkfleeiw dvhaippsvq 661 shlgitqeen erleraermr asvggaitag idcdsastsa aaaaaqhqpq pqpqpqpssl 721 tqndsqhqtq pqlqpqlppq lqgqlqpqlq pqlqtqlqpq iqpqpqllpv sapvpasvta 781 pgslsaysts seymggsaai gpitpattss itaavtasst tsavpmgngv gvgvgvggnv 841 smyanaqtam almgvalhsh qeqliggvav ksehstta
```

The DBD is characterized by the presence of two cysteine zinc fingers between which are two amino acid motifs, the P-box and the D-box, which confer specificity for response elements. These domains may be either native, modified, or chimeras of different domains of heterologous receptor proteins. The EcR, like a subset of the nuclear receptor family, also possesses less well-defined regions responsible for heterodimerization properties. Because the domains of nuclear receptors are modular in nature, the LBD, DBD, and AD may be interchanged.

In another embodiment, the transcription factor comprises a AD, a DBD that recognizes a response element associated with the therapeutic protein or therapeutic polynucleotide whose expression is to be modulated; and a Group H nuclear receptor LBD. In certain embodiments, the Group H nuclear receptor LBD comprises a substitution mutation.

Figure 2:
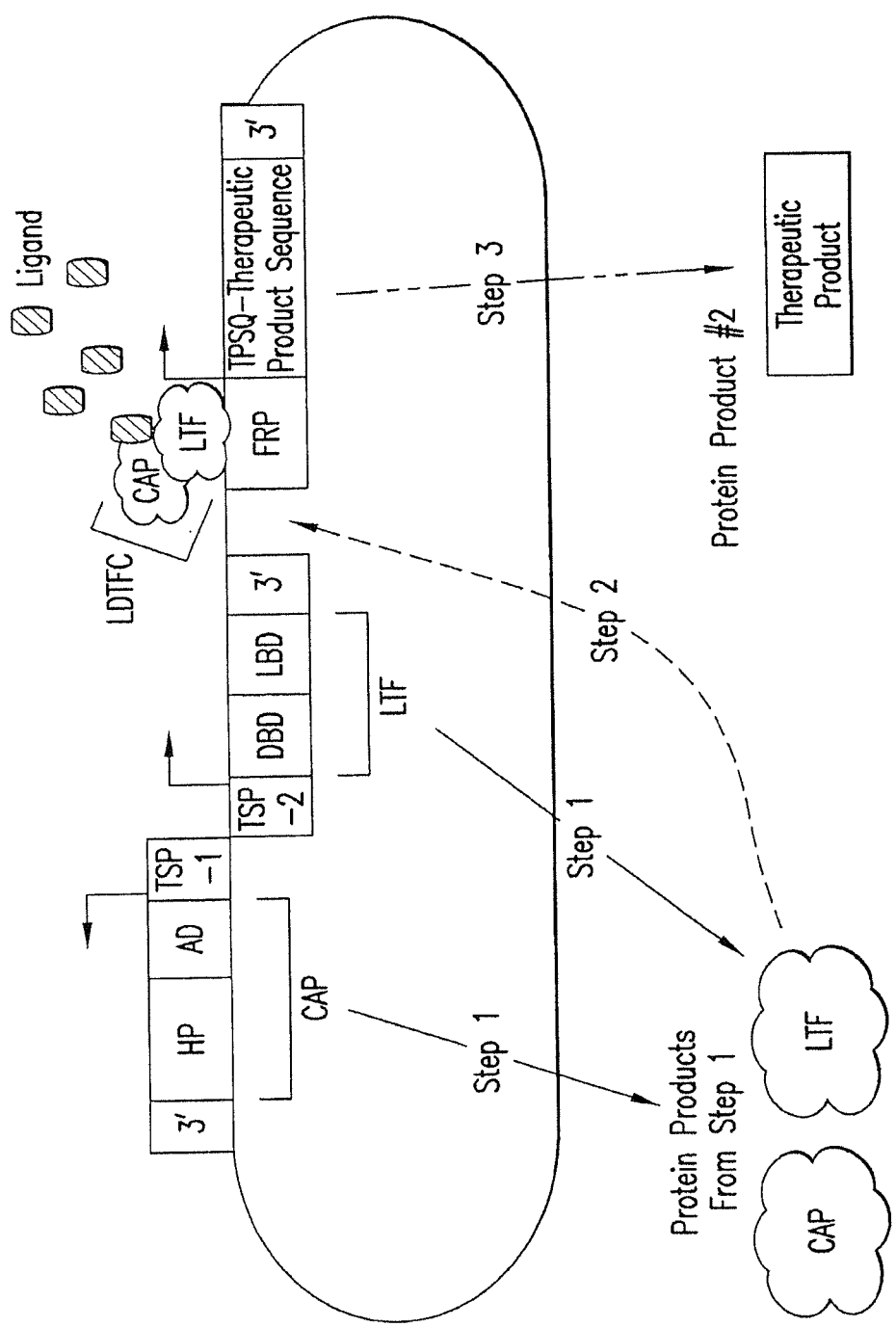
FIG. 2 shows an embodiment of the therapeutic gene switch of the invention in which two transcription factor sequences (CAP and LTF) encoding two separate portions of a ligand-dependent transcription factor complex are under the control of different promoters. The terms AD, HP, CAP, DBD, LBD, LTF, "Therapeutic Product Sequence," "Therapeutic Product," TSP, LDTFC, and FRP are defined in the legend to FIG. 1. "TSP-1" and "TSP-2" represent two different therapeutic switch promoters, each of which is, independently, either a constitutive promoter or a promoter activated under conditions associated with a disease, disorder, or condition. In one embodiment TSP-1 is a constitutive promoter and TSP-2 is a promoter activated under conditions associated with a disease, disorder, or condition. CAP and LTF combine to form a LDTFC which in combination with ligand activates a FRP.

In another embodiment, the gene switch comprises a first transcription factor sequence, e.g., a CAP, under the control of a first therapeutic switch promoter (TSP-1) and a second transcription factor sequence, e.g., a LTF, under the control of a second therapeutic switch promoter (TSP-2), wherein the proteins encoded by said first transcription factor sequence and said second transcription factor sequence interact to form a protein complex (LDTFC), i.e., a "dual switch"- or "two-hybrid"-based gene switch. The first and second TSPs may be the same or different. In this embodiment, the presence of two different TSPs in the gene switch that are required for therapeutic molecule expression enhances the specificity of the therapeutic method (see FIG. 2). FIG. 2 also demonstrates the ability to modify the therapeutic gene switch to treat any disease, disorder, or condition simply by inserting the appropriate TSPs.

In a further embodiment, both the first and the second transcription factor sequence, e.g., a CAP or a LTF, are under the control of a single therapeutic switch promoter (e.g. TSP-1 in FIG. 1). Activation of this promoter will generate both CAP and LTF with a single open reading frame. This can be achieved with the use of a transcriptional linker such as an IRES (internal ribosomal entry site). In this embodiment, both portions of the ligand-dependent transcription factor complex will be synthesized upon activation of TSP-1. TSP-1 can be a constitutive promoter or only activated under conditions associated with the disease, disorder, or condition.

Figure 4:
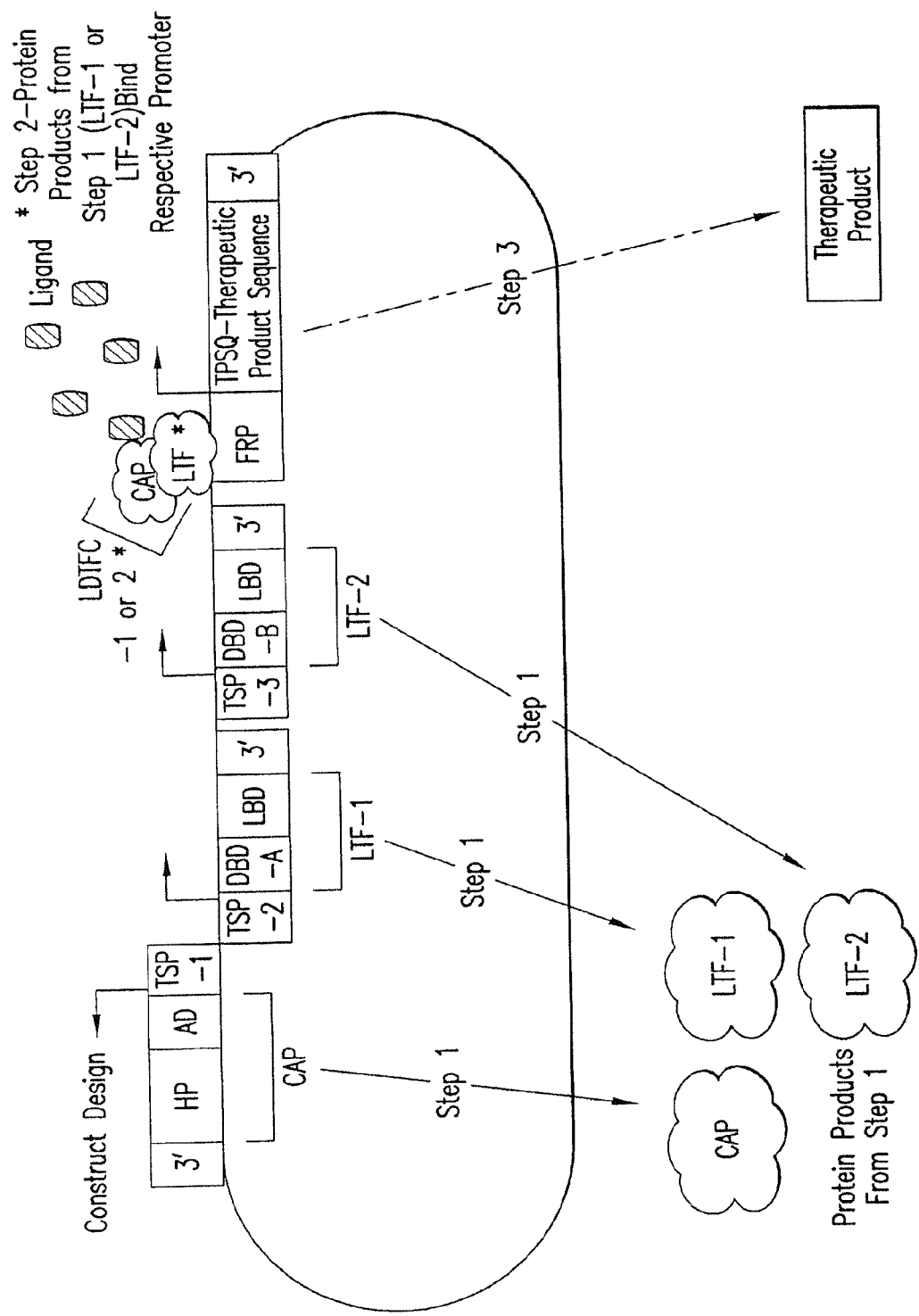
FIG. 4 shows an embodiment of the therapeutic gene switch of the invention in which three transcription factor sequences encoding CAP and two separate LTF portions of a ligand-dependent transcription factor complex are under the control of different promoters. The terms AD, HP, CAP, DBD, LBD, LTF, "Therapeutic Product Sequence," "Therapeutic Product," TSP, LDTFC, and FRP are defined in the legend to FIG. 1. TSP-1, TSP-2, and TSP-3 represent three different therapeutic switch promoters, each of which is, independently, either a constitutive promoter or a promoter activated under conditions associated with a disease, disorder, or condition. In one embodiment, TSP-1 is a constitutive promoter and TSP-2 and TSP-3 are different promoters, each of which is independently activated under conditions associated with a disease, disorder, or condition. Either LTF-1 or LTF-2 may combine with CAP to form LDTFC-1 or LDTFC-2. Either LDTFC-1 or LDTFC-2, in combination with ligand, activates FRP.

In a further embodiment, one transcription factor sequence, e.g. a LTF, is under the control of a therapeutic switch promoter only activated under conditions associated with the disease, disorder, or condition (e.g., TSP-2 or TSP-3 in FIG. 4) and the other transcription factor sequence, e.g., CAP, is under the control of a constitutive therapeutic switch promoter (e.g., TSP-1 in FIG. 4). In this embodiment, one portion of the ligand-dependent transcription factor complex will be constitutively present while the second portion will only be synthesized under conditions associated with the disease, disorder, or condition.

Figure 3:
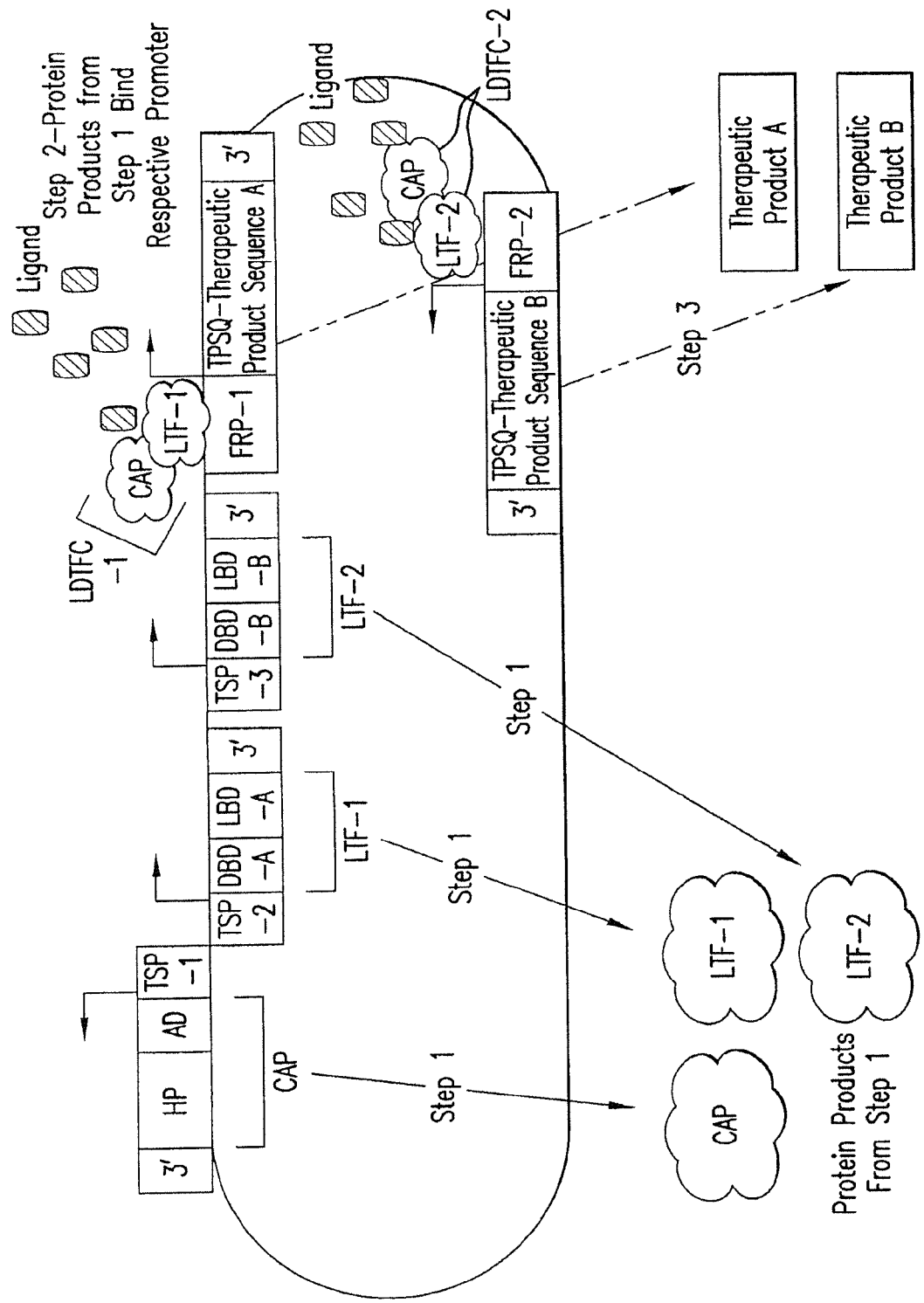
FIG. 3 shows an embodiment of the therapeutic gene switch of the invention in which three transcription factor sequences (CAP, LTF-1, and LTF-2), which may combine to form two separate LDTFCs under the control of different promoters. The terms AD, HP, CAP, DBD, LBD, LTF, "Therapeutic Product Sequence," "Therapeutic Product," TSP, LDTFC, and FRP are defined in the legend to FIG. 1. DBD-A represents a first DNA binding domain which is fused with an LBD to form LTF-1, DBD-B represents a second DNA binding domain which is fused with an LBD to form LTF-2. "Therapeutic Product A" represents a first therapeutic polypeptide or therapeutic polynucleotide; "Therapeutic Product B" represents a second therapeutic polypeptide or therapeutic polynucleotide; and TSP-1, TSP-2, and TSP-3 represent three different therapeutic switch promoters, each of which is, independently, either a constitutive promoter or a promoter activated under conditions associated with a disease, disorder, or condition. In one embodiment, TSP-1 is a constitutive therapeutic switch promoter and TSP-2, and TSP-3 are different therapeutic switch promoters, each of which is independently activated under conditions associated with a disease, disorder, or condition. CAP and LTF-1 combine to form LDTFC-1 which in combination with ligand activates FRP-1. CAP and LTF-2 combine to form LDTFC-2 which in combination with ligand activates FRP-2.

In another embodiment, one transcription factor sequence, e.g., CAP, is under the control of a first TSP (e.g., TSP-1 in FIG. 3) and two or more different second transcription factor sequences, e.g., LTF-1 and LTF-2 are under the control of different TSPs (e.g., TSP-2 and TSP-3 in FIG. 3). In this embodiment, each of the LTFs may have a different DBD that recognizes a different factor-regulated promoter sequence (e.g., DBD-A binds to a response element associated with factor-regulated promoter-1 (FRP-1) and DBD-B binds to a response element associated with factor-regulated promoter-2 (FRP-2). Each of the factor-regulated promoters may be operably linked to a different therapeutic gene. In this manner, multiple treatments may be provided simultaneously.

In one embodiment, the first transcription factor sequence encodes a polypeptide comprising a AD, a DBD that recognizes a response element associated with the therapeutic product sequence whose expression is to be modulated; and a Group H nuclear receptor LBD, and the second transcription factor sequence encodes a transcription factor comprising a nuclear receptor LBD selected from the group consisting of a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see WO 01/70816 A2 and US 2004/0096942 A1). The "partner" nuclear receptor ligand binding domain may further comprise a truncation mutation, a deletion mutation, a substitution mutation, or another modification.

In another embodiment, the gene switch comprises a first transcription factor sequence encoding a first polypeptide comprising a nuclear receptor LBD and a DBD that recognizes a response element associated with the therapeutic product sequence whose expression is to be modulated, and a second transcription factor sequence encoding a second polypeptide comprising an AD and a nuclear receptor LBD, wherein one of the nuclear receptor LBDs is a Group H nuclear receptor LBD. In a preferred embodiment, the first polypeptide is substantially free of an AD and the second polypeptide is substantially free of a DBD. For purposes of the invention, "substantially free" means that the protein in question does not contain a sufficient sequence of the domain in question to provide activation or binding activity.

In another aspect of the invention, the first transcription factor sequence encodes a protein comprising a heterodimerization partner and an AD (a "CAP") and the second transcription factor sequence encodes a protein comprising a DBD and a LBD (a "LTF").

When only one nuclear receptor LBD is a Group H LBD, the other nuclear receptor LBD may be from any other nuclear receptor that forms a dimer with the Group H LBD. For example, when the Group H nuclear receptor LBD is an EcR LBD, the other nuclear receptor LBD "partner" may be from an EcR, a vertebrate RXR, an invertebrate RXR, an ultraspiracle protein (USP), or a chimeric nuclear receptor comprising at least two different nuclear receptor LBD polypeptide fragments selected from the group consisting of a vertebrate RXR, an invertebrate RXR, and a USP (see WO 01/70816 A2, International Patent Application No. PCT/US02/05235 and US 2004/0096942 A1, incorporated herein by reference in their entirety). The "partner" nuclear receptor ligand binding domain may further comprise a truncation mutation, a deletion mutation, a substitution mutation, or another modification.

In one embodiment, the vertebrate RXR LBD is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR LBD comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

The ligand, when combined with the LBD of the nuclear receptor(s), which in turn are bound to the response element of a FRP associated with a therapeutic product sequence, provides external temporal regulation of expression of the therapeutic product sequence. The binding mechanism or the order in which the various components of this invention bind to each other, that is, for example, ligand to LBD, DBD to response element, AD to promoter, etc., is not critical.

In a specific example, binding of the ligand to the LBD of a Group H nuclear receptor and its nuclear receptor LBD partner enables expression of the therapeutic product sequence. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and AD, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563 (1988)) or LexA protein from *Escherichia coli* (see Brent et al., *Cell* 43:729 (1985)), or synthetic response elements specific for targeted interactions with proteins designed, modified, and selected for such specific interactions (see, for example, Kim et al., *Proc. Natl. Acad. Sci. USA*, 94:3616 (1997)) to accommodate hybrid receptors. Another advantage of two-hybrid systems is that they allow choice of a promoter used to drive the gene expression according to a desired end result. Such double control may be particularly important in areas of gene therapy, especially when cytotoxic proteins are produced, because both the timing of expression as well as the cells wherein expression occurs may be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

The DNA binding domain of the first hybrid protein binds, in the presence or absence of a ligand, to the DNA sequence of a response element to initiate or suppress transcription of downstream gene(s) under the regulation of this response element.

The functional LDTFC, e.g., an EcR complex, may also include additional protein(s) such as immunophilins. Additional members of the nuclear receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., *Curr. Opin. Cell Biol.* 9:222 (1997)). Also, protein cofactors generally known as corepressors (also known as repressors, silencers, or silencing mediators) may be required to effectively inhibit transcriptional activation in the absence of ligand. These corepressors may interact with the unliganded EcR to silence the activity at the response element. Current evidence suggests that the binding of ligand changes the conformation of the receptor, which results in release of the corepressor and recruitment of the above described coactivators, thereby abolishing their silencing activity. Examples of corepressors include N-CoR and SMRT (for review, see Horwitz et al., *Mol Endocrinol.* 10:1167 (1996)). These cofactors may either be endogenous within the cell or organism, or may be added exogenously as transgenes to be expressed in either a regulated or unregulated fashion.

B. Rapamycin Based Gene Switch

The present invention further provides a gene switch system which utilizes FK506 binding protein as the ligand-dependent transcription factor complex and rapamycin as the ligand. In one embodiment, the construct encoding the gene switch comprises
 (a) a first polynucleotide encoding a first chimeric protein which binds to rapamycin or an analog thereof and which comprises at least one FK506-binding protein (FKBP) domain and at least one protein domain heterologous thereto, wherein the FKBP domain comprises a peptide sequence selected from:
  (1) a naturally occurring FKBP
  (2) a variant of a naturally occurring FKBP in which up to 10 amino acid residues have been deleted, inserted, or replaced with substitute amino acids, and
  (3) an FKBP encoded by a DNA sequence which selectively hybridizes to a DNA sequence encoding an FKBP of (1) or (2);
 (b) a second polynucleotide encoding a second chimeric protein which forms a complex with both (a) rapamycin or a rapamycin analog and (b) the first chimeric protein, and which comprises at least one FKBP:rapamycin binding (FRB) domain and at least one protein domain heterologous thereto, wherein the FRB domain comprises a peptide sequence selected from:
  (4) a naturally occurring FRB domain,
  (5) a variant of a naturally occurring FRB domain in which up to 10 amino acid residues have been deleted, inserted, or replaced with substitute amino acids, and
  (6) an FRB domain encoded by a DNA sequence which selectively hybridizes to a DNA sequence encoding an FRB of (4) or (5).

In this gene switch system, each of the first polynucleotide and the second polynucleotide are under the control of one or more therapeutic switch promoters as described elsewhere herein. Furthermore, in certain embodiments, at least one protein domain heterologous to the FKBP and/or FRB domains in the first and second chimeric protein may be one or more "action" or "effector" domains. Effector domains may be selected from a wide variety of protein domains including DNA binding domains, transcription activation domains, cellular localization domains and signaling domains (i.e., domains which are capable upon clustering or multimerization, of triggering cell growth, proliferation, differentiation, apoptosis, gene transcription, etc.).

In certain embodiments, one fusion protein contains at least one DNA binding domain (e.g., a GAL4 or ZFHD1 DNA-binding domain) and another fusion protein contains at least one transcription activation domain (e.g., a VP16 or p65 transcription activation domain). Ligand-mediated association of the fusion proteins represents the formation of a transcription factor complex and leads to initiation of transcription of a target gene linked to a DNA sequence recognized by (i.e., capable of binding with) the DNA-binding domain on one of the fusion proteins. Information regarding the gene expression system as well as the ligand is disclosed in U.S. Pat. Nos. 6,187,757 B1, 6,649,595 B1, 6,509,152 B1, 6,479,653 B1, and 6,117,680 B1.

In other embodiments, the present invention provides a gene switch system which comprises polynucleotides encoding two fusion proteins which self-aggregate in the absence of a ligand, wherein (a) the first fusion protein comprises a conditional aggregation domain which binds to a selected ligand and a transcription activation domain, and (b) the second fusion protein comprising a conditional aggregation domain which binds to a selected ligand and a DNA binding domain, and (c) in the absence of ligand, the cells express a gene operably linked to regulatory DNA to which said DNA binding domain binds. Modified cells comprising the gene switch system are expanded in the presence of the ligand in an amount sufficient for repression of the gene. Ligand removal induces expression of the encoded protein that causes cell death. The nucleic acids encoding the two fusion proteins are under the control of at least one conditional promoter. The gene expression system utilizing conditional aggregation domains is disclosed in U.S. Publication No. 2002/0048792.

C. Procaryotic Repressor/Operator Based Gene Switch System

In one embodiment, the present invention provides gene switch system comprising (a) a first polynucleotide coding for a transactivator fusion protein comprising a prokaryotic tetracycline ("tet") repressor and a eucaryotic transcriptional activator protein domain; and (b) a second polynucleotide coding for a therapeutic protein or therapeutic polypeptide, wherein said second polynucleotide is operably linked to a minimal promoter and at least one tet operator sequence. The first polynucleotide coding for a transactivator fusion protein may comprise therapeutic switch promoter as described elsewhere herein. The expression of the lethal protein is up-regulated in the absence of tetracycline. (see, e.g., Gossen et al. (1992) *Proc. Natl. Acad. Sci.* 89: 5547-5551; Gossen et al. (1993) *TIBS* 18: 471-475; Furth et al. (1994) *Proc. Natl. Acad. Sci.* 91: 9302-9306; and Shockett et al. (1995) *Proc. Natl. Acad. Sci.* 92: 6522-6526). The TetO expression system is disclosed in U.S. Pat. No. 5,464,758 B1.

In another embodiment, the gene switch system comprises the lactose ("Lac") repressor-operator systems from the bacterium *Escherichia coli*. The gene switch system of the present invention may also comprise (a) a first polynucleotide coding for a transactivator fusion protein comprising a prokaryotic lac I repressor and a eucaryotic transcriptional activator protein domain; and (b) a second polynucleotide coding for a therapeutic protein or therapeutic polypeptide, wherein said second polynucleotide is operably linked to a therapeutic switch promoter. In the Lac system, a lac operon is inactivated in the absence of lactose, or synthetic analogs such as isopropyl-b-D-thiogalactoside.

Additional gene switch systems include those described in the following: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. No. 7,304,162; U.S. Pat. No. 7,304,161; MX234742; KR10-0563143; AU765306; AU2002-248500; and AU2002-306550.

D. Combination of the Gene Switch Systems

The present invention provides nucleic acid compositions, modified cells, and bioreactors comprising two or more gene switch systems comprising different ligand-dependent transcription factor complexes which are activated by an effective amount of one or more ligands, wherein the two or more gene switch systems comprise a first gene switch and a second gene switch, both of which selectively induce expression of one or more therapeutic polypeptides or therapeutic polynucleotides, upon binding to one or more ligands. Within the scope of the present invention are any numbers of and/or combinations of gene switch systems.

In one embodiment, the present invention provides a nucleic acid composition comprising:

(c) a first gene switch system which comprises:
  i. a first gene expression cassette comprising a polynucleotide encoding a first hybrid polypeptide which comprises:
    1. a transactivation domain, which activates a factor-regulated promoter operably associated with a polynucleotide encoding a therapeutic polypeptide or therapeutic polynucleotide; and
    2. a heterodimer partner domain,
  ii. a second gene expression cassette comprising a polynucleotide encoding a second hybrid polypeptide which comprises:
    1. a DNA-binding domain, which recognizes a factor-regulated promoter operably associated with a polynucleotide encoding a therapeutic polypeptide or therapeutic polynucleotide; and
    2. a ligand binding domain; and
  iii. a third gene expression cassette comprising a polynucleotide encoding a therapeutic polypeptide or therapeutic polynucleotide comprising:
    1. a factor-regulated promoter, which is activated by the transactivation domain of the second hybrid polypeptide; and,
    2. a polynucleotide encoding a therapeutic polypeptide or therapeutic polynucleotide, and b. a second gene expression system which comprises:
  i. a first gene expression cassette comprising a polynucleotide encoding a first hybrid polypeptide which comprises:
    1. a transactivation domain, which activates a factor-regulated promoter operably associated with a polynucleotide encoding a therapeutic polypeptide or therapeutic polynucleotide; and
    2. a heterodimer partner domain,
  ii. a second gene expression cassette comprising a polynucleotide encoding a second hybrid polypeptide which comprises:
    1. a DNA-binding domain, which recognizes a factor-regulated promoter operably associated with a polynucleotide encoding a therapeutic polypeptide or therapeutic polynucleotide; and
    2. a ligand binding domain; and
  iii. a third gene expression cassette comprising a polynucleotide encoding a therapeutic polypeptide or therapeutic polynucleotide comprising:
    1. a factor-regulated promoter, which is activated by the transactivation domain of the second hybrid polypeptide; and,
    2. a polynucleotide encoding a therapeutic polypeptide or therapeutic polynucleotide.

The multiple inducible gene expression systems provide for expression of a given therapeutic polynucleotide or therapeutic polypeptide under conditions associated with different diseases, disorders or conditions, or expression of multiple therapeutic polypeptides or therapeutic polynucleotides either under the same conditions associated with the same disease disorder or condition, or under different conditions associated with different diseases, disorders, or conditions.

In certain embodiments, the combination of two or more gene switch systems may be (1) a dual-switch ecdysone receptor based gene expression system and (2) a single-switch ecdysone receptor based gene switch. In other embodiments, the combination may be (1) an single- or dual-switch ecdysone receptor based gene switch and (2) a rapamycin based gene switch. Alternatively, the combination of gene switch systems may be two identical rapamycin based gene switch systems disclosed above. Any possible combinations of the gene switch systems are within the scope of the invention.

Ligands

The ligand for a ligand-dependent transcription factor complex of the invention binds to the protein complex comprising one or more of the ligand binding domain, the heterodimer partner domain, the DNA binding domain, and the transactivation domain. The choice of ligand to activate the ligand-dependent transcription factor complex depends on the type of the gene switch utilized.

For example, a ligand for the edysone receptor based gene switch may be selected from any suitable ligands. Both naturally occurring ecdysone or ecdyson analogs (e.g., 20-hydroxyecdysone, muristerone A, ponasterone A, ponasterone B, ponasterone C, 26-iodoponasterone A, inokosterone or 26-mesylinokosterone) and non-steroid inducers may be used as a ligand for gene switch of the present invention. U.S. Pat. No. 6,379,945 B1, describes an insect steroid receptor isolated from *Heliothis virescens* ("HEcR") which is capable of acting as a gene switch responsive to both steroid and certain non-steroidal inducers. Non-steroidal inducers have a distinct advantage over steroids, in this and many other systems which are responsive to both steroids and non-steroid inducers, for a number of reasons including, for example: lower manufacturing cost, metabolic stability, absence from insects, plants, or mammals, and environmental acceptability. U.S. Pat. No. 6,379,945 B1 describes the utility of two dibenzoylhydrazines, 1,2-dibenzoyl-1-tert-butyl-hydrazine and tebufenozide (N-(4-ethylbenzoyl)-N'-(3,5-dimethylbenzoyl)-N'-tert-butyl-hydrazine) as ligands for an ecdysone-based gene switch. Also included in the present invention as a ligand are other dibenzoylhydrazines, such as those disclosed in U.S. Pat. No. 5,117,057 B1. Use of tebufenozide as a chemical ligand for the ecdysone receptor from *Drosophila melanogaster* is also disclosed in U.S. Pat. No. 6,147,282. Additional, non-limiting examples of ecdysone ligands are 3,5-di-tert-butyl-4-hydroxy-N-isobutyl-benzamide, 8-O-acetylharpagide, a 1,2-diacyl hydrazine, an N'-substituted-N,N'-disubstituted hydrazine, a dibenzoylalkyl cyanohydrazine, an N-substituted-N-alkyl-N,N-diaroyl hydrazine, an N-substituted-N-acyl-N-alkyl, carbonyl hydrazine or an N-aroyl-N'-alkyl-N'-aroyl hydrazine. (See U.S. Pat. No. 6,723,531).

In one embodiment, the ligand for an ecdysone based gene switch system is a diacylhydrazine ligand or chiral diacylhydrazine ligand. The ligand used in the gene switch system may be compounds of Formula I

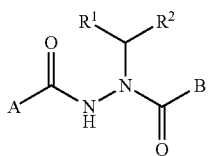

Formula I wherein

A is alkoxy, arylalkyloxy or aryloxy;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

or pharmaceutically acceptable salts, hydrates, crystalline forms or amorphous forms thereof.

In another embodiment, the ligand may be enantiomerically enriched compounds of Formula II

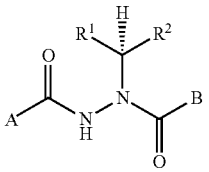

Formula II wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly S;

or pharmaceutically acceptable salts, hydrates, crystalline forms or amorphous forms thereof.

In certain embodiments, the ligand may be enantiomerically enriched compounds of Formula III

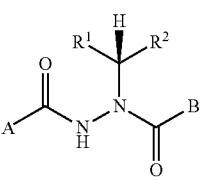

Formula III wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocyclo, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly R;

or pharmaceutically acceptable salts, hydrates, crystalline forms or amorphous forms thereof.

In one embodiment, a ligand may be (R)-3,5-dimethylbenzoic acid N-(1-tert-butyl-butyl)-N'-(2-ethyl-3-methoxybenzoyl)-hydrazide having an enantiomeric excess of at least 95% or a pharmaceutically acceptable salt, hydrate, crystalline form or amorphous form thereof.

The diacylhydrazine ligands of Formula I and chiral diacylhydrazine ligands of Formula II or III, when used with an ecdysone-based gene switch system, provide the means for external temporal regulation of expression of a therapeutic polypeptide or therapeutic polynucleotide of the present invention.

The ligands used in the present invention may form salts. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are used, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The ligands which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, pi crates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The ligands which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Non-limiting examples of the ligands for the inducible gene expression system utilizing the FK506 binding domain are FK506, Cyclosporin A, or Rapamycin. FK506, rapamycin, and their analogs are disclosed in U.S. Pat. Nos. 6,649,595 B2 and 6,187,757. See also U.S. Pat. Nos. 7,276,498 and 7,273,874.

The ligands described herein may be administered alone or as part of a pharmaceutical composition comprising a pharmaceutically acceptable carrier. In one embodiment, the pharmaceutical composition are in the form of solutions, suspensions, tablets, capsules, ointments, elixirs, or injectable compositions.

Pharmaceutical Compositions

Pharmaceutically acceptable carriers include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the is dissolved or suspended in suitable liquids, such as fatty oils, or liquid paraffin, optionally with stabilizers.

Fatty oils may comprise mono-, di- or triglycerides. Mono-, di- and triglycerides include those that are derived from $C_6$, $C_8$, $C_{10}$, $C_{12}$, $C_{14}$, $C_{16}$, $C_{18}$, $C_{20}$ and $C_{22}$ acids. Exemplary diglycerides include, in particular, diolein, dipalmitolein, and mixed caprylin-caprin diglycerides. Triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX 355. Other triglycerides are caprylic-capric acid triglycerides such as known and commercially available under the trade name MYRITOL, including the product MYRITOL 813. Further triglycerides of this class are CAPMUL MCT, CAPTEX 200, CAPTEX 300, CAPTEX 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS). Examples of such compositions are described in U.S. Pat. No. 6,267,985.

In another embodiment, the pharmaceutically acceptable carrier comprises LABRASOL (Gattefosse SA), which is PEG-8 caprylic/capric glycerides. In another embodiment, the pharmaceutically acceptable carrier comprises PL90G, vitamin E TPGS, and Miglyol 812N.

Possible pharmaceutical preparations which can be used rectally include, for example, suppositories, which consist of a combination of one or more of the ligands with a suppository base. Suitable suppository bases are, for example, natural or synthetic triglycerides, or paraffin hydrocarbons. In addition, it is also possible to use gelatin rectal capsules which consist of a combination of the ligand with a base. Possible base materials include, for example, liquid triglycerides, polyethylene glycols, or paraffin hydrocarbons.

Suitable formulations for parenteral administration include aqueous solutions of the ligand in water-soluble form, for example, water-soluble salts and alkaline solutions. In addition, suspensions of the ligand as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions may be formulated as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams may be formulated from a mixture of mineral oil, self-emulsifying beeswax and water in which ligand, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a suspension of the ligand in a vegetable oil such as almond oil with warm soft paraffin and allowing the mixture to cool. A typical example of such an ointment is one which includes about 30% almond oil and about 70% white soft paraffin by weight.

Lotions may be conveniently prepared by preparing a suspension of the ligand in a suitable high molecular weight alcohol such as propylene glycol or polyethylene glycol.

Examples of antioxidants which may be added to the pharmaceutical compositions include BHA and BHT.

In one embodiment, the pharmaceutical composition comprises 30 mg ligand per mL LABRASOL in a solid gelatin capsule. In another embodiment, the capsule contains 1, 2, 3, 4, 5, 6, 7, 8, 9, 10, 15, 20, 25, 30, 35, 40, 45, 50, 55, 60, 65, 70, 75, 80, 85, 90, 95 or 100 mg ligand.

Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression. In one embodiment, 0.1 to 7.5 mg/kg is administered to the subject. In another embodiment, 0.1 to 3 mg/kg is administered to the subject. In another embodiment, 0.1 to 3 mg/kg is administered.

Suitable routes of administering the pharmaceutical compositions include oral, rectal, topical (including dermal, buccal and sublingual), vaginal, parenteral (including subcutaneous, intramuscular, intravenous, intradermal, intrathecal, intra-tumoral and epidural) and by naso-gastric tube. It will be understood by those skilled in the art that the route of administration will depend upon the condition being treated and may vary with factors such as the condition of the recipient. The pharmaceutical compositions may be administered one or more times daily.

Therapeutic Molecules

The therapeutic molecule, e.g., the polynucleotide encoding a therapeutic polypeptide or therapeutic polynucleotide may be any sequence that encodes a polypeptide or polynucleotide that is useful for the treatment, amelioration, or prevention of a disease, disorder, or condition. Therapeutic polypeptides may be any polypeptide known to be effective for treating, ameliorating, or preventing a disease, disorder, or condition. Examples of classes of therapeutic polypeptides that may be used in the invention include, without limitation, cytokines, chemokines, hormones, antibodies, engineered immunoglobulin-like molecules, single chain antibodies, fusion proteins, enzymes, immune co-stimulatory molecules, immunomodulatory molecules, transdominant negative mutants of target proteins, toxins, conditional toxins, antigens, tumor suppressor proteins, growth factors, membrane proteins, vasoactive proteins and peptides, anti-viral proteins or variants thereof. Therapeutic polynucleotides include, without limitation, antisense sequences, small interfering RNAs, ribozymes, and RNA external guide sequences. Therapeutic polynucleotides may be targeted to any transcript associated with a particular disease, disorder, or condition and for which it is desired to decrease or eliminate expression. Numerous genes exhibiting elevated expression during a disease, disorder, or condition are known in the art, including the genes listed in Tables 1-3 above.

The polynucleotide encoding a therapeutic polypeptide or therapeutic polynucleotide is operably linked to or operably associated with a factor-regulated promoter comprising at least one response element that is recognized by the DBD of the ligand-dependent transcription factor complex encoded by the gene switch. In one embodiment, the promoter comprises 1, 2, 3, 4, 5, 6, 7, 8, 9, 10, or more copies of the response element. Promoters comprising the desired response elements may be naturally occurring promoters or artificial promoters created using techniques that are well known in the art, e.g., one or more response elements operably linked to a minimal promoter.

Specific therapeutic polypeptides which may be expressed using a therapeutic gene-switch include, but are not limited to antibodies, including monoclonal antibodies, minimal antibodies, fusion proteins, endogenous protein mimetics, enzymes, hormones, cytokines, chemokines, growth factors, and fragments, variants or derivatives of any such polypeptides. Non-limiting representative therapeutic molecules are described below. All references to these molecules, including patent publications, scientific literature, and polynucleotide and polypeptide sequence accession numbers, are hereby incorporated by reference in their entireties.

Monoclonal Antibodies

Therapeutic gene-switch constructs of the present invention may be used to express therapeutic monoclonal antibodies, or fragments, variants or analogs thereof (collectively "monoclonal antibodies"). Such monoclonal antibodies are useful for treatment of diseases and disorders including, without limitation, cancer, autoimmune diseases (e.g., MS, Crohn's disease, rheumatoid arthritis), cancer, infectious diseases, inflammatory diseases, allergies, heart diseases, and transplantation rejection. Antibodies for use in the present invention include any known therapeutic monoclonal antibodies including, but not limited to those listed below, monoclonal antibodies which bind to the same epitope or target as any known monoclonal antibodies. Monoclonal antibody constructs suitable for expression via therapeutic gene switch constructs include multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), and fragments comprising either a VL or VH domain. ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains.

In certain embodiments, the present invention includes therapeutic gene switch constructs which encode monoclonal antibodies against antigens including, but not limited to CTLA4, CD25, HER-2/neu (ErbB2), CD20, TNFα, EGFR, and VEGF.

Anti-CTLA4 antibodies employable in the present invention, and methods of producing them, are described in the International Application No. PCT/US99/30895, published on Jun. 29, 2000 as WO 00/37504 (e.g., ticilimumab, also known as 11.2.1 and CP-675,206), European Patent Appl. No. EP 1262193 A1, published Apr. 12, 2002, U.S. patent application Ser. No. 09/472,087, now issued as U.S. Pat. No. 6,682,736, U.S. patent application Ser. No. 09/948,939, now published as U.S. Pat. App. Pub. No. 2002/0086014 (e.g., ipilimumab, also known as 10D1 and MDX-010, Medarex, Princeton, N.J.), Anti-CD25 antibodies employable in the present invention include, without limitation, Daclizumab. See, e.g., U.S. Pat. No. 5,530,101. Daclizumab (brand name: Zenapax®, marketed by Roche) is a humanized IgG1 monoclonal antibody directed against CD25 (IL-2 receptor). Functioning as an IL-2 receptor antagonist, it binds with high affinity to the Tac subunit of the high-affinity IL-2 receptor complex. Daclizumab is indicated for the prophylaxis of acute organ rejection in renal transplant patients when used in combination with cyclosporine and corticosteroids.

Anti-HER-2/neu (ErbB2) antibodies employable in the invention include, without limitation, Trastuzumab. See, e.g., U.S. Pat. No. 5,677,171. Trastuzumab (brand name: Herceptin®, marketed by Genentech) is a humanized, monoclonal antibody targeted against the extracellular domain of the c-erbB2/HER2/neu protein, a transmembrane receptor protein (structurally related to the Epidermal Growth Factor receptor) which is overexpressed in certain types of breast cancer. As a mediator of antibody-dependent cellular cytotoxicity, trastuzumab is preferentially toxic to HER2-expressing cancer cells.

Anti-CD20 antibodies employable in the invention include, without limitation rituximab (see, e.g., U.S. Pat. No. 5,736,137). Rituximab (brand name: Rituxan®, marketed by Biogen Idec and Genentech) is a chimeric (murine/human) monoclonal IgG1κ antibody. Rituximab was initially designed and licensed for treatment of non-Hodgkin's lymphoma, and more recently has been licensed for treatment of anti-TNF refractory rheumatoid arthritis.

Anti-TNFα antibodies employable in the invention include, without limitation, Adalimumab (see, e.g., U.S. Pat. No. 7,223,394), and Infliximab (see, e.g., U.S. Pat. No. 7,138,118). Adalimumab, (brand name: Humira®, marketed by Abbott) is a recombinant human IgG1κ monoclonal antibody which binds specifically to TNFα, thereby blocking interaction of TNFα with the p55 and p75 surface TNF receptors. Adalimumab is licensed for use in rheumatoid arthritis, and juvenile idiopathic arthritis. Additional indications for adalimumab include Crohn's disease, plaque psoriasis, psoriatic arthritis, and ankylosing spondylitis. Infliximab (brand name: Remicade, marketed by Centocor) is a recombinant chimeric IgG1κ monoclonal antibody which binds specifically to TNFα, thereby blocking interaction of TNFα with the p55 and p75 surface TNF receptors. Infliximab is licensed for use in Crohn's disease. Additional indications include rheumatoid arthritis, psoriatic arthritis, severe chronic plaque psoriasis, and ankylosing spondylitis.

Anti EGFR (Epidermal Growth Factor Receptor) antibodies employable in the invention include, without limitation, Cetuximab (see, e.g., U.S. Pat. No. 6,217,866). Cetuximab (brand name: Erbitux®, marketed by Imclone and Bristol-Meyers Squibb (North America) and by Merck KGaA (other areas) is a chimeric monoclonal antibody which binds specifically to EGFR. Cetuximab is indicated for metastatic colorectal cancer; and head and neck cancer.

Anti-VEGF antibodies employable in the invention include, without limitation, Bevacizumab (see, e.g., U.S. Pat. No. 6,383,486). Bevacizumab (brand name: Avastin®, marketed by Genentech) is a human monoclonal antibody that inhibits the function of vascular endothelial growth factor (VEGF), thus inhibiting tumor neoangiogenesis. Bevacizumab is indicated for treatment in combination with other anti-cancer chemotherapeutics for the first- and second-line treatment of patients with metastatic colorectal cancer and first-line treatment of patients with recurrent or metastatic non-squamous non-small cell lung cancer (NSCLC).

Fusion Proteins

Therapeutic gene-switch constructs of the present invention may be used to express therapeutic fusion proteins, such as a chimeric TNFα binding protein 2. Tumor necrosis factor binding protein 2 (Enbrel) is produced from the membrane form by proteolytic processing. Enbrel is a recombinant fusion protein consisting of two soluble TNF receptors joined by the Fc fragment of a human IgG1 molecule. It binds to TNF-alpha and blocks TNF-alpha interaction with its receptor. Enbrel is used to treat moderate to severe rheumatoid arthritis. The amino acid sequence coding for Enbrel is available from public database as accession number P20333.

The polynucleotide sequences of Enbrel are available from public databases as accession numbers DD292498 and DD 292499, sequences of which are incorporated by reference herein.

Enzymes

Therapeutic gene-switch constructs of the present invention may be used to express therapeutic enzymes, including tissue plasminogen activator. Plasminogen activator, tissue type isoform 3 preproprotein (tPA) is a secreted scrine protease which converts the proenzyme plasminogen to plasmin, a fibrinolytic enzyme. This enzyme plays a role in cell migration and tissue remodeling. The amino acid sequences coding for tPA are available from public databases as accession numbers NP_127509 and NP_000921 (both human), sequences of which are incorporated by reference herein.

The polynucleotide sequences coding for tPA are available from public databases as accession numbers NM_033011 and NM_000930 (both human), sequences of which are incorporated by reference herein.

Endogenous Protein Mimetics

Therapeutic gene-switch constructs of the present invention may be used to express therapeutic mimetics of endogenous proteins, such as the following.

Alphanate (Coagulation factor III), along with calcium and phospholipid, acts as a cofactor for factor IXa when it converts factor X to the activated form of factor Xa. Alphanate is purified Factor VIII (also know as Antihemophilic factor) and von Willebrand factor. Alphanate is approved for the prevention and control of bleeding in patients with Factor VIII deficiency due to hemophilia A or acquired Factor VIII deficiency. The amino acid sequences coding for factor VIII are available from public databases as accession numbers AAA52485 (human); and AAA37385 (mouse), sequences of which are incorporated by reference herein.

The polynucleotide sequences coding for factor VIII are available from public databases as accession numbers M14113 (human); and L05573 (mouse), sequences of which are incorporated by reference herein.

Aralast (Alpha-1 proteinase inhibitor) amino acid sequences are available from public databases as accession numbers AAB59375 (human alpha 1-antitrypsin); AAC28869 (mouse alpha-1 protease inhibitor); and AAA40788 (rat alpha-1-antitrypsin), sequences of which are incorporated by reference herein.

The polynucleotide sequences coding for alpha-1 proteinase inhibitor are available from public databases as accession numbers K01396 (human); M75721 (mouse); and M32247 (rat), sequences of which are incorporated by reference herein.

Nesiritide (Natrecor®) is a recombinant form of human B-type natriuretic peptide (hBNP) that has been approved for the intravenous treatment of patients with acute decompensated congestive heart failure (CHF) who have dyspnea at rest or with minimal activity. The amino acid sequence coding for Brain natriuretic peptide is available from public database as accession number NP_002512, sequence of which is incorporated by reference herein.

The polynucleotide sequence coding for brain natriuretic peptide is available from public database as accession number NM_002521, sequence of which is incorporated by reference herein.

The amino acid sequence coding for human insulin is available from public database as accession number AAH05255, sequence of which is incorporated by reference herein.

The polynucleotide sequence coding for human insulin is available from public database as accession number BC005255, sequence of which is incorporated by reference herein.

Granulocyte/macrophage colony-stimulating factor (GM-CSF) is a cytokine that functions as a white blood cell growth factor, stimulates stems cells to produce granulocytes (neutrophils, eosinophils, and basophils) and monocytes. The amino acid sequences coding for granulocyte/macrophage colony-stimulating factor (GM-CSF) are available from public databases as accession numbers AAA52122 (human); NP_034099 (mouse); NP_001032749 (rat Csf2ra); and NP_598239 (Csf2rb), sequences of which are incorporated by reference herein.

The polynucleotide sequences coding for GM-CSF are available from public databases as accession numbers M11734 (human); NM_009969 (mouse); NM_001037660 (rat Csf2ra); and NM_133555 (rat Csf2rb), sequences of which are incorporated by reference herein.

The amino acid sequences coding for erythropoietin are available from public databases as accession numbers AAH93628 (human); AAI19266 (mouse); and BAA01593 (rat), sequences of which are incorporated by reference herein.

The polynucleotide sequences coding for erythropoietin are available from public databases as accession numbers BC093628 (human); BC119265 (mouse); and D10763 (rat), sequences of which are incorporated by reference herein.

The amino acid sequences coding for growth hormone are available from public databases as accession numbers AAA98618 (human); NP_032143 (mouse); and NP_001030020 (rat), sequences of which are incorporated by reference herein.

The polynucleotide sequences coding for growth hormone are available from public databases as accession numbers M13438 (human); NM_008117 (mouse); and NM_001034848 (rat), sequences of which are incorporated by reference herein.

Recombinant Protein

Therapeutic gene-switch constructs of the present invention may be used to express therapeutic recombinant proteins, such as the botulinum toxin. The botulinum toxin inhibits neurotransmitter acetylcholine release at nerve terminals, and is available under the name BOTOX for the treatment of strabismus and blepharospasm associated with dystonia and cervical dystonia. BOTOX is also used for the treatment of hemifacial spasm and a number of other neurological disorders characterized by abnormal muscle contraction. The amino acid sequence coding for botulinum neurotoxin type A precursor (BoNT/A) (Bontoxilysin-A) (BOTOX) are available from public databases as accession numbers P10845.

Treatment of Cardiovascular Diseases

The present invention is further directed to a method of treating, ameliorating, or preventing cardiovascular disease, comprising administering to a subject in need of such treatment a therapeutic gene product which ameliorates, prevents, or treats cardiovascular related diseases under control of the switch proteins referenced earlier. Such treatment may be delivered directly to the subject to be treated, or via a bioreactor containing encapsulated or non-encapsulated non-modified or genetically modified cells which secrete one or more therapeutic proteins or therapeutic polypeptides as described elsewhere herein. According to this embodiment, the cell will express one or more therapeutic gene products effective in treating cardiovascular disease when transplanted into a subject, e.g., into an infarct zone of a cardiovascular disease patient. Examples of such therapeutic gene products are described in more detail below. In certain embodiments, a genetically modified cell of the present invention expresses the one or more therapeutic gene products constitutively, i.e., one or more heterologous therapeutic gene products are expressed in the cell continuously. Alternatively, expression of one, two, three, or more heterologous therapeutic gene products expressed by the cell is controlled by a therapeutic gene switch. In certain aspects, bioreactors for treatment, amelioration, or prevention of cardiovascular disease comprise encapsulated cells, e.g., the cells are encapsulated in an alginate-based formulation. Examples and methods of cell encapsulation, to provide, e.g., a physical or immunological barrier from the subject being treated, are described in detail elsewhere herein.

The invention further provides a nucleic acid composition comprising one or more polynucleotides which express therapeutic gene products, e.g., therapeutic polypeptides and/or therapeutic polynucleotides, useful for the treatment, amelioration, or prevention of cardiovascular disease through operable association with a promoter. In certain embodiments a promoter controlling expression of a therapeutic gene product is activated by a ligand-dependent transcription factor complex, where at least a portion of the transcription factor is expressed via operable linkage to one or more therapeutic switch promoter, where the activity of the therapeutic switch promoters is constitutive and/or is modulated under conditions associated with a tissue type or associated with a disease, disorder, or condition. In embodiments relating to the treatment, amelioration, or prevention of cardiovascular disease, a therapeutic switch promoter could be, for example, a heart-specific promoter, or a promoter which is activated during conditions such as congestive heart failure, ischemic heart disease, hypertensive heart disease, coronary artery disease, peripheral vascular disease and ischemic cardiac events, e.g., myocardial infarction, heart attack, heart failure, arrhythmia, myocardial rupture, pericarditis, and cardiogenic shock. Exemplary promoters are presented in Tables 1-3. Additional promoters are described elsewhere herein, for example in Examples 1-8. Additional promoters can also be easily identified via methods described herein.

Examples of therapeutic switch promoters useful for regulated gene switch expression in cardiac cells or under conditions related to cardiac diseases, disorders, or conditions include, without limitation: the S100A6 promoter, which is tissue-specific for cardiac myocytes (Tsoporis et al., *J. Biol. Chem.* (2008) (Epub ahead of print; PMID: 18753141)); Atrial Naturetic Factor (ANF) promoter, Alpha-myosin heavy chain promoter, c-fos promoter, BNP promoter, or alpha actins promoter, all of which are tissue-specific for cardiomyocytes (Nelson et al., *J. Mol. Cell. Cardiol.* 39(3):479 (2005)); Erythropoietin promoter, which is activated in myocardium under ischemic conditions (Su et al., *Proc. Natl. Acad. Sci. U.S.A.* 99(14):9480 (2002)); AlphaB-Crystallin (CRYAB) promoter including, for example, a BRG1-response element, which is tissue-specific for vertebrate eye lens (Duncan B. and Zhao K. *DNA Cell. Biol.* 26(10):745 (2007)); AlphaB-Crystallin (CRYAB) promoter with cis-acting regulatory elements, e.g., alpha BE-1, alpha BE-2, alpha BE-3, and MRF, which is tissue-specific for skeletal muscle (Gopal-Srivastava et al., *J. Mol. Cell Biol.* 15(12):7081 (1995)); NCX1 promoter, which is tissue-specific for cardiomyocytes (Xu et al., *J. Biol. Chem.* 281(45):34430 (2006)); Beta myosin heavy chain promoter, which is tissue-specific for cardiomyocytes (Nelson et al., *J. Mol. Cell Cardiol.* 39(3):479 (2005), Ross et al., *Development.* 122(6):1799 (1996), and Lee et al., *Mol. Cell. Biol.* 14(2):1220 (1994)), Myosin light chain-2 ventricular promoter including an HF-1a/HF-1b/MEF-2 combinatorial element (Ross et al., *Development.* 122(6):1799 (1996)) or an HF-1a/HF-1b element and an HF-3 regulatory element, (Lee et al., *Mol. Cell. Biol.* 14(2):1220 (1994)), which is tissue-specific for cardiac ventricles; Myosin light chain promoters, e.g., MLC1F and MLC3F, which are differentially activated during skeletal muscle development (Kelly et al., *J. Cell. Biol.* 129(2):383 (1995)); Myosin light chain 2v (MLC-2v) promoter, which is tissue-specific for cardiac muscles (Su et al., *Proc. Natl. Acad. Sci. USA.* 101(46): 16280 (2004)); and Cardiac troponin I (TnIc) promoter, which is tissue-specific and developmental stage-specific in cardiac muscles (Bhaysar et al., *J. Mol. Cell Cardiol.* 32(1): 95 (2000)).

The invention further provides one or more vectors comprising the aforementioned nucleic acid composition, and one or more genetically modified cells comprising such vectors. Such cells may be allogeneic, autologous, or xenogeneic relative to the subject to be treated. The invention further provides one or more encapsulation methodologies for the treatment, amelioration, or prevention of cardiovascular disease, comprising the aforementioned modified cells, where the cells have been treated in such a way as to be protected from a subject's immune system upon introduction into the subject. Such treatments include, without limitation, provision of a conformal coating, microencapsulation, or macroencapsulation.

Cardiovascular diseases include, but are not limited to congestive heart failure, ischemic heart disease, hypertensive heart disease, coronary artery disease, peripheral vascular disease and ischemic cardiac events, e.g., myocardial infarction, heart attack, heart failure, arrhythmia, myocardial rupture, pericarditis, and cardiogenic shock. Causes of such events include, without limitation, thrombosis, embolism, atherosclerosis, and stenosis. Populations predisposed include, without limitation, smokers, persons with diabetes, hypertension, or dyslipidemia.

Suitable therapeutic molecules for the treatment, amelioration, or prevention of cardiovascular disease include, without limitation, pro-angiogenic factors, cardioprotective factors, and cardioregenerative factors.

The therapeutic molecules useful for the present invention to prevent, treat, or ameliorate cardiovascular diseases include, without limitation, the atrial natriuretic factor (ANF), carperitide, brain Natriuretic factor (BNP), nesiritide, relaxin, vascular endothelial growth factor (VEGF165), hepatocyte growth factor (HGF), Angiopoietin-1 (Ang-1), basic fibroblast growth factor (bFGF), fibroblast growth factor 4 (FGF-4), insulin-like growth factor 1 (IGF-1), hypoxia-inducible factor1-alpha (HIF1-alpha), erythropoietin, tissue plasminogen activator (tPA), growth hormone, Stromal-Derived Factor-1 (SDF-1), sarco-endoplasmic reticulum Ca2+-ATPase (SERCA2a), adenylycyclase type VI (AC6), S100A1, parvalbumin, phosphatase inhibitor 2, and phosphatase inhibitor 1. These molecules are known to exert the effects on cardiac tissues through various mechanisms, e.g., hemodynamics, angiogenesis, cardiac regeneration, anti-fibrosis, and/or cardiac repair. These therapeutic molecules may provide multiple therapeutic actions and may be used in combination with each other or other molecules that are known in public.

In one embodiment, pro-angiogenic gene therapy clinical trials for the treatment, amelioration, or prevention of cardiovascular disease are currently being performed using therapeutic proteins useful for promoting neo-vascularization. These include, without limitation, pro-angiogenic factors such as VEGF, HGF, bFGF, Ang-1, FGF-4, TGF-1, and HIF1-alpha as well as fragments, variants and derivatives thereof. Identification of suitable molecules for promoting neo-vascularization are well within the capabilities of a person of ordinary skill in the art Such pro-angiogenic factors stimulate neo-angiogenesis to supply oxygen and nutrients within the infarct zone. This will limit infarct zone expansion and sustain any cardiac progenitors that migrate into the infarct.

Indeed, pro-angionic factor VEGF165 is known to induce neovascularization (Benest et al., *Microcirculation.* 13(6): 423 (2006); Riley et al., *Biomaterials.* 27(35):5935 (2006); Shyu et al., *Life Sci.* 73(5):563 (2003); Arsic et al., *Mol Ther.* 7(4):450 (2003); Ye et al., *J. Heart Lung Transplant.* 24(9): 1393 (2005); Lubiatowski et al., *Plast. Reconstr. Surg.* 110(1):149 (2002) (Erratum in: *Plast. Reconstr. Surg.* 111 (3):1380 (2003)); Kim et al., *Ann. Thorac. Surg.* 83(2):640 (2007) (Comment in: *Ann. Thorac. Surg.* 83(2):646 (2007)); Thurston G., *J. Anat.* 200(6):575 (2002); Ryu et al., *Mol. Ther.* 13(4):705 (2006); Chac et al., *Arterioscler. Thromb. Vasc. Biol.* 20(12):2573 (2000); and Chen et al., *Acta. Pharmacol. Sin.* 28(4):493 (2007)). The shortcomings of early clinical trials in therapeutic neovascularization have been partly attributed to the single administration of high doses of growth factor. See Zacchigna et al., *Hum. Gene Ther.* 18(6):515 (2007) and Yla-Herttuala et al., *J Am Coll Cardiol.* 49(10):1015 (2007) (Comment in: *J Am Coll Cardiol.* 50(2):186 (2007)). Since then, preclinical data on VEGF expression and release has suggested that prolonged exposure results in the formation of stable vessels, whereas short-term delivery merely produces leaky vessels that regress easily. High local concentrations caused, for example, by VEGF-A-producing myoblasts results in leaky and abnormal vessels, whereas moderate amounts of the growth factor initiated the growth of healthy vessels. See Arsic et al., *Mol Ther.* 7(4):450 (2003); Benest et al., *Microcirculation.* 13(6):423 (2006); Yamauchi et al., *J Gene Med.* 5(11):994 (2003); Jiang et al., *Acta Cardiol.* 61(2):145 (2006); Ozawa et al., *J Clin Invest.* 113(4):516 (2004). Additionally, the combination of VEGF (initiation of angiogenesis) and Ang-1 (maturation of vessels) has been shown to result in more stable vascular growth. See Thurston G., *J Anat.* 200(6):575 (2002); Jiang et al., *Acta Cardiol.* 61(2): 145 (2006); Benest et al., *Microcirculation.* 13(6):423

(2006); Zhou et al., *Gene Ther.* 12(3):196 (2005) (Erratum in: *Gene Ther.* 12(6):552 (2005); Liu et al., *Scand Cardiovasc J.* 41(2):95 (2007); Shyu et al., *Life Sci.* 73(5):563 (2003); Yamauchi et al., *J Gene Med.* 5(11):994 (2003); Arsic et al., *Mol Ther.* 7(4):450 (2003); Ye et al., *J Heart Lung Transplant.* 24(9):1393 (2005); Ye et al., *Eur J Heart Fail.* 9(1):15 (2007); Lubiatowski et al., *Plast Reconstr Surg.* 110(1):149 (2002) (Erratum in: *Plast Reconstr Surg.* 111(3):1380 (2003)); Ryu et al., *Mol Ther.* 13(4):705 (2006); Chen et al., *Eur J Pharmacol.* 568(1-3):222 (2007); Chae et al., *Arterioscler Thromb Vasc Biol.* 20(12):2573 (2000); and Chen et al., *Acta Pharmacol Sin.* 28(4):493 (2007).

Therefore, pro-angiogenic factor VEGF165 is known to prevent, treat or ameliorate various cardiovascular disease (Yamauchi et al., *J Gene Med.* 5(11):994 (2003) and Xu et al., *Cytotherapy.* 6(3):204 (2004) (Comment in: *Cytotherapy.* 7(1):74 (2005))) including, without limitation, myocardial infarction (Zhou et al., *Gene Ther.* 12(3):196 (2005) (Erratum in: *Gene Ther.* 12(6):552 (2005); Ye et al., *Circulation.* 116(11 Suppl):I113 (2007); Liu et al., *Scand Cardiovasc J.* 41(2):95 (2007); Ye et al., *Eur. J. Heart Fail.* 7(6):945 (2005); Zhang et al., *Cell Transplant.* 14(10):787 (2005); Bonaros et al., *Interact. Cardiovasc. Thorac. Surg.* 7(2):249 (2008); Shyu et al., *J. Biomed. Sci.* 13(1):47 (2006); Ventura et al., *J Biol Chem.* 282(19):14243 (2007); Sugimoto et al., *Jpn. J. Thorac. Cardiovasc. Surg.* 51(5):192 (2003); Yau et al., *Ann. Thorac. Surg.* 83(3):1110 (2007) (Comment in: *Ann Thorac Surg.* 83(3):1119 (2007)); Rong et al., *Chin. Med. J. (Engl).* 121(4):347 (2008); Yang et al., *Cardiology.* 107(1):17 (2007); Wang et al., *J. Mol. Cell Cardiol.* 40(5):736 (2006); Chen et al., *Eur J Clin Invest.* 35(11):677 (2005); Suzuki et al., *Circulation.* 104(12 Suppl 1):1207 (2001); Ye et al., *Ann. Acad. Med. Singapore.* 32(5 Suppl):S21 (2003); and Haider et al., *J Mol Med.* 82(8):539 (2004) (Comment in: *J Mol Med.* 82(8):485 (2004))) or ischemia or reperfusion injury (Becker et al., *Int J Cardiol.* 113(3):348 (2006); Gao et al., *Can. J. Cardiol.* 23(11):891 (2007); Ye et al. *Eur J Heart Fail.* 9(1):15 (2007); Chen et al., *Eur. J. Pharmacol.* 568(1-3):222 (2007); and Jiang et al., *Acta Cardiol.* 61(2):145 (2006)).

Furthermore, another pro-angiogenic factor HGF (human nucleotide sequence accession No.: M29145, human amino acid sequence accession No.: NP_000592.3), which provides multipotent actions, are useful for the present invention. HGF, mediated by c-Met receptor, provides a pro-angiogenic effect through mitogenic activity on endothelial cells, a cardioprotective anti-apoptotic effect on cardiomyocytes, an anti-fibrotic effect through suppression of TGF-beta1 signaling, and is a type I collagen regenerative factor through mobilization of CD117(+)/c-Met(+) stem cells into ischemic myocardium. See Li et al., *Chin Med J (Engl)* 121(4):336 (2008); Guo et al., *Arch. Med. Res.* 39(2):179 (2008); Ventura et al., *J. Biol. Chem.* 282(19):14243 (2007); Yang et al., *Gene Ther.* 13(22):1564 (2006); Tambara et al., *Circulation.* 112(9 Suppl):I129 (2005); Zhang et al., *Tissue Eng. Part A.* 14(6):1025 (2008); and Sakaguchi et al., *Ann. Thorac. Surg.* 79(5):1627 (2005).

Similarly, bFGF (amino acid sequence accession no. NP_001997) has been shown to have the added effect of cardioprotection by promoting angiogenesis, neovascularization, and tissue regeneration. (Doi et al., *Heart Vessels.* 22(2):104 (2007); Fujita et al., *J. Surg. Res.* 126(1):27 (2005); Fujita et al., *Wound Repair Regen.* 15(1):58 (2007); Hosaka et al., *Circulation.* 110(21):3322 (2004); Iwakura et al., *Heart Vessels.* 18(2):93 (2003); Lai et al., *Tissue Eng.* 12(9):2499 (2006); Nakajima et al., *J. Artif. Organs.* 7(2):58 (2004); Perets et al., *J. Biomed. Mater. Res. A.* 65(4):489 (2003); Pike et al., *Biomaterials.* 27(30):5242 (2006); Sakakibara et al., *J Thorac Cardiovasc Surg.* 124(1):50 (2002); Sakakibara et al., *Eur J Cardiothorac Surg.* 24(1): 105 (2003); Shao et al., *Circ J.* 70(4):471 (2006); Tabata Y. and Ikada Y., *Biomaterials.* 20(22):2169 (1999); Yamamoto et al., *Artif. Organs.* 27(2):181 (2003); Yamamoto et al., *Jpn. Circ. J.* 65(5):439 (2001); Yang et al., *Ophthalmic Res.* 32(1):19 (2000); and Zhu et al., *Chin. Med. Sci. J.* 15(4):210 (2000)) In certain embodiments, bFGF may be used to prevent, treat, or ameliorate osteoarthritis. See Inoue et al., *Arthritis Rheum.* 54(1):264 (2006);

IGF-1 (human amino acid sequence accession No.: NP_001104753.1) is also known to exert multipotent function of protecting cardiomyocytes from apoptosis and enhancing neovascularization (Su et al., *Am J Physiol Heart Circ Physiol.* 284(4):H1429 (2003); Chao et al., *J. Gene Med.* (4):277 (2003); Rabinovsky E. D. and Draghia-Akli R., *Mol Ther.* 9(1):46 (2004); and Barton et al., *Circulation.* 112(9 Suppl):146 (2005)) and may be used in the present invention.

In addition, FGF-4 may be used as a therapeutic molecule to prevent, treat, or ameliorate chronic ischemic heart disease by inducing myocardial angio-/arteriogenesis. (Kapur N. K. and Rade J. J., *Trends Cardiovasc. Med.* 18(4):133 (2008); Henry et al., *J. Am. Coll. Cardiol.* 50(11):1038 (2007); Grines et al., *Am. J. Cardiol.* 92(9B):24N (2003); (no author listed) *BioDrugs.* 16(1):75 (2002)).

Furthermore, HIF1-alpha gene therapy, e.g., HIF1-alpha (aa 1-390)/VP16 (aa 413-490), is known to treat, prevent, or ameliorate ischemic disease by enhancing BNP gene expression (Rajagopalan et al., *Circulation.* 115(10):1234 (2007) (Comment in: *Circulation.* 115(10):1180 (2007)); Wilhide M. E. and Jones W. K., *Mol Pharmacol.* 69(6):1773 (2006) (Comment on: *Mol Pharmacol.* 69(6):1953 (2006)); Luo et al., *Mol Pharmacol.* 69(6):1953 (2006) (Comment in: *Mol. Pharmacol.* 69(6):1773 (2006)) or improve angiogenesis in myocardial infarction (Shyu et al., *Cardiovasc Res.* 54(3): 576 (2002); Vincent et al., *Circulation.* 102(18):2255 (2000)).

In certain embodiments, cardioprotective factors for the treatment, amelioration, or prevention of cardiovascular diseases are provided, either alone, or in combination with angiogenic factors and/or cardioregenerative factors. Cardioprotective molecules provide anti-fibrotic, anti-apoptotic signal to resident cardiomyocytes, limiting infact zone size and supplying survival signals to migrating stem cells. In certain embodiments, the cardioprotective factor is erythropoietin alfa (EPO) (human amino acid accession no. CAA26095.1), e.g., human erythropoietin alfa or EPO-GEN®, manufactured by Amgen. Erythropoietin has been shown to have cardioprotective, angiogenic and neuroprotective effects (Ben-Dor et al., *Cardiovasc Drugs Ther.* 21(5):339 (2007); Lin et al., *Circ J.* 71(1):132 (2007); Prunier et al., *Am J Physiol Heart Circ Physiol.* 292(1):H522 (2007)).

Other cardioprotective hormones demonstrated to be protective against experimental myocardial ischemia-reperfusion injury include, without limitation, adrenomedullin, bradykinin, relaxin, ANF, also known as atrial natriuretic peptide (ANP, human nucleotide sequence accession No.: NM_006172, human amino acid sequence accession No.: NP_006163), BNP, also known as B-type natriuretic peptide or GC-B (human amino acid sequence accession No.: NP_002512.1; human nucleotide sequence accession No.: M25296), C-type natriuretic peptide (CNP), carperitide, tissue plasminogen activator (tPA) and urocortins. Many have also been shown to reduce fibrosis or mediate hemodynamics. Nesiritide (brand name Natrecor®, marketed by Scios), a recombinant form of human B-type natriuretic peptide, ANF, and Carperitide are used in the treatment, amelioration, or prevention of acute decompensated heart failure, and may also be used in the present invention (Burnett J. C. Jr., *J. Cardiol.* 48(5):235 (2006)).

Relaxin (human amino acid accession no. NP_604390.1), known for its effects on the female reproductive system, is also a potent vasodilator of the systemic and coronary circulation by a mechanism of action involving nitric oxide, and influences cardiac beating rate. Relaxin is also known as a cardiovascular drug that may prevent, treat, or ameliorate ischemic heart disease (acute and chronic myocardial infarction), cardiac fibrosis, and obliterative peripheral arterial disease and restore cardiac function in cell transplantation. (Nistri et al., *Pharmacol. Res.* 57(1):43 (2008); Samuel et al., *Adv. Exp. Med. Biol.* 612:88 (2007); Du X J., *J. Cell Mol. Med.* 11(5):1101 (2007); Formigli et al., *J. Cell Mol. Med.* 11(5):1087 (2007); Bathgate et al., *Mol. Cell Endocrinol.* 280(1-2):30 (2008); Nistri et al., *Cardiovasc. Hematol. Agents Med. Chem.* 5(2):101 (2007); Moore et al., *Endocrinology.* 148(4):1582 (2007); Lekgabe et al., *Endocrinology.* 147(12):5575 (2006); Samuel et al., *Pharmacol. Ther.* 112(2):529 (2006); Zhang et al., *Peptides.* 26(9):1632 (2005); Perna et al., *Ann. N.Y. Acad. Sci.* 1041:431 (2005); Perna et al., *FASEB J.* 19(11):1525 (2005); Samuel et al., *Endocrinology.* 145(9):4125 (2004); Masini et al., *Br J Pharmacol.* 137(3):337 (2002); Ndisang et al., *Inflamm. Res.* 50 Suppl. 2:S122-3 (2001); Dschietzig et al., *FASEB. J.* 15(12):2187 (2001); Bani et al., *Am J Pathol.* 152(5):1367 (1998); and Masini et al., *Inflamm. Res.* 45 Suppl 1:S27 (1996))

In certain embodiments, therapeutic proteins of the invention useful for the treatment, amelioration, or prevention of cardiovascular diseases have multiple therapeutic benefits. For example, in the early phase after myocardial infarction, elevated (SDF-1, human nucleotide sequence accession No.: U16752, human amino acid sequence accession No.: NP_954637) levels have been reported in the infarct zone. This provides the required stimulus for mobilization of stem cells from BM niches to the damaged site as part of a natural repair process. SDF-1 recruits bone marrow haematopoietic stem cells (primarily $CD31^+$, $C-kit^+$ and $CD34^+$ cells) to the infarcted heart resulting in both neoangiogenic and cardioprotective activities. Furthermore, SDF-1 activates the cell-survival factor protein kinase B (PKB/Akt) via the G protein-coupled receptor CXCR4 regenerative factors. See also U.S. Patent Appl. Publ. No. 20060111290 A1; Elmadbouh et al., *J Mol Cell Cardiol.* 42(4):792 (2007); Bonaros et al., *Interact Cardiovasc Thorac Surg.* 7(2):249 (2008); Zhang et al., *J Mol Cell Cardiol.* 44(2):281 (2008); Ma et al., *Basic Res Cardiol.* 100(3):217 (2005); and Zhang et al., *Tissue Eng.* 13(8):2063 (2007).

In addition, tPA (human amino acid accession no. 28274638), e.g., human tissue Plasminogen Activator or Retavase®, manufactured by PDL BioPharma, Inc. is known to prevent, treat, or ameliorate post cardiac transplant complications by inhibiting graft atherosclerosis (Scholl et al., *J Heart Lung Transplant.* 20(3):322 (2001); Dunn et al., *Circulation.* 93(7):1439 (1996) (Comment in: *Circulation.* 93(7):1319 (1996)); and Gong et al., *Gene Ther.* 14(21): 1537 (2007)). Furthermore, the growth hormone is also known to prevent, treat, or ameliorate cardiovascular disease and may be used in the present invention (Isgaard J. and Bergh C. H., *BioDrugs.* 12(4):245 (1999); Fazio et al., *J. Clin. Endocrinol. Metab.* 92(11):4218 (2007); Climent et al., *Curr Med Chem.* 14(13):1399 (2007); Perez-Berbel et al., *Int J Cardiol.* 124(3):393 (2008) (Comment on: *Int J Cardiol.* 110(3):313 (2006)); and Le Corvoisier et al., *J Clin Endocrinol Metab.* 92(1):180 (2007)) by promoting angiogenesis and attenuate apoptosis (Rong et al., *Chin Med J (Engl).* 121(4):347 (2008)).

In other embodiments, the therapeutic molecules that restore cardiac function are included in the present invention. Cardiac repair molecules include, but are not limited to, SERCA2a, AC6, S100A1, parvalbumin, phosphatase inhibitor 2 and phosphatase inhibitor 1. For example, SERCA2a is known to improve cardiac contractility in vivo and in vitro and cardiac function in heart failure (Asahi et al., *Proc Natl Acad Sci USA.* 101(25):9199 (2004); Cavagna et al., *J Physiol.* 528 Pt 1:53 (2000); Chaudhri et al., *Mol Cell Biochem.* 251(1-2):103 (2003); Davia et al., *J Mol Cell Cardiol.* 33(5):1005 (2001); del Monte et al., *Circulation.* 100(23):2308 (1999) (Comment in: *Circulation.* 100(23): 2303 (1999); del Monte et al., *Circulation.* 104(12):1424 (2001); Hajjar et al., *Circ Res.* 81(2):145 (1997) (Comment in: *Circ Res.* 88(4):373 (2001) and *Circulation.* 101(7):790 (2000)); Kawase et al., *J Am Coll Cardiol.* 51(11):1112 (2008); Maier et al., *Cardiovasc Res.* 67(4):636 (2005) (Comment in: *Cardiovasc Res.* 67(4):581 (2005); Meyer M. and Dillmann W. H., *Cardiovasc Res.* 37(2):360 (1998); Miyamoto et al., *Proc Natl Acad Sci USA.* 97(2):793 (2000); Muller et al., *Cardiovasc Res.* 59(2):380 (2003); Sakata et al., *J Mol Cell Cardiol.* 42(4):852 (2007); Sakata et al., *Am J Physiol Heart Circ Physiol.* 292(2):H1204 (2007); Schmidt et al., *Circulation.* 101(7):790 (2000) (Comment in: *Circulation.* 101(7):738 (2000), *Circ Res.* 81(2):145 (1997), *Circ Res.* 83(9):889 (1998), and *Circulation.* 95(2):423 (1997)) Suarez et al., *Am J Physiol Heart Circ Physiol.* 287(5):H2164 (2004); Terracciano et al., *Cell Calcium.* 31(6):299 (2002); Trost et al., *Diabetes.* 51(4):1166 (2002); and Vetter et al., *FASEB J.* 16(12):1657 (2002))

Furthermore, AC6 is known to restore affinity of SERCA2a to calcium and maximum velocity of cardiac calcium uptake by sarcoplasmic reticulum in cardiomyopathy (Gao et al., *Proc Natl Acad Sci USA.* 95(3):1038 (1998); Roth et al., *Circulation.* 99(24):3099 (1999); Lai et al., *Circulation.* 102(19):2396 (2000); Roth et al., *Circulation.* 105(16):1989 (2002) (Comment in: *Circulation.* 105(16): 1876 (2002)); Gao et al., *Cardiovasc Res.* 56(2):197 (2002) (Comment in: *Cardiovasc Res.* 56(2):181 (2002)); Roth et al., *Basic Res Cardiol.* 98(6):380 (2003); Roth et al., *Am J Physiol Heart Circ Physiol.* 287(1):H172 (2004); Gao et al., *J Biol Chem.* 279(37):38797 (2004); Tang et al., *Am J Physiol Heart Circ Physiol.* 287(5):H1906 (2004); Lai et al., *Circulation.* 110(3):330 (2004) (Comment in: *Circulation.* 110(3):242 (2004); Roth et al., *Hum Gene Ther.* 15(10):989 (2004); Timofeyev et al., *J Mol Cell Cardiol.* 41(1):170 (2006) (Comment in: *J Mol Cell Cardiol.* 41(3):424 (2006); Takahashi et al., *Circulation.* 114(5):388 (2006) (Erratum in: *Circulation.* 114(11):e497 (2006); Comment in: *Circulation.* 114(5):365 (2006); Sastry et al., *J Am Coll Cardiol.* 48(3): 559 (2006); Rebolledo et al., *Hum Gene Ther.* 17(10):1043 (2006); Hammond H. K., *Ann N Y Acad Sci.* 1080:426 (2006); Phan et al., *Trends Cardiovasc Med.* 17(7):215 (2007); Tang et al., *Circulation.* 117(1):61 (2008); and Lai et al., *J Am Coll Cardiol.* 51(15):1490 (2008)).

In certain embodiments, the Ca2+-binding protein S100A1 may restore cardiac function and therefore be used in the present invention. S100A1 is known to increase myocardial contraction in vivo and reduce propensity toward heart failure after myocardial infarction. (Most et al., *J Clin Invest.* 114(11):1550 (2004); Most et al., *Circulation.* 114(12):1258 (2006); Pleger et al., *Mol Ther.* 12(6):1120 (2005); Pleger et al., *Eur J Med Res.* 11(10):418 (2006);

Remppis et al., *J Gene Med.* 6(4):387 (2004); Most et al., *Am J Physiol Regul Integr Comp Physiol.* 293(2):R568 (2007); Remppis et al., *Basic Res Cardiol.* 97 Suppl 1:156 (2002); Pleger et al., *Circulation.* 115(19):2506 (2007); and Most et al., *J Biol Chem.* 278(36):33809 (2003)). Other non-limiting examples of the therapeutic molecules that improve or restore cardiac function are: paralbumin (Hirsch et al., *Am J Physiol Heart Circ Physiol.* 286(6):H2314 (2004); Michele et al., *Mol Ther.* 10(2):399 (2004); and Sakata et al., *J Mol Cell Cardiol.* 42(4):852 (2007)), phosphatase inhibitor 2 (Yamada et al., *FASEB J.* 20(8):1197 (2006); Gupta et al., *Mol Cell Biochem.* 269(1-2):49 (2005); and Kirchhefer et al., *Cardiovasc Res.* 68(1):98 (2005)) and phosphatase inhibitor 1 (Gupta et al., *Mol Cell Biochem.* 269(1-2):49 (2005) and Gupta et al., *Am J Physiol Heart Circ Physiol.* 285(6):H2373 (2003))

Additional therapeutic molecules that may be useful for the present invention to prevent, treat, or ameliorate a disease or disorder include, but are not limited to, monoclonal antibodies (e.g., HERCEPTIN®-HC, HERCEPTIN®-LC, TICILIMUMAB®-HC, TICILIMUMAB®-LC, ZENAPAX®-HC, ZENAPAX®-LC, HUMIRA®-HC, HUMIRA®-LC, RITUXAN®-HC, RITUXAN®-LC, IPILIMUMAB®-HC, IPILIMUMAB®-LC, AVASTIN®-HC, AVASTIN®-LC, ERBITUX®-HC, ERBITUX®-HC, and ERBITUX®-LC), recombinant enzymes (e.g., RETAVASE®, ACTRAPID®-A chain, ACTRAPID®-B chain, NEULASTA®, pre-pro insulin, EPOGEN®, and NORDITROPIN®), fusion protein (e.g., ENBREL®), or any purified proteins (e.g., ALPHANATE® and ARALAST®). In addition, identification of suitable therapeutic molecules for preventing, treating, or ameliorating a particular disease or disorder is well within the capabilities of a person of ordinary in the art.

Vectors and Host Cells

To introduce the polynucleotides into the cells, a vector can be used. The vector may be, for example, a plasmid vector or a single- or double-stranded RNA or DNA viral vector. Such vectors may be introduced into cells by well-known techniques for introducing DNA and RNA into cells. Viral vectors may be replication competent or replication defective. In the latter case, viral propagation generally will occur only in complementing viral competent cells.

Thus, at a minimum, the vectors must include the polynucleotides of the invention. Other components of the vector may include, but are not limited to, selectable markers, chromatin modification domains, additional promoters driving expression of other polypeptides that may also be present on the vector (e.g., a lethal polypeptide), genomic integration sites, recombination sites, and molecular insertion pivots. The vectors may comprise any number of these additional elements, either within or not within the polynucleotides, such that the vector can be tailored to the specific goals of the therapeutic methods desired.

In one embodiment of the present invention, the vectors that are introduced into the cells further comprise a "selectable marker gene" which, when expressed, indicates that the therapeutic gene switch construct of the present invention has been integrated into the genome of the modified cell. In this manner, the selector gene can be a positive marker for the genome integration. While not critical to the methods of the present invention, the presence of a selectable marker gene allows the practitioner to select for a population of live cells where the vector construct has been integrated into the genome of the cells. Thus, certain embodiments of the present invention comprise selecting cells where the vector has successfully been integrated. As used herein, the term "select" or variations thereof, when used in conjunction with cells, is intended to mean standard, well-known methods for choosing cells with a specific genetic make-up or phenotype. Typical methods include, but are not limited to, culturing cells in the presence of antibiotics, such as G418, neomycin and ampicillin. Other examples of selectable marker genes include, but are not limited to, genes that confer resistance to dihydrofolate reductase, hygromycin, or mycophenolic acid. Other methods of selection include, but are not limited to, a selectable marker gene that allows for the use of thymidine kinase, hypoxanthine-guanine phosphoribosyl-transferase or adenine phosphoribosyltransferase as selection agents. Cells comprising a vector construct comprising an antibiotic resistance gene or genes would then be capable of tolerating the antibiotic in culture. Likewise, cells not comprising a vector construct comprising an antibiotic resistance gene or genes would not be capable of tolerating the antibiotic in culture.

As used herein, a "chromatin modification domain" (CMD) refers to nucleotide sequences that interact with a variety of proteins associated with maintaining and/or altering chromatin structure, such as, but not limited to, DNA insulators. See Ciavatta et al., *Proc. Nat'l Acad. Sci. U.S.A.,* 103:9958 (2006), which is incorporated by reference herein. Examples of CMDs include, but are not limited to, the chicken β-globulin insulator and the chicken hypersensitive site 4 (cHS4). The use of different CMD sequences between one or more gene programs (i.e., a promoter, coding sequence, and 3' regulatory region), for example, can facilitate the use of the differential CMD DNA sequences as "mini homology arms" in combination with various microorganism or in vitro recombineering technologies to "swap" gene programs between existing multigenic and monogenic shuttle vectors. Other examples of chromatin modification domains are known in the art or can be readily identified.

Particular vectors for use with the present invention are expression vectors that code for polypeptides or polynucleotides. Generally, such vectors comprise cis-acting control regions effective for expression in a modified cell, operatively linked to the polynucleotide to be expressed. Appropriate trans-acting factors are supplied by the modified cell, supplied by a complementing vector or supplied by the vector itself upon introduction into the cell.

A great variety of expression vectors can be used to express polypeptides or polynucleotides. Such vectors include chromosomal, episomal and virus-derived vectors, e.g., vectors derived from bacterial plasmids, from bacteriophage, from yeast episomes, from yeast chromosomal elements, from viruses such as adeno-associated viruses, lentiviruses, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or express polynucleotides or polypeptides in a cell may be used for expression in this regard.

The polynucleotide sequence in the expression vector is operatively linked to appropriate expression control sequence(s) including, for instance, a promoter to direct mRNA transcription. Representatives of additional promoters include, but are not limited to, constitutive promoters and tissue specific or inducible promoters. Examples of constitutive eukaryotic promoters include, but are not limited to, the promoter of the mouse metallothionein I gene (Hamer et al., *J. Mol. Appl. Gen.* 1:273 (1982)); the TK promoter of Herpes virus (McKnight, *Cell* 31:355 (1982)); the SV40 early promoter (Benoist et al., *Nature* 290:304 (1981)); and the vaccinia virus promoter. All of the above listed references are incorporated by reference herein. Additional examples of the promoters that could be used to drive expression of a protein or polynucleotide include, but are not limited to, tissue-specific promoters and other endogenous promoters for specific proteins, such as the albumin promoter (hepatocytes), a proinsulin promoter (pancreatic beta cells) and the like. In general, expression constructs will contain sites for transcription, initiation and termination and, in the transcribed region, a ribosome binding site for translation. The coding portion of the mature transcripts expressed by the constructs may include a translation initiating AUG at the beginning and a termination codon (UAA, UGA or UAG) appropriately positioned at the end of the polypeptide to be translated.

In addition, the constructs may contain control regions that regulate, as well as engender expression. Generally, such regions will operate by controlling transcription, such as repressor binding sites and enhancers, among others.

Examples of eukaryotic vectors include, but are not limited to, pW-LNEO, pSV2CAT, pOG44, pXT1 and pSG available from Stratagene; pSVK3, pBPV, pMSG and pSVL available from Amersham Pharmacia Biotech; and pCM-VDsRed2-express, pIRES2-DsRed2, pDsRed2-Mito, and pCMV-EGFP available from Clontech. Many other vectors are well-known and commercially available.

Particularly useful vectors, which comprise molecular insertion pivots for rapid insertion and removal of elements of gene programs, are described in United States Published Patent Application No. 2004/0185556, U.S. patent application Ser. No. 11/233,246 and International Published Application Nos. WO 2005/040336 and WO 2005/116231, all of which are incorporated by reference. An example of such vectors is the UltraVector™ Production System (Intrexon Corp., Blacksburg, Va.), as described in WO 2007/038276, incorporated herein by reference. As used herein, a "gene program" is a combination of genetic elements comprising a promoter (P), an expression sequence (E) and a 3' regulatory sequence (3), such that "PE3" is a gene program. The elements within the gene program can be easily swapped between molecular pivots that flank each of the elements of the gene program. A molecular pivot, as used herein, is defined as a polynucleotide comprising at least two non-variable rare or uncommon restriction sites arranged in a linear fashion. In one embodiment, the molecular pivot comprises at least three non-variable rare or uncommon restriction sites arranged in a linear fashion. Typically any one molecular pivot would not include a rare or uncommon restriction site of any other molecular pivot within the same gene program. Cognate sequences of greater than 6 nucleotides upon which a given restriction enzyme acts are referred to as "rare" restriction sites. There are, however, restriction sites of 6 bp that occur more infrequently than would be statistically predicted, and these sites and the endonucleases that cleave them are referred to as "uncommon" restriction sites. Examples of either rare or uncommon restriction enzymes include, but are not limited to, AsiS I, Pac I, Sbf I, Fse I, Asc I, Mlu I, SnaB I, Not I, Sal I, Swa I, Rsr II, BSiW I, Sfo I, Sgr AI, AflIII, Pvu I, Ngo MIV, Ase I, Flp I, Pme I, Sda I, Sgf I, Srf I, and Sse8781 I.

The vector may also comprise restriction sites for a second class of restriction enzymes called homing endonuclease (HE) enzymes. HE enzymes have large, asymmetric restriction sites (12-40 base pairs), and their restriction sites are infrequent in nature. For example, the HE known as I-SceI has an 18 bp restriction site (5'TAGGGATAACA-GGGTAAT3' (SEQ ID NO:4)), predicted to occur only once in every $7 \times 10^{10}$ base pairs of random sequence. This rate of occurrence is equivalent to only one site in a genome that is 20 times the size of a mammalian genome. The rare nature of HE sites greatly increases the likelihood that a genetic engineer can cut a gene program without disrupting the integrity of the gene program if HE sites were included in appropriate locations in a cloning vector plasmid.

Selection of appropriate vectors and promoters for expression in a host cell is a well-known procedure, and the requisite techniques for vector construction and introduction into the host cell, as well as its expression in the host cell are routine skills in the art.

The introduction of the polynucleotides into the cells can be a transient transfection, stable transfection, or can be a locus-specific insertion of the vector. Transient and stable transfection of the vectors into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods in Molecular Biology (1986); Keown et al., 1990, Methods Enzymol. 185: 527-37; Sambrook et al., 2001, Molecular Cloning, A Laboratory Manual, Third Edition, Cold Spring Harbor Laboratory Press, N.Y., which are hereby incorporated by reference. These stable transfection methods result in random insertion of the vector into the genome of the cell. Further, the copy number and orientation of the vectors are also, generally speaking, random.

In another embodiment, locus-specific insertion may be carried out by recombinase-site specific gene insertion. Briefly, bacterial recombinase enzymes, such as, but not limited to, PhiC31 integrase can act on "pseudo" recombination sites within the human genome. These pseudo recombination sites can be targets for locus-specific insertion using the recombinases. Recombinase-site specific gene insertion is described in Thyagarajan et al., *Mol. Cell Biol.* 21:3926 (2001), which is hereby incorporated by reference. Other examples of recombinases and their respective sites that may be used for recombinase-site specific gene insertion include, but are not limited to, serine recombinases such as R4 and TP901-1 and recombinases described in WO 2006/083253, incorporated herein by reference.

In order to stably integrate the one or more gene expression systems in the genome of a modified cell, any known methods of integration may be used for the purpose of this invention. In one embodiment, locus-specific insertion may be carried out by recombinase-site specific gene insertion. Briefly, bacterial recombinase enzymes, such as, but not limited to, PhiC31 integrase may act on "pseudo" recombination sites within the human genome. See US publication No. 2004/0003420 A1; Groth et al., *Proc. Natl. Acad. Science*, 97, 5995-6000 (2000). These pseudo recombination sites may be targets for locus-specific insertion using the recombinases. Recombinase-site specific gene insertion is described in Thyagarajan, B. et al., *Mol. Cell Biol.* 21(12): 3926-34 (2001).

In certain embodiments, the first inducible gene expression system further comprises an integrase, which will stably integrate the first gene switch system into pseudo-sites within the genome of the targeted cells. A second gene switch system may also comprise an integrase, which will integrate the second gene switch system into the pseudo-sites within the genome of the targeted cells. The first gene switch system may further comprise an integrase acceptor site, which may allow integration of the second inducible gene switch system in the pre-positioned acceptor site within the genome of the targeted cells.

The following polypeptide sequence was reported as a polypeptide sequence encoding the *Streptomyces* phase PhiC31 integrase polypeptide sequence and has the accession number NP_047974 in Genbank.

```
Streptomyces phage phiC31 integrase (605 aa)
                                                       (SEQ ID NO: 6)
  1 mdtyagaydr qsrerenssa aspatqrsan edkaadlgre verdggrfrf vghfseapgt 61 safgtaerpe ferilnecra grinmiivyd vsrfsrlkvm daipivsell algvtivstq 121 egvfrqgnvm dlihlimrld ashkesslks akildtknlq relggyvggk apygfelvse 181 tkeitrngrm vnvvinklah sttpltgpfe fepdvirwww reikthkhlp fkpgsqaaih 241 pgsitglckr mdadavptrg etigkktass awdpatvmri lrdpriagfa aeviykkkpd 301 gtpttkiegy riqrdpitlr pveldcgpii epaewyelqa wldgrgrgkg lsrgqailsa 361 mdklycecga vmtskrgees ikdsyrcrrr kvvdpsapgq hegtcnvsma aldkfvaeri 421 fnkirhaegd eetlallwea arrfgkltea peksgeranl vaeradalna leelyedraa 481 gaydgpvgrk hfrkqqaalt lrqqgaeerl aeleaaeapk lpldqwfped adadptgpks 541 wwgrasvddk rvfvglfvdk ivvtksttgr gqgtpiekra sitwakpptd ddeddaqdgt 601 edvaa
```

Other examples of recombinases and their respective sites that may be used for recombinase-site specific gene insertion include, but are not limited to, serine recombinases such as R4 and TP901-1. Site-specific recombinases (SSRs), such as the bacteriophage Pl-derived Cre recombinase recognize specific DNA sequences ("recognition sites," "recognition sequences," or "integrase acceptor site") and catalyze recombination between two recognition sites. Cre recombinase, for example, recognizes the 34 base pair (bp) loxP motif (Austin et al., *Cell* 25, 729-736 (1981)). If the two sites are located on the same DNA molecule in the same orientation, the intervening DNA sequence is excised by the recombinase from the parental molecule as a closed circle, leaving one recognition site on each of the reaction products. If the two sites are in inverted orientation, the recognition-site flanked region is inverted through recombinase mediated recombination. Alternatively, if the two recognition sites are located on different molecules, recombinase-mediated recombination will lead to integration of a circular molecule or translocation between two linear molecules.

In addition to Crc, a few recombinases have been shown to exhibit some activity in mammalian cells. The best characterized examples are the yeast derived FLP and Kw recombinases, which exhibit optimal activity at 30° C. and are unstable at 37° C. (Buchholz et al., *Nature Biotech.*, 16, 657-662 (1998); Ringrose et al., *Eur. J. Biochem.*, 248, 903-912). Other recombinases that show some activity in mammalian cells include a mutant integrase of phage lambda, the integrases of phage HK022, mutant gamma delta-resolvase and beta-recombinase (Lorbach et al., *J. Mol. Biol.*, 296, 1175-81 (2000); Kolot et al., *Moi. Biol. Rep.* 26, 207-213 (1999); Schwikardi et al., *FEBS Lett.*, 471, 147-150 (2000); Diaz et al., *J. Biol. Chem.*, 274, 6634-6640 (1999)). Moreover, an improved version of the phiC31 integrase has been developed. This modified C31-Int (C31-Int (CNLS)) carries a C-terminal nuclear localization signal (NLS) and displays a recombination efficiency in mammalian cells that is significantly enhanced over the wild type form and is comparable to that of Cre recombinase (EP 1205490; US Publication No. 2004/0003420 A1). This makes the C31-Int a valuable tool for mammalian genome modification.

In one embodiment of the invention, the vector is inserted into a bio-neutral site in the genome. A bio-neutral site is a site in the genome where insertion of the polynucleotides interferes very little, if any, with the normal function of the cell. Bio-neutral sites may be analyzed using available bioinformatics. Many bio-neutral sites are known in the art, e.g., the ROSA-equivalent locus. Other bio-neutral sites may be identified using routine techniques well known in the art. Characterization of the genomic insertion site(s) is performed using methods known in the art. To control the location, copy number and/or orientation of the polynucleotides when introducing the vector into the cells, methods of locus-specific insertion may be used. Methods of locus-specific insertion are well-known in the art and include, but are not limited to, homologous recombination and recombinase-mediated genome insertion. Of course, if locus-specific insertion methods are to be used in the methods of the present invention, the vectors may comprise elements that aid in this locus-specific insertion, such as, but not limited to, homologous recombination. For example, the vectors may comprise one, two, three, four or more genomic integration sites (GISs). As used herein, a "genomic integration site" is defined as a portion of the vector sequence which nucleotide sequence is identical or nearly identical to portions of the genome within the cells that allows for insertion of the vector in the genome. In particular, the vector may comprise two genomic insertion sites that flank at least the polynucleotides. Of course, the GISs may flank additional elements, or even all elements present on the vector.

In a further embodiment, the vector may comprise a chemo-resistance gene, e.g., the multidrug resistance gene mdr1, dihydrofolate reductase, or $O^6$-alkylguanine-DNA alkyltransferase. The chemo-resistance gene may be under the control of a constitutive (e.g., CMV) or inducible (e.g., RheoSwitch®) promoter. In this embodiment, if it is desired to treat a disease in a subject while maintaining the modified cells within the subject, a clinician may apply a chemotherapeutic agent to destroy diseased cells while the modified cells would be protected from the agent due to expression of a suitable chemo-resistance gene and may continue to be used for treatment, amelioration, or prevention of a disease, disorder, or condition. By placing the chemo-resistance gene under an inducible promoter, the unnecessary expression of the chemo-resistance gene can be avoided, yet it will still be available in case continued treatment is needed. If the modified cells themselves become diseased, they could still be destroyed by inducing expression of a lethal polypeptide as described below.

The methods of the invention are carried out by introducing the polynucleotides encoding the gene switch and the therapeutic polypeptide or therapeutic polynucleotide into cells of a subject. Any method known for introducing a polynucleotide into a cell known in the art, such as those described above, can be used.

When the polynucleotides are to be introduced into cells ex vivo, the cells may be obtained from a subject by any technique known in the art, including, but not limited to, biopsies, scrapings, and surgical tissue removal. The isolated cells may be cultured for a sufficient amount of time to allow the polynucleotides to be introduced into the cells, e.g., 2, 4, 6, 8, 10, 12, 18, 24, 36, 48, hours or more. Methods for culturing primary cells for short periods of time are well known in the art. For example, cells may be cultured in plates (e.g., in microwell plates) either attached or in suspension.

For ex vivo therapeutic methods, cells are isolated from a subject and cultured under conditions suitable for introducing the polynucleotides into the cells. Once the polynucleotides have been introduced into the cells, the cells are incubated for a sufficient period of time to allow the ligand-dependent transcription factor complex to be expressed, e.g., 0.5, 1, 2, 3, 4, 5, 6, 7, 8, 9, 10, 12, 18, or 24 hours or more. At some point after the introduction of the polynucleotides into the cells (either before or after significant levels of the ligand-dependent transcription factor complex is expressed), the cells are introduced back into the subject. Reintroduction may be carried out by any method known in the art, e.g., intravenous infusion or direct injection into a tissue or cavity. In one embodiment, the presence of the polynucleotides in the cells is determined prior to introducing the cells back into the subject. In another embodiment, cells containing the polynucleotides are selected (e.g., based on the presence of a selectable marker in the polynucleotides) and only those cells containing the polynucleotides are reintroduced into the subject. After the cells are reintroduced to the subject, ligand is administered to the subject to induce expression of the therapeutic polypeptide or therapeutic polynucleotide. In an alternative embodiment, the ligand may be added to the cells even before the cells are reintroduced to the subject such that the therapeutic polypeptide or therapeutic polynucleotide is expressed prior to reintroduction of the cells. The ligand may be administered by any suitable method, either systemically (e.g., orally, intravenously) or locally (e.g., intraperitoneally, intrathecally, intraventricularly, direct injection into the tissue or organ where the cells were reintroduced). The optimal timing of ligand administration can be determined for each type of cell and disease, disorder, or condition using only routine techniques.

In a different embodiment, the ex vivo therapeutic methods may be carried out using non-autologous cells, e.g., cells that are allogeneic or xenogeneic to the subject, instead of autologous cells from the subject. The polynucleotides may be introduced into the non-autologous cells ex vivo to produce modified cells and the modified cells may then be introduced into the subject. The non-autologous cells may be any cells that are viable after transplantation into a subject, including, without limitation, stem cells (such as embryonic stem cells or hematopoietic stem cells) and fibroblasts.

The in vivo therapeutic methods of the invention involve direct in vivo introduction of the polynucleotides into the cells of the subject. The polynucleotides may be introduced into the subject systemically or locally (e.g., at the site of the disease, disorder, or condition). Once the polynucleotides have been introduced to the subject, the ligand may be administered to induce expression of the therapeutic polypeptide or therapeutic polynucleotide. The ligand may be administered by any suitable method, either systemically (e.g., orally, intravenously) or locally (e.g., intraperitoneally, intrathecally, intraventricularly, direct injection into the tissue or organ where the disease, disorder, or condition is occurring). The optimal timing of ligand administration can be determined for each type of cell and disease, disorder, or condition using only routine techniques.

In one embodiment, the ligand may be administered to the subject continuously or intermittently, and the pattern of ligand administration may be altered as necessary depending on the status of the disease, disorder, or condition. The level of expression of the therapeutic polypeptide or therapeutic polynucleotide can be modulated both by the schedule of ligand administration and the amount of ligand that is administered, permitting careful control of the therapeutic treatment.

The therapeutic methods of the invention may also be coupled with diagnostic technologies in order to improve treatment outcomes in various approaches that are known in the art as pharmacodiagnostics or theranostics. For example, administration of the ligand may be coordinated with monitoring of the status or progression of the disease, disorder, or condition. In one embodiment, the polynucleotides of the invention are introduced into a cell together with one or more polynucleotides designed to diagnose or monitor a disease, disorder, or condition. In another embodiment, the diagnostic polynucleotides are present on the same vector comprising the polynucleotides of the invention. In this embodiment, the therapeutic treatment and the diagnostic test for monitoring effectiveness of the treatment are administered together in one unit, ensuring that all cells that receive the treatment also receive the diagnostic test. In one embodiment, the diagnostic polynucleotides comprise a diagnostic switch promoter (i.e., a promoter whose activity is modulated during a disease, disorder, or condition) operably linked to a reporter gene, and monitoring of the status of the disease, disorder, or condition involves detecting the level of expression of the reporter gene.

In another theranostic embodiment of the invention, the level of expression of a therapeutic polypeptide or therapeutic polynucleotide is monitored through detecting the level of expression of a reporter gene, wherein the level of expression of the reporter directly correlates with the level of expression of the therapeutic polypeptide or therapeutic polynucleotide. For example, the level of expression of a therapeutic protein such as interleukin-12 may be monitored non-invasively in various tissues through a bioneutral reporter such as the human type 2 somatostatin receptor, which may be imaged with a radiolabeled somatostatin analog (see, e.g., Zinn et al., *J. Nucl. Med* 41:887-895 (2000)). The reporter may be linked to the same promoter as the therapeutic polypeptide or polynucleotide, or may be placed under a different promoter that is modulated by the therapeutic polypeptide or polynucleotide.

An additional embodiment of the invention relates to methods for expressing a therapeutic polypeptide or therapeutic polynucleotide in a subject, comprising:

(a) introducing into cells of said subject (1) a polynucleotide encoding a gene switch, said gene switch comprising at least one transcription factor sequence, wherein said at least one transcription factor sequence encodes a ligand-dependent transcription factor complex, operably linked to a therapeutic switch promoter, wherein the promoter is activated during said disease, disorder, or condition, and (2) a polynucleotide encoding a therapeutic polypeptide or therapeutic polynucleotide linked to a promoter which is activated by said ligand-dependent transcription factor complex, to produce modified cells; and (b) administering ligand to said subject to induce expression of said therapeutic polypeptide or therapeutic polynucleotide.

In one embodiment, the methods for expressing a therapeutic polypeptide or therapeutic polynucleotide in a subject may be carried out using laboratory animals (e.g., mice, rats, cats, dogs, monkeys) or farm animals (e.g., pigs, sheep, cows). For example, methods of expressing therapeutic products in animals may be carried out for research purposes or for the large scale production of therapeutic polypeptides or therapeutic polynucleotides.

A further embodiment of the invention relates to methods for expressing a therapeutic polypeptide or therapeutic polynucleotide in a cell, comprising:

(a) introducing into said cell (1) a polynucleotide encoding a gene switch, said gene switch comprising at least one transcription factor sequence, wherein said at least one transcription factor sequence encodes a ligand-dependent transcription factor complex, operably linked to a therapeutic switch promoter, wherein the promoter is activated during said disease, disorder, or condition, and (2) a polynucleotide encoding a therapeutic polypeptide or therapeutic polynucleotide linked to a promoter which is activated by said ligand-dependent transcription factor complex, to produce a modified cell; and (b) administering ligand to said modified cell to induce expression of said therapeutic polypeptide or therapeutic polynucleotide.

Another embodiment of the invention is a method for expressing a therapeutic polypeptide or therapeutic polynucleotide in one or more modified cells, comprising:

(a) introducing into a cell (1) a first polynucleotide encoding a gene switch, said gene switch comprising at least one transcription factor sequence, wherein said at least one transcription factor sequence encodes a ligand-dependent transcription factor complex through operable association with a therapeutic switch promoter, wherein said therapeutic switch promoter is activated under conditions associated with a disease, disorder, or condition, and (2) a second polynucleotide encoding a therapeutic polypeptide or therapeutic polynucleotide operably associated with a factor-regulated promoter which is activated by said ligand-dependent transcription factor complex, thereby producing a modified cell; and (b) administering ligand to said modified cell to induce expression of said therapeutic polypeptide or therapeutic polynucleotide.

In one embodiment, the methods for expressing a therapeutic polypeptide or therapeutic polynucleotide in a cell may be carried out in vitro, e.g., in cells in culture. For example, in vitro methods of therapeutic product expression may be carried out for research use or for the large scale production of therapeutic polypeptides or therapeutic polynucleotides.

In any embodiments described herein, the polynucleotides or vector comprising the polynucleotides may comprise a sequence encoding a lethal polypeptide that can be turned on to express a product that will kill a cell containing the polynucleotides or vector. Lethal polypeptide expression can be used to eliminate the modified cells from a subject, either because treatment is no longer needed or because of a problem with the modified cells (e.g., hyperproliferation or toxicity). A lethal polypeptide, as used herein, is a polypeptide that, when expressed, is lethal to the cell that expresses the polypeptide, either because the polypeptide itself is lethal or the polypeptide produces a compound that is lethal. As used herein, a lethal polypeptide includes polypeptides that induce cell death in any fashion, including but not limited to, necrosis, apoptosis and cytotoxicity. Examples of lethal polypeptides include, but are not limited to, apoptosis inducing tumor suppressor genes such as, but not limited to, p53, Rb and BRCA-1, toxins such as diphtheria toxin (DTA), shigella neurotoxin, botulism toxin, tetanus toxin, cholera toxin, CSE-V2 and other variants of scorpion protein toxins to name a few, suicide genes such as cytosine deaminase and thymidine kinase, and cytotoxic genes, e.g., tumor necrosis factor, interferon-alpha. The present invention is not limited by the identity of the lethal polypeptide, provided that the polypeptide is capable of being lethal to the cell in which it is expressed. If the modified cells are short-lived cells (e.g., cells with a limited lifespan (e.g., about 10 days or less, such as dendritic cells), it may not be necessary to include a lethal polypeptide in the polynucleotides or vector as the cells will be naturally removed over a short period of time.

For each of the methods described above, in one embodiment, the polynucleotide encoding the gene switch and the polynucleotide encoding the therapeutic polypeptide or therapeutic polynucleotide linked to a promoter are part of one larger polynucleotide, e.g., a vector. In another embodiment, the polynucleotide encoding the gene switch and the polynucleotide encoding the therapeutic polypeptide or therapeutic polynucleotide linked to a promoter are separate polynucleotides, which may be combined to form a "nucleic acid composition."

In one aspect, the invention relates to polynucleotides that may be used in the methods of the invention. In one embodiment, the polynucleotide encodes a gene switch, the gene switch comprising at least one transcription factor sequence, wherein said at least one transcription factor sequence encodes a ligand-dependent transcription factor complex, operably linked to a therapeutic switch promoter, wherein the activity of the promoter is modulated during said disease, disorder, or condition. In another embodiment, the polynucleotide further encodes a therapeutic polypeptide or therapeutic polynucleotide linked to a factor-regulated promoter which is activated by said ligand-dependent transcription factor complex. In one embodiment, the gene switch is an EcR-based gene switch. In another embodiment, the gene switch comprises a first transcription factor sequence under the control of a first therapeutic switch promoter and a second transcription factor sequence under the control of a second therapeutic switch promoter, wherein the proteins encoded by said first transcription factor sequence and said second transcription factor sequence interact to form a protein complex which functions as a ligand-dependent transcription factor complex. In one embodiment, the first therapeutic switch promoter and the second therapeutic switch promoter are different. In another embodiment, the first therapeutic switch promoter and the second therapeutic switch promoter are the same. In another embodiment, the first transcription factor sequence encodes a protein comprising a heterodimer partner and a transactivation domain and the second transcription factor sequence encodes a protein comprising a DNA binding domain and a ligand-binding domain. In a further embodiment, the polynucleotide also encodes a lethal polypeptide operably linked to an inducible promoter.

Another aspect of the invention relates to vectors comprising any of the polynucleotides described above. In one embodiment, the vector is a plasmid vector or a viral vector.

In another aspect, the invention provides kits that may be used in conjunction with methods of the invention. Kits according to this aspect of the invention may comprise one or more containers, which may contain one or more components selected from the group consisting of one or more nucleic acid molecules, restriction enzymes and one or more cells comprising such nucleic acid molecules. Kits of the invention may further comprise one or more containers containing supporting cells suitable for supporting the cells of the invention in culture, one or more containers containing cell culture media suitable for culturing cells of the invention, one or more containers containing antibiotics suitable for use in culturing cells of the invention, one or more containers containing buffers, one or more containers containing transfection reagents, one or more containers containing substrates for enzymatic reactions, and/or one or more ligands for gene switch activation.

Kits of the invention may contain a wide variety of nucleic acid molecules that can be used with the invention. Examples of nucleic acid molecules that can be supplied in kits of the invention include those that contain promoters, sequences encoding gene switches, enhancers, repressors, selection markers, transcription signals, translation signals, primer hybridization sites (e.g., for sequencing or PCR), recombination sites, restriction sites and polylinkers, sites that suppress the termination of translation in the presence of a suppressor tRNA, suppressor tRNA coding sequences, sequences that encode domains and/or regions, origins of replication, telomeres, centromeres, and the like. In one embodiment, kits may comprise a polynucleotide comprising a gene switch without any therapeutic switch promoters, the polynucleotide being suitable for insertion of any therapeutic switch promoters of interest. Nucleic acid molecules of the invention may comprise any one or more of these features in addition to polynucleotides as described above.

Kits of the invention may comprise containers containing one or more recombination proteins. Suitable recombination proteins include, but are not limited to, Cre, Int, IHF, Xis, Flp, Fis, Hin, Gin, Cin, Tn3 resolvase, ΦC31, TndX, XerC, and XerD. Other suitable recombination sites and proteins are those associated with the GATEWAY™ Cloning Technology available from Invitrogen Corp., Carlsbad, Calif., and described in the product literature of the GATEWAY™ Cloning Technology (version E, Sep. 22, 2003), the entire disclosures of which are incorporated herein by reference.

Kits of the invention can also be supplied with primers. These primers will generally be designed to anneal to molecules having specific nucleotide sequences. For example, these primers can be designed for use in PCR to amplify a particular nucleic acid molecule. Sequencing primers may also be supplied with the kit.

One or more buffers (e.g., one, two, three, four, five, eight, ten, fifteen) may be supplied in kits of the invention. These buffers may be supplied at working concentrations or may be supplied in concentrated form and then diluted to the working concentrations. These buffers will often contain salt, metal ions, co-factors, metal ion chelating agents, etc. for the enhancement of activities or the stabilization of either the buffer itself or molecules in the buffer. Further, these buffers may be supplied in dried or aqueous forms. When buffers are supplied in a dried form, they will generally be dissolved in water prior to use.

Kits of the invention may contain virtually any combination of the components set out above or described elsewhere herein. As one skilled in the art would recognize, the components supplied with kits of the invention will vary with the intended use for the kits. Thus, kits may be designed to perform various functions set out in this application and the components of such kits will vary accordingly.

EXAMPLES

The examples which follow further illustrate the invention, but should not be construed to limit the scope of the invention in any way. The practice of the present invention, including the following examples will employ, unless otherwise indicated, conventional techniques of cell biology, cell culture, molecular biology, transgenic biology, microbiology, and recombinant DNA, which are within the skill of the art. Such techniques are explained fully in the literature. See, for example, Molecular Cloning: A Laboratory Manual (3-Volume Set), J. Sambrook, D. W. Russell, Cold Spring Harbor Laboratory Press (2001); Genes VIII, B. Lewin, Prentice Hall (2003); PCR Primer, C. W. Dieffenbach and G. S. Dveksler, CSHL Press (2003); DNA Cloning, D. N. Glover ed., Volumes I and II (1985); Oligonucleotide Synthesis: Methods and Applications (Methods in Molecular Biology), P. Herdewijn (Ed.), Humana Press (2004); Culture of Animal Cells: A Manual of Basic Technique, 4th edition, R. I. Freshney, Wiley-Liss (2000); Oligonucleotide Synthesis, M. J. Gait (Ed.), (1984); Mullis et. al U.S. Pat. No. 4,683,195; Nucleic Acid Hybridization, B. D. Hames & S. J. Higgins eds. (1984); Nucleic Acid Hybridization, M. L. M. Anderson, Springer (1999); Animal Cell Culture and Technology, 2nd edition, M. Butler, BIOS Scientific Publishers (2004); Immobilized Cells and Enzymes: A Practical Approach (Practical Approach Series), J. Woodward, IRL Press (1992); Transcription And Translation, B. D. Hames & S. J. Higgins (Eds.) (1984); Culture Of Animal Cells, R. I. Freshney, Alan R. Liss, Inc., (1987); A Practical Guide To Molecular Cloning, 3rd edition, B. Perbal, John Wiley & Sons Inc. (1988); Gene Transfer Vectors For Mammalian Cells, J. H. Miller and M. P. Calos eds., Cold Spring Harbor Laboratory (1987); Methods In Enzymology, Vols. 154 and 155, Wu et. al (Eds.); Immunochemical Methods In Cell And Molecular Biology, Mayer and Walker, (Eds.), Academic Press, London (1987); and in Ausubel et. al, Current Protocols in Molecular Biology, John Wiley and Sons, Baltimore, Md. (1989).

Example 1

Figure 5:
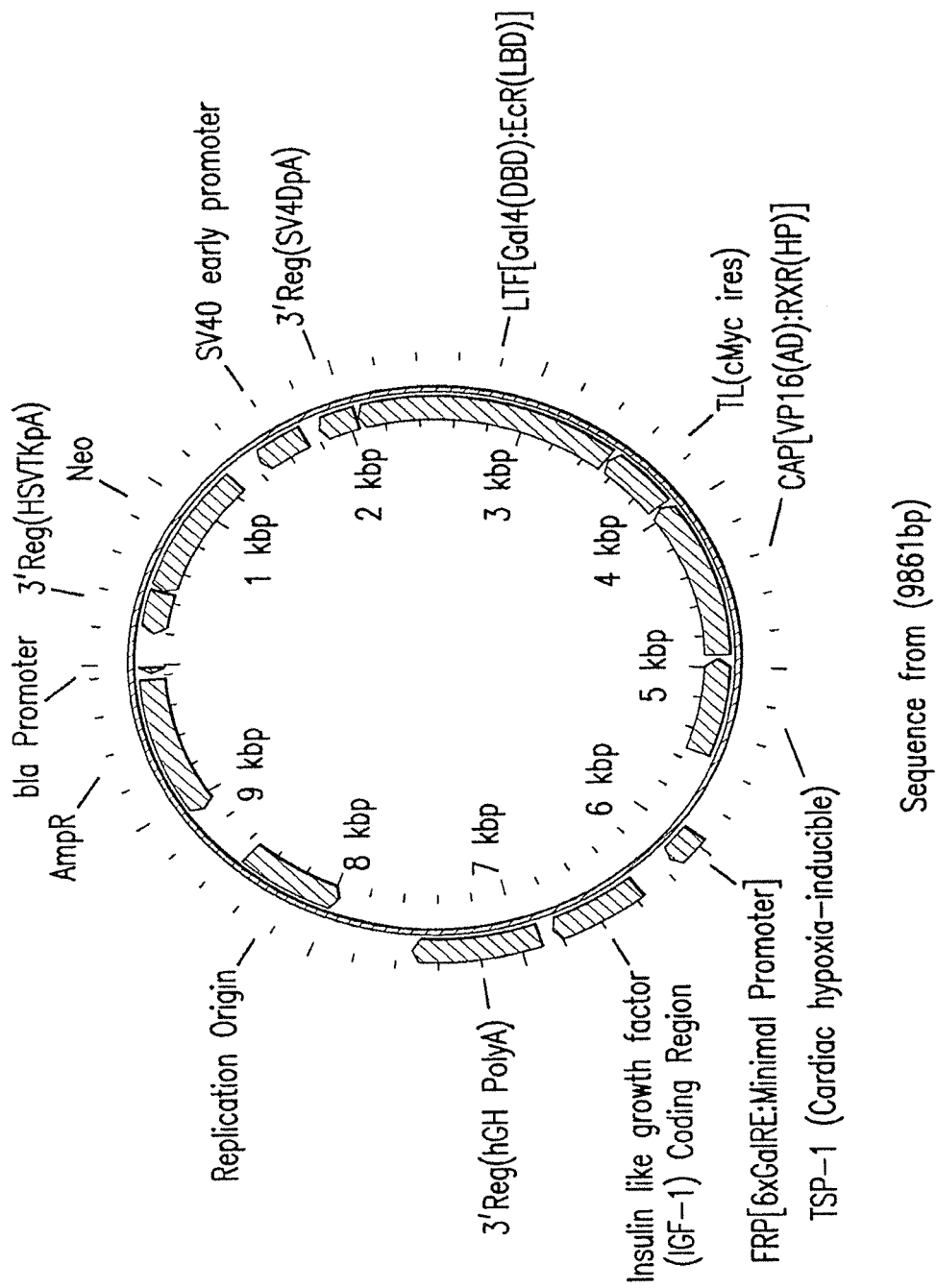
FIG. 5 is a diagram of a vector constructed under the scheme shown in FIG. 1, and engineered to express insulin growth factor-1 (IGF-1) under hypoxic conditions such as cardiac ischemia.

This example describes a gene therapy vector useful for the treatment of ischemic heart disease through the promotion of angiogenesis. Insulin like growth factor 1 is a hormone that may be useful in the treatment of ischemic heart disease. (IGF-1, GenBank Accession No.: NP_001104753.1, SEQ ID NO:20). Use of IGF-1 in preclinical models is associated with improved cardiac function, anti-apoptosis, neo-vascularization and cardiac muscle regeneration (reviewed in Santini, M. P., et al. *Novartis Found Symp.* 274:228-38 (2006); discussion 239-43, 272-6; and Saetrum Opgaard, O., and Wang, P. H. *Growth Horm IGF Res.* 15:89-94 (2005)). For this purpose, an example of inducible IGF-1 expression, in response to ischemia and/or inflammation is given. An inducible expression system for the expression if IGF-1 upon administration of ligand, under hypoxic conditions which occur in ischemic tissue is shown in FIG. 5.

SEQ ID NO: 20:
MGKISSLPTQLFKCCFCDFLKVKMHTMSSSHLFYLALCLLTFTSSATAGP

ETLCGAELVDALQFVCGDRGFYFNKPTGYGSSSRRAPQTGIVDECCFRSC

DLRRLEMYCAPLKPAKSARSVRAQRHTDMPKTQKYQPPSTNKNTKSQRRK

GSTFEERK

The complete nucleotide sequence of the construct shown in FIG. 5 is presented as SEQ ID NO:7. The nucleotide coordinates for salient elements of the construct are shown in Table 4.

TABLE 4

| Label | Direction | Length | Start | End |
|---|---|---|---|---|
| 3'Reg(HSVTKpA) | reverse | 259 | 197 | 455 |
| Neo | reverse | 795 | 462 | 1256 |
| SV40 early promoter | reverse | 278 | 1446 | 1723 |
| 3'Reg(SV40pA) | reverse | 221 | 1830 | 2050 |
| LTF[Gal4(DBD):EcR(LBD)] | reverse | 1467 | 2057 | 3523 |
| TL (cMyc ires) | reverse | 408 | 3536 | 3943 |
| CAP[VP16(AD):RXR(HP)] | reverse | 975 | 3950 | 4924 |
| TSP-1 (Cardiac hypoxia-inducible) | reverse | 578 | 4958 | 5535 |
| FRP[6xGalRE:Minimal Promoter] | forward | 189 | 5946 | 6134 |
| Insulin like growth factor (IGF-1) Coding Region | forward | 477 | 6348 | 6824 |
| 3'Reg(hGH PolyA) | forward | 627 | 6897 | 7523 |
| Replication Origin | reverse | 589 | 7957 | 8545 |
| AmpR | reverse | 858 | 8920 | 9777 |
| bla Promoter | reverse | 39 | 9811 | 9849 |

The vector shown in FIG. 5 is modeled according to the gene switch system shown in FIG. 1. Under this system, both the CAP subunit, and the LTF subunit of the ligand-dependent transcription factor complex (LDTFC) are expressed through operable association with a single therapeutic switch promoter (TSP-1) via use of an internal ribosome entry site (IRES). The promoter utilized in this system is a UV-conformed synthetic hypoxia-inducible promoter.

The coding region for the therapeutic product, IGF-1, is operably associated with a factor-regulated promoter (FRP) which is activated upon contact with the LDTFC in the presence of ligand.

The construct shown in FIG. 5 is inserted into a suitable vector system, for example, a viral vector, for delivery to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of gene therapy vectors are well known in the art. Upon delivery the vector will be taken up by cells, e.g., cardiac cells, and the transcription factor may be expressed under the appropriate physiological conditions. The LTF encoded by the vector will be expressed under hypoxic conditions associated with, e.g., cardiac ischemia. Ligand will be administered to the subject to be treated which will combine with the expressed LDTFC to drive expression of TGF-1 under control of the factor-regulated promoter. IGF-1 expression in turn promotes targeted angiogenesis in the ischemic tissue.

Example 2

This example describes a bioreactor/cell therapy vector useful for the treatment of ischemic cardiovascular disease through the promotion of angiogenesis and cardioprotection. The vector, shown in FIG. 6, will confer expression of human basic fibroblast growth factor (bFGF, GenBank Accession No.: NP_001997, SEQ ID NO:21) upon administration of ligand, under hypoxic conditions which occur in ischemic tissue.

SEQ ID NO: 21:
MVGVGGGDVEDVTPRPGGCQISGRGARGCNGIPGAAAWEAALPRRRPRRH

PSVNPRSRAAGSPRTRGRRTEERPSGSRLGDRGRGRALPGGRLGGRGRGR

APERVGGRGRGRGTAAPRAAPAARGSRPGPAGTMAAGSITTLPALPEDGG

SGAFPPGHFKDPKRLYCKNGGFFLRIHPDGRVDGVREKSDPHIKLQLQAE

ERGVVSIKGVCANRYLAMKEDGRLLASKCVTDECFFFERLESNNYNTYRS

RKYTSWYVALKRTGQYKLGSKTGPGQKAILFLPMSAKS

Figure 6:
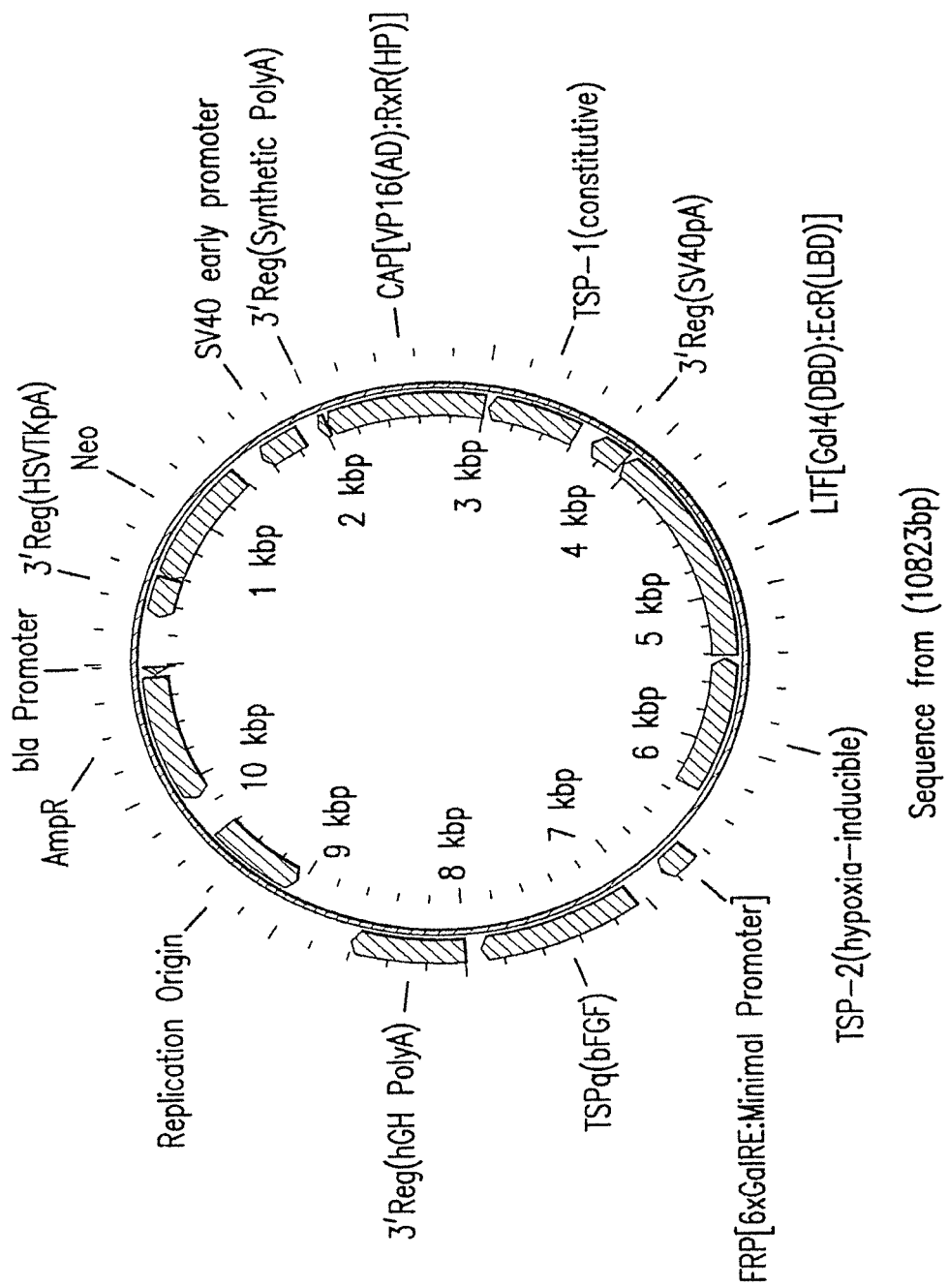
FIG. 6 is a diagram of a vector constructed under the scheme shown in FIG. 2, and engineered to express basic fibroblast growth factor (bFGF) under hypoxic conditions such as cardiac ischemia.

The complete nucleotide sequence of the construct shown in FIG. 6 is presented as SEQ ID NO:8. The nucleotide coordinates for salient elements of the construct are shown in Table 5.

TABLE 5

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1 (constitutive) | reverse | 571 | 3026 | 3596 |
| 3'Reg(SV40pA) | reverse | 221 | 3719 | 3939 |
| LTF[Gal4(DBD):EcR(LBD)] | reverse | 1467 | 3946 | 5412 |
| TSP-2(hypoxia-inducible) | reverse | 870 | 5446 | 6315 |
| FRP[6x GalRE:Minimal Promoter] | forward | 189 | 6648 | 6836 |
| TSPq(bFGF) | forward | 867 | 7050 | 7916 |
| 3'Reg(hGH PolyA) | forward | 627 | 7989 | 8615 |
| Replication Origin | reverse | 589 | 9049 | 9637 |
| AmpR | reverse | 858 | 9882 | 10739 |
| bla Promoter | reverse | 39 | 10773 | 10811 |

The vector shown in FIG. 6 is modeled according to the gene switch system shown in FIG. 2. Under this system, the CAP subunit of the LDTFC is expressed through operable association with a first, constitutive therapeutic switch promoter, TSP-1, and the LTF subunit of the LDTFC is expressed through operable association with a second, inducible therapeutic switch promoter (TSP-2). The promoter used in this construct is the hypoxia-inducible control promoter-1.

The coding region for the therapeutic product, bFGF, is operably associated with a FRP which is activated upon contact with the LDTFC in the presence of ligand.

The construct shown in FIG. 6 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and the LTF encoded by the vector will be expressed under hypoxic conditions associated with, e.g., cardiac ischemia. Ligand will be administered to the subject to be treated which will combine with the expressed LDTFC to drive expression of bFGF under control of the FRP. bFGF expression in turn promotes targeted angiogenesis and/or cardioprotection in the ischemic tissue.

Example 3

This example describes a bioreactor/cell therapy vector useful for the treatment of ischemic cardiovascular disease through the promotion of cardioprotection. The vector, shown in FIG. 7, will confer expression of human erythropoietin (EPO, GenBank Accession No.: CAA26095.1, SEQ ID NO:22) upon administration of ligand, under hypoxic conditions which occur in ischemic tissue. Erythropoietin has been shown to function in cardioprotection and anti-remodeling, in response to ischemia.

```
SEQ ID NO: 22:
MGVHECPAWLWLLLSLLSLPLGLPVLGAPPRLICDSRVLQRYLLEAKEAE

NITTGCAEHCSLNENITVPDTKVNEYAWKRMEVGQQAVEVWQGLALLSEA

VLRGQALLVNSSQPWEPLQLHVDKAVSGLRSLTTLLRALGAQKEAISPPD

AASAAPLRTITADTFRKLFRVYSNFLRGKLKLYTGEACRTGDR
```

Figure 7:
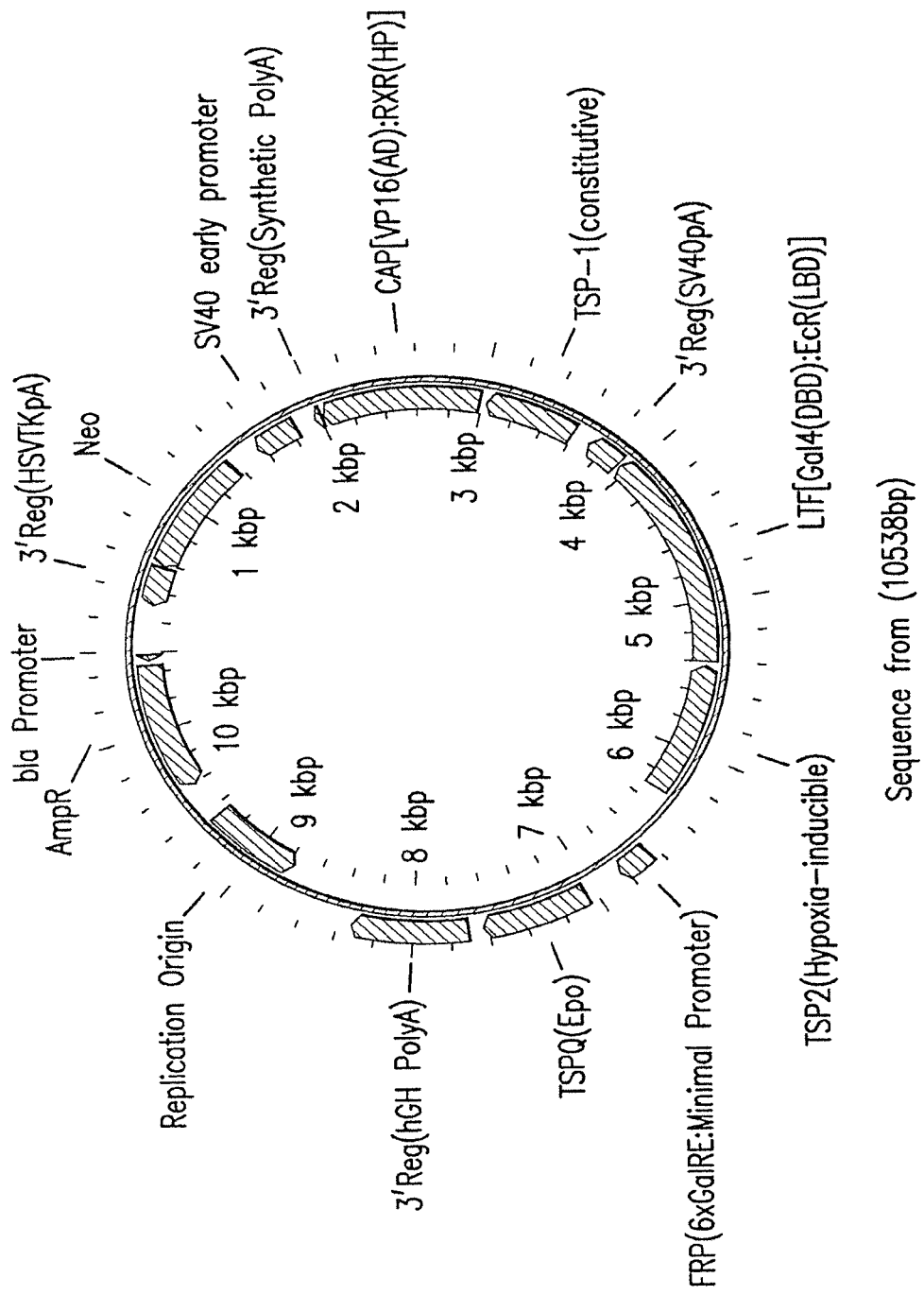
FIG. 7 is a diagram of a vector constructed under the scheme shown in FIG. 2, and engineered to express erythropoietin (EPO) under hypoxic conditions such as cardiac ischemia.

The complete nucleotide sequence of the construct shown in FIG. 7 is presented as SEQ ID NO:9. The nucleotide coordinates for salient elements of the construct are shown in Table 6.

TABLE 6

| Label | Direction | Length | Start | End |
| --- | --- | --- | --- | --- |
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1(constitutive) | reverse | 571 | 3026 | 3596 |
| 3'Reg(SV40pA) | reverse | 221 | 3719 | 3939 |
| LTF[Gal4(DBD):EcR(LBD)] | reverse | 1467 | 3946 | 5412 |
| TSP2(Hypoxia-inducible) | reverse | 870 | 5446 | 6315 |
| FRP(6x GalRE:minimal promoter) | forward | 189 | 6648 | 6836 |
| TSPQ(Epo) | forward | 582 | 7050 | 7631 |
| 3'Reg(hGH PolyA) | forward | 627 | 7704 | 8330 |
| Replication Origin | reverse | 589 | 8764 | 9352 |
| AmpR | reverse | 858 | 9597 | 10454 |
| bla Promoter | reverse | 39 | 10488 | 10526 |

The vector shown in FIG. 7 is modeled according to the gene switch system shown in FIG. 2. Under this system, the CAP subunit of the LDTFC is expressed through operable association with a first, constitutive therapeutic switch promoter (TSP-1), and the LTF subunit of the LDTFC is expressed through operable association with a second, inducible therapeutic switch promoter (TSP-2). The inducible therapeutic switch promoter used in this vector is the hypoxia-inducible control promoter-1.

The coding region for the therapeutic product, EPO, is operably associated with a FRP which is activated upon contact with the LDTFC in the presence of ligand.

The construct shown in FIG. 7 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and LTF encoded by the vector will be expressed under hypoxic conditions associated with, e.g., cardiac ischemia. Ligand will be administered to the subject to be treated which will combine with the expressed LDTFC to drive expression of EPO under control of the FRP. EPO expression in turn promotes targeted cardioprotection in the ischemic tissue.

Example 4

This example describes a bioreactor/cell therapy vector useful for the treatment of ischemic cardiovascular disease through the promotion of antiogenesis and hemodynamics. The vector, shown in FIG. 8, will confer expression of human brain natriuretic factor (BNP, GenBank Accession No.: NP_002512, SEQ ID NO:23) upon administration of ligand, under hypoxic conditions which occur in ischemic tissue. BNP, as well as other natriuretic peptides, such as relaxin, ANF, CNP and adrenomodulin, has been shown to function in cardioprotection, vasodilation and anti-remodeling, in the heart. For this purpose, an example of inducible expression of BNP, in response to ischemia is given.

```
SEQ ID NO: 23:
MDPQTAPSRALLLLLFLHLAFLGGRSHPLGSPGSASDLETSGLQEQRNHL

QGKLSELQVEQTSLEPLQESPRPTGVWKSREVATEGIRGHRKMVLYTLRA

PRSPKMVQGSGCFGRKMDRISSSSGLGCKVLRRH
```

Figure 8:
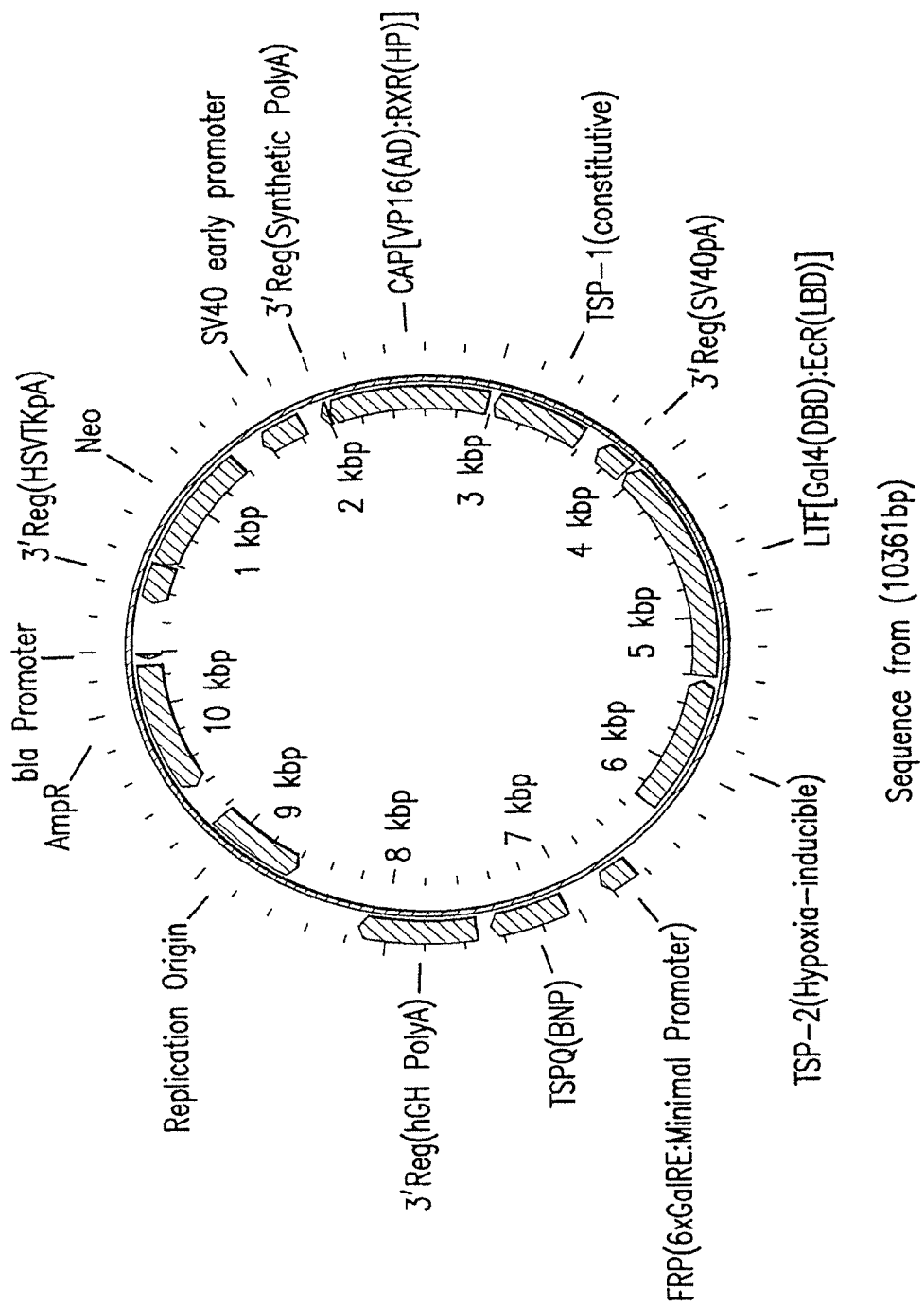
FIG. 8 is a diagram of a vector constructed under the scheme shown in FIG. 2, and engineered to express human B-type natriuretic peptide (BNP) under hypoxic conditions such as cardiac ischemia.

The complete nucleotide sequence of the construct shown in FIG. 8 is presented as SEQ ID NO:10. The nucleotide coordinates for salient elements of the construct are shown in Table 7.

TABLE 7

| Label | Direction | Length | Start | End |
| --- | --- | --- | --- | --- |
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1(constitutive) | reverse | 571 | 3026 | 3596 |
| 3'Reg(SV40pA) | reverse | 221 | 3719 | 3939 |

TABLE 7-continued

| Label | Direction | Length | Start | End |
|---|---|---|---|---|
| LTF[GAL4(DBD):EcR(LBD)] | reverse | 1467 | 3946 | 5412 |
| TSP-2(Hypoxia-inducible) | reverse | 870 | 5446 | 6315 |
| FRP(6x GalRE:Minimal Promoter) | forward | 189 | 6648 | 6836 |
| TSPQ(BNP) | forward | 405 | 7050 | 7454 |
| 3'Reg(hGH PolyA) | forward | 627 | 7527 | 8153 |
| Replication Origin | reverse | 589 | 8587 | 9175 |
| AmpR | reverse | 858 | 9420 | 10277 |
| bla Promoter | reverse | 39 | 10311 | 10349 |

The vector shown in FIG. 8 is modeled according to the gene switch system shown in FIG. 2. Under this system, the CAP subunit of the LDTFC is expressed through operable association with a first, constitutive therapeutic switch promoter (TSP-1), and the LTF subunit of the LDTFC is expressed through operable association with a second, inducible therapeutic switch promoter (TSP-2). The inducible TSP-2 used in this vector is the hypoxia-inducible control promoter-1.

The coding region for the therapeutic product, BNP, is operably associated with a FRP which is activated upon contact with the LDTFC in the presence of ligand.

The construct shown in FIG. 8 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and the LTF encoded by the vector will be expressed under hypoxic conditions associated with, e.g., cardiac ischemia. Ligand will be administered to the subject to be treated which will combine with the expressed LDTFC to drive expression of BNP under control of the FRP. BNP expression in turn promotes targeted cardioprotection, vasodilation and anti-remodeling in the ischemic tissue.

Example 5

This example describes a bioreactor/cell therapy vector useful for the treatment of ischemic cardiovascular disease through the breakdown of fibrin deposition in the heart. The vector, shown in FIG. 9, will confer expression of human tissue plasminogen activator (tPA, GenBank Accession No.: AAO34406, SEQ ID NO:24) upon administration of ligand, under inflammatory conditions which occur in ischemic tissue. Tissue plasminogen activator is a serine protease that catalyzes the conversion of plasminogen to the activated enzyme plasmin, that degrades fibrin. The use of recombinant tPA has been proven effective as a thrombolytic, for the breakdown of fibrin clots, in diseases such as pulmonary embolism, myocardial infarction and stroke. In addition to clot formation, excess fibrin deposition in the heart and vasculature is associated with insulin resistant diabetes, atherosclerosis and myocardial infarction in response to inflammation. For this purpose, an example of inducible expression of tPA, in response to ischemia is given.

SEQ ID NO: 24:
MDAMKRGLCCVLLLCGAVFVSPSQEIHARFRRGARSYQVICRDEKTQMIY

QQHQSWLRPVLRSNRVEYCWCNSGRAQCHSVPVKSCSEPRCFNGGTCQQA

LYFSDFVCQCPEGFAGKCCEIDTRATCYEDQGISYRGTWSTAESGAECTN

WNSSALAQKPYSGRRPDAIRLGLGNHNYCRNPDRDSKPWCYVFKAGKYSS

EFCSTPACSEGNSDCYFGNGSAYRGTHSLTESGASCLPWNSMILIGNVYT

AQNPSAQALGLGKHNYCRNPDGDAKPWCHVLKNRRLTWEYCDVPSCSTCG

LRQYSQPQFRIKGGLFADIASHPWQAAIFAKHRRSPGERFLCGGILISSC

WILSAAHCFQERFPPHHLTVILGRTYRVVPGEEEQKFEVEKYIVHKEFDD

DTYDNDIALLQLKSDSSRCAQESSVVRTVCLPPADLQLPDWTECELSGYG

KHEALSPFYSERLKEAHVRLYPSSRCTSQHLLNRTVTDNMLCAGDTRSGG

PQANLHDACQGDSGGPLVCLNDGRMTLVGIISWGLGCGQKDVPGVYTKVT

NYLDWIRDNMRP

Figure 9:
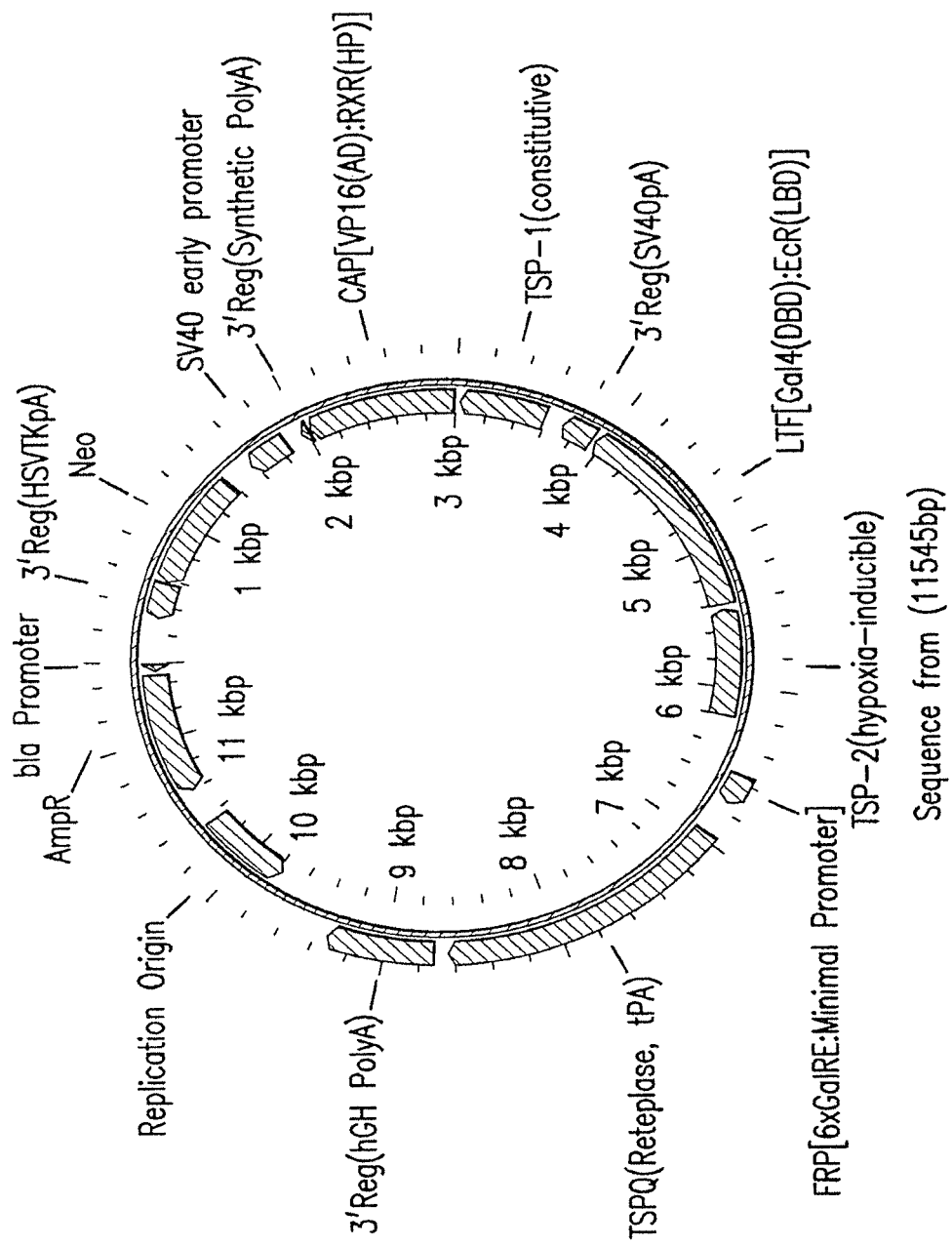
FIG. 9 is a diagram of a vector constructed under the scheme shown in FIG. 2, and engineered to express tissue plasminogen activator (tPA) under inflammatory conditions such as cardiac ischemia.

The complete nucleotide sequence of the construct shown in FIG. 9 is presented as SEQ ID NO:11. The nucleotide coordinates for salient elements of the construct are shown in Table 8.

TABLE 8

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1 (constitutive) | reverse | 571 | 3026 | 3596 |
| 3'Reg(SV40pA) | reverse | 221 | 3719 | 3939 |
| LTF[GAL4(DBD):EcR(LBD)] | reverse | 1467 | 3946 | 5412 |
| TSP-2 (hypoxia inducible) | reverse | 770 | 5446 | 6215 |
| FRP[6xGalRE:Minimal Promoter] | forward | 189 | 6548 | 6736 |
| TPSQ (Reteplase, tPA) | forward | 1689 | 6950 | 8638 |
| 3'Reg(hGH PolyA) | forward | 627 | 8711 | 9337 |
| Replication Origin | reverse | 589 | 9771 | 10359 |
| AmpR | reverse | 858 | 10604 | 11461 |
| bla Promoter | reverse | 39 | 11495 | 11533 |

The vector shown in FIG. 9 is modeled according to the gene switch system shown in FIG. 2. Under this system, the CAP subunit of the LDTFC is expressed through operable association with a first, constitutive therapeutic switch promoter (TSP-1), and the LTF subunit of the LDTFC is expressed through operable association with a second, inducible therapeutic switch promoter (TSP-2). The inducible therapeutic switch promoter used in this vector is the human Plexin D1 promoter.

The coding region for the therapeutic product, tPA, is operably associated with a FRP which is activated upon contact with the LDTFC in the presence of ligand.

The construct shown in FIG. 9 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and the LTF encoded by the vector will be expressed in the event of an inflammatory response associated with, e.g., cardiac ischemia. Ligand will be administered to the subject to be treated which will combine with the expressed LDTFC to drive expression of tPA under control of the FRP. tPA expression in turn promotes targeted break-up of fibrin deposition in the ischemic tissue.

Example 6

This example describes a bioreactor/cell therapy vector useful for the treatment of ischemic cardiovascular disease through the promotion of cardioprotection, antiogenesis and hemodynamics. The vector, shown in FIG. 10, will confer expression of two therapeutic polypeptides, human relaxin (GenBank Accession No.: NP_604390.1, SEQ ID NO:25) and human hepatocyte growth factor (HGF, GenBank Accession No.: NP_000592.3, SEQ ID NO:26) upon administration of ligand, under inflammatory conditions and/or hypoxia, respectively, both of which occur in ischemic tissue. Relaxin is a potent vasodilator of the systemic and coronary circulation by a mechanism of action involving nitric oxide, and influences cardiac beating rate. HGF provides a pro-angiogenic effect, a cardioprotective anti-apoptotic effect, an anti-fibrotic effect, and is a type I collagen regenerative factor in ischemic myocardium. For this purpose, an example of separately controlled inducible expression of relaxin and HGF in response to ischemia is given.

SEQ ID NO: 25:
MPRLFFFHLLGVCLLLNQFSRAVADSWMEEVIKLCGRELVRAQIAICGMS

TWSKRSLSQEDAPQTPRPVAEIVPSFINKDTETINMMSEEVANLPQELKL

TLSEMQPALPQLQQHVPVLKDSSLLFEEFKKLIRNRQSEAADSSPSELKY

LGLDTHSRKKRQLYSALANKCCHVGCTKRSLARFC

SEQ ID NO: 26:
MWVTKLLPALLLQHVLLHLLLLPIAIPYAEGQRKRRNTIHEFKKSAKTTL

IKIDPALKIKTKKVNTADQCANRCTRNKGLPFTCKAFVFDKARKQCLWFP

FNSMSSGVKKEFGHEFDLYENKDYIRNCIIGKGRSYKGTVSITKSGIKCQ

PWSSMIPHEHSFLPSSYRGKDLQENYCRNPRGEEGGPWCFTSNPEVRYEV

CDIPQCSEVECMTCNGESYRGLMDHTESGKICQRWDHQTPHRHKFLPERY

PDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLR

ENYCRNPDGSESPWCFTTDPNIRVGYCSQIPNCDMSHGQDCYRGNGKNYM

-continued
GNLSQTRSGLTCSMWDKNMEDLHRHIFWEPDASKLNENYCRNPDDDAHGP

WCYTGNPLIPWDYCPISRCEGDTTPTIVNLDHPVISCAKTKQLRVVNGIP

TRTNIGWMVSLRYRNKHICGGSLIKESWVLTARQCFPSRDLKDYEAWLGI

HDVHGRGDEKCKQVLNVSQLVYGPEGSDLVLMKLARPAVLDDEVSTIDLP

NYGCTIPEKTSCSVYGWGYTGLINYDGLLRVAHLYIMGNEKCSQHHRGKV

TLNESEICAGAEKIGSGPCEGDYGGPLVCEQHKMRMVLGVIVPGRGCAIP

NRPGIFVRVAYYAKWIHKIILTYKVPQS

Figure 10:
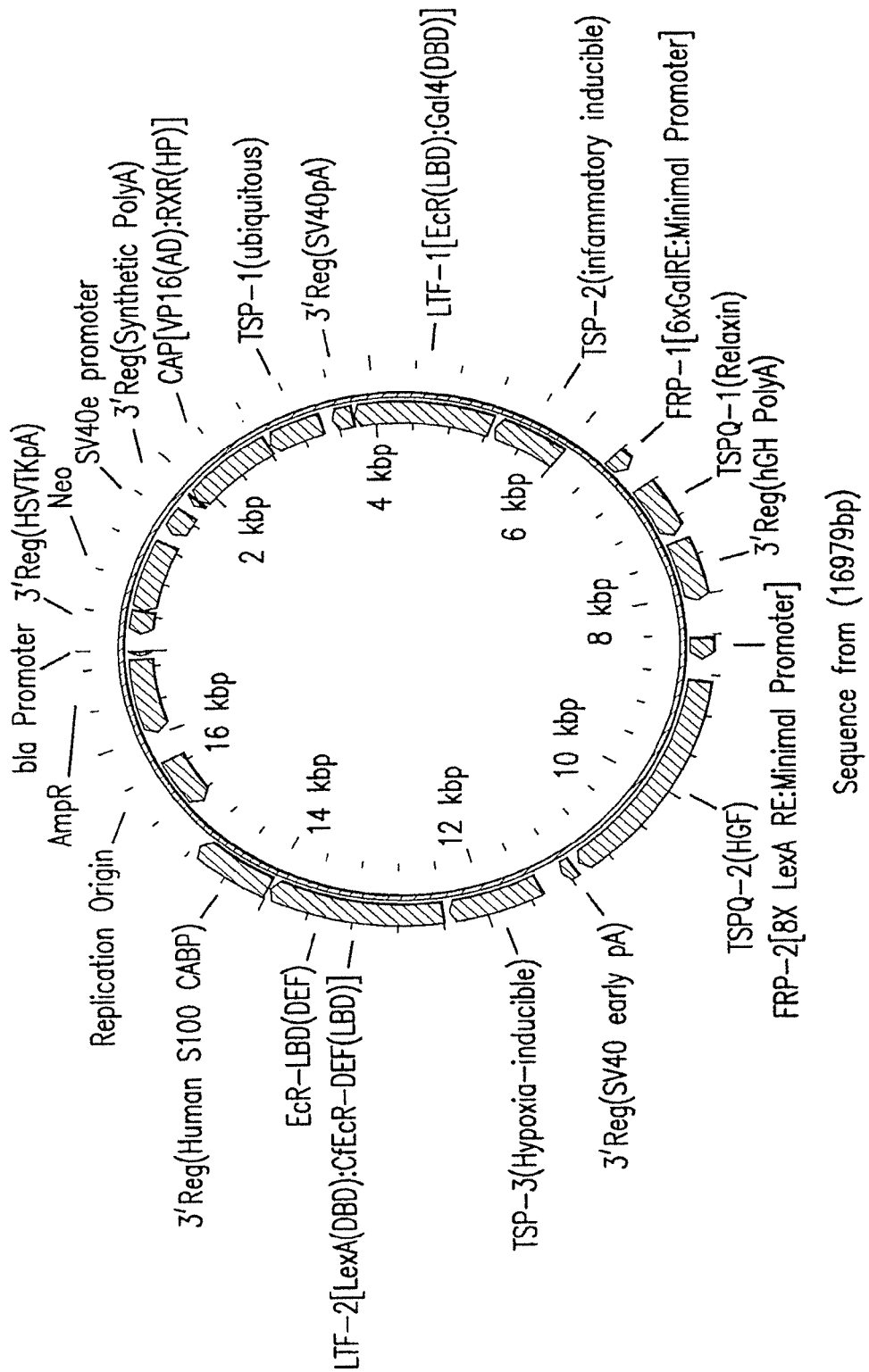
FIG. 10 is a diagram of a vector constructed under the scheme shown in FIG. 3, and engineered to express relaxin under inflammatory conditions and/or hepatocyte growth factor under hypoxic conditions, both conditions being associated with cardiac ischemia.

The complete nucleotide sequence of the construct shown in FIG. 10 is presented as SEQ ID NO:13. The nucleotide coordinates for salient elements of the construct are shown in Table 9.

TABLE 9

| Label | Direction | Length | Start | End |
|---|---|---|---|---|
| 3'Reg(HSVTKpA) | reverse | 259 | 197 | 455 |
| NEO | reverse | 804 | 462 | 1265 |
| SV40e Promoter | reverse | 280 | 1385 | 1664 |
| 3'Reg(Synthetic PolyA) | reverse | 49 | 1782 | 1830 |
| CAP[VP16(AD):RxR(HP)] | reverse | 975 | 1837 | 2811 |
| TSP-1(ubiquitous) | reverse | 571 | 2845 | 3415 |
| 3'Reg(SV40pA) | reverse | 221 | 3538 | 3758 |
| LTF-1[EcR(LBD):Gal4(DBD)] | reverse | 1467 | 3765 | 5231 |
| TSP-2(inflammatory inducible) | reverse | 770 | 5265 | 6034 |
| FRP-1[6x GalRE:Minimal Promoter] | forward | 189 | 6405 | 6593 |
| TPSQ-1(Relaxin) | forward | 558 | 6807 | 7364 |
| 3'Reg(hGH PolyA) | forward | 627 | 7437 | 8063 |
| FRP-2[8X LexA RE:Minimal Promoter] | forward | 216 | 8437 | 8652 |
| TPSQ-2(HGF) | forward | 2187 | 8866 | 11052 |
| 3'Reg(SV40 early pA) | forward | 135 | 11112 | 11246 |
| TSP-3(Hypoxia-inducible) | forward | 870 | 11478 | 12347 |
| LTF-2[LexA(DBD) CfEcR-DEF(LBD)] | forward | 1629 | 12381 | 14009 |
| EcR-LBD (DEF) | forward | 1014 | 12996 | 14009 |
| 3'Reg(Human S100 CABP) | forward | 765 | 14016 | 14780 |
| Replication Origin | reverse | 589 | 15114 | 15702 |
| AmpR | reverse | 858 | 16038 | 16895 |
| bla Promoter | reverse | 39 | 16929 | 16967 |

The vector shown in FIG. 10 is modeled according to the gene switch system shown in FIG. 3. Under this system, the CAP subunit of the LDTFC is expressed through operable association with a first, constitutive therapeutic switch promoter (TSP-1), a first LTF (LTF-1) subunit is expressed through operable association with a second, inducible therapeutic switch promoter (TSP-2), and a second LTF (LTF-2) subunit is expressed through operable association with a third, inducible therapeutic switch promoter (TSP-3). TSP-2 in this vector is the human Plexin D1 promoter and TSP-3 in this vector is the hypoxia-inducible control promoter 1.

The coding region for the first therapeutic product, relaxin, is operably associated with a first FRP (FRP-1) having response elements which recognize the first DNA binding domain DBD-A of LTF-1, and the coding region for the second therapeutic product, HGF, is operably associated with a second FRP (FRP-2) having response elements which recognize the second DNA binding domain (DBD-B) of LTF-2. Both FRPs are activated upon contact with the respective LDTFC in the presence of ligand.

The construct shown in FIG. 10 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of cell-based therapies are well known in the art. Upon delivery the vector will be taken up by cells, e.g., cardiac cells, and the LTF-1 and/or LTF-2 will be expressed in the event of an inflammatory response and/or hypoxia associated with, e.g., cardiac ischemia. One or more ligands will be administered to the subject to be treated which will combine with the expressed LDTFC(s) to drive expression of relaxin and/or HGF under control of FRPs.

Example 7

This example describes a bioreactor/cell therapy vector useful for the treatment of ischemic cardiovascular disease through the promotion of cardiac repair and cardioprotection. The vector, shown in FIG. 11, will confer expression of human EPO (see Example 3) upon administration of ligand, under hypoxic conditions which occur in ischemic tissue. EPO has been shown to function in cardioprotection and anti-remodeling, in response to ischemic. In this example, EPO expression is specifically limited to cardiac tissue.

Figure 11:
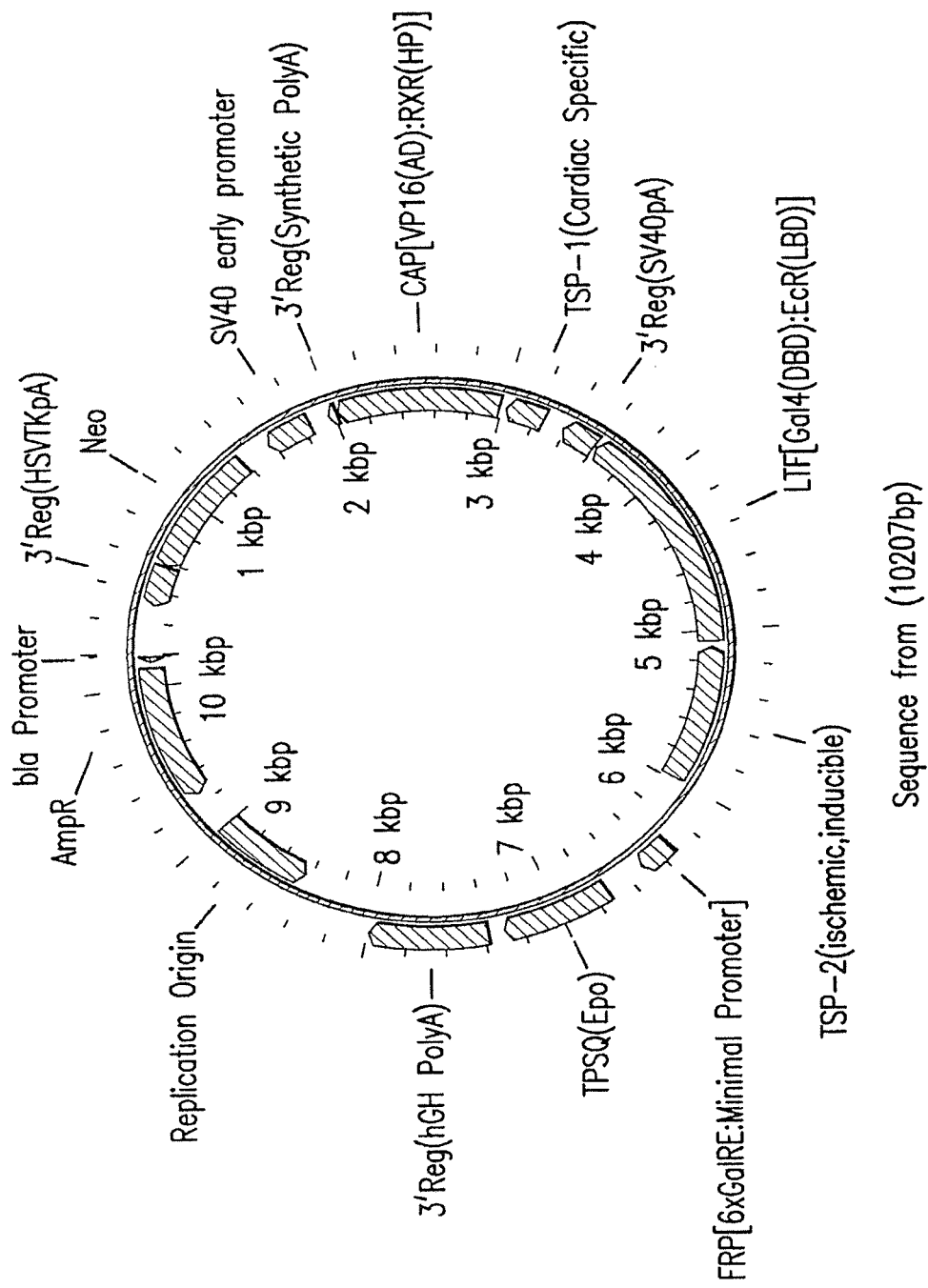
FIG. 11 is a diagram of a vector constructed under the scheme shown in FIG. 2, and engineered to express EPO under hypoxic conditions such as cardiac ischemia with expression being limited to cardiac myocytes.

The vector shown in FIG. 11 is modeled according to the gene switch system shown in FIG. 2. Under this system, the CAP subunit is expressed through operable association with a promoter which is specific for cardiac tissue (Nxc1 cardiomyocyte-specific promoter), and the LTF subunit is expressed through operable association with the hypoxia-inducible control promoter-1.

The coding region for the therapeutic product, EPO, is operably associated with a FRP which is activated upon contact with the LDTFC in the presence of ligand.

The complete nucleotide sequence of the construct shown in FIG. 11 is presented as SEQ ID NO:12. The nucleotide coordinates for salient elements of the construct are shown in Table 10.

The construct shown in FIG. 11 is inserted into a suitable vector system, for example, a viral vector, for delivery to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of gene therapy vectors are well known in the art. Upon delivery the vector will be taken up by cells, e.g., cardiac cells, and the LDTFC may be expressed under the appropriate physiological conditions. The LDTFC encoded by the vector will be expressed specifically in cardiomyocytes under hypoxic conditions associated with, e.g., cardiac ischemia. Ligand will be administered to the subject to be treated which will combine with the expressed LDTFC to drive expression of EPO under control of the FRP. EPO expression in turn promotes targeted cardioprotection in the ischemic tissue.

Example 8

This example describes a gene therapy vector useful for the treatment of ischemic heart disease through the promotion of cardiac repair and angiogenesis. The vector, shown in FIG. 12, will confer expression of human IGF-1 (see Example 1) upon administration of ligand, under either hypoxic conditions in an inflammatory response, both of which may occur in ischemic tissue. For this purpose, an example of inducible IGF-1 expression, in response to hypoxia and/or an inflammatory response is given. In this example, inducible expression if IGF-1 is specifically limited to cardiomyocytes.

Figure 12:
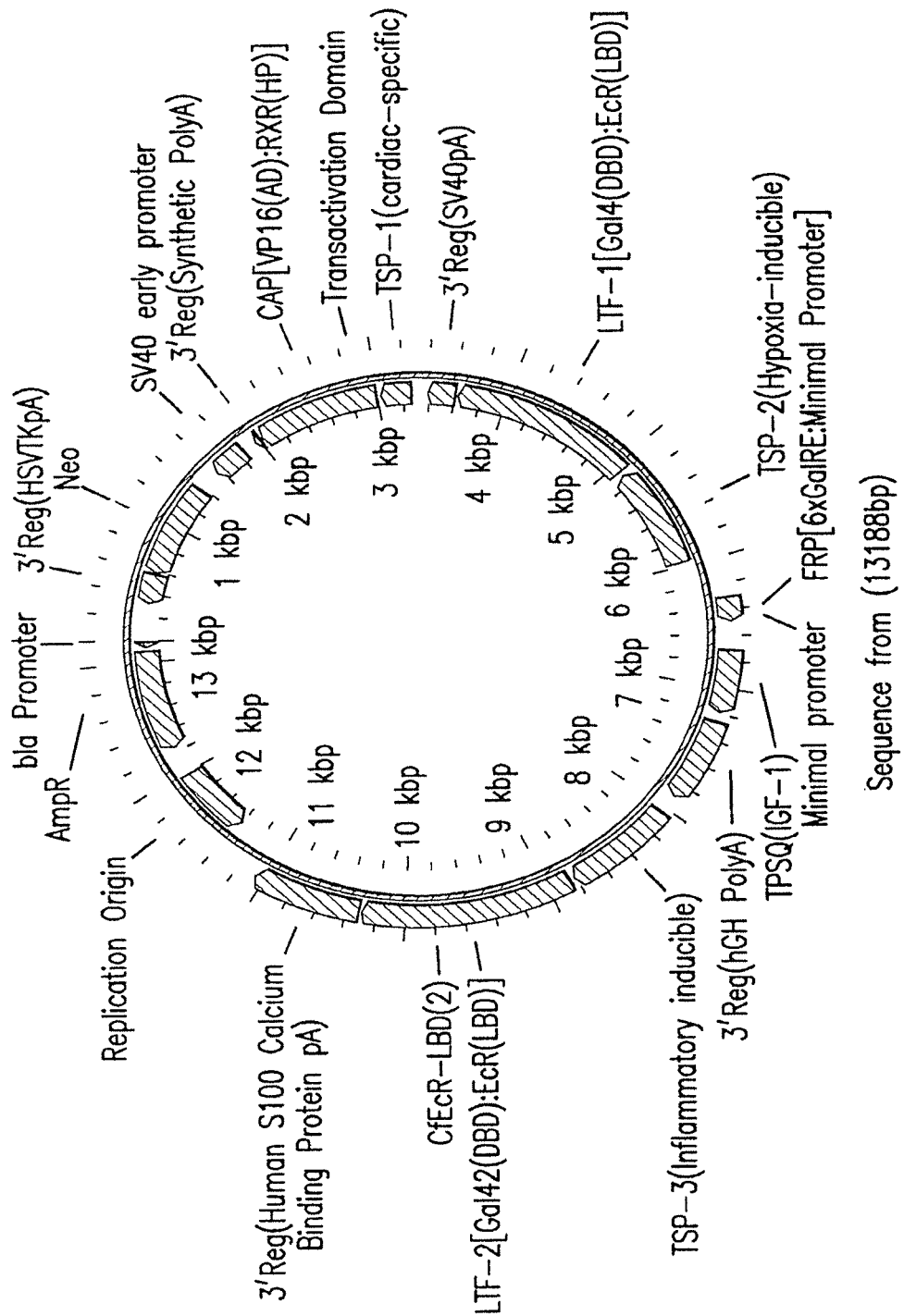
FIG. 12 is a diagram of a vector constructed under the scheme shown in FIG. 4, and engineered to express IGF-1 under either inflammatory conditions or hypoxic conditions such as cardiac ischemia with expression being limited to cardiac myocytes.

The vector shown in FIG. 12 is modeled according to the gene switch system shown in FIG. 4. Under this system, the CAP subunit is expressed through operable association with a promoter which is specific for cardiac tissue (Nxc1 cardiomyocyte-specific promoter), and LTF subunits (LTF-1 and LTF-2) of the LDTFC are expressed through either of two inducible TSPs, the first through operable association with the hypoxia-inducible control promoter-1, and the second through operable association with the human plexin D1 promoter.

The coding region for the therapeutic product, IGF-1, is operably associated with a FRP which is activated upon contact with the LDTFC in the presence of ligand.

The complete nucleotide sequence of the construct shown in FIG. 12 is presented as SEQ ID NO:14. The nucleotide coordinates for salient elements of the construct are shown in Table 11.

TABLE 10

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| TSP-1(Cardiac Specific) | reverse | 240 | 3026 | 3265 |
| 3'Reg(SV40pA) | reverse | 221 | 3388 | 3608 |
| LTF[Gal4(DBD):EcR(LBD)] | reverse | 1467 | 3615 | 5081 |
| TSP-2(ischemic, inducible) | reverse | 870 | 5115 | 5984 |
| FRP[6x GalRE:Minimal Promoter] | forward | 189 | 6317 | 6505 |
| TPSQ (Epo) | forward | 582 | 6719 | 7300 |
| 3'Reg(hGH PolyA) | forward | 627 | 7373 | 7999 |
| Replication Origin | reverse | 589 | 8433 | 9021 |
| AmpR | reverse | 858 | 9266 | 10123 |
| bla Promoter | reverse | 39 | 10157 | 10195 |

TABLE 11

| Label | Direction | Length | Start | End |
|---|---|---|---|---|
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| Transactivation Domain | reverse | 261 | 2732 | 2992 |
| TSP-1(cardiac-specific) | reverse | 240 | 3026 | 3265 |
| 3'Reg(SV40pA) | reverse | 221 | 3388 | 3608 |
| LTF-1[Gal4(DBD):EcR(LBD)] | reverse | 1467 | 3615 | 5081 |
| TSP-2(Hypoxia-inducible) | reverse | 870 | 5115 | 5984 |
| FRP[6xGalRE:Minimal promoter] | forward | 189 | 6317 | 6505 |
| Minimal promoter | forward | 60 | 6446 | 6505 |
| TPSQ (IGF-1) | forward | 477 | 6719 | 7195 |
| 3'Reg(hGH PolyA) | forward | 627 | 7268 | 7894 |
| TSP-3(Inflammatory inducible) | forward | 770 | 8040 | 8809 |
| LTF-2[Gal42(DBD):EcR(LBD)] | forward | 1467 | 8843 | 10309 |

TABLE 11-continued

| Label | Direction | Length | Start | End |
| --- | --- | --- | --- | --- |
| CfEcR-LBD(2) | forward | 1014 | 9296 | 10309 |
| 3'Reg(Human S100 Calcium Binding Protein pA) | forward | 765 | 10316 | 11080 |
| Replication Origin | reverse | 589 | 11414 | 12002 |
| AmpR | reverse | 858 | 12247 | 13104 |
| bla Promoter | reverse | 39 | 13138 | 13176 |

The construct shown in FIG. 12 is inserted into a suitable vector system, for example, a viral vector, for delivery to a subject in need of treatment for ischemic heart disease.

The vector may be delivered to a subject systemically, for example, via intravenous infusion, or may be delivered directly to cardiac tissue, e.g., via angioplasty. Methods for systemic and/or local administration of gene therapy vectors are well known in the art. Upon delivery the vector will be taken up by cells, e.g., cardiac cells, and the LDTFC may be expressed under the appropriate physiological conditions. The LDTFC encoded by the vector will be expressed specifically in cardiomyocytes under hypoxic conditions, and/or in the event of an inflammatory response, associated with, e.g., cardiac ischemia. Ligand will be administered to the subject to be treated which will combine with the expressed transcription factor to drive expression of IGF-1 under control of the FRP. IGF-1 expression in turn promotes targeted angiogenesis in the ischemic tissue.

Example 9

This example describes a bioreactor/cell therapy vector useful for the treatment of rheumatoid arthritis, active ankylosing spondylitis or plaque psoriasis or for inhibition of structural damage by the active arthritis ("RA or related diseases"). Conventional treatment of RA and related diseases includes traditional Disease Modifying Anti-Rheumatic Drugs (DMARDs) as well as biologic DMARDs such as etanercept, infliximab, and adalimumab. For example, etanercept (Enbrel®), manufactured by Amgen, is a fusion protein that contains two extracellular domains of human TNF-alpha receptor 2 fused to a Fc portion by a hinge peptide. See U.S. Pat. No. 7,276,477 (incorporated herein by reference in its entirety). Etanercept should be administered s.c. once or twice a week. Use of the etanercept gene switch system utilizing inflammation or cytokine response promoters may therefore increase convenience and safety by limiting any production of etanercept in the absence of TNF activation.

Figure 13:
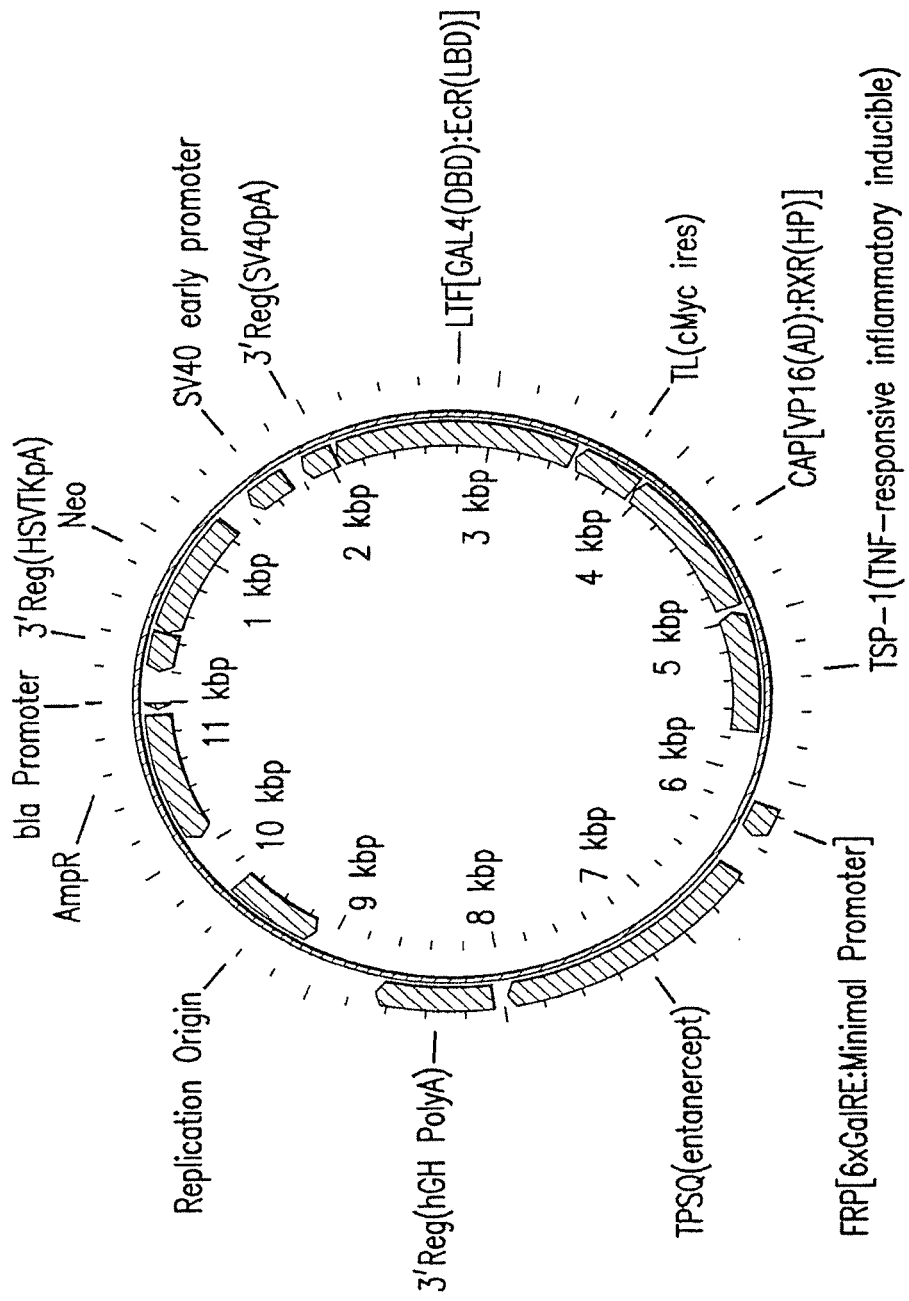
FIG. 13 is a diagram of a vector constructed under the scheme shown in FIG. 1, and engineered to express tumor necrosis factor binding protein 2 (Enbrel®) under inflammatory conditions such as rheumatoid arthritis.

The complete nucleotide sequence of the construct shown in FIG. 13 is presented as SEQ ID NO: 16. The nucleotide coordinates for salient elements of the construct are shown in Table 12.

TABLE 12

| Label | Direction | Length | Start | End |
| --- | --- | --- | --- | --- |
| 3'Reg(HSVTKpA) | reverse | 259 | 197 | 455 |
| Neo | reverse | 795 | 462 | 1256 |
| SV40 early promoter | reverse | 278 | 1446 | 1723 |
| 3'Reg(SV40pA) | reverse | 221 | 1830 | 2050 |
| LTF[GAL4(DBD):EcR(LBD)] | reverse | 1467 | 2057 | 3523 |
| TL(cMyc ires) | reverse | 408 | 3536 | 3943 |
| CAP[VP16(AD):RxR(HP)] | reverse | 975 | 3950 | 4924 |
| TSP-1(TNF-responsive inflammatory inducible) | reverse | 800 | 4958 | 5757 |
| FRP[6x GalRE:Minimal Promoter] | forward | 189 | 6168 | 6356 |

TABLE 12-continued

| Label | Direction | Length | Start | End |
| --- | --- | --- | --- | --- |
| TPSQ(entanercept) | forward | 1407 | 6570 | 7976 |
| 3'Reg(hGH PolyA) | forward | 627 | 8049 | 8675 |
| Replication Origin | reverse | 589 | 9109 | 9697 |
| AmpR | reverse | 858 | 10072 | 10929 |
| bla Promoter | reverse | 39 | 10963 | 11001 |

The vector shown in FIG. 13 is modeled according to the gene switch system shown in FIG. 1. Under this system, both the CAP subunit and the LTF subunit of the LDTFC are expressed through operable association with a single TSP-1 via use of an internal ribosome entry site (IRES). The promoter utilized in this system is a vascular cell adhesion molecule (VCAM1) promoter, which is activated by TNF-alpha. Another example of the TNF-alpha regulated promoters that may be used for the invention is human pentraxin 3 (PTX3) promoter, which is responsive to TNF-alpha or Interleukin (IL)-1 beta. See Basile et al., *J. Biol. Chem.* 272(13): 8172 (1997).

The coding region for the therapeutic product, etanercept, is operably associated with a FRP which is activated upon contact with the LDTFC in the presence of ligand.

The construct shown in FIG. 13 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for RA.

The cells may be delivered to a subject systemically, for example, via intravenous infusion, or may be delivered directly to joints. Systemic and/or local administration of gene therapy cells are well known in the art. Upon delivery of the cells, the LDTFC may be expressed under the appropriate physiological conditions. The LDTFC encoded by the vector will be expressed in the presence of TNF-alpha associated with, e.g., RA. Ligand will be administered to the subject to be treated which will combine with the expressed LDTFC to drive expression of etanercept under control of the TNF-alpha regulated promoter. Etanercept expression in turn captures TNF-alpha and reduces the TNF-alpha concentration in the tissues.

Example 10

This example describes a bioreactor/cell therapy vector useful for the treatment of RA and related disease through reducing the TNF-alpha level. The vector shown in FIG. 14 will confer expression of etanercept upon administration of ligand, under either the presence of TNF-alpha and/or severe inflammation, both of which may occur in RA or related diseases. For this purpose, an example of inducible etanercept expression, in response to the presence of TNF-alpha and/or an inflammatory response is given.

Figure 14:
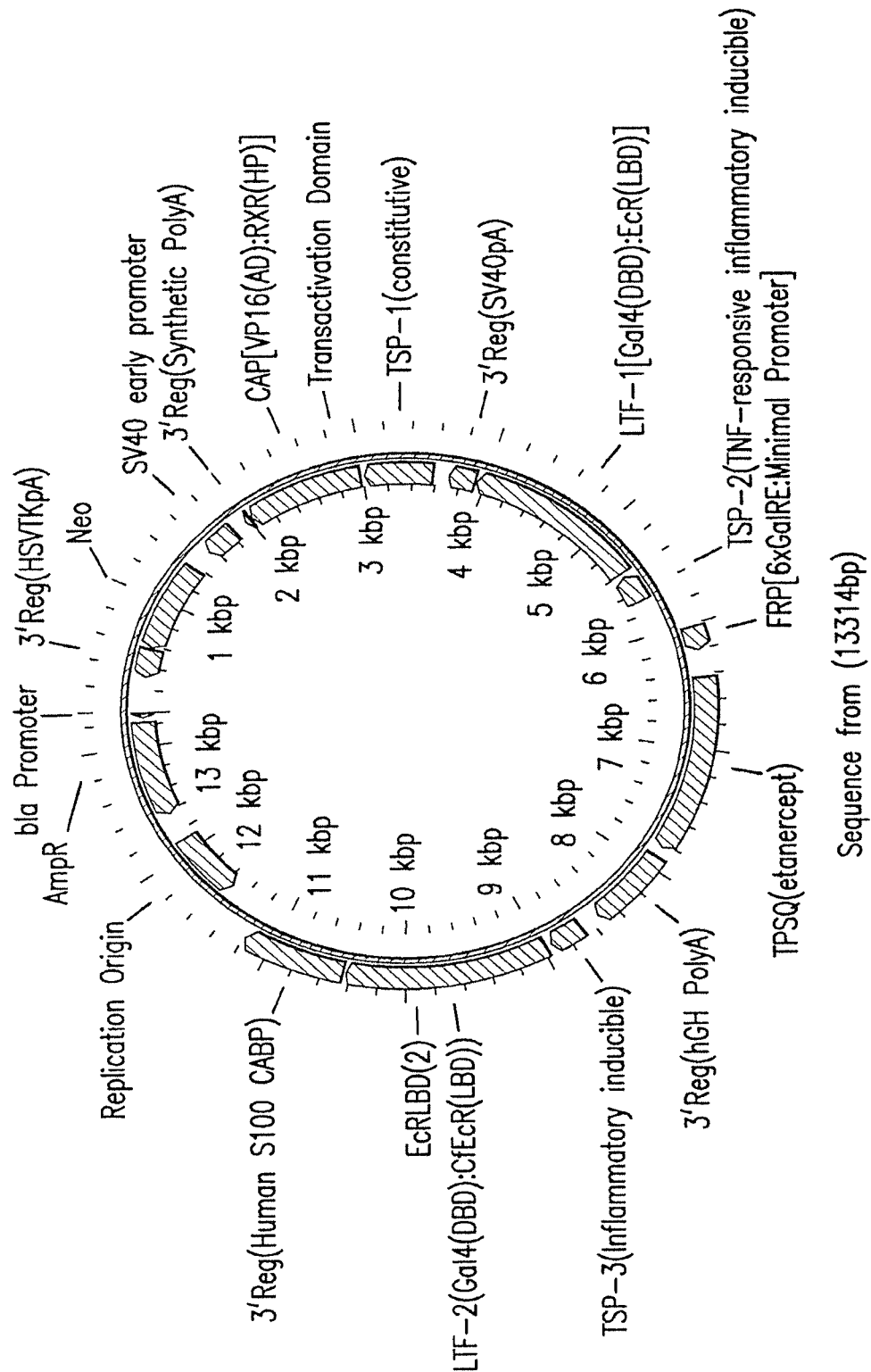
FIG. 14 is a diagram of a vector constructed under the scheme shown in FIG. 4, and engineered to express tumor necrosis factor binding protein 2 (Enbrel®) either in response to TNF alpha expression or under inflammatory conditions, both conditions associated with rheumatoid arthritis.

The vector shown in FIG. 14 is modeled according to the gene switch system shown in FIG. 4. Under this system, the CAP subunit is expressed through operable association with a constitutive promoter (TSP-1), and a LTF subunit of a LDTFC is expressed by either of two inducible transcription cassettes, the first (LTF-1) through operable association with human plasminogen activator inhibitor type-2 (PAI2) promoter (TSP-2), and the second (LTF-2) through operable association with the human scrum amyloid A1 (SAA1) promoter (TSP-3). The human PAI2 promoter is activated in the presence of TNF-alpha. See Mahony et al. *Eur. J. Biochem.* 263(3) (1999) and Matsuo et al., *Biochem. J.* 405: 605 (2007). The SAA1 promoter is upregulated not directly by proinflammatory cytokines such as TNF-alpha, but by other acute inflammatory signals such as glucocorticoid. See Kumon et al., *Scandinavian J. Immunol.* 56: 504 (2002).

The coding region for the therapeutic product, etanercept, is operably associated with a FRP which is activated upon contact with the LDTFC in the presence of ligand.

The complete nucleotide sequence of the construct shown in FIG. 14 is presented as SEQ ID NO: 15. The nucleotide coordinates for salient elements of the construct are shown in Table 13.

TABLE 13

| Label | Direction | Length | Start | End |
| --- | --- | --- | --- | --- |
| 3'Reg(HSVTKpA) | reverse | 259 | 318 | 576 |
| Neo | reverse | 795 | 583 | 1377 |
| SV40 early promoter | reverse | 278 | 1567 | 1844 |
| 3'Reg(Synthetic PolyA) | reverse | 49 | 1963 | 2011 |
| CAP[VP16(AD):RxR(HP)] | reverse | 975 | 2018 | 2992 |
| Transactivation Domain | reverse | 261 | 2732 | 2992 |
| TSP-1(constitutive) | reverse | 571 | 3026 | 3596 |
| 3'Reg(SV40pA) | reverse | 221 | 3719 | 3939 |
| LTF-1[Gal4(DBD):EcR(LBD)] | reverse | 1467 | 3946 | 5412 |
| TSP-2(TNF-responsive Inflammatory inducible) | reverse | 252 | 5446 | 5697 |
| FRP[6x GalRE:Minimal Promoter] | forward | 189 | 6030 | 6218 |
| TPSQ(etanercept) | forward | 1407 | 6432 | 7838 |
| 3'Reg(hGH PolyA) | forward | 627 | 7911 | 8537 |
| TSP-3(Inflammatory inducible) | forward | 253 | 8683 | 8935 |
| LTF-2(Gal4(DBD):CfEcR (LBD)) | forward | 1467 | 8969 | 10435 |
| EcRLBD(2) | forward | 1014 | 9422 | 10435 |
| 3'Reg(Human S100 CABP) | forward | 765 | 10442 | 11206 |
| Replication Origin | reverse | 589 | 11540 | 12128 |
| AmpR | reverse | 858 | 12373 | 13230 |
| bla Promoter | reverse | 39 | 13264 | 13302 |

The construct shown in FIG. 14 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for RA.

The cells may be delivered to a subject systemically, for example, via intravenous infusion, or may be delivered directly to joints. Methods for systemic and/or local administration of gene therapy cells are well known in the art. Upon delivery of the cells, the LDTFC may be expressed under the appropriate physiological conditions. The LDTFC encoded by the vector will be expressed specifically in the administered cells under the presence of TNF-alpha and/or severe inflammation. Ligand will be administered to the subject to be treated which will combine with the expressed LDTFC to drive expression of etanercept under control of the FRP. Etanercept expression in turn captures TNF-alpha and reduces the TNF-alpha concentration in the tissues.

Example 11

This example describes a bioreactor/cell therapy vector useful for the treatment of RA. The vector will confer expression of two therapeutic polypeptides, etanercept and human erythropoietin (EPO) upon administration of ligand, under the presence of TNF-alpha and/or inflammatory conditions, respectively, both of which occur in RA patients. EPO induces erythrogenesis in anemic RA patients. See Mercuriali et al. *Transfusion* 34(6): 501 (2003). For this purpose, an example of separately controlled inducible expression of etanercept and EPO in response to RA and anemia, respectively, is given.

Figure 15:
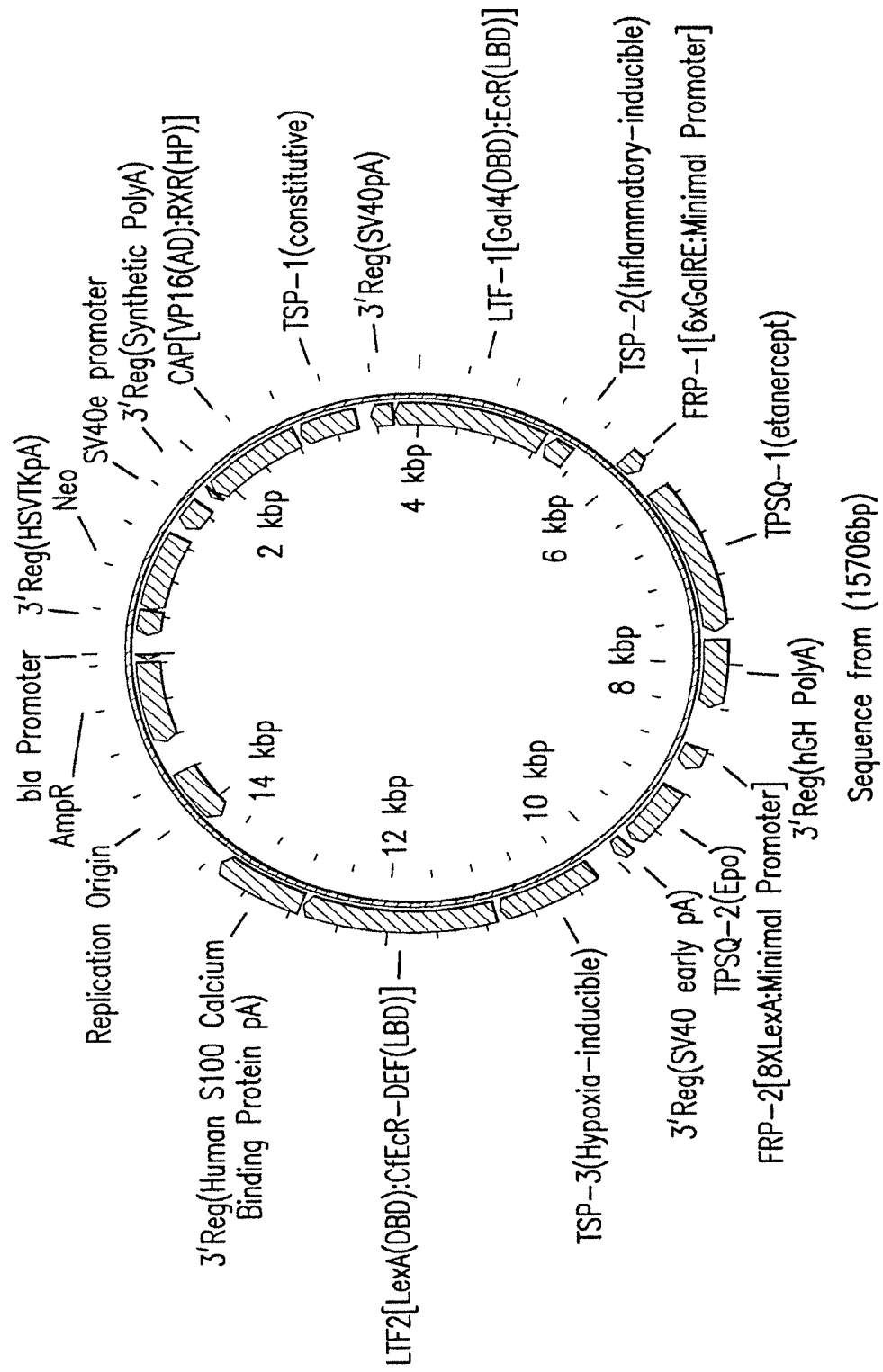
FIG. 15 is a diagram of a vector constructed under the scheme shown in FIG. 3, and engineered to express tumor necrosis factor binding protein 2 (Enbrel®) under inflammatory conditions and/or EPO under HIF-driven hypoxic conditions, both conditions being associated with rheumatoid arthritis.

The complete nucleotide sequence of the construct shown in FIG. 15 is presented as SEQ ID NO: 17. The nucleotide coordinates for salient elements of the construct are shown in Table 14.

TABLE 14

| Label | Direction | Length | Start | End |
| --- | --- | --- | --- | --- |
| 3'Reg(HSVTKpA) | reverse | 259 | 197 | 455 |
| NEO | reverse | 804 | 462 | 1265 |
| SV40e Promoter | reverse | 280 | 1385 | 1664 |
| 3'Reg(Synthetic PolyA) | reverse | 49 | 1782 | 1830 |
| CAP[VP16(AD):RxR(HP)] | reverse | 975 | 1837 | 2811 |
| TSP-1(constitutive) | reverse | 571 | 2845 | 3415 |
| 3'Reg(SV40pA) | reverse | 221 | 3538 | 3758 |
| LTF-1[Gal4(DBD):EcR(LBD)] | reverse | 1467 | 3765 | 5231 |
| TSP-2(Inflammatory-inducible) | reverse | 253 | 5265 | 5517 |
| FRP-1[6x GalRE:Minimal promoter] | forward | 189 | 5888 | 6076 |
| TPSQ-1(etanercept) | forward | 1407 | 6290 | 7696 |
| 3'Reg(hGH PolyA) | forward | 627 | 7769 | 8395 |
| FRP-2[8X LexA:Minimal Promoter] | forward | 216 | 8769 | 8984 |
| TPSQ-2(Epo) | forward | 582 | 9198 | 9779 |
| 3'Reg(SV40 early pA) | forward | 135 | 9839 | 9973 |
| TSP-3(Hypoxia-inducible) | forward | 870 | 10205 | 11074 |
| LTF2[LexA(DBD):CfEcR-DEF(LBD)] | forward | 1629 | 11108 | 12736 |
| 3'Reg(Human S100 Calcium Binding Protein pA) | forward | 765 | 12743 | 13507 |
| Replication Origin | reverse | 589 | 13841 | 14429 |
| AmpR | reverse | 858 | 14765 | 15622 |
| bla Promoter | reverse | 39 | 15656 | 15694 |

The vector shown in FIG. 15 is modeled according to the gene switch system shown in FIG. 3. Under this system, the CAP subunit of the LDTFC is expressed through operable association with a first, constitutive TSP-1, a first LTF subunit of a LDTFC (LTF-1) is expressed through operable association with a second, inducible TSP-2, and a second LTF subunit of a LDTFC (LTF-2) is expressed through operable association with a third, inducible TSP-3. The second inducible TSP-2 used in this vector is the human serum amyloid A1 (SAA1) promoter and the third inducible TSP-3 used in this vector is the hypoxia-inducible control promoter 1.

The coding region for the first therapeutic product, etanercept, is operably associated with a first FPR-1 having response elements which recognize the first DNA binding domain (DBD-A) associated with LTF-1, and the coding region for the second therapeutic product, EPO, is operably associated with a second FPR-2 having response elements which recognize the second DNA binding domain (DBD-B)

associated with LTF-2. Both factor-regulated promoters are activated upon contact with the respective LDTFC in the presence of ligand.

The construct shown in FIG. 15 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for RA.

The cells may be delivered to a subject systemically, for example, via intravenous infusion, or may be delivered directly to joints. Methods for systemic and/or local administration of gene therapy cells are well known in the art. Upon delivery of the cells, the LDTFC(s) may be expressed under the appropriate condition. One or more ligands will be administered to the subject to be treated which will combine with the expressed LDTFC(s) to drive expression of etanercept and/or EPO under control of FRP-1 or FRP-2. Etanercept expression in turn captures TNF-alpha and reduces the TNF-alpha concentration in the tissues, and EPO expression induces erythrogenesis and improves anemia.

Example 12

Figure 16:
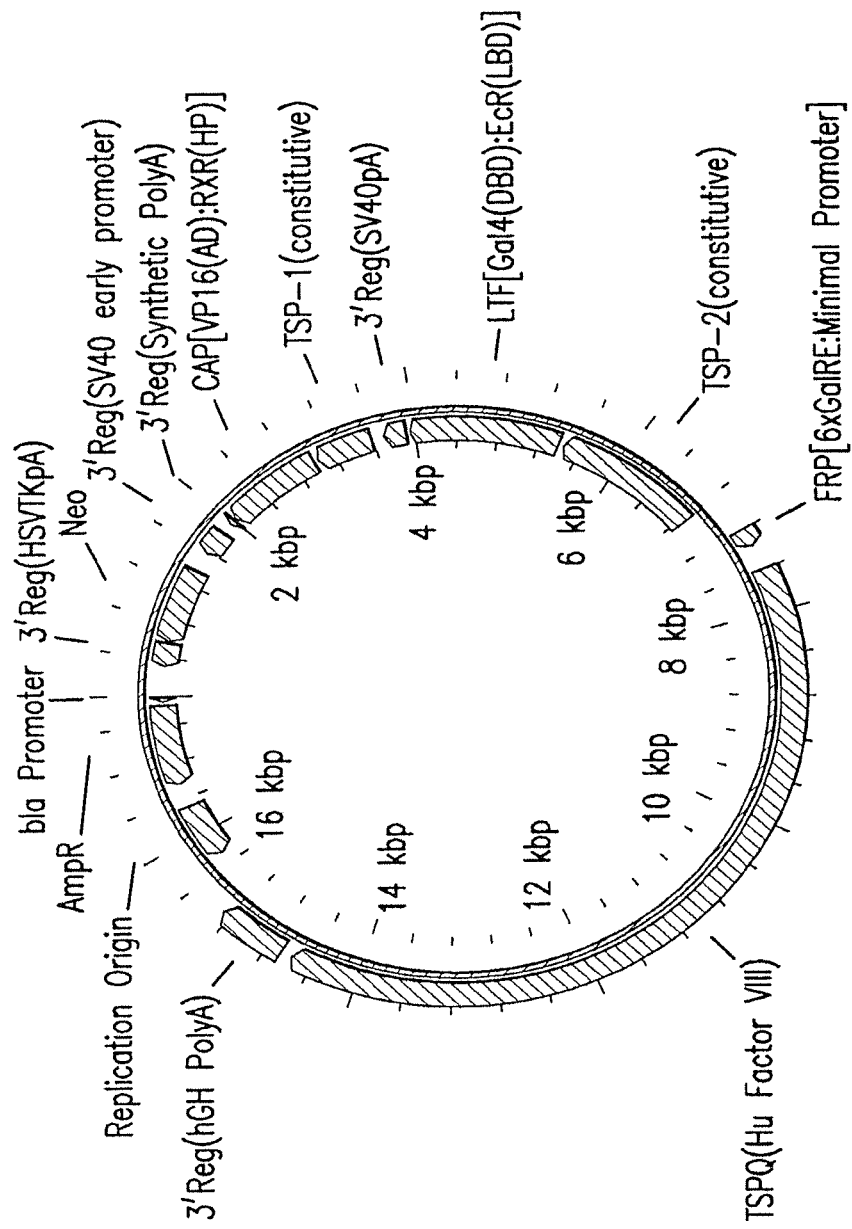
FIG. 16 is a diagram of a vector constructed under the scheme shown in FIG. 1, and engineered to express human factor VIII:C constitutively.

This example describes a bioreactor/cell therapy vector useful for the treatment of hemophilia. Hemophilia is caused by lack of either Factor VIII or Factor IX. Deficiency of Factor VIII is called hemophilia A, and deficiency of Factor IX is called hemophilia B. Hemophilia A or B may be treated by administering recombinantly produced Factor VIII or IX, respectively. See Garcia-Martin et al., *J. Gene Med.* 4(2): 215 (2002). For example, recombinantly produced Factor VIII that may be used in the present invention includes, without limitation, full length Factor VIII such as RECOMBINATE® (marketed by Baxter), BIOCLATE® (marketed by Aventis), KOGENATE® (marketed by Bayer), HELIXATE® (marketed by Aventis), or ADVATE® (marketed by Baxter), B-domain deleted Factor VIII such as REFACTO® and XYNTHA® (both marked by Genetics Institute and Wyeth), or Factor VIII and von Willebrand Factor complex such as ALPHANATE® (marketed by Grifols Biologicals, Inc.). For this purpose, an example of inducible ALPHANATE® expression for a bioreactor/cell therapy in response to administration of ligand is shown in FIG. 16. Use of bioreactor/cell therapy improves problems of stability and continuous infusion. See Pipe S. W., *J. Thromb. Haemost.* 3(8): 1692 (2005).

The complete nucleotide sequence of the construct shown in FIG. 16 is presented as SEQ ID NO: 18. The nucleotide coordinates for salient elements of the construct are shown in Table 15.

TABLE 15

| Label | Direction | Length | Start | End |
|---|---|---|---|---|
| 3'Reg(HSVTKpA) | reverse | 259 | 318 | 576 |
| Neo | reverse | 795 | 583 | 1377 |
| 3'Reg(SV40 early promoter) | reverse | 278 | 1567 | 1844 |
| 3'Reg(Synthetic PolyA) | reverse | 49 | 1963 | 2011 |

TABLE 15-continued

| Label | Direction | Length | Start | End |
|---|---|---|---|---|
| CAP[VP16(AD):RxR(HP)] | reverse | 975 | 2018 | 2992 |
| TSP-1(constitutive) | reverse | 571 | 3026 | 3596 |
| 3'Reg(SV40pA) | reverse | 221 | 3719 | 3939 |
| LTF[Gal4(DBD):EcR(LBD)] | reverse | 1467 | 3946 | 5412 |
| TSP-2(constitutive) | reverse | 1417 | 5446 | 6862 |
| FRP[6xGalRE:Minimal promoter] | forward | 189 | 7195 | 7383 |
| TSPQ(Hu Factor VIII) | forward | 7002 | 7597 | 14598 |
| 3'Reg(hGH PolyA) | forward | 627 | 14671 | 15297 |
| Replication Origin | reverse | 589 | 15731 | 16319 |
| AmpR | reverse | 858 | 16564 | 17421 |
| bla Promoter | reverse | 39 | 17455 | 17493 |

The vector shown in FIG. 16 is modeled according to the gene switch system shown in FIG. 2. Under this system, the CAP subunit is expressed through operable association with a first, constitutive promoter (TSP-1), and the LTF subunit of the LDTFC is expressed through operable association with a second, constitutive promoter (TSP-2). The promoter utilized for the first constitutive promoter is UbC (short) promoter, and the promoter utilized for the second constitutive promoter is UbB (short) promoter.

The coding region for the therapeutic product, ALPHANATE®, is operably associated with a FRP which is activated upon contact with the LDTFC in the presence of ligand.

The construct shown in FIG. 16 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for hemophilia.

The cells may be delivered to a subject systemically, for example, via intravenous infusion. Systemic and/or local administration of gene therapy cells are well known in the art. Upon delivery the cells, the LDTFC may be expressed constitutively. Ligand will be administered to the subject to be treated which will combine with the expressed LDTFC to drive expression of ALPHANATE® under control of the factor regulated promoter. ALPHANATE® expression in turn treats the symptoms of hemophilia.

Example 13

Figure 17:
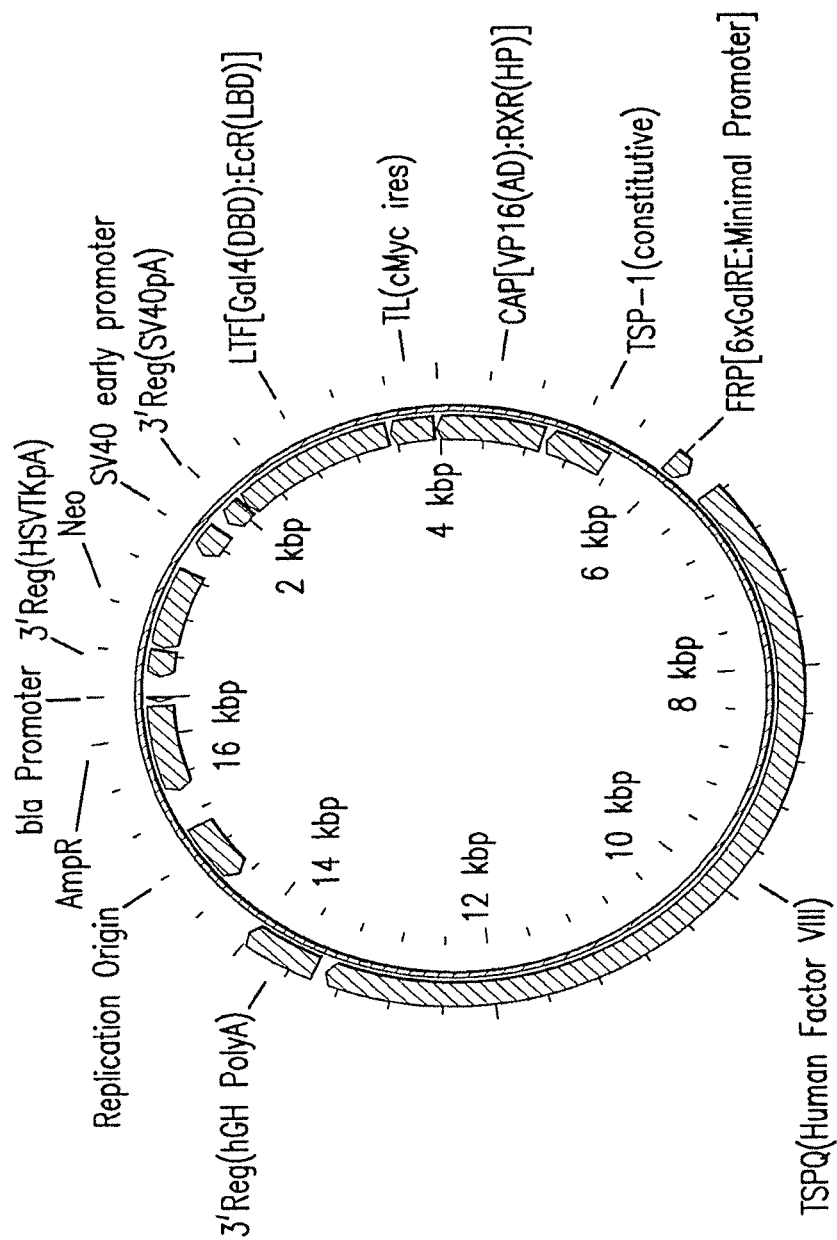
FIG. 17 is a diagram of a vector constructed under the scheme shown in FIG. 2, and engineered to express human factor VIII:C under hypoxic conditions associated with hemophilia.

This example describes a bioreactor/cell therapy vector useful for the treatment of hemophilia. The vector shown in FIG. 17 is modeled according to the gene switch system shown in FIG. 1. Under this system, both CAP subunit, and the LTF subunit of the LDTFC are expressed through operable association with a single constitutive promoter (TSP-1) via use of an internal ribosome entry site (IRES). The constitutive promoter is UbC (short) promoter.

The coding region for the therapeutic product, ALPHANATE®, is operably associated with a FRP which is activated upon contact with the LDTFC in the presence of ligand.

The complete nucleotide sequence of the construct shown in FIG. 17 is presented as SEQ ID NO: 19. The nucleotide coordinates for salient elements of the construct are shown in Table 16.

TABLE 16

(MOD 8361)

| Label | Direction | Length | Start | End |
|---|---|---|---|---|
| 3'Reg(HSVTKpA) | reverse | 259 | 197 | 455 |
| Neo | reverse | 795 | 462 | 1256 |
| SV40 early promoter | reverse | 278 | 1446 | 1723 |
| 3'Reg(SV40pA) | reverse | 221 | 1830 | 2050 |
| LTF[Gal4(DBD):EcR(LBD)] | reverse | 1467 | 2057 | 3523 |
| TL(cMyc ires) | reverse | 408 | 3536 | 3943 |
| CAP[VP16(AD):RxR(HP)] | reverse | 975 | 3950 | 4924 |
| TSP-1(constitutive) | reverse | 571 | 4958 | 5528 |
| FRP[6x GalRE:Minimal Promoter] | forward | 189 | 5939 | 6127 |
| TSPQ(Human Factor VIII) | forward | 7002 | 6341 | 13342 |
| 3'Reg(hGH PolyA) | forward | 627 | 13415 | 14041 |
| Replication Origin | reverse | 589 | 14475 | 15063 |
| AmpR | reverse | 858 | 15438 | 16295 |
| bla Promoter | reverse | 39 | 16329 | 16367 |

The construct shown in FIG. 17 may be prepared in a vector suitable for introduction into cells prior to introduction into the subject to be treated. The cells may be autologous cells removed from the subject to be treated or non-autologous allogeneic or xenogeneic cells, either primary cells or cell-lines maintained in culture. The vector is introduced into the cells via any standard method, e.g., transfection, transduction, lipofection, or electroporation, to produce modified cells. Following introduction of the vector, the modified cells may optionally be treated to produce a barrier system, e.g., the cells may be coated or encapsulated so as to provide immunoisolation. The modified cells will then be formulated as a bioreactor for administration to a subject in need of treatment for hemophilia.

The cells may be delivered to a subject systemically, for example, via intravenous infusion. Systemic and/or local administration of gene therapy cells are well known in the art. Upon delivery the cells, the LDTFC may be expressed constitutively. Ligand will be administered to the subject to be treated which will combine with the expressed LDTFC to drive expression of ALPHANATE® under control of the factor regulated promoter. ALPHANATE® expression in turn treats the symptoms of hemophilia.

Additional embodiments of the invention include the following:

E1. A method for treating, ameliorating, or preventing a disease or disorder in a subject, comprising:
  (a) introducing into cells of said subject (1) a polynucleotide encoding a gene switch, said gene switch comprising at least one transcription factor sequence, wherein said at least one transcription factor sequence encodes a ligand-dependent transcription factor, operably linked to a therapeutic switch promoter, wherein the promoter is activated during said disease or disorder, and (2) a polynucleotide encoding a therapeutic polypeptide or therapeutic polynucleotide linked to a promoter which is activated by said ligand-dependent transcription factor, to produce modified cells; and
  (b) administering ligand to said subject to induce expression of said therapeutic polypeptide or therapeutic polynucleotide;
wherein said therapeutic polypeptide or therapeutic polynucleotide is expressed at a level sufficient to treat, ameliorate, or prevent said disease or disorder.

E2. A method for expressing a therapeutic polypeptide or therapeutic polynucleotide in a subject, comprising:
  (a) introducing into cells of said subject (1) a polynucleotide encoding a gene switch, said gene switch comprising at least one transcription factor sequence, wherein said at least one transcription factor sequence encodes a ligand-dependent transcription factor, operably linked to a therapeutic switch promoter, wherein the promoter is activated during said disease or disorder, and (2) a polynucleotide encoding a therapeutic polypeptide or therapeutic polynucleotide linked to a promoter which is activated by said ligand-dependent transcription factor, to produce modified cells; and
  (b) administering ligand to said subject to induce expression of said therapeutic polypeptide or therapeutic polynucleotide.

E3. The method of E1 or E2, wherein said polynucleotides are introduced into cells that have been isolated from said subject to produce modified cells, and the modified cells are re-introduced into said subject.

E4. The method of E1 or E2, wherein said method is carried out in vivo.

E5. The method of E1 or E2, wherein said gene switch is an ecdysone receptor (EcR)-based gene switch.

E6. The method of E5, wherein said ligand binds to the EcR ligand binding domain.

E7. The method of E6, wherein said ligand is a diacylhydrazine.

E8. The method of E7, wherein said ligand is selected from the group consisting of RG-115819, RG-115932, and RG-115830.

E9. The method of E6, wherein said ligand is an amidoketone or oxadiazoline.

E10. The method of E1 or E2, wherein said gene switch comprises a first transcription factor sequence under the control of a first therapeutic switch promoter and a second transcription factor sequence under the control of a second therapeutic switch promoter, wherein the proteins encoded by said first transcription factor sequence and said second transcription factor sequence interact to form a protein complex which functions as a ligand-dependent transcription factor.

E11. The method of E10, wherein said first therapeutic switch promoter and said second therapeutic switch promoter are different.

E12. The method of E10, wherein said first therapeutic switch promoter and said second therapeutic switch promoter are the same.

E13. The method of E10, wherein said first transcription factor sequence encodes a protein comprising a heterodimer partner and a transactivation domain.

E14. The method of E10, wherein said second transcription factor sequence encodes a protein comprising a DNA binding domain and a ligand-binding domain.

E15. The method of E1 or E2, wherein one of said polynucleotides further encodes a lethal polypeptide operably linked to an inducible promoter.

E16. A method for expressing a therapeutic polypeptide or therapeutic polynucleotide in a cell, comprising:
  (a) introducing into said cell (1) a polynucleotide encoding a gene switch, said gene switch comprising at least one transcription factor sequence, wherein said at least one transcription factor sequence encodes a ligand-dependent transcription factor, operably linked to a therapeutic switch promoter, wherein the promoter is activated during said disease or disorder, and (2) a polynucleotide encoding a therapeutic polypeptide or therapeutic polynucleotide linked to a promoter which is activated by said ligand-dependent transcription factor, to produce a modified cell; and (b) administering ligand to said modified cell to induce expression of said therapeutic polypeptide or therapeutic polynucleotide.

E17. The method of E16, wherein said method is carried out in vitro.

E18. The method of E16, wherein said method is carried out ex vivo in a cell that has been isolated from a subject.

E19. The method of E16, wherein said method is carried out in vivo.

E20. The method of E16, wherein said gene switch is an EcR-based gene switch.

E21. The method of E20, wherein said ligand binds to the EcR ligand binding domain.

E22. The method of E21, wherein said ligand is a diacylhydrazine.

E23. The method of E22, wherein said ligand is selected from the group consisting of RG-115819, RG-115932, and RG-115830.

E24. The method of E21, wherein said ligand is an amidoketone or oxadiazoline.

E25. The method of E16, wherein said gene switch comprises a first transcription factor sequence under the control of a first therapeutic switch promoter and a second transcription factor sequence under the control of a second therapeutic switch promoter, wherein the proteins encoded by said first transcription factor sequence and said second transcription factor sequence interact to form a protein complex which functions as a ligand-dependent transcription factor.

E26. The method of E25, wherein said first therapeutic switch promoter and said second therapeutic switch promoter are different.

E27. The method of E25, wherein said first therapeutic switch promoter and said second therapeutic switch promoter are the same.

E28. The method of E25, wherein said first transcription factor sequence encodes a protein comprising a heterodimer partner and a transactivation domain.

E29. The method of E25, wherein said second transcription factor sequence encodes a protein comprising a DNA binding domain and a ligand-binding domain.

E30. The method of E16, wherein one of said polynucleotides further encodes a lethal polypeptide operably linked to an inducible promoter.

E31. A polynucleotide encoding a gene switch, said gene switch comprising at least one transcription factor sequence, wherein said at least one transcription factor sequence encodes a ligand-dependent transcription factor, operably linked to a therapeutic switch promoter, wherein the activity of the promoter is modulated during said disease or disorder.

E32. The polynucleotide of E31, further encoding a reporter gene linked to a promoter which is activated by said ligand-dependent transcription factor.

E33. The polynucleotide of E31, wherein said gene switch is an EcR-based gene switch.

E34. The polynucleotide of E31, wherein said gene switch comprises a first transcription factor sequence under the control of a first therapeutic switch promoter and a second transcription factor sequence under the control of a second therapeutic switch promoter, wherein the proteins encoded by said first transcription factor sequence and said second transcription factor sequence interact to form a protein complex which functions as a ligand-dependent transcription factor.

E35. The polynucleotide of E34, wherein said first therapeutic switch promoter and said second therapeutic switch promoter are different.

E36. The polynucleotide of E34, wherein said first therapeutic switch promoter and said second therapeutic switch promoter are the same.

E37. The polynucleotide of E34, wherein said first transcription factor sequence encodes a protein comprising a heterodimer partner and a transactivation domain.

E38. The polynucleotide of E34, wherein said second transcription factor sequence encodes a protein comprising a DNA binding domain and a ligand-binding domain.

E39. The polynucleotide of E31, wherein said polynucleotide further encodes a lethal polypeptide operably linked to an inducible promoter.

E40. A vector comprising the polynucleotide of E31.

E41. The vector of E40, which is a plasmid vector.

E42. The vector of E40, which is a viral vector.

E43. A kit comprising the polynucleotide of E31.

E44. A kit comprising the vector of E42.

The present invention further relates to instructions for performing one or more methods of the invention. Such instructions can instruct a user of conditions suitable for performing methods of the invention. Instructions of the invention can be in a tangible form, for example, written instructions (e.g., typed on paper), or can be in an intangible form, for example, accessible via a computer disk or over the internet.

It will be recognized that a full text of instructions for performing a method of the invention or, where the instructions are included with a kit, for using the kit, need not be provided. One example of a situation in which a kit of the invention, for example, would not contain such full length instructions is where the provided directions inform a user of the kits where to obtain instructions for practicing methods for which the kit can be used. Thus, instructions for performing methods of the invention can be obtained from internet web pages, separately sold or distributed manuals or other product literature, etc. The invention thus includes kits that direct a kit user to one or more locations where instructions not directly packaged and/or distributed with the kits can be found. Such instructions can be in any form including, but not limited to, electronic or printed forms.

Having now fully described the invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A composition comprising: (1) a first polynucleotide encoding a gene switch, said gene switch comprising at least one transcription factor sequence, wherein said at least one transcription factor sequence encodes a ligand-dependent transcription factor in operable association with a hypoxia-inducible promoter, wherein the hypoxia-inducible promoter is a nucleic acid sequence at least 95% identical to the sequence from nucleotide 4958 to nucleotide 5535 of SEQ ID NO: 7, and
   (2) a second polynucleotide encoding a therapeutic polypeptide or therapeutic polynucleotide operably associated with a transcription factor-regulated promoter which is activated by said ligand-dependent transcription factor, wherein a ligand is capable of inducing expression of said therapeutic polypeptide or therapeutic polynucleotide, wherein said composition is for use in treating, ameliorating, or preventing a disease or disorder.

2. The composition of claim 1, wherein said first and second polynucleotides are part of one larger polynucleotide.

3. The composition of claim 1, wherein the ligand capable of inducing expression of said therapeutic polypeptide or therapeutic polynucleotide is a diacylhydrazine.

4. The composition of claim 1, wherein the ligand capable of inducing expression of said therapeutic polypeptide or therapeutic polynucleotide is selected from the group consisting of RG-115819, RG-115932, and RG-115830.

* * * * *

SEQUENCE LISTING

<160> NUMBER OF SEQ ID NOS: 26

<210> SEQ ID NO 1
<211> LENGTH: 17
<212> TYPE: DNA

```
<213> ORGANISM: Artificial Sequence
<220> FEATURE:
<223> OTHER INFORMATION: Synthetic ecdysone receptor response element
<220> FEATURE:
<221> NAME/KEY: misc_feature
<222> LOCATION: (9)..(9)
<223> OTHER INFORMATION: n is a, c, g, or t

<400> SEQUENCE: 1
rrggttcant gacacyy                                                        17

<210> SEQ ID NO 2
<211> LENGTH: 13
<212> TYPE: DNA
<213> ORGANISM: Artificial Sequence
<220> FEATURE:
<223> OTHER INFORMATION: Synthetic ecdysone receptor response element
<220> FEATURE:
<221> NAME/KEY: misc_feature
<222> LOCATION: (7)..(7)
<223> OTHER INFORMATION: n is a, c, g, or t

<400> SEQUENCE: 2
aggtcanagg tca                                                            13

<210> SEQ ID NO 3
<211> LENGTH: 15
<212> TYPE: DNA
<213> ORGANISM: Artificial Sequence
<220> FEATURE:
<223> OTHER INFORMATION: Synthetic ecdysone receptor response element

<400> SEQUENCE: 3
gggttgaatg aattt                                                          15

<210> SEQ ID NO 4
<211> LENGTH: 18
<212> TYPE: DNA
<213> ORGANISM: Artificial Sequence
<220> FEATURE:
<223> OTHER INFORMATION: Synthetic I-SceI homing endonuclease
      restriction site

<400> SEQUENCE: 4
tagggataac agggtaat                                                       18

<210> SEQ ID NO 5
<211> LENGTH: 878
<212> TYPE: PRT
<213> ORGANISM: Drosophila melanogaster
<220> FEATURE:
<223> OTHER INFORMATION: Ecdysone receptor

<400> SEQUENCE: 5
```

| Met | Lys | Arg | Arg | Trp | Ser | Asn | Asn | Gly | Gly | Phe | Met | Arg | Leu | Pro | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Ser | Ser | Ser | Glu | Val | Thr | Ser | Ser | Ser | Asn | Gly | Leu | Val | Leu | Pro |
|-----|-----|-----|-----|-----|-----|-----|-----|-----|-----|-----|-----|-----|-----|-----|-----|
|     |     | 20  |     |     |     |     | 25  |     |     |     |     | 30  |     |     |     |

| Ser | Gly | Val | Asn | Met | Ser | Pro | Ser | Ser | Leu | Asp | Ser | His | Asp | Tyr | Cys |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Asp | Gln | Asp | Leu | Trp | Leu | Cys | Gly | Asn | Glu | Ser | Gly | Ser | Phe | Gly | Gly |
|-----|-----|-----|-----|-----|-----|-----|-----|-----|-----|-----|-----|-----|-----|-----|-----|
|     |     | 50  |     |     |     |     | 55  |     |     |     |     | 60  |     |     |     |

| Ser | Asn | Gly | His | Gly | Leu | Ser | Gln | Gln | Gln | Gln | Ser | Val | Ile | Thr | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Met | His | Gly | Cys | Ser | Ser | Thr | Leu | Pro | Ala | Gln | Thr | Thr | Ile | Ile |
|-----|-----|-----|-----|-----|-----|-----|-----|-----|-----|-----|-----|-----|-----|-----|-----|

-continued

```
                85                  90                  95
Pro Ile Asn Gly Asn Ala Asn Gly Asn Gly Gly Ser Thr Asn Gly Gln
            100                 105                 110
Tyr Val Pro Gly Ala Thr Asn Leu Gly Ala Leu Ala Asn Gly Met Leu
            115                 120                 125
Asn Gly Gly Phe Asn Gly Met Gln Gln Gln Ile Gln Asn Gly His Gly
            130                 135                 140
Leu Ile Asn Ser Thr Thr Pro Ser Thr Pro Thr Thr Pro Leu His Leu
145                 150                 155                 160
Gln Gln Asn Leu Gly Gly Ala Gly Gly Gly Ile Gly Gly Met Gly
                165                 170                 175
Ile Leu His His Ala Asn Gly Thr Pro Asn Gly Leu Ile Gly Val Val
            180                 185                 190
Gly Gly Gly Gly Val Gly Leu Gly Val Gly Gly Gly Val Gly
            195                 200                 205
Gly Leu Gly Met Gln His Thr Pro Arg Ser Asp Ser Val Asn Ser Ile
            210                 215                 220
Ser Ser Gly Arg Asp Asp Leu Ser Pro Ser Ser Leu Asn Gly Tyr
225                 230                 235                 240
Ser Ala Asn Glu Ser Cys Asp Ala Lys Lys Ser Lys Lys Gly Pro Ala
                245                 250                 255
Pro Arg Val Gln Glu Glu Leu Cys Leu Val Cys Gly Asp Arg Ala Ser
            260                 265                 270
Gly Tyr His Tyr Asn Ala Leu Thr Cys Glu Gly Cys Lys Gly Phe Phe
            275                 280                 285
Arg Arg Ser Val Thr Lys Ser Ala Val Tyr Cys Cys Lys Phe Gly Arg
            290                 295                 300
Ala Cys Glu Met Asp Met Tyr Met Arg Arg Lys Cys Gln Glu Cys Arg
305                 310                 315                 320
Leu Lys Lys Cys Leu Ala Val Gly Met Arg Pro Glu Cys Val Val Pro
            325                 330                 335
Glu Asn Gln Cys Ala Met Lys Arg Arg Glu Lys Lys Ala Gln Lys Glu
            340                 345                 350
Lys Asp Lys Met Thr Thr Ser Pro Ser Ser Gln His Gly Gly Asn Gly
            355                 360                 365
Ser Leu Ala Ser Gly Gly Gly Gln Asp Phe Val Lys Lys Glu Ile Leu
            370                 375                 380
Asp Leu Met Thr Cys Glu Pro Pro Gln His Ala Thr Ile Pro Leu Leu
385                 390                 395                 400
Pro Asp Glu Ile Leu Ala Lys Cys Gln Ala Arg Asn Ile Pro Ser Leu
            405                 410                 415
Thr Tyr Asn Gln Leu Ala Val Ile Tyr Lys Leu Ile Trp Tyr Gln Asp
            420                 425                 430
Gly Tyr Glu Gln Pro Ser Glu Glu Asp Leu Arg Arg Ile Met Ser Gln
            435                 440                 445
Pro Asp Glu Asn Glu Ser Gln Thr Asp Val Ser Phe Arg His Ile Thr
450                 455                 460
Glu Ile Thr Ile Leu Thr Val Gln Leu Ile Val Glu Phe Ala Lys Gly
465                 470                 475                 480
Leu Pro Ala Phe Thr Lys Ile Pro Gln Glu Asp Gln Ile Thr Leu Leu
            485                 490                 495
Lys Ala Cys Ser Ser Glu Val Met Met Leu Arg Met Ala Arg Arg Tyr
            500                 505                 510
```

Asp His Ser Ser Asp Ser Ile Phe Phe Ala Asn Asn Arg Ser Tyr Thr
    515                 520                 525

Arg Asp Ser Tyr Lys Met Ala Gly Met Ala Asp Asn Ile Glu Asp Leu
530                 535                 540

Leu His Phe Cys Arg Gln Met Phe Ser Met Lys Val Asp Asn Val Glu
545                 550                 555                 560

Tyr Ala Leu Leu Thr Ala Ile Val Ile Phe Ser Asp Arg Pro Gly Leu
                565                 570                 575

Glu Lys Ala Gln Leu Val Glu Ala Ile Gln Ser Tyr Tyr Ile Asp Thr
            580                 585                 590

Leu Arg Ile Tyr Ile Leu Asn Arg His Cys Gly Asp Ser Met Ser Leu
        595                 600                 605

Val Phe Tyr Ala Lys Leu Leu Ser Ile Leu Thr Glu Leu Arg Thr Leu
    610                 615                 620

Gly Asn Gln Asn Ala Glu Met Cys Phe Ser Leu Lys Leu Lys Asn Arg
625                 630                 635                 640

Lys Leu Pro Lys Phe Leu Glu Glu Ile Trp Asp Val His Ala Ile Pro
                645                 650                 655

Pro Ser Val Gln Ser His Leu Gln Ile Thr Gln Glu Glu Asn Glu Arg
            660                 665                 670

Leu Glu Arg Ala Glu Arg Met Arg Ala Ser Val Gly Gly Ala Ile Thr
        675                 680                 685

Ala Gly Ile Asp Cys Asp Ser Ala Ser Thr Ser Ala Ala Ala Ala
    690                 695                 700

Ala Gln His Gln Pro Gln Pro Gln Pro Gln Pro Gln Pro Ser Ser Leu
705                 710                 715                 720

Thr Gln Asn Asp Ser Gln His Gln Thr Gln Pro Gln Leu Gln Pro Gln
                725                 730                 735

Leu Pro Pro Gln Leu Gln Gly Gln Leu Gln Pro Gln Leu Gln Pro Gln
            740                 745                 750

Leu Gln Thr Gln Leu Gln Pro Gln Ile Gln Pro Gln Pro Gln Leu Leu
        755                 760                 765

Pro Val Ser Ala Pro Val Pro Ala Ser Val Thr Ala Pro Gly Ser Leu
    770                 775                 780

Ser Ala Val Ser Thr Ser Ser Glu Tyr Met Gly Gly Ser Ala Ala Ile
785                 790                 795                 800

Gly Pro Ile Thr Pro Ala Thr Thr Ser Ser Ile Thr Ala Ala Val Thr
                805                 810                 815

Ala Ser Ser Thr Thr Ser Ala Val Pro Met Gly Asn Gly Val Gly Val
            820                 825                 830

Gly Val Gly Val Gly Asn Val Ser Met Tyr Ala Asn Ala Gln Thr
        835                 840                 845

Ala Met Ala Leu Met Gly Val Ala Leu His Ser His Gln Glu Gln Leu
    850                 855                 860

Ile Gly Gly Val Ala Val Lys Ser Glu His Ser Thr Thr Ala
865                 870                 875

<210> SEQ ID NO 6
<211> LENGTH: 605
<212> TYPE: PRT
<213> ORGANISM: Streptomyces sp.
<220> FEATURE:
<223> OTHER INFORMATION: Streptomyces phage phiC31 integrase

<400> SEQUENCE: 6

-continued

```
Met Asp Thr Tyr Ala Gly Ala Tyr Asp Arg Gln Ser Arg Glu Arg Glu
1               5                   10                  15

Asn Ser Ser Ala Ala Ser Pro Ala Thr Gln Arg Ser Ala Asn Glu Asp
            20                  25                  30

Lys Ala Ala Asp Leu Gln Arg Glu Val Glu Arg Asp Gly Gly Arg Phe
        35                  40                  45

Arg Phe Val Gly His Phe Ser Glu Ala Pro Gly Thr Ser Ala Phe Gly
    50                  55                  60

Thr Ala Glu Arg Pro Glu Phe Glu Arg Ile Leu Asn Glu Cys Arg Ala
65              70                  75                  80

Gly Arg Leu Asn Met Ile Ile Val Tyr Asp Val Ser Arg Phe Ser Arg
                85                  90                  95

Leu Lys Val Met Asp Ala Ile Pro Ile Val Ser Glu Leu Leu Ala Leu
        100                 105                 110

Gly Val Thr Ile Val Ser Thr Gln Glu Gly Val Phe Arg Gln Gly Asn
            115                 120                 125

Val Met Asp Leu Ile His Leu Ile Met Arg Leu Asp Ala Ser His Lys
    130                 135                 140

Glu Ser Ser Leu Lys Ser Ala Lys Ile Leu Asp Thr Lys Asn Leu Gln
145                 150                 155                 160

Arg Glu Leu Gly Gly Tyr Val Gly Gly Lys Ala Pro Tyr Gly Phe Glu
                165                 170                 175

Leu Val Ser Glu Thr Lys Glu Ile Thr Arg Asn Gly Arg Met Val Asn
            180                 185                 190

Val Val Ile Asn Lys Leu Ala His Ser Thr Thr Pro Leu Thr Gly Pro
    195                 200                 205

Phe Glu Phe Glu Pro Asp Val Ile Arg Trp Trp Trp Arg Glu Ile Lys
210                 215                 220

Thr His Lys His Leu Pro Phe Lys Pro Gly Ser Gln Ala Ala Ile His
225                 230                 235                 240

Pro Gly Ser Ile Thr Gly Leu Cys Lys Arg Met Asp Ala Asp Ala Val
                245                 250                 255

Pro Thr Arg Gly Glu Thr Ile Gly Lys Lys Thr Ala Ser Ser Ala Trp
            260                 265                 270

Asp Pro Ala Thr Val Met Arg Ile Leu Arg Asp Pro Arg Ile Ala Gly
    275                 280                 285

Phe Ala Ala Glu Val Ile Tyr Lys Lys Lys Pro Asp Gly Thr Pro Thr
290                 295                 300

Thr Lys Ile Glu Gly Tyr Arg Ile Gln Arg Asp Pro Ile Thr Leu Arg
305                 310                 315                 320

Pro Val Glu Leu Asp Cys Gly Pro Ile Ile Glu Pro Ala Glu Trp Tyr
                325                 330                 335

Glu Leu Gln Ala Trp Leu Asp Gly Arg Gly Arg Gly Lys Gly Leu Ser
            340                 345                 350

Arg Gly Gln Ala Ile Leu Ser Ala Met Asp Lys Leu Tyr Cys Glu Cys
    355                 360                 365

Gly Ala Val Met Thr Ser Lys Arg Gly Glu Glu Ser Ile Lys Asp Ser
370                 375                 380

Tyr Arg Cys Arg Arg Lys Val Val Asp Pro Ser Ala Pro Gly Gln
385                 390                 395                 400

His Glu Gly Thr Cys Asn Val Ser Met Ala Ala Leu Asp Lys Phe Val
                405                 410                 415
```

```
Ala Glu Arg Ile Phe Asn Lys Ile Arg His Ala Glu Gly Asp Glu Glu
            420                 425                 430

Thr Leu Ala Leu Leu Trp Glu Ala Ala Arg Arg Phe Gly Lys Leu Thr
        435                 440                 445

Glu Ala Pro Glu Lys Ser Gly Glu Arg Ala Asn Leu Val Ala Glu Arg
    450                 455                 460

Ala Asp Ala Leu Asn Ala Leu Glu Glu Leu Tyr Glu Asp Arg Ala Ala
465                 470                 475                 480

Gly Ala Tyr Asp Gly Pro Val Gly Arg Lys His Phe Arg Lys Gln Gln
                485                 490                 495

Ala Ala Leu Thr Leu Arg Gln Gln Gly Ala Glu Glu Arg Leu Ala Glu
            500                 505                 510

Leu Glu Ala Ala Glu Ala Pro Lys Leu Pro Leu Asp Gln Trp Phe Pro
        515                 520                 525

Glu Asp Ala Asp Ala Asp Pro Thr Gly Pro Lys Ser Trp Trp Gly Arg
    530                 535                 540

Ala Ser Val Asp Asp Lys Arg Val Phe Val Gly Leu Phe Val Asp Lys
545                 550                 555                 560

Ile Val Val Thr Lys Ser Thr Thr Gly Arg Gly Gln Gly Thr Pro Ile
                565                 570                 575

Glu Lys Arg Ala Ser Ile Thr Trp Ala Lys Pro Pro Thr Asp Asp Asp
            580                 585                 590

Glu Asp Asp Ala Gln Asp Gly Thr Glu Asp Val Ala Ala
        595                 600                 605

<210> SEQ ID NO 7
<211> LENGTH: 9861
<212> TYPE: DNA
<213> ORGANISM: Artificial Sequence
<220> FEATURE:
<223> OTHER INFORMATION: Synthetic hypoxia-inducible gene switch
      constructor expressing IGF-1

<400> SEQUENCE: 7
taaacaaata ggggttccgc gcacatttcc ccgaaaagtg ccacctgacg tactgaggac      60
gccagggttt tcccagtcac gacgttgtaa acgacggcc agtagcagac aagcccgtca     120
gggcgcgtca gcgggtgttg gcgggtgtcg gggatttagg tgacactata ggctgagcgc    180
cgcacaggca tctagaggct atggcagggc ctgccgcccc gacgttggct gcgagccctg    240
ggccttcacc cgaacttggg gggtggggtg gggaaaagga agaaacgcgg gcgtattggc    300
cccaatgggg tctcggtggg gtatcgacag agtgccagcc ctgggaccga accccgcgtt    360
tatgaacaaa cgacccaaca ccgtgcgttt tattctgtct ttttattgcc gtcatagcgc    420
gggttccttc cggtattgtc tccttccgtg tttcaatcga ttcaaaagaa ctcgtccagc    480
agacggtaaa aagcaatgcg ttgagaatcc ggtgcagcaa tgccatacag caccagaaag    540
cgatcagccc attcaccgcc cagttcttca gcaatgtcac gggttgccag tgcgatgtcc    600
tgatagcgat cagccacgcc caggcgaccg cagtcgataa agccggagaa acggccgttt    660
tccaccataa tgtttggcag acaagcatcg ccgtgggtca caaccaggtc ctcgccatct    720
ggcatacgtg ctttcaggcg tgcgaacagt tctgccggtg ccagacctg atgttcctcg    780 tccaggtcat cctgatcaac caggccagct tccatgcgag tgcgtgcgcg ctcgatacgg    840
tgtttagctt ggtgatcgaa tgggcaagta gctgggtcca gggtatgcag acggcgcata    900
gcatcagcca tgatggaaac cttttctgcc ggtgccagat gagaggacag cagatcctgg    960
```

```
cctggaacct cgcccagcag cagccagtcg cggccagcct cggtcacaac atccagcaca    1020
gctgcgcatg gaacgccggt agtagccagc caggacagac gagctgcttc atcttgcagt    1080
tcgttcagtg cgccggacag atcggtctta acaaacagca ccggacggcc ttgagcggac    1140
agacggaaca cagctgcgtc ggagcaaccg atagtctgtt gagcccagtc atagccaaac    1200
agacgttcca cccaagcagc cggagaacca gcgtgcagac cgtcttgttc aatcatggtg    1260
gcaattgggt gtctgagcga tgtggctcgg ctggcgacgc aaaagaagat gcggctgact    1320
gtcgaacagg aggagcagag agcgaagcgg gaggctgcgg gctcaatttg catgctttag    1380
ttcctcacct tgtcgtatta tactatgccg atatactatg ccgatgatta attgtcaacg    1440
tatacggaat agctctgagg ccgaggcagc ttcggcctct gcataaataa aaaaaattag    1500
tcagccatgg ggcggagaat gggcggaact gggcggagtt aggggcggga tgggcggagt    1560
taggggcggg actatggttg ctgactaatt gagatgcttg ctttgcatac ttctgcctgc    1620
tggggagcct ggggactttc cacacctggt tgctgactaa ttgagatgct tgctttgcat    1680
acttctgcct gctggggagc ctgggacctt ccacaccct aacctcgagg ccatcgtggc    1740
acgccagggt tttcccagtc acgacgttgt aaaacgacgg ccagtgctct ctccccgc    1800 gggaggtttt ataaatccga ctgtctagat accacatttg tagaggtttt acttgcttta    1860
aaaaacctcc cacatctccc cctgaacctg aaacataaaa tgaatgcaaa tgttttatta    1920
acttgtttat tgcagcttat aatggttaca aattaagcaa tagcatcaca aatttcacaa    1980
attaagcatt ttttcactg cattctagtt gtggtttgtc caaactcatc aatgtatctt    2040
atcatgtcta atcgattcac aggttggtgg ggctctccag gatgggggg gctgggtgt    2100 ggctcatgtc ggccacgtcc caaatctcct ccaggaaggg gggcagcttc ctgttcttca    2160
gcttcaggct gatacacata ttgctgttct gcattcccag ggtcctcagc tcgctcagga    2220
tgctcaggat cttgccgtag atcacgctgc tcctggcgct gccgctcagc tggttcagga    2280
tgtagatcct cagggtgttc aggtagtacc tctggatctc ctccaccagc tggggctgct    2340
ccaggccggg cctgtcgctg aagatcacca cggcggtcag cagggcgtag tggatgttgt    2400
ccagggccat gctgtacata catctgcaga agtgcaggag gtcctcgatc acctcggcca    2460
tgccagcctt cctgtagttg tccctggtgt aagcctggtt gttggcgaac aggatgctgt    2520
cgctggcggc gtcgtacctc ctggccaccc tcagcatcat cacctcgctg ctgcaagcct    2580
tcagcagggt gatctggtcg ggctggctga tcttggcgaa tccgggcagg cccttggcga    2640
actccacgat cagctgcacg gtcaggatgg tcatctcggt gatctgcctg aaggggtgt    2700 cgctctcctc gttctcgtcg tcggcctgct gccaggtctg ggtgatcctt ttcaggtcct    2760
cgtcgctggg ctgctcgtag ccgtcctgat accagatcag cctggcgatc aggaactgct    2820
ggttggcggt cagctggggg atgttcttct gcctgttggt caccagcagc ttgtcgctca    2880
ggaacctggg cacgacctcg tgaatcctgg cggcctcggg ggggggggc tcgcactgca    2940 tgatgggggg catgtggtca tcgacggtgg tggtgctcac gggcagcttg tccttctcct    3000
tctgggcctt cttctccttc cttttcatgg cgcactgggt ctcgggcacc acgcactcgg    3060
gcctgatccc gggaaactcg gggctcacgg tcagctgcct ctggcccttg ttgctgctct    3120
cctcgctgct gctggtggcg ctgatcctgt gctgcctcag ggtcagggc atgtcggtct    3180 ccacgctggc cagcctgtcg gtcacggcgt cctgttcac gttgtcctgc acgaacaggc    3240
cggtcagcag ggccttgatg tcttgcaggc tgtccatctt caggatcatg tccaggtcct    3300
ccctggggaa gatcagcagg aacagctgct ccagcctctc cagcctgctc tccacctcgg    3360
```

```
tcaggtgggc cctggtcagg gggctcctct tggtcttggg gctgtatctg cactcccagt    3420
tgttcttcag gcacttggcg cacttgggct tctccttgct gcacttcagc ttcttcagcc    3480
tgcagatgtc gcaagcctgc tcgatgctgc tcagcagctt catggtggca gatctggtcg    3540
cgggaggctg ctggttttcc actacccgaa aaaaatccag cgtctaagca gctgcaagga    3600
gagcctttca gagaagcggg tcctggcagc ggcggggaag tgtccccaaa tgggcagaat    3660
agcctccccg cgtcgggaga gtcgcgtcct tgctcgggtg ttgtaagttc cagtgcaaag    3720
tgcccgcccg ctgctatggg caaagtttcg tggatgcggc tagggttgcg caccgctggc    3780
tgggggatca gcgggagggc tgggccagag gcgaagcccc ctattcgctc cggatctccc    3840
ttcccaggac gcccgcagcg cagctctgct cgccgggctc ctccacccta gcccgccgcc    3900
cgctcgctcc ctctgcctct cgctggaatt actacagcga gttgccggct cagctgtcgc    3960
tggggctctc cagcatctcc atcaggaagg tgtcgatggg cacgtcgccg atcagcctga    4020
agaagaacag gtgctccagg cacttcaggc cgatgctcct caggctgggc agcctcagca    4080
gcagcttggc gaatctgccg ggctcgtcgg ggtgggtggt cctggtgtac tcctccaggg    4140
cggcgtacac cttctccctc agcagctcca cctcctgggc gcttttcagg cccctcacct    4200
cggggttgaa caggatgatg gccctcaggc agcccagctc ggtcttgtcc atcctcatgt    4260
ccctcatctt gctcaccagc tcggtcagca ccctgtcgaa gatggcgccc actccggcgc    4320
tgtgggcgct gttcctatgg acgtgcaggc cggtggccag caggatgccg tccctcacgt    4380
cgatgctcct gtggctgaag ctggcgatca gcagctcgtt ccatccgcc ctcagcagga    4440
tcacctggtc gtccaggggc aggctgctga agtggggaat cctcttggcc cactccacca    4500
gggtgaacag ctgcttgtcg gcggcctggc agatgttggt cacggggtcg ttggggctgc    4560
tgccgctgcc gccggttccg ccggggccct ccacgccctg gtcgcttttc tgctccacgg    4620
cgagttcggc ctccagaatc ctgtccacgg gcatctccat atggccgccg tactcgtcga    4680
tgcccagggc gtcggtgaac atctgctcga actcgaagtc ggccatgtcc agggcgccgt    4740
aggggcgct gtcgtggggg gtgaagccgg ggccggggct gtcgccgtcg cccagcatgt    4800
ccaggtcgaa gtcgtccagg gcgtcggcgt gggccatggc cacgtcctcg ccgtccaggt    4860
gcagctcgtc gcccaggctc acgtcggtgg gggggccac cttccttttc ttcttggggc    4920
ccatggtggc caattgcccc cccccccccc cgcatgcggc tggctgctgc ctctgaagaa    4980
ttcaaggagc ctgctggtcg gcccctgctg tggaacaata aatacctctt ccctgggtt    5040
aaaaataacc ccatgaccac ttttggcagt tgtaggtgag gcagaggcca cctaagcccc    5100
cccacccat gccgttcttc tgaagtaaga gccgttcaaa gtccgacacc gcctgggtg    5160
gacacgtgag acccaaaaat gccttcaagg ttaaagagac agtggctggg gcctggcctg    5220
ggaacgatgc tctgtgctct gggtcctgcc attgccgaca ggcgctgtgt gagacagcac    5280
gtagggcgac aggcgctgtg tgagacagca cgtaggcga caggcgctgt gtgagacagc    5340
acgtagggcg acaggcgctg tgtgagacag cacgtagggc gacaggcgct gtgtgagaca    5400
gcacgtaggg cgacaggcgc tgtgtgagac agcacgtagg gcgacaggcg ctgtgtgaga    5460
cagcacgtag ggcgacaggc gctgtgtgag acagcacgta gggcgacagg cgctgtgtga    5520
gacagcacgt agggcctcga gtaggcgaga ccaatgggtg cgccatgggc tcttccaaaa    5580
atttaggtga cactataggg caccgctcgc acctgcgcac aggcataagc caaatggaac    5640
tacgagacct gcatcgtggt gtaactataa cggtcctaag gtagcgaccg cggagactag    5700
```

```
gtgtatttat ctaagcgatc gcttaattaa ggccggccgc cgcaataaaa tatctttatt    5760
ttcattacat ctgtgtgttg gttttttgtg tgaatccata gtactaacat acgctctcca    5820
tcaaaacaaa acgaaacaaa acaaactagc aaaataggct gtccccagtg caagtccagg    5880
tgccagaaca tttctctatc cataatgcag gggtaccggg tgatgacggt gaaaacctcc    5940
aattgcggag tactgtcctc cgagcggagt actgtcctcc gagcggagta ctgtcctccg    6000
agcggagtac tgtcctccga gcggagtact gtcctccgag cggagtactg tcctccgagc    6060
ggagagtccc cggggaccta gagggtatat aatgggtgcc ttagctggtg tgtgacctca    6120
tcttcctgta cgcccctgca ggggcgcgcc acgcgtcgaa gaaggtgagt aatcttaaca    6180
tgctcttttt tttttttttt gctaatccct tttgtgtgct gatgttagga tgacatttac    6240
aacaaatgtt tgttcctgac aggaaaaacc ttgctgggta ccttcgttgc cggacacttc    6300
ttgtcctcta ctttggaaaa aaggaattga gagccgctag cgccaccatg ggaaaaatca    6360
gcagcctgcc cacccaatta tttaagtgct gcttttgtga tttcttgaag gtgaagatgc    6420
acaccatgtc ctcctcgcat ctgttctacc tggcgctgtg cctgctgacc ttcaccagct    6480
ctgccacggc tggaccggag accctctgcg gggccgagct ggtggatgcc ctgcaattcg    6540
tgtgtggaga caggggcttc tacttcaaca agcccacagg gtatggctcc agcagtcgga    6600
gagcccccca gacaggcatc gtggatgagt gctgcttcag aagctgtgat ctaaggaggc    6660
tggagatgta ttgcgcaccc ctcaagcctg ccaagtcagc tcgctctgtc cgtgcccagc    6720
gccacaccga catgcccaag acccagaagt atcagccccc atctaccaac aagaacacga    6780
agtctcagag aaggaaagga agtacatttg aagaacgcaa gtagatcgat gcgcaaagc     6840 tttcgcgata ggcgagacca atgggtgtgt acgtagcggc cgcgtcgacg atagcttgat    6900
gggtggcatc cctgtgaccc ctccccagtg cctctcctgg ccctggaagt tgccactcca    6960
gtgcccacca gccttgtcct aataaaatta agttgcatca ttttgtctga ctaggtgtcc    7020
ttctataata ttatggggtg gagggggggtg gtatggagca aggggcaagt tgggaagaca    7080
acctgtaggg cctgcggggt ctattgggaa ccaagctgga gtgcagtggc acaatcttgg    7140
ctcactgcaa tctccgcctc ctgggttcaa gcgattctcc tgcctcagcc tcccgagttg    7200
ttgggattcc aggcatgcat gaccaggctc agctaatttt tgttttttttg gtagagacgg    7260 ggtttcacca tattggccag gctggtctcc aactcctaat ctcaggtgat ctacccacct    7320
tggcctccca aattgctggg attacaggcg tgaaccactg ctcccttccc tgtccttctg    7380
attttaaaat aactatacca gcaggaggac gtccagacac agcataggct acctggccat    7440
gcccaaccgg tgggacattt gagttgcttg cttggcactg tcctctcatg cgttgggtcc    7500
actcagtaga tgcctgttga attctgattt aaatcggtcc gcgtacgcg tggtaggtcc     7560 gaacgaatcc atggattacc ctgttatccc tactcaagga catcatccct ttagtgaggg    7620
ttaattcacg cagtgggtac ggaactaaag gcagcacaca tcgtgtaatc atggtcatag    7680
ctgtttcctg tgtgaaattg ttatccgcta cgtctctccc ccgcagtaag gctagatta    7740 actcgtctcg tgaatatccg gaactccctt tagtgagggt taattgcgtt gcgctcactg    7800
cccgctttcc agtcgggaaa cctgtcgtgc cagcttaatc atggtcatag ctgtttcctg    7860
tgtgaaattg ttatccgcta ccggaaacgc ttccttcatg tgagcaaaag gccagcaaaa    7920
ggccaggaac cgtaaaaagg ccgcgttgct ggcgtttttc cataggctcc gccccctga    7980 cgagcatcac aaaaatcgac gctcaagtca gaggtggcga aacccgacag gactataaag    8040
ataccaggcg tttccccctg gaagctccct cgtgcgctct cctgttccga ccctgccgct    8100
```

```
taccggatac ctgtccgcct ttctcccttc gggaagcgtg gcgctttctc atagctcacg    8160
ctgtaggtat ctcagttcgg tgtaggtcgt tcgctccaag ctgggctgtg tgcacgaacc    8220
ccccgttcag cccgaccgct gcgccttatc cggtaactat cgtcttgagt ccaacccggt    8280
aagacacgac ttatcgccac tggcagcagc cactggtaac aggattagca gagcgaggta    8340
tgtaggcggt gctacagagt tcttgaagtg gtggcctaac tacggctaca ctagaagaac    8400
agtatttggt atctgcgctc tgctgaagcc agttaccttc ggaaaaagag ttggtagctc    8460
ttgatccggc aaacaaacca ccgctggtag cggtggtttt tttgtttgca agcagcagat    8520
tacgcgcaga aaaaaggat ctcaagaaga tcctttgatc ttttctacgg ggtctgacgc     8580
tcagtggaac gaaaactcac gttaagggat tttggtcatg cctaggacga aggaggtcg    8640 tgaaatggat aaaaaatac agcgttttc atgtacaact atactagttg tagtgcctaa     8700
ataatgcttt taaaacttaa aaataatcta tgtcgggtgc ggagaaagag gtaatgaaat   8760
ggcaaatcaa tgtcctcagc gaaatggcat acgagtaaac ttggtctgac accgctgcat   8820
gagattatca aaaaggatct tcacctagat ccttttaaat taaaaatgaa gttttaaatc   8880
aatctaaagt atatatgagt aaacttggtc tgacagttac caatgcttaa tcagtgaggc   8940
acctatctca gcgatctgtc tatttcgttc atccatagtt gcctgactcc ccgtcgtgta   9000
gataactacg atacgggagg gcttaccatc tggccccagt gctgcaatga taccgcgaga   9060
cccacgctca ccggctccag atttatcagc aataaaccag ccagccggaa gcgccagcg    9120 cagaagtggt cctgcaactt tatccgcctc catccagtct attaactgtt gccgggaagc   9180
tagagtaagt agttcgccag ttaatagttt gcggagcgtt gttgccattg ctacaggcat   9240
cgtggtgtca cgctcgtcgt ttggtatggc ttcattcagc tccggttccc aacgatcaag   9300
gcgagttaca tgatccccca tgttgtgcaa aaaagcggtt agctccttcg gtcctccgat   9360
ggttgtcaga agtaagttgg ccgcagtgtt atcactcatg gttatggcag cactgcataa   9420
ttctcttact gtcatgccat ccgtaagatg cttttctgtg actggtgagt attcaaccaa   9480
gtcattctga gaatagtgta tgcggcgacc gagttgctct tgcccggcgt caatacggga   9540
taataccgcg ccacatagca gaactttaaa agtgctcatc attgggaagc gttcttcggg   9600
gcgaaaactc tcaaggatct taccgctgtt gagatccagt tcgatgtaac ccacacgagc   9660
acccaactga tcttcagcat cttttacttt caccagcgtt tctgggtgag caaaaacagg   9720
aaggcaaaat gccgcaaaaa agggaataag ggcgacacgg aaatgttgaa tactcatacg   9780 cttcctttt caatagtatt gaagcattta tcagggttat tgtctcggga gcgaatacat   9840
atttgaatgt atttagaaaa a                                              9861
```

<210> SEQ ID NO 8
<211> LENGTH: 10823
<212> TYPE: DNA
<213> ORGANISM: Artificial Sequence
<220> FEATURE:
<223> OTHER INFORMATION: Synthetic ubiquitous and hypoxia inducible
      promoter gene switch construct expressing bFGF

<400> SEQUENCE: 8

```
taaacaaata gggttccgc gcacatttcc ccgaaaagtg ccacctgacg tactgaggac      60
gccagggttt tcccagtcac gacgttgtaa aacgacggcc agtagcagac aagcccgtca    120
gggcgcgtca gcgggtgttg gcctaggac gaaaggaggt cgtgaaatgg ataaaaaaat    180
acagcgtttt tcatgtacaa ctatactagt tgtagtgcct aaataatgct tttaaaactt   240
```

```
aaaaataatc aatgtcctca gcggggtgtc ggggatttag gtgacactat aggctgagcg     300
ccgcacaggc atctagaggc tatggcaggg cctgccgccc cgacgttggc tgcgagccct     360
gggccttcac ccgaacttgg ggggtggggt ggggaaaagg aagaaacgcg ggcgtattgg     420
ccccaatggg gtctcggtgg ggtatcgaca gagtgccagc cctgggaccg aaccccgcgt     480
ttatgaacaa acgacccaac accgtgcgtt ttattctgtc tttttattgc cgtcatagcg     540
cgggttcctt ccgtattgt ctccttccgt gtttcaatcg attcaaaaga actcgtccag      600
cagacggtaa aaagcaatgc gttgagaatc cggtgcagca atgccataca gcaccagaaa     660
gcgatcagcc cattcaccgc ccagttcttc agcaatgtca cgggttgcca gtgcgatgtc     720
ctgatagcga tcagccacgc ccaggcgacc gcagtcgata aagccggaga acggccgtt     780 ttccaccata atgtttggca gacaagcatc gccgtgggtc acaaccaggt cctcgccatc     840
tggcatacgt gctttcaggc gtgcgaacag ttctgccggt gccagaccct gatgttcctc     900
gtccaggtca tcctgatcaa ccaggccagc ttccatgcga gtgcgtgcgc gctcgatacg     960
gtgtttagct tggtgatcga atgggcaagt agctgggtcc agggtatgca gacggcgcat    1020
agcatcagcc atgatggaaa ccttttctgc cggtgccaga tgagaggaca gcagatcctg    1080
gcctggaacc tcgcccagca gcagccagtc gcggccagcc tcggtcacaa catccagcac    1140
agctgcgcat ggaacgccgg tagtagccag ccaggacaga cgagctgctt catcttgcag    1200
ttcgttcagt gcgccggaca gatcggtctt aacaaacagc accggacggc cttgagcgga    1260
cagacggaac acagctgcgt cggagcaacc gatagtctgt tgagcccagt catagccaaa    1320
cagacgttcc acccaagcag ccggagaacc agcgtgcaga ccgtcttgtt caatcatggt    1380
ggcaattggg tgtctgagcg atgtggctcg gctggcgacg caaagaaga tgcggctgac     1440 tgtcgaacag gaggagcaga gagcgaagcg ggaggctgcg ggctcaattt gcatgcttta    1500
gttcctcacc ttgtcgtatt atactatgcc gatatactat gccgatgatt aattgtcaac    1560
gtatacggaa tagctctgag gccgaggcag cttcggcctc tgcataaata aaaaaaatta    1620
gtcagccatg gggcggagaa tgggcggaac tgggcggagt tagggcgggg atgggcggag    1680 ttagggcgg gactatggtt gctgactaat tgagatgctt gctttgcata cttctgcctg     1740
ctggggagcc tggggacttt ccacacctgg ttgctgacta attgagatgc ttgctttgca    1800
tacttctgcc tgctggggag cctggggact ttccacaccc taacctcgag gccatcgtgg    1860
cacgccaggg ttttcccagt cacgacgttg taaaacgacg gccagtgctc ttctcccccg    1920
cgggaggttt tataaatccg actgtctaga ttgttgttaa atcacacaaa aaaccaacac    1980
acagatgtaa tgaaaataaa gatatttat tatcgattca gctgtcgctg gggctctcca     2040
gcatctccat caggaaggtg tcgatgggca cgtcgccgat cagcctgaag aagaacaggt    2100
gctccaggca cttcaggccg atgctcctca ggctgggcag cctcagcagc agcttggcga    2160
atctgccggg ctcgtcgggg tgggtggtcc tggtgtactc ctccagggcg gcgtacacct    2220
tctccctcag cagctccacc tcctgggcgc ttttcaggcc cctcacctcg ggttgaaca    2280 ggatgatggc cctcaggcag cccagctcgg tcttgtccat cctcatgtcc ctcatcttgc    2340
tcaccagctc ggtcagcacc ctgtcgaaga tggcgcccac tccggcgctg tgggcgctgt    2400
tcctatggac gtgcaggccg gtggccagca ggatgccgtc cctcacgtcg atgctcctgt    2460
ggctgaagct ggcgatcagc agctcgttcc atcggccct cagcaggatc acctggtcgt     2520
ccaggggcag gctgctgaag tggggaatcc tcttggccca ctccaccagg gtgaacagct    2580
```

```
gcttgtcggc ggcctggcag atgttggtca cggggtcgtt ggggctgctg ccgctgccgc      2640
cggttccgcc ggggccctcc acgcctggt cgcttttctg ctccacggcg agttcggcct       2700
ccagaatcct gtccacgggc atctccatat ggccgccgta ctcgtcgatg cccagggcgt      2760
cggtgaacat ctgctcgaac tcgaagtcgg ccatgtccag ggcgccgtag ggggcgctgt      2820 cgtgggggt gaagccgggg ccggggctgt cgccgtcgcc cagcatgtcc aggtcgaagt       2880
cgtccagggc gtcggcgtgg gccatggcca cgtcctcgcc gtccaggtgc agctcgtcgc      2940
ccaggctcac gtcggtgggg ggggccacct tcctttcttt cttggggccc atggtggcca     3000
attgcccccc cccccccccg catgccgtct aacaaaaaag ccaaaaacgg ccagaattta      3060
gcggacaatt tactagtcta acactgaaaa ttacatattg acccaaatga ttacatttca     3120
aaaggtgcct aaaaaacttc acaaaacaca ctcgccaacc ccgagcgcac gtacccagcc     3180
cagcagcccg ctactcacca agtgacgatc acagcgatcc acaaacaaga accgcgaccc     3240
aaatcccggc tgcgacggaa ctagctgtgc cacaccggc gcgtccttat ataatcatcg      3300
gcgttcaccg ccccacggag atccctccgc agaatcgccg agaagggact acttttcctc     3360
gcctgttccg ctctctggaa agaaaaccag tgccctagag tcacccaagt cccgtcctaa     3420
aatgtccttc tgctgatact ggggttctaa ggccgagtct tatgagcagc gggccgctgt     3480
cctgagcgtc cgggcggaag gatcaggacg ctcgctgcgc ccttcgtctg acgtggcagc     3540
gctcgccgtg aggaggggg cgcccgcggg aggcgccaaa accggcgcg gaggccctcg      3600 agtaggcgag accaatgggt gcgccatggg ctcttccaaa aatttaggtg acactatagg     3660
gcaccgctcg cacctgcgca caggcccgcg gctacaaact cgaacgatc attctagata    3720 ccacatttgt agaggtttta cttgctttaa aaaacctccc acatctcccc ctgaacctga     3780
aacataaaat gaatgcaaat gttttattaa cttgtttatt gcagcttata atggttacaa     3840
attaagcaat agcatcacaa atttcacaaa ttaagcattt ttttcactgc attctagttg     3900
tggtttgtcc aaactcatca atgtatctta tcatgtctaa tcgattcaca ggttggtggg    3960
gctctccagg atggggggg gctgggtgtg gctcatgtcg gccacgtccc aaatctcctc     4020
caggaagggg ggcagcttcc tgttcttcag cttcaggctg atacacatat tgctgttctg    4080
cattcccagg gtcctcagct cgctcaggat gctcaggatc ttgccgtaga tcacgctgct    4140
cctggcgctg ccgctcagct ggttcaggat gtagatcctc agggtgttca ggtagtacct    4200
ctggatctcc tccaccagct ggggctgctc caggccgggc ctgtcgctga agatcaccac    4260
ggcggtcagc agggcgtagt ggatgttgtc cagggccatg ctgtacatac atctgcagaa    4320
gtgcaggagg tcctcgatca cctcggccat gccagccttc ctgtagttgt ccctggtgta    4380
agcctggttg ttggcgaaca ggatgctgtc gctggcggcg tcgtacctcc tggccaccct    4440
cagcatcatc acctcgctgc tgcaagcctt cagcagggtg atctggtcgg gctggctgat   4500
cttggcgaat ccgggcaggc ccttggcgaa ctccacgatc agctgcacgg tcaggatggt    4560
catctcggtg atctgcctga aggggtgtc gctctcctcg ttctcgtcgt cggcctgctg    4620
ccaggtctgg gtgatccttt tcaggtcctc gtcgctgggc tgctcgtagc cgtcctgata    4680
ccagatcagc ctggcgatca ggaactgctg gttggcggtc agctggggga tgttcttctg    4740
cctgttggtc accagcagct tgtcgctcag gaacctgggc acgacctcgt gaatcctggc    4800
ggcctcgggg gggggggct cgcactgcat gatggggggc atgtggtcat cgacggtggt    4860
ggtgctcacg ggcagcttgt ccttctcctt ctggccttc ttctccttcc ttttcatggc     4920
gcactgggtc tcgggcacca cgcactcggg cctgatcccg ggaaactcgg ggctcacggt    4980
```

```
cagctgcctc tggcccttgt tgctgctctc ctcgctgctg ctggtggcgc tgatcctgtg   5040
ctgcctcagg gtcaggggca tgtcggtctc cacgctggcc agcctgtcgg tcacggcgtc   5100
cttgttcacg ttgtcctgca cgaacaggcc ggtcagcagg gccttgatgt cttgcaggct   5160
gtccatcttc aggatcatgt ccaggtcctc cctgggaag atcagcagga acagctgctc    5220
cagcctctcc agcctgctct ccacctcggt caggtgggcc ctggtcaggg ggctcctctt   5280
ggtcttgggg ctgtatctgc actcccagtt gttcttcagg cacttggcgc acttgggctt   5340
ctccttgctg cacttcagct tcttcagcct gcagatgtcg caagcctgct cgatgctgct   5400
cagcagcttc atggtggcca attgcccccc ccccccccg catgcacagg aagatgagct    5460
cacacaccag ctaaggcacc cattatatac cctctaggtc ttcgcggacg tgcgggaacc   5520
cacgtggggg ctccgtcacg tactccgagt cccgcacgca ctcagcgtcg ctctggggcc   5580
ccacgtccgg ccctgacgtg cggcttcgtt tgtcacgtcg cggacgtgcg gaacccacg    5640 tgggggctcc gtcacgtact ccgagtcccg cacgcactca gcgtcgctct ggggccccac   5700
gtccggccct gacgtgcggc ttcgtttgtc acgtcgcgga cgtgcgggaa cccacgtggg   5760
ggctccgtca cgtactccga gtcccgcacg cactcagcgt cgctctgggg ccccacgtcc   5820
ggccctgacg tgcggcttcg tttgtcacgt cgcggacgtg cgggaaccca cgtggggct    5880 ccgtcacgta ctccgagtcc cgcacgcact cagcgtcgct ctggggcccc acgtccggcc   5940
ctgacgtgcg gcttcgtttg tcacgtcgcg gacgtgcggg aacccacgtg gggctccgt    6000 cacgtactcc gagtcccgca cgcactcagc gtcgctctgg ggccccacgt ccggccctga   6060
cgtgcggctt cgtttgtcac gtcgcggacg tgcgggaacc cacgtggggg ctccgtcacg   6120
tactccgagt cccgcacgca ctcagcgtcg ctctggggcc ccacgtccgg ccctgacgtg   6180
cggcttcgtt tgtcacgtcg cggacgtgcg ggaacccacg tggggctcc gtcacgtact    6240 ccgagtcccg cacgcactca gcgtcgctct ggggccccac gtccggccct gacgtgcggc   6300
ttcgtttgtc acgtcctcga gtggtaatac aatggccggt tcccatggac ctgcatcgtg   6360
gtgtaactat aacggtccta aggtagcgac cgcggagact aggtgtattt atctaagcga   6420
tcgcttaatt aaggccggcc gccgcaataa aatatcttta ttttcattac atctgtgtgt   6480
tggttttttg tgtgaatcca tagtactaac atacgctctc catcaaaaca aaacgaaaca   6540
aaacaaacta gcaaaatagg ctgtccccag tgcaagtcca ggtgccagaa catttctcta   6600
tccataatgc aggggtaccg ggtgatgacg gtgaaaacct ccaattgcgg agtactgtcc   6660
tccgagcgga gtactgtcct ccgagcggag tactgtcctc cgagcggagt actgtcctcc   6720
gagcggagta ctgtcctccg agcggagtac tgtcctccga gcggagagtc ccggggacc    6780 tagagggtat ataatgggtg ccttagctgg tgtgtgacct catcttcctg tacgccctg    6840 caggggcgcg ccacgcgtcg aagaaggtga gtaatcttaa catgctcttt ttttttttt    6900 ttgctaatcc cttttgtgtg ctgatgttag gatgacattt acaacaaatg tttgttcctg   6960
acaggaaaaa ccttgctggg taccttcgtt gccggacact tcttgtcctc tactttggaa   7020
aaaaggaatt gagagccgct agcgccacca tggtgggtgt ggggggtgga gatgtagaag   7080
atgtgacgcc caggcccggc gggtgccaga ttagcggacg cggtgccaga ggctgcaacg   7140
gcatccccgg cgcagccgcc tgggaagccg ctctccccag gcggcgtccc agaaggcacc   7200
catccgtgaa cccaggagc agagccgccg gatcgccgcg caccagggc agaagaacag      7260 aggaacggcc gagcggcagc agactggggg acagaggcag aggcagagcg ctgccgggcg   7320
```

```
ggaggctggg gggccggggc cggggccgtg ccccggagcg ggtcggaggc cggggccggg    7380
gccgggggac ggcggctccc cgcgcggctc cagcggctcg ggctccaga cccgccccg     7440 cagggacaat ggccgccggg agcatcacca cgctgcccgc cttgcccgag gatggcggca    7500
gcggcgcttt cccgcccggc cacttcaagg accccaagcg gctgtactgc aaaaacgggg    7560
gcttcttcct gcgcatccac cccgacggcc gagttgacgg ggtccgggag aagtccgacc    7620
ctcacatcaa gctacaactt caagcagagg agagaggagt tgtgtctatc aaaggagtgt    7680
gtgctaaccg ttacctggct atgaaggaag atggaagatt actggcttct aaatgtgtta    7740
cggatgagtg tttcttttt gaacgattgg aatctaataa ctacaatact tacagaagca    7800
ggaaatacac cagttggtat gtggcactga acgaactgg gcagtataaa cttggcagca    7860
aaacaggacc tgggcagaaa gctatacttt ttcttccaat gtctgctaag agctgaatcg    7920
attgcgcaaa gctttcgcga taggcgagac caatgggtgt gtacgtagcg gccgcgtcga    7980
cgatagcttg atgggtggca tccctgtgac ccctccccag tgcctctcct ggccctggaa    8040
gttgccactc cagtgcccac cagccttgtc ctaataaaat taagttgcat cattttgtct    8100
gactaggtgt ccttctataa tattatgggg tggaggggggg tggtatggag caaggggcaa    8160
gttgggaaga caacctgtag ggcctgcggg gtctattggg aaccaagctg gagtgcagtg    8220
gcacaatctt ggctcactgc aatctccgcc tcctgggttc aagcgattct cctgcctcag    8280
cctcccgagt tgttgggatt ccaggcatgc atgaccaggc tcagctaatt tttgtttttt    8340
tggtagagac ggggtttcac catattggcc aggctggtct ccaactccta atctcaggtg    8400
atctacccac cttggcctcc caaattgctg ggattacagg cgtgaaccac tgctcccttc    8460
cctgtccttc tgattttaaa ataactatac cagcaggagg acgtccagac acagcatagg    8520
ctacctggcc atgcccaacc ggtgggacat ttgagttgct tgcttggcac tgtcctctca    8580
tgcgttgggt ccactcagta gatgcctgtt gaattctgat ttaaatcggt ccgcgtacgg    8640
cgtggtaggt ccgaacgaat ccatggatta ccctgttatc cctactcaag gacatcatcc    8700 cctttagtgag ggttaattca cgcagtgggt acggaactaa aggcagcaca catcgtgtaa    8760
tcatggtcat agctgtttcc tgtgtgaaat tgttatccgc tacgtctctc ccccgcagta    8820
agggctagat taactcgtct cgtgaatatc cggaactccc tttagtgagg gttaattgcg    8880
ttgcgctcac tgcccgcttt ccagtcggga aacctgtcgt gccagcttaa tcatggtcat    8940 agctgttcc tgtgtgaaat tgttatccgc taccggaaac gcttccttca tgtgagcaaa    9000
aggccagcaa aaggccagga accgtaaaaa ggccgcgttg ctggcgtttt tccataggct    9060
ccgcccccct gacgagcatc acaaaaatcg acgctcaagt cagaggtggc gaaacccgac    9120
aggactataa agataccagg cgtttccccc tggaagctcc ctcgtgcgct ctcctgttcc    9180
gaccctgccg cttaccggat acctgtccgc ctttctccct tcgggaagcg tggcgctttc    9240
tcatagctca cgctgtaggt atctcagttc ggtgtaggtc gttcgctcca agctgggctg    9300
tgtgcacgaa ccccccgttc agcccgaccg ctgcgcctta ccggtaact atcgtcttga    9360 gtccaacccg gtaagacacg acttatcgcc actggcagca gccactggta acaggattag    9420
cagagcgagg tatgtaggcg gtgctacaga gttcttgaag tggtggccta actacggcta    9480
cactagaaga acagtatttg gtatctgcgc tctgctgaag ccagttacct tcggaaaaag    9540
agttggtagc tcttgatccg gcaaacaaac caccgctggt agcggtggtt ttttgtttg    9600 caagcagcag attacgcgca gaaaaaaagg atctcaagaa gatcctttga tcttttctac    9660
ggggtctgac gctcagtgga acgaaaactc acgttaaggg attttggtca tgatctatgt    9720
```

```
cgggtgcgga gaaagaggta atgaaatggc atacgagtaa acttggtctg acaccgctgc    9780
atgagattat caaaaaggat cttcacctag atccttttaa attaaaaatg aagttttaaa    9840
tcaatctaaa gtatatatga gtaaacttgg tctgacagtt accaatgctt aatcagtgag    9900
gcacctatct cagcgatctg tctatttcgt tcatccatag ttgcctgact ccccgtcgtg    9960
tagataacta cgatacggga gggcttacca tctggcccca gtgctgcaat gataccgcga   10020
gacccacgct caccggctcc agatttatca gcaataaacc agccagccgg aagcgccgag   10080
cgcagaagtg gtcctgcaac tttatccgcc tccatccagt ctattaactg ttgccgggaa   10140
gctagagtaa gtagttcgcc agttaatagt ttgcggagcg ttgttgccat tgctacaggc   10200
atcgtggtgt cacgctcgtc gtttggtatg gcttcattca gctccggttc ccaacgatca   10260
aggcgagtta catgatcccc catgttgtgc aaaaaagcgg ttagctcctt cggtcctccg   10320
atggttgtca gaagtaagtt ggccgcagtg ttatcactca tggttatggc agcactgcat   10380
aattctctta ctgtcatgcc atccgtaaga tgcttttctg tgactggtga gtattcaacc   10440
aagtcattct gagaatagtg tatgcggcga ccgagttgct cttgcccggc gtcaatacgg   10500
gataataccg cgccacatag cagaacttta aaagtgctca tcattgggaa gcgttcttcg   10560
gggcgaaaac tctcaaggat cttaccgctg ttgagatcca gttcgatgta acccacacga   10620
gcacccaact gatcttcagc atcttttact ttcaccagcg tttctgggtg agcaaaaaca   10680
ggaaggcaaa atgccgcaaa aaagggaata agggcgacac ggaaatgttg aatactcata   10740
cgcttccttt ttcaatagta ttgaagcatt tatcagggtt attgtctcgg gagcgaatac   10800
atatttgaat gtatttagaa aaa                                            10823
```

<210> SEQ ID NO 9
<211> LENGTH: 10538
<212> TYPE: DNA
<213> ORGANISM: Artificial Sequence
<220> FEATURE:
<223> OTHER INFORMATION: Synthetic ubiquitous and hypoxia inducible gene
      switch construct expressing EPO

<400> SEQUENCE: 9

```
taaacaaata ggggttccgc gcacatttcc ccgaaaagtg ccacctgacg tactgaggac      60
gccagggttt tcccagtcac gacgttgtaa aacgacggcc agtagcagac aagcccgtca     120
gggcgcgtca gcgggtgttg gccctaggac gaaaggaggt cgtgaaatgg ataaaaaaat     180
acagcgtttt tcatgtacaa ctatactagt tgtagtgcct aaataatgct tttaaaactt     240
aaaaataatc aatgtcctca gcggggtgtc ggggatttag gtgacactat aggctgagcg     300
ccgcacaggc atctagaggc tatggcaggg cctgccgccc cgacgttggc tgcgagccct     360
gggccttcac ccgaacttgg ggggtggggt ggggaaaagg aagaaacgcg ggcgtattgg     420
ccccaatggg gtctcggtgg ggtatcgaca gagtgccagc cctgggaccg aaccccgcgt     480
ttatgaacaa acgacccaac accgtgcgtt ttattctgtc tttttattgc cgtcatagcg     540
cgggttcctt ccggtattgt ctccttccgt gtttcaatcg attcaaaaga actcgtccag     600
cagacggtaa aaagcaatgc gttgagaatc cggtgcagca atgccataca gcaccagaaa     660
gcgatcagcc cattcaccgc ccagttcttc agcaatgtca cgggttgcca gtgcgatgtc     720
ctgatagcga tcagccacgc ccaggcgacc gcagtcgata agccggagaa acggccgtt     780
ttccaccata atgtttggca gacaagcatc gccgtgggtc acaaccaggt cctcgccatc     840
tggcatacgt gctttcaggc gtgcgaacag ttctgccggt gcagaccct gatgttcctc     900
```

```
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaagaaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatatttat tatcgattca gctgtcgctg gggctctcca   2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg gggttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta tcgtcgatg cccagggcgt   2760
cggtgaacat ctgctcgaac tcgaagtcgg ccatgtccag ggcgccgtag ggggcgctgt   2820
cgtgggggt gaagccgggg ccgggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tcctttttctt cttggggccc atggtggcca   3000
attgcccccc cccccccccg catgccgtct aacaaaaaag ccaaaacgg ccagaattta   3060
gcggacaatt tactagtcta acactgaaaa ttacatattg acccaaatga ttacatttca   3120
aaaggtgcct aaaaaacttc acaaaacaca ctcgccaacc ccgagcgcac gtacccagcc   3180
cagcagcccg ctactcacca agtgacgatc acagcgatcc acaaacaaga accgcgaccc   3240
```

```
aaatcccggc tgcgacggaa ctagctgtgc cacacccggc gcgtccttat ataatcatcg  3300
gcgttcaccg ccccacggag atccctccgc agaatcgccg agaagggact acttttcctc  3360
gcctgttccg ctctctggaa agaaaaccag tgccctagag tcacccaagt cccgtcctaa  3420
aatgtccttc tgctgatact ggggttctaa ggccgagtct tatgagcagc gggccgctgt  3480
cctgagcgtc cgggcggaag gatcaggacg ctcgctgcgc ccttcgtctg acgtggcagc  3540
gctcgccgtg aggaggggg cgcccgcggg aggcgccaaa accggcgcg gaggccctcg  3600
agtaggcgag accaatgggt gcgccatggg ctcttccaaa aatttaggtg acactatagg  3660
gcaccgctcg cacctgcgca caggcccgcg gctacaaact acgaacgatc attctagata  3720
ccacatttgt agaggtttta cttgctttaa aaaacctccc acatctcccc ctgaacctga  3780
aacataaaat gaatgcaaat gttttattaa cttgtttatt gcagcttata atggttacaa  3840
attaagcaat agcatcacaa atttcacaaa ttaagcattt ttttcactgc attctagttg  3900
tggtttgtcc aaactcatca atgtatctta tcatgtctaa tcgattcaca ggttggtggg  3960
gctctccagg atggggggg gctgggtgtg gctcatgtcg gccacgtccc aaatctcctc  4020
caggaagggg ggcagcttcc tgttcttcag cttcaggctg atacacatat tgctgttctg  4080
cattcccagg gtcctcagct cgctcaggat gctcaggatc ttgccgtaga tcacgctgct  4140
cctggcgctg ccgctcagct ggttcaggat gtagatcctc agggtgttca ggtagtacct  4200
ctggatctcc tccaccagct ggggctgctc caggccgggc ctgtcgctga agatcaccac  4260
ggcggtcagc agggcgtagt ggatgttgtc cagggccatg ctgtacatac atctgcagaa  4320
gtgcaggagg tcctcgatca cctcggccat gccagccttc ctgtagttgt ccctggtgta  4380
agcctggttg ttggcgaaca ggatgctgtc gctggcggcg tcgtacctcc tggccaccct  4440
cagcatcatc acctcgctgc tgcaagcctt cagcagggtg atctggtcgg gctggctgat  4500
cttggcgaat ccgggcaggc ccttggcgaa ctccacgatc agctgcacgg tcaggatggt  4560
catctcggta atctgcctga aggggtgtc gctctcctcg ttctcgtcgt cggcctgctg  4620
ccaggtctgg gtgatccttt tcaggtcctc gtcgctgggc tgctcgtagc cgtcctgata  4680
ccagatcagc ctggcgatca ggaactgctg gttggcggtc agctggggga tgttcttctg  4740
cctgttggtc accagcagct tgtcgctcag gaacctgggc acgacctcgt gaatcctggc  4800
ggcctcgggg ggggggggct cgcactgcat gatgggggg atgtggtcat cgacggtggt  4860
ggtgctcacg ggcagcttgt ccttctcctt ctgggccttc ttctccttcc ttttcatggc  4920
gcactgggtc tcgggcacca cgcactcggg cctgatcccg ggaaactcgg ggctcacggt  4980
cagctgcctc tggcccttgt tgctgctctc ctcgctgctg ctggtggcgc tgatcctgtg  5040
ctgcctcagg gtcaggggca tgtcggtctc cacgctggcc agcctgtcgg tcacggcgtc  5100
cttgttcacg ttgtcctgca cgaacaggcc ggtcagcagg gccttgatgt cttgcaggct  5160
gtccatcttc aggatcatgt ccaggtcctc cctggggaag atcagcagga acagctgctc  5220
cagcctctcc agcctgctct ccacctcggt caggtgggcc ctggtcaggg gctcctcttc  5280
ggtcttgggg ctgtatctgc actccagtt gttcttcagg cacttggcgc acttgggctt  5340
ctccttgctg cacttcagct tcttcagcct gcagatgtcg caagcctgct cgatgctgct  5400
cagcagcttc atggtggcca attgcccccc cccccccccg catgcacagg aagatgagct  5460
cacacaccag ctaaggcacc cattatatac cctctaggtc ttcgcggacg tgcgggaacc  5520
cacgtggggg ctccgtcacg tactccgagt cccgcacgca ctcagcgtcg ctctgggcc  5580
ccacgtccgg ccctgacgtg cggcttcgtt tgtcacgtcg cggacgtgcg ggaacccacg  5640
```

```
tgggggctcc gtcacgtact ccgagtcccg cacgcactca gcgtcgctct ggggccccac    5700
gtccggccct gacgtgcggc ttcgtttgtc acgtcgcgga cgtgcgggaa cccacgtggg    5760
ggctccgtca cgtactccga gtcccgcacg cactcagcgt cgctctgggg cccacgtcc     5820 ggccctgacg tgcggcttcg tttgtcacgt cgcggacgtg cgggaaccca cgtgggggct    5880
ccgtcacgta ctccgagtcc cgcacgcact cagcgtcgct ctgggccccc acgtccggcc    5940
ctgacgtgcg gcttcgtttg tcacgtcgcg gacgtgcggg aacccacgtg ggggctccgt    6000
cacgtactcc gagtcccgca cgcactcagc gtcgctctgg ggcccacgt ccggccctga     6060 cgtgcggctt cgtttgtcac gtcgcggacg tgcgggaacc cacgtggggg ctccgtcacg    6120
tactccgagt cccgcacgca ctcagcgtcg ctctggggcc ccacgtccgg ccctgacgtg    6180
cggcttcgtt tgtcacgtcg cggacgtgcg ggaacccacg tggggctcc gtcacgtact     6240 ccgagtcccg cacgcactca gcgtcgctct ggggccccac gtccggccct gacgtgcggc    6300
ttcgtttgtc acgtcctcga gtggtaatac aatggccggt tcccatggac ctgcatcgtg    6360
gtgtaactat aacggtccta aggtagcgac cgcggagact aggtgtattt atctaagcga    6420
tcgcttaatt aaggccggcc gccgcaataa aatatcttta ttttcattac atctgtgtgt    6480 tggtttttg tgtgaatcca tagtactaac atacgctctc catcaaaaca aaacgaaaca     6540
aaacaaacta gcaaaatagg ctgtccccag tgcaagtcca ggtgccagaa catttctcta    6600
tccataatgc aggggtaccg ggtgatgacg gtgaaaacct ccaattgcgg agtactgtcc    6660
tccgagcgga gtactgtcct ccgagcggag tactgtcctc cgagcggagt actgtcctcc    6720
gagcggagta ctgtcctccg agcggagtac tgtcctccga gcggagagtc cccggggacc    6780
tagagggtat ataatgggtg ccttagctgg tgtgtgacct catcttcctg tacgccctg     6840 caggggcgcg ccacgcgtcg aagaaggtga gtaatcttaa catgctcttt ttttttttt     6900 ttgctaatcc cttttgtgtg ctgatgttag gatgacattt acaacaaatg tttgttcctg    6960
acaggaaaaa ccttgctggg taccttcgtt gccggacact tcttgtcctc tactttggaa    7020
aaaaggaatt gagagccgct agcgccacca tggggtgca tgaatgtcct gcctggctgt     7080
ggcttctcct gtccctgctg tcgctccctc tgggcctccc agtcctgggc gctccaccac    7140
gcctcatctg tgacagccga gtcctggaga gatacctgtt ggaggccaag gaagccgaga    7200
atatcacgac gggctgtgct gaacactgct ccttgaatga gaatatcact gtcccagaca    7260
ccaaagttaa tttctatgcc tggaagcgga tggaggtcgg gcagcaggcc gtagaagtct    7320
ggcagggcct ggccctgctg tcggaagctg tcctgcgggg ccaggccctg ttggtcaaca    7380
gcagccagcc gtgggagccc ctgcaactgc atgtggataa agccgtcagt ggccttcgca    7440
gcctcaccac tctgcttcgg gctctgcgag cccagaagga agccatctcc cctcagatg     7500 cggccagcgc cgctccactc cgaacaatca ctgctgacac tttccgcaaa ctgttccgag    7560
tctactccaa tttcctccgg ggaaagctga agctgtacac aggggaggct gcaggacag     7620 gggacagatg aatcgattgc gcaaagcttt cgcgataggc gagaccaatg ggtgtgtacg    7680
tagcggccgc gtcgacgata gcttgatggg tggcatccct gtgacccctc ccagtgcct     7740 ctcctggccc tggaagttgc cactccagtg cccaccagcc ttgtcctaat aaaattaagt    7800
tgcatcattt tgtctgacta ggtgtccttc tataatatta tggggtggag ggggtggta     7860 tggagcaagg gcaagttgg gaagacaacc tgtagggcc gcggggtcta ttgggaacca     7920
agctggagtg cagtggcaca atcttggctc actgcaatct ccgcctcctg ggttcaagcg    7980
```

```
attctcctgc ctcagcctcc cgagttgttg ggattccagg catgcatgac caggctcagc   8040
taattttttgt tttttttggta gagacggggt ttcaccatat tggccaggct ggtctccaac   8100
tcctaatctc aggtgatcta cccaccttgg cctcccaaat tgctgggatt acaggcgtga   8160
accactgctc ccttccctgt ccttctgatt ttaaaataac tataccagca ggaggacgtc   8220
cagacacagc ataggctacc tggccatgcc caaccggtgg gacatttgag ttgcttgctt   8280
ggcactgtcc tctcatgcgt tgggtccact cagtagatgc ctgttgaatt ctgatttaaa   8340
tcggtccgcg tacggcgtgg taggtccgaa cgaatccatg gattaccctg ttatccctac   8400
tcaaggacat catcccttta gtgagggtta attcacgcag tgggtacgga actaaaggca   8460
gcacacatcg tgtaatcatg gtcatagctg tttcctgtgt gaaattgtta tccgctacgt   8520
ctctcccccg cagtaagggc tagattaact cgtctcgtga atatccggaa ctcccttttag   8580
tgagggttaa ttgcgttgcg ctcactgccc gctttccagt cgggaaacct gtcgtgccag   8640
cttaatcatg gtcatagctg tttcctgtgt gaaattgtta tccgctaccg gaaacgcttc   8700
cttcatgtga gcaaaaggcc agcaaaaggc caggaaccgt aaaaaggccg cgttgctggc   8760
gttttttccat aggctccgcc cccctgacga gcatcacaaa aatcgacgct caagtcagag   8820
gtggcgaaac ccgacaggac tataaagata ccaggcgttt ccccctggaa gctccctcgt   8880
gcgctctcct gttccgaccc tgccgcttac cggatacctg tccgcctttc tcccttcggg   8940
aagcgtggcg ctttctcata gctcacgctg taggtatctc agttcggtgt aggtcgttcg   9000
ctccaagctg ggctgtgtgc acgaaccccc cgttcagccc gaccgctgcg ccttatccgg   9060
taactatcgt cttgagtcca acccggtaag acacgactta tcgccactgg cagcagccac   9120
tggtaacagg attagcagag cgaggtatgt aggcggtgct acagagttct tgaagtggtg   9180
gcctaactac ggctacacta agaacagt atttggtatc tgcgctctgc tgaagccagt   9240
taccttcgga aaaagagttg gtagctcttg atccggcaaa caaaccaccg ctggtagcgg   9300
tggttttttt gtttgcaagc agcagattac gcgcagaaaa aaaggatctc aagaagatcc   9360
tttgatcttt tctacggggt ctgacgctca gtggaacgaa aactcacgtt aagggatttt   9420
ggtcatgatc tatgtcgggt gcggagaaag aggtaatgaa atggcatacg agtaaacttg   9480
gtctgacacc gctgcatgag attatcaaaa aggatcttca cctagatcct tttaaattaa   9540
aaatgaagtt ttaaatcaat ctaaagtata tatgagtaaa cttggtctga cagttaccaa   9600
tgcttaatca gtgaggcacc tatctcagcg atctgtctat ttcgttcatc catagttgcc   9660
tgactccccg tcgtgtagat aactacgata cgggagggct taccatctgg ccccagtgct   9720
gcaatgatac cgcgagaccc acgctcaccg gctccagatt tatcagcaat aaaccagcca   9780
gccggaagcg ccgagcgcag aagtggtcct gcaactttat ccgcctccat ccagtctatt   9840
aactgttgcc gggaagctag agtaagtagt tcgccagtta atagtttgcg gagcgttgtt   9900
gccattgcta caggcatcgt ggtgtcacgc tcgtcgtttg gtatggcttc attcagctcc   9960
ggttcccaac gatcaaggcg agttacatga tcccccatgt tgtgcaaaaa agcggttagc  10020
tccttcggtc ctccgatggt tgtcagaagt aagttggccg cagtgttatc actcatggtt  10080
atggcagcac tgcataattc tcttactgtc atgccatccg taagatgctt ttctgtgact  10140
ggtgagtatt caaccaagtc attctgagaa tagtgtatgc ggcgaccgag ttgctcttgc  10200
ccggcgtcaa tacgggataa taccgcgcca catagcagaa ctttaaaagt gctcatcatt  10260
gggaagcgtt cttcggggcg aaaactctca aggatcttac cgctgttgag atccagttcg  10320
atgtaaccca cacgagcacc caactgatct tcagcatctt ttactttcac cagcgtttct  10380
```

```
gggtgagcaa aaacaggaag gcaaaatgcc gcaaaaaagg gaataagggc gacacggaaa    10440
tgttgaatac tcatacgctt cctttttcaa tagtattgaa gcatttatca gggttattgt    10500
ctcgggagcg aatacatatt tgaatgtatt tagaaaaa                            10538
```

<210> SEQ ID NO 10
<211> LENGTH: 10361
<212> TYPE: DNA
<213> ORGANISM: Artificial Sequence
<220> FEATURE:
<223> OTHER INFORMATION: Synthetic ubiquitous and hypoxia inducible gene switch construct expressing BNP

<400> SEQUENCE: 10

```
taaacaaata gggttccgc gcacatttcc ccgaaaagtg ccacctgacg tactgaggac       60
gccagggttt tcccagtcac gacgttgtaa acgacggcc agtagcagac aagcccgtca      120
gggcgcgtca gcgggtgttg gccctaggac gaaaggaggt cgtgaaatgg ataaaaaaat     180
acagcgtttt tcatgtacaa ctatactagt tgtagtgcct aaataatgct tttaaaactt    240
aaaaataatc aatgtcctca gcggggtgtc ggggatttag gtgacactat aggctgagcg    300
ccgcacaggc atctagaggc tatggcaggg cctgccgccc cgacgttggc tgcgagccct    360
gggccttcac ccgaacttgg ggggtggggt ggggaaaagg aagaaacgcg ggcgtattgg    420
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccgtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
ctgatagcga tcagccacgc ccaggcgacc gcagtcgata aagccggaga acggccgtt    780 ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgctttta  1500 gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctgggggag cctggggact ttccacaccc taacctcgag gccatcgtgg   1860
```

```
cacgccaggg ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatatttat tatcgattca gctgtcgctg gggctctcca    2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg cgtacacct    2220 tctccctcag cagctccacc tcctgggcgc ttttcaggcc cctcacctcg gggttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgcctggt cgcttttctg ctccacggcg agttcggcct    2700
ccagaatcct gtccacgggc atctccatat ggccgccgta ctcgtcgatg cccagggcgt   2760
cggtgaacat ctgctcgaac tcgaagtcgg ccatgtccag ggcgccgtag ggggcgctgt   2820 cgtgggggt gaagccgggg ccggggctgt cgccgtcgcc cagcatgtcc aggtcgaagt    2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc ccccccccg catgccgtct aacaaaaaag ccaaaaacgg ccagaattta   3060
gcggacaatt tactagtcta acactgaaaa ttacatattg acccaaatga ttacatttca   3120
aaaggtgcct aaaaaacttc acaaaacaca ctcgccaacc ccgagcgcac gtacccagcc   3180
cagcagcccg ctactcacca agtgacgatc acagcgatcc acaaacaaga accgcgaccc   3240
aaatcccggc tgcgacggaa ctagctgtgc cacacccggc gcgtccttat ataatcatcg   3300
gcgttcaccg ccccacggag atccctccgc agaatcgccg agaagggact acttttcctc   3360
gcctgttccg ctctctggaa agaaaaccag tgccctagag tcacccaagt cccgtcctaa   3420
aatgtccttc tgctgatact gggttctaa ggccgagtct tatgagcagc gggccgctgt    3480
cctgagcgtc cgggcggaag gatcaggacg ctcgctgcgc ccttcgtctg acgtggcagc   3540
gctcgccgta aggagggggg cgcccgcggg aggcgccaaa acccggcgcg gaggccctcg   3600
agtaggcgag accaatgggt gcgccatggg ctcttccaaa aatttaggtg acactatagg   3660
gcaccgctcg cacctgcgca caggcccgcg gctacaaact acgaacgatc attctagata   3720
ccacatttgt agaggtttta cttgcttta aaaacctccc acatctcccc ctgaacctga    3780
aacataaaat gaatgcaaat gttttattaa cttgtttatt gcagcttata atggttacaa   3840
attaagcaat agcatcacaa atttcacaaa ttaagcattt ttttcactgc attctagttg   3900
tggtttgtcc aaactcatca atgtatctta tcatgtctaa tcgattcaca ggttggtggg   3960
gctctccagg atggggggg gctgggtgtg gctcatgtcg gccacgtccc aaatctcctc   4020
caggaagggg ggcagcttcc tgttcttcag cttcaggctg atacacatat tgctgttctg   4080
cattcccagg gtcctcagct cgctcaggat gctcaggatc ttgccgtaga tcacgctgct   4140
cctggcgctg ccgctcagct ggttcaggat gtagatcctc agggtgttca ggtagtacct   4200
```

```
ctggatctcc tccaccagct ggggctgctc caggccgggc ctgtcgctga agatcaccac    4260
ggcggtcagc agggcgtagt ggatgttgtc cagggccatg ctgtacatac atctgcagaa    4320
gtgcaggagg tcctcgatca cctcggccat gccagccttc ctgtagttgt ccctggtgta    4380
agcctggttg ttggcgaaca ggatgctgtc gctggcggcg tcgtacctcc tggccaccct    4440
cagcatcatc acctcgctgc tgcaagcctt cagcagggtg atctggtcgg gctggctgat    4500
cttggcgaat ccgggcaggc ccttggcgaa ctccacgatc agctgcacgg tcaggatggt    4560
catctcggtg atctgcctga aggggtgtc gctctcctcg ttctcgtcgt cggcctgctg    4620
ccaggtctgg gtgatccttt tcaggtcctc gtcgctgggc tgctcgtagc cgtcctgata    4680
ccagatcagc ctggcgatca ggaactgctg gttggcggtc agctggggga tgttcttctg    4740
cctgttggtc accagcagct tgtcgctcag gaacctgggc acgacctcgt gaatcctggc    4800
ggcctcgggg gggggggct cgcactgcat gatgggggc atgtggtcat cgacggtggt    4860
ggtgctcacg ggcagcttgt ccttctcctt ctgggccttc ttctccttcc ttttcatggc    4920
gcactgggtc tcgggcacca cgcactcggg cctgatcccg ggaaactcgg ggctcacggt    4980
cagctgcctc tggcccttgt tgctgctctc ctcgctgctg ctggtggcgc tgatcctgtg    5040
ctgcctcagg tcaggggca tgtcggtctc cacgctggcc agcctgtcgg tcacggcgtc    5100
cttgttcacg ttgtcctgca cgaacaggcc ggtcagcagg gccttgatgt cttgcaggct    5160
gtccatcttc aggatcatgt ccaggtcctc cctggggaag atcagcagga acagctgctc    5220
cagcctctcc agcctgctct ccacctcggt caggtgggcc ctggtcaggg ggctcctctt    5280
ggtcttgggg ctgtatctgc actcccagtt gttcttcagg cacttggcgc acttgggctt    5340
ctccttgctg cacttcagct tcttcagcct gcagatgtcg caagcctgct cgatgctgct    5400
cagcagcttc atggtggcca attgcccccc cccccccccg catgcacagg aagatgagct    5460
cacacaccag ctaaggcacc cattatatac cctctaggtc ttcgcggacg tgcgggaacc    5520
cacgtggggg ctccgtcacg tactccgagt cccgcacgca ctcagcgtcg ctctggggcc    5580
ccacgtccgg ccctgacgtg cggcttcgtt tgtcacgtcg cggacgtgcg ggaacccacg    5640
tgggggctcc gtcacgtact ccgagtcccg cacgcactca gcgtcgctct ggggccccac    5700
gtccggccct gacgtgcggc ttcgtttgtc acgtcgcgga cgtgcgggaa cccacgtggg    5760
ggctccgtca cgtactccga gtcccgcacg cactcagcgt cgctctgggg ccccacgtcc    5820
ggccctgacg tgcggcttcg tttgtcacgt cgcggacgtg cgggaaccca cgtggggct    5880 ccgtcacgta ctccgagtcc cgcacgcact cagcgtcgct ctggggcccc acgtccggcc    5940
ctgacgtgcg gcttcgtttg tcacgtcgcg gacgtgcggg aacccacgtg gggctccgt    6000 cacgtactcc gagtcccgca cgcactcagc gtcgctctgg ggccccacgt ccggccctga    6060
cgtgcggctt cgtttgtcac gtcgcggacg tgcgggaacc cacgtggggg ctccgtcacg    6120
tactccgagt cccgcacgca ctcagcgtcg ctctggggcc ccacgtccgg ccctgacgtg    6180
cggcttcgtt tgtcacgtcg cggacgtgcg ggaacccacg tggggctcc gtcacgtact    6240 ccgagtcccg cacgcactca gcgtcgctct ggggccccac gtccggccct gacgtgcggc    6300
ttcgtttgtc acgtcctcga gtggtaatac aatggccggt tccatggac ctgcatcgtg    6360 gtgtaactat aacggtccta aggtagcgac cgcggagact aggtgtattt atctaagcga    6420
tcgcttaatt aaggccggcc gccgcaataa aatatcttta ttttcattac atctgtgtgt    6480
tggttttttg tgtgaatcca tagtactaac atacgctctc catcaaaaca aaacgaaaca    6540
aaacaaacta gcaaaatagg ctgtccccag tgcaagtcca ggtgccagaa catttctcta    6600
```

```
tccataatgc aggggtaccg ggtgatgacg gtgaaaacct ccaattgcgg agtactgtcc     6660
tccgagcgga gtactgtcct ccgagcggag tactgtcctc cgagcggagt actgtcctcc     6720
gagcggagta ctgtcctccg agcggagtac tgtcctccga gcggagagtc cccggggacc     6780
tagagggtat ataatgggtg ccttagctgg tgtgtgacct catcttcctg tacgccctg      6840 caggggcgcg ccacgcgtcg aagaaggtga gtaatcttaa catgctcttt tttttttttt     6900
ttgctaatcc cttttgtgtg ctgatgttag gatgacattt acaacaaatg tttgttcctg     6960
acaggaaaaa ccttgctggg taccttcgtt gccggacact tcttgtcctc tactttggaa     7020
aaaaggaatt gagagccgct agcgccacca tggaccccca gacagcacct agcagagccc     7080
tcctgctcct gctgttcttg catctggctt tcctgggagg tcgttcccac ccgctgggca     7140
gccccggttc agcctcggac ttggaaacgt ccggggttaca ggagcagcgc aaccatttgc    7200 agggcaaaact gtcggagctg caagtggagc agacatccct ggagcccctc caggagagcc    7260
cccgtcccac aggtgtctgg aagtccagag aggtagccac cgagggcatc cgtgggcacc    7320
gcaaaatggt cctctacacc ctgcgggcac cacgaagccc aagatggtg caagggtctg      7380 gctgctttgg gaggaagatg gaccggatca gctccagcag cggcctgggc tgcaaagtgc     7440
tgagaaggca ctaaatcgat tgcgcaaagc tttcgcgata ggcgagacca tgggtgtgt     7500 acgtagcggc cgcgtcgacg atagcttgat gggtggcatc cctgtgaccc ctccccagtg     7560
cctctcctgg ccctggaagt tgccactcca gtgcccacca gccttgtcct aataaaatta     7620
agttgcatca ttttgtctga ctaggtgtcc ttctataata ttatgggggtg gagggggtg     7680 gtatggagca aggggcaagt tgggaagaca acctgtaggg cctgcggggt ctattgggaa     7740
ccaagctgga gtgcagtggc acaatcttgg ctcactgcaa tctccgcctc ctgggttcaa     7800
gcgattctcc tgcctcagcc tcccgagttg ttgggattcc aggcatgcat gaccaggctc     7860
agctaatttt tgttttttttg gtagagacgg ggtttcacca tattggccag gctggtctcc     7920
aactcctaat ctcaggtgat ctaccccct tggcctccca aattgctggg attacaggcg       7980
tgaaccactg ctcccttccc tgtccttctg atttaaaat aactatacca gcaggaggac       8040
gtccagacac agcataggct acctggccat gcccaaccgg tgggacattt gagttgcttg     8100
cttggcactg tcctctcatg cgttgggtcc actcagtaga tgcctgttga attctgattt     8160
aaatcggtcc gcgtacggcg tggtaggtcc gaacgaatcc atggattacc ctgttatccc     8220
tactcaagga catcatccct ttagtgaggg ttaattcacg cagtgggtac ggaactaaag     8280
gcagcacaca tcgtgtaatc atggtcatag ctgtttcctg tgtgaaattg ttatccgcta     8340
cgtctctccc ccgcagtaag ggctagatta actcgtctcg tgaatatccg gaactcccttt   8400 tagtgagggt taattgcgtt gcgctcactg cccgctttcc agtcgggaaa cctgtcgtgc     8460
cagcttaatc atggtcatag ctgtttcctg tgtgaaattg ttatccgcta ccggaaacgc     8520
ttccttcatg tgagcaaaag gccagcaaaa ggccaggaac cgtaaaaagg ccgcgttgct     8580
ggcgtttttc cataggctcc gcccccctga cgagcatcac aaaaatcgac gctcaagtca     8640
gaggtggcga aacccgacag gactataaag ataccaggcg tttccccctg gaagctccct     8700
cgtgcgctct cctgttccga ccctgccgct taccggatac ctgtccgcct ttctcccttc     8760
gggaagcgtg gcgctttctc atagctcacg ctgtaggtat ctcagttcgg tgtaggtcgt     8820
tcgctccaag ctgggctgtg tgcacgaacc ccccgttcag cccgaccgct gcgccttatc     8880
cggtaactat cgtcttgagt ccaacccggt aagacacgac ttatcgccac tggcagcagc     8940
```

```
cactggtaac aggattagca gagcgaggta tgtaggcggt gctacagagt tcttgaagtg    9000
gtggcctaac tacggctaca ctagaagaac agtatttggt atctgcgctc tgctgaagcc    9060
agttaccttc ggaaaaagag ttggtagctc ttgatccggc aaacaaacca ccgctggtag    9120
cggtggtttt tttgtttgca agcagcagat tacgcgcaga aaaaaaggat ctcaagaaga    9180
tcctttgatc ttttctacgg ggtctgacgc tcagtggaac gaaaactcac gttaagggat    9240
tttggtcatg atctatgtcg ggtgcggaga agaggtaat gaaatggcat acgagtaaac    9300
ttggtctgac accgctgcat gagattatca aaaaggatct tcacctagat ccttttaaat    9360
taaaaatgaa gttttaaatc aatctaaagt atatatgagt aaacttggtc tgacagttac    9420
caatgcttaa tcagtgaggc acctatctca gcgatctgtc tatttcgttc atccatagtt    9480
gcctgactcc ccgtcgtgta gataactacg atacgggagg gcttaccatc tggccccagt    9540
gctgcaatga taccgcgaga cccacgctca ccggctccag atttatcagc aataaaccag    9600
ccagccggaa gcgccagcg cagaagtggt cctgcaactt tatccgcctc catccagtct    9660
attaactgtt gccgggaagc tagagtaagt agttcgccag ttaatagttt gcggagcgtt    9720
gttgccattg ctacaggcat cgtggtgtca cgctcgtcgt ttggtatggc ttcattcagc    9780
tccggttccc aacgatcaag gcgagttaca tgatccccca tgttgtgcaa aaaagcggtt    9840
agctccttcg gtcctccgat cgttgtcaga agtaagttgg ccgcagtgtt atcactcatg    9900
gttatggcag cactgcataa ttctcttact gtcatgccat ccgtaagatg cttttctgtg    9960
actggtgagt attcaaccaa gtcattctga gaatagtgta tgcggcgacc gagttgctct   10020
tgcccggcgt caatacggga taataccgcg ccacatagca gaactttaaa agtgctcatc   10080
attgggaagc gttcttcggg gcgaaaactc tcaaggatct taccgctgtt gagatccagt   10140
tcgatgtaac ccacacgagc acccaactga tcttcagcat cttttacttt caccagcgtt   10200
tctgggtgag caaaaacagg aaggcaaaat gccgcaaaaa agggaataag ggcgacacgg   10260
aaatgttgaa tactcatacg cttccttttt caatagtatt gaagcattta tcagggttat   10320
tgtctcggga gcgaatacat atttgaatgt atttagaaaa a                       10361
```

<210> SEQ ID NO 11
<211> LENGTH: 11545
<212> TYPE: DNA
<213> ORGANISM: Artificial Sequence
<220> FEATURE:
<223> OTHER INFORMATION: Synthetic ubiquitous and Plexin D1 inducible
      gene switch expressing tPA

<400> SEQUENCE: 11

```
taaacaaata ggggttccgc gcacatttcc ccgaaaagtg ccacctgacg tactgaggac      60
gccagggttt tcccagtcac gacgttgtaa aacgacggcc agtagcagac aagcccgtca     120
gggcgcgtca gcgggtgttg gccctaggac gaaaggaggt cgtgaaatgg ataaaaaaat     180
acagcgtttt tcatgtacaa ctatactagt tgtagtgcct aaataatgct tttaaaactt     240
aaaaataatc aatgtcctca gcggggtgtc ggggatttag gtgacactat aggctgagcg     300
ccgcacaggc atctagaggc tatggcaggg cctgccgccc cgacgttggc tgcgagccct     360
gggccttcac ccgaacttgg ggggtggggt ggggaaaagg aagaaacgcg ggcgtattgg     420
ccccaatggg gtctcggtgg ggtatcgaca gagtgccagc cctgggaccg aaccccgcgt     480
ttatgaacaa acgacccaac accgtgcgtt ttattctgtc tttttattgc cgtcatagcg     540
cgggttcctt ccggtattgt ctccttccgt gtttcaatcg attcaaaaga actcgtccag     600
```

```
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
ctgatagcga tcagccacgc ccaggcgacc gcagtcgata aagccggaga acggccgtt     780 ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa cctttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatattttat tatcgattca gctgtcgctg ggctctcca    2040 gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg cgtacacct    2220 tctccctcag cagctccacc tcctgggcgc ttttcaggcc cctcacctcg gggttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta tcgtcgatg cccagggcgt    2760 cggtgaacat ctgctcgaac tcgaagtcgg ccatgtccag ggcgccgtag ggggcgctgt   2820 cgtgggggt gaagccgggg ccgggctgt cgccgtcgcc cagcatgtcc aggtcgaagt    2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
```

```
attgccccccc ccccccccccg catgccgtct aacaaaaaag ccaaaaacgg ccagaattta    3060
gcggacaatt tactagtcta acactgaaaa ttacatattg acccaaatga ttacatttca    3120
aaaggtgcct aaaaaacttc acaaaacaca ctcgccaacc ccgagcgcac gtacccagcc    3180
cagcagcccg ctactcacca agtgacgatc acagcgatcc acaaacaaga accgcgaccc    3240
aaatcccggc tgcgacggaa ctagctgtgc cacacccggc gcgtccttat ataatcatcg    3300
gcgttcaccg ccccacggag atccctccgc agaatcgccg agaagggact acttttcctc    3360
gcctgttccg ctctctggaa agaaaaccag tgccctagag tcacccaagt cccgtcctaa    3420
aatgtccttc tgctgatact ggggttctaa ggccgagtct tatgagcagc gggccgctgt    3480
cctgagcgtc cgggcggaag gatcaggacg ctcgctgcgc ccttcgtctg acgtggcagc    3540
gctcgccgtg aggaggggggg cgcccgcggg aggcgccaaa accggcgcg gaggccctcg    3600
agtaggcgag accaatgggt gcgccatggg ctcttccaaa aatttaggtg acactatagg    3660
gcaccgctcg cacctgcgca caggcccgcg gctacaaact acgaacgatc attctagata    3720
ccacatttgt agaggtttta cttgctttaa aaaacctccc acatctcccc ctgaacctga    3780
aacataaaat gaatgcaaat gttttattaa cttgtttatt gcagcttata atggttacaa    3840
attaagcaat agcatcacaa atttcacaaa ttaagcattt ttttcactgc attctagttg    3900
tggtttgtcc aaactcatca atgtatctta tcatgtctaa tcgattcaca ggttggtggg    3960
gctctccagg atgggggggg gctgggtgtg gctcatgtcg gccacgtccc aaatctcctc    4020
caggaagggg ggcagcttcc tgttcttcag cttcaggctg atacacatat tgctgttctg    4080
cattcccagg gtcctcagct cgctcaggat gctcaggatc ttgccgtaga tcacgctgct    4140
cctggcgctg ccgctcagct ggttcaggat gtagatcctc agggtgttca ggtagtacct    4200
ctggatctcc tccaccagct ggggctgctc caggccgggc ctgtcgctga agatcaccac    4260
ggcggtcagc agggcgtagt ggatgttgtc cagggccatg ctgtacatac atctgcagaa    4320
gtgcaggagg tcctcgatca cctcggccat gccagccttc ctgtagttgt ccctggtgta    4380
agcctggttg ttggcgaaca ggatgctgtc gctggcggcg tcgtacctcc tggccacccct    4440
cagcatcatc acctcgctgc tgcaagcctt cagcagggtg atctggtcgg gctggctgat    4500
cttggcgaat ccgggcaggc ccttggcgaa ctccacgatc agctgcacgg tcaggatggt    4560
catctcggtg atctgcctga aggggtgtc gctctcctcg ttctcgtcgt cggcctgctg    4620
ccaggtctgg gtgatccttt tcaggtcctc gtcgctgggc tgctcgtagc cgtcctgata    4680
ccagatcagc ctggcgatca ggaactgctg gttggcggtc agctggggga tgttcttctg    4740
cctgttggtc accagcagct tgtcgctcag gaacctgggc acgacctcgt gaatcctggc    4800
ggcctcgggg gggggggct cgcactgcat gatgggggc atgtggtcat cgacggtggt    4860
ggtgctcacg ggcagcttgt ccttctcctt ctgggccttc ttctccttcc ttttcatggc    4920
gcactgggtc tcgggcacca cgcactcggg cctgatcccg ggaaactcgg gctcacggt    4980
cagctgcctc tggcccttgt tgctgctctc ctcgctgctg ctggtggcgc tgatcctgtg    5040
ctgcctcagg gtcaggggca tgtcggtctc cacgctggcc agcctgtcgg tcacggcgtc    5100
cttgttcacg ttgtcctgca cgaacaggcc ggtcagcagg gccttgatgt cttgcaggct    5160
gtccatcttc aggatcatgt ccaggtcctc cctggggaag atcagcagga acagctgctc    5220
cagcctctcc agcctgctct ccacctcggt caggtgggcc ctggtcaggg gctcctctct    5280
ggtcttgggg ctgtatctgc actcccagtt gttcttcagg cacttggcgc acttgggctt    5340
```

| | |
|---|---|
| ctccttgctg cacttcagct tcttcagcct gcagatgtcg caagcctgct cgatgctgct | 5400 |
| cagcagcttc atggtggcca attgcccccc ccccccccg catgcccgg aggcggcggg | 5460 |
| aggcgggggg cgggtccggg ccacgatgcg cttcctgccc gcgccagccg ccccgaccc | 5520 |
| cggcgtccgg gcccggatca gcctcgccgc gcagtccggg ggcggggcgg gggcggctcc | 5580 |
| gctgcggaca cgccctcact ccccgccccg gccccgcccg ccccggaac cccgcctgc | 5640 |
| ccctggccgc cctgggccac gccccgccgt ccgcgggtcc cgccgcccgc gccctccagg | 5700 |
| acccgcccgc ggccccaggg tccctccccg tagccgccgc cgccgtcgct cgctctcctc | 5760 |
| gctctttcct cccacttggc cgcttggcct gcctcgctcg cgcctgtttt ctcttttccg | 5820 |
| ccctctcccc caccccgcct ctccctctct ctgtgtctct cggtctctgc gcctctccgc | 5880 |
| ctctgtcccc accccaaact ccgcgcgtgt ggcgcttctc cgggttctgc ctctgcttct | 5940 |
| ccttctccct ccgactccgc ttcgctctcc agtccctggc agccccgccc ccggcccttt | 6000 |
| ctagtctcct tctctctcct gctccgtttt tccgtccctg acgctcgctc cctctctccg | 6060 |
| tggctcccctc tgcctccccc tcggaccctc cgtccctctc tcggtccctc tgagctcccc | 6120 |
| tttccttctc cctctgcctt cccgaaccct gtgtctcccc tccacactca gcctccctcc | 6180 |
| accacctttc tcaggcactg tccaggcctt cgctcctcga gtggtaatac aatggccggt | 6240 |
| tcccatggac ctgcatcgtg gtgtaactat aacggtccta aggtagcgac cgcggagact | 6300 |
| aggtgtattt atctaagcga tcgcttaatt aaggccggcc gccgcaataa aatatcttta | 6360 |
| ttttcattac atctgtgtgt tggtttttg tgtgaatcca tagtactaac atacgctctc | 6420 |
| catcaaaaca aaacgaaaca aaacaaacta gcaaaatagg ctgtccccag tgcaagtcca | 6480 |
| ggtgccagaa catttctcta tccataatgc aggggtaccg ggtgatgacg gtgaaaacct | 6540 |
| ccaattgcgg agtactgtcc tccgagcgga gtactgtcct ccgagcggag tactgtcctc | 6600 |
| cgagcggagt actgtcctcc gagcggagta ctgtcctccg agcggagtac tgtcctccga | 6660 |
| gcggagagtc cccgggggacc tagagggtat ataatgggtg ccttagctgg tgtgtgacct | 6720 |
| catcttcctg tacgcccctg caggggcgcg ccacgcgtcg aagaaggtga gtaatcttaa | 6780 |
| catgctcttt ttttttttt ttgctaatcc cttttgtgtg ctgatgttag gatgacattt | 6840 |
| acaacaaatg tttgttcctg acaggaaaaa ccttgctggg taccttcgtt gccggacact | 6900 |
| tcttgtcctc tactttggaa aaaggaatt gagagccgct agcgccacca tggatgcaat | 6960 |
| gaagcggggg ctctgctgtg tgctgctgct gtgtggagca gtgttcgttt cgcccagcca | 7020 |
| ggaaatccat gcccgattca gaaggggcgc aagaagctac caagtgatct gccgggatga | 7080 |
| aaaaacgcag atgatatacc agcaacatca gtcatggctg cgccctgtgc tcagaagcaa | 7140 |
| ccgggtggga tattgctggt gcaacagtgg cagggcacag tgccacagcg tccctgtcaa | 7200 |
| aagttgcagc gagccaaggt gtttcaacgg gggcacctgt cagcaggccc tgtacttctc | 7260 |
| agatttcgtg tgccagtgcc ccgaaggatt tgctgggaag tgctgtgaaa tagataccag | 7320 |
| ggccacctgt tacgaggacc agggcatcag ctacaggggc acctgagca cagcggagag | 7380 |
| tggcgctgag tgtaccaact ggaacagcag cgcgttggcc cagaagccct acagcgggcg | 7440 |
| gaggccagat gccatcagac tcggcctggg gaaccacaac tactgccgga acccagatcg | 7500 |
| agactcaaag ccctggtgct acgtctttaa ggcggggaag tacagctcag agttctgctc | 7560 |
| caccccctgcc tgctctgagg gaaacagtga ctgctacttt gggaatgggt cagcctaccg | 7620 |
| tggcacgcac agcctcaccg agtcgggtgc ctcctgcctc ccgtggaaca gcatgatcct | 7680 |
| gataggcaat gtttacacag cacagaaccc cagtgcccag gcactgggcc tgggcaaaca | 7740 |

```
taattactgc cggaatcctg atggggatgc caagccctgg tgccacgtcc tgaagaaccg   7800
caggctgacg tgggagtatt gcgatgtgcc cagctgctcc acctgtggcc tgagacagta   7860
cagccagcct cagtttcgca tcaaaggcgg cctgttcgcc gacatcgcct cccacccctg   7920
gcaggctgcc atctttgcca agcacaggag gtcgcccgga gagcggttcc tgtgcggggg   7980
catactcatc agctcctgct ggattctctc tgccgcccac tgcttccagg agaggtttcc   8040
gccccaccac ctgacggtga tcttgggcag aacataccgg tggtccctg gcgaggagga    8100
gcagaaattt gaagtcgaaa atacattgt ccataaggag ttcgatgatg acacttacga    8160
caatgacatt gcgctgctgc aactgaaatc ggattcgtcc cgctgtgccc aggagagcag   8220
cgtggtcaga accgtgtgcc ttcccccggc ggacctccag ctgccggact ggacggagtg   8280
tgagctgtcc ggctacggca agcatgaggc cctgtctcct ttctattcgg agcggctgaa   8340
ggaggctcat gtcagactgt acccatccag ccgctgcaca tcacaacatt tacttaacag   8400
aacagtcacc gacaacatgc tgtgtgctgg agacactcgg agcggcggcc cccaggcaaa   8460
cttgcacgac gcctgccagg gcgattcggg aggccccctg gtgtgtctga acgatggccg   8520
catgactttg gtgggcatca tcagctgggg cctgggctgt ggacagaagg atgtgcccgg   8580
cgtgtacacc aaggttacca actacctaga ctggattcgt gacaacatgc gaccgtgaat   8640
cgattgcgca aagctttcgc gataggcgag accaatgggt gtgtacgtag cggccgcgtc   8700
gacgatagct tgatgggtgg catccctgtg accctcccc agtgcctctc ctggccctgg    8760
aagttgccac tccagtgccc accagccttg tcctaataaa attaagttgc atcattttgt   8820
ctgactaggt gtccttctat aatattatgg ggtggagggg ggtggtatgg agcaaggggc   8880
aagttgggaa gacaacctgt agggcctgcg gggtctattg gaaccaagc tggagtgcag    8940
tggcacaatc ttggctcact gcaatctccg cctcctgggt tcaagcgatt ctcctgcctc   9000
agcctcccga gttgttggga ttccaggcat gcatgaccag gctcagctaa tttttgtttt   9060
tttggtagag acggggtttc accatattgg ccaggctggt ctccaactcc taatctcagg   9120
tgatctaccc accttggcct cccaaattgc tgggattaca ggcgtgaacc actgctccct   9180
tccctgtcct tctgattta aaataactat accagcagga ggacgtccag acacagcata    9240
ggctacctgg ccatgcccaa ccggtgggac atttgagttg cttgcttggc actgtcctct   9300
catgcgttgg gtccactcag tagatgcctg ttgaattctg atttaaatcg gtccgcgtac   9360
ggcgtggtag gtccgaacga atccatggat taccctgtta tccctactca aggacatcat   9420
ccctttagtg agggttaatt cacgcagtgg gtacggaact aaaggcagca cacatcgtgt   9480
aatcatggtc atagctgttt cctgtgtgaa attgttatcc gctacgtctc tcccccgcag   9540
taagggctag attaactcgt ctcgtgaata tccggaactc cctttagtga gggttaattg   9600
cgttgcgctc actgcccgct ttccagtcgg gaaacctgtc gtgccagctt aatcatggtc   9660
atagctgttt cctgtgtgaa attgttatcc gctaccggaa acgcttcctt catgtgagca   9720
aaaggccagc aaaaggccag gaaccgtaaa aaggccgcgt tgctggcgtt tttccatagg   9780
ctccgccccc ctgacgagca tcacaaaaat cgacgctcaa gtcagaggtg gcgaaacccg   9840
acaggactat aaagatacca ggcgtttccc cctggaagct ccctcgtgcg ctctcctgtt   9900
ccgaccctgc cgcttaccgg atacctgtcc gcctttctcc cttcgggaag cgtggcgctt   9960
tctcatagct cacgctgtag gtatctcagt tcggtgtagg tcgttcgctc caagctgggc  10020
tgtgtgcacg aaccccccgt tcagcccgac cgctgcgcct tatccggtaa ctatcgtctt  10080
```

```
gagtccaacc cggtaagaca cgacttatcg ccactggcag cagccactgg taacaggatt    10140
agcagagcga ggtatgtagg cggtgctaca gagttcttga agtggtggcc taactacggc    10200
tacactagaa gaacagtatt tggtatctgc gctctgctga agccagttac cttcggaaaa    10260
agagttggta gctcttgatc cggcaaacaa accaccgctg gtagcggtgg ttttttttgtt    10320 tgcaagcagc agattacgcg cagaaaaaaa ggatctcaag aagatccttt gatcttttct    10380
acggggtctg acgctcagtg gaacgaaaac tcacgttaag gattttggt catgatctat    10440 gtcgggtgcg gagaagagg taatgaaatg gcatacgagt aaacttggtc tgacaccgct    10500
gcatgagatt atcaaaaagg atcttcacct agatcctttt aaattaaaaa tgaagtttta    10560
aatcaatcta agtatatat gagtaaactt ggtctgacag ttaccaatgc ttaatcagtg    10620
aggcacctat ctcagcgatc tgtctatttc gttcatccat agttgcctga ctccccgtcg    10680
tgtagataac tacgatacgg gagggcttac catctggccc cagtgctgca atgataccgc    10740
gagacccacg ctcaccggct ccagatttat cagcaataaa ccagccagcc ggaagcgccg    10800
agcgcagaag tggtcctgca actttatccg cctccatcca gtctattaac tgttgccggg    10860
aagctagagt aagtagttcg ccagttaata gtttgcggag cgttgttgcc attgctacag    10920
gcatcgtggt gtcacgctcg tcgtttggta tggcttcatt cagctccggt tcccaacgat    10980
caaggcgagt tacatgatcc cccatgttgt gcaaaaaagc ggttagctcc ttcggtcctc    11040
cgatggttgt cagaagtaag ttggccgcag tgttatcact catggttatg gcagcactgc    11100
ataattctct tactgtcatg ccatccgtaa gatgcttttc tgtgactggt gagtattcaa    11160
ccaagtcatt ctgagaatag tgtatgcggc gaccgagttg ctcttgcccg gcgtcaatac    11220
gggataatac cgcgccacat agcagaactt taaaagtgct catcattggg aagcgttctt    11280
cggggcgaaa actctcaagg atcttaccgc tgttgagatc cagttcgatg taacccacac    11340
gagcacccaa ctgatcttca gcatctttta ctttcaccag cgtttctggg tgagcaaaaa    11400
caggaaggca aaatgccgca aaaaagggaa taagggcgac acggaaatgt tgaatactca    11460
tacgcttcct ttttcaatag tattgaagca tttatcaggg ttattgtctc gggagcgaat    11520
acatatttga atgtatttag aaaaa                                          11545
```

<210> SEQ ID NO 12
<211> LENGTH: 10207
<212> TYPE: DNA
<213> ORGANISM: Artificial Sequence
<220> FEATURE:
<223> OTHER INFORMATION: Synthetic NxcI cardomyocyte promoter hypoxia
      inducible gene switch expressing EPO

<400> SEQUENCE: 12

```
taaacaaata ggggttccgc gcacatttcc ccgaaaagtg ccacctgacg tactgaggac      60
gccagggttt tcccagtcac gacgttgtaa aacgacggcc agtagcagac aagcccgtca     120
gggcgcgtca gcgggtgttg gcccctaggac gaaaggaggt cgtgaaatgg ataaaaaaat    180
acagcgtttt tcatgtacaa ctatactagt tgtagtgcct aaataatgct tttaaaactt    240
aaaaataatc aatgtcctca gcggggtgtc ggggatttag gtgacactat aggctgagcg    300
ccgcacaggc atctagaggc tatggcaggg cctgccgccc cgacgttggc tgcgagccct    360
gggccttcac ccgaacttgg ggggtggggt ggggaaaagg aagaaacgcg ggcgtattgg    420
ccccaatggg gtctcggtgg ggtatcgaca gagtgccagc cctgggaccg aacccgcgt    480 ttatgaacaa acgacccaac accgtgcgtt ttattctgtc tttttattgc cgtcatagcg    540
```

```
cgggttcctt ccggtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
ctgatagcga tcagccacgc ccaggcgacc gcagtcgata aagccggaga aacggccgtt    780
ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtgcaga ccgtcttgtt caatcatggt   1380
ggcaattggg tgtctgagcg atgtggctcg gctggcgacg caaagaaga tgcggctgac   1440 tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt tagggggcggg atgggcggag   1680 ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggt ttttcccagt cacgacgttg taaaacgacg gccagtgctc ttctcccccg   1920
cgggaggttt tataaatccg actgtctaga ttgttgttaa atcacacaaa aaaccaacac   1980
acagatgtaa tgaaaataaa gatattttat tatcgattca gctgtcgctg gggctctcca   2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg gggttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgcctggt cgcttttctg ctccacgcg agttcggcct   2700 ccagaatcct gtccacgggc atctccatat ggccgccgta ctcgtcgatg cccagggcgt   2760
cggtgaacat ctgctcgaac tcgaagtcgg ccatgtccag ggcgccgtag ggggcgctgt   2820
cgtggggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
```

```
ccaggctcac gtcggtgggg ggggccacct tccttttctt cttggggccc atggtggcca    3000 attgccccc ccccccccg catgcccag tatgatgcct tctctaaatt taccagaaag      3060
aaaggacctg ggatgcttgt cctttaagtg tctctaaaca tggtttgcat agctggatct    3120
cagcttatct gtgcctttcg gctttcgctt ccatacatgg atctgttccc aacagtaact    3180
ccaagctgtc gaaaagaagc tatctggcag ctctctgctt catccaacac atggatgata    3240
aaaatacaca tatagcgatt cttccctcga gtaggcgaga ccaatgggtg cgccatgggc    3300
tcttccaaaa atttaggtga cactataggg caccgctcgc acctgcgcac aggcccgcgg    3360
ctacaaacta cgaacgatca ttctagatac cacatttgta gaggttttac ttgctttaaa    3420
aaacctccca catctccccc tgaacctgaa acataaaatg aatgcaaatg ttttattaac    3480
ttgtttattg cagcttataa tggttacaaa ttaagcaata gcatcacaaa tttcacaaat    3540
taagcatttt tttcactgca ttctagttgt ggtttgtcca aactcatcaa tgtatcttat    3600
catgtctaat cgattcacag gttggtgggg ctctccagga tgggggggg ctgggtgtgg    3660 ctcatgtcgg ccacgtccca atctcctcc aggaaggggg gcagcttcct gttcttcagc    3720
ttcaggctga tacacatatt gctgttctgc attcccaggg tcctcagctc gctcaggatg    3780
ctcaggatct tgccgtagat cacgctgctc ctggcgctgc cgctcagctg gttcaggatg    3840
tagatcctca gggtgttcag gtagtacctc tggatctcct ccaccagctg gggctgctcc    3900
aggccgggcc tgtcgctgaa gatcaccacg gcggtcagca gggcgtagtg gatgttgtcc    3960
agggccatgc tgtacataca tctgcagaag tgcaggaggt cctcgatcac ctcggccatg    4020
ccagccttcc tgtagttgtc cctggtgtaa gcctggttgt tggcgaacag gatgctgtcg    4080
ctggcggcgt cgtacctcct ggccaccctc agcatcatca cctcgctgct gcaagccttc    4140
agcagggtga tctggtcggg ctggctgatc ttggcgaatc cggcaggcc cttggcgaac    4200 tccacgatca gctgcacggt caggatggtc atcgcgtga tctgcctgaa gggggtgtcg    4260
ctctcctcgt tctcgtcgtc ggcctgctgc caggtctggg tgatccttt caggtcctcg    4320 tcgctgggct gctcgtagcc gtcctgatac cagatcagcc tggcgatcag gaactgctgg    4380
ttggcggtca gctggggat gttcttctgc ctgttggtca ccagcagctt gtcgctcagg    4440
aacctgggca cgacctcgtg aatcctggcg gcctcggggg ggggggctc gcactgcatg    4500 atgggggca tgtggtcatc gacggtggtg gtgctcacgg gcagcttgtc cttctccttc    4560
tgggccttct tctccttcct tttcatggcg cactgggtct cgggcaccac gcactcgggc    4620 ctgatccgg gaaactcggg gctcacggtc agctgcctct ggcccttgtt gctgctctcc    4680
tcgctgctgc tggtggcgct gatcctgtgc tgcctcaggg tcagggcat gtcggtctcc    4740 acgctggcca gcctgtcggt cacggcgtcc ttgttcacgt tgtcctgcac gaacaggccg    4800
gtcagcaggg ccttgatgtc ttgcaggctg tccatcttca ggatcatgtc caggtcctcc    4860
ctggggaaga tcagcaggaa cagctgctcc agcctctcca gcctgctctc cacctcggtc    4920
aggtgggccc tggtcagggg gctcctcttg gtcttgggc tgtatctgca ctcccagttg    4980
ttcttcaggc acttggcgca cttgggcttc tccttgctgc acttcagctt cttcagcctg    5040
cagatgtcgc aagcctgctc gatgctgctc agcagcttca tggtggccaa ttgccccccc    5100 ccccccgc atgcacagga agatgagctc acacaccagc taaggcaccc attatatacc    5160
ctctaggtct tcgcggacgt gcgggaaccc acgtgggggc tccgtcacgt actccgagtc    5220
ccgcacgcac tcagcgtcgc tctggggccc cacgtccggc cctgacgtgc ggcttcgttt    5280
```

```
gtcacgtcgc ggacgtgcgg gaacccacgt gggggctccg tcacgtactc cgagtcccgc   5340
acgcactcag cgtcgctctg gggcccacg tccggccctg acgtgcggct tcgtttgtca    5400
cgtcgcggac gtgcgggaac ccacgtgggg gctccgtcac gtactccgag tcccgcacgc   5460
actcagcgtc gctctgggc cccacgtccg gccctgacgt gcggcttcgt tgtcacgtc     5520
gcggacgtgc gggaacccac gtgggggctc cgtcacgtac tccgagtccc gcacgcactc   5580
agcgtcgctc tggggcccca cgtccggccc tgacgtgcgg cttcgtttgt cacgtcgcgg   5640
acgtgcggga acccacgtgg gggctccgtc acgtactccg agtcccgcac gcactcagcg   5700
tcgctctggg gccccacgtc cggccctgac gtgcggcttc gtttgtcacg tcgcggacgt   5760
gcgggaaccc acgtggggc tccgtcacgt actccgagtc ccgcacgcac tcagcgtcgc    5820
tctggggccc cacgtccggc cctgacgtgc ggcttcgttt gtcacgtcgc ggacgtgcgg   5880
gaacccacgt gggggctccg tcacgtactc cgagtcccgc acgcactcag cgtcgctctg   5940
gggcccacg tccggccctg acgtgcggct tcgtttgtca cgtcctcgag tggtaataca    6000
atggccggtt cccatggacc tgcatcgtgg tgtaactata acggtcctaa ggtagcgacc   6060
gcggagacta ggtgtattta tctaagcgat cgcttaatta aggccggccg ccgcaataaa   6120
atatctttat tttcattaca tctgtgtgtt ggttttttgt gtgaatccat agtactaaca   6180
tacgctctcc atcaaaacaa aacgaaacaa aacaaactag caaaataggc tgtccccagt   6240
gcaagtccag gtgccagaac atttctctat ccataatgca ggggtaccgg gtgatgacgg   6300
tgaaaacctc caattgcgga gtactgtcct ccgagcggag tactgtcctc cgagcggagt   6360
actgtcctcc gagcggagta ctgtcctccg agcggagtac tgtcctccga gcggagtact   6420
gtcctccgag cggagagtcc ccggggacct agagggtata taatgggtgc cttagctggt   6480
gtgtgacctc atcttcctgt acgccctgc aggggcgcgc cacgcgtcga agaaggtgag    6540
taatcttaac atgctctttt tttttttttt tgctaatccc ttttgtgtgc tgatgttagg   6600
atgacattta caacaaatgt tgttcctga caggaaaaac cttgctgggt accttcgttg     6660
ccggacactt cttgtcctct actttggaaa aaggaattg agagccgcta gcgccaccat    6720
gggggtgcat gaatgtcctg cctggctgtg gcttctcctg tccctgctgt cgctccctct   6780
gggcctccca gtcctgggcg ctccaccacg cctcatctgt gacagccgag tcctggagag   6840
atacctgttg gaggccaagg aagccgagaa tatcacgacg ggctgtgctg aacactgctc   6900
cttgaatgag aatatcactg tcccagacac caaagttaat ttctatgcct ggaagcggat   6960
ggaggtcggg cagcaggccg tagaagtctg gcagggcctg gccctgctgt cggaagctgt   7020
cctgcggggc caggccctgt tggtcaacag cagccagccg tgggagcccc tgcaactgca   7080
tgtggataaa gccgtcagtg gccttcgcag cctcaccact ctgcttcggg ctctgcgagc   7140
ccagaaggaa gccatctccc ctccagatgc ggccagcgcc gctccactcc gaacaatcac   7200
tgctgacact ttccgcaaac tgttccgagt ctactccaat ttcctccggg gaaagctgaa   7260
gctgtacaca ggggaggctt gcaggacagg ggacagatga atcgattgcg caaagctttc   7320
gcgataggcg agaccaatgg gtgtgtacgt agcggccgcg tcgacgatag cttgatgggt   7380
ggcatccctg tgacccctcc ccagtgcctc tcctggccct ggaagttgcc actccagtgc   7440
ccaccagcct tgtcctaata aaattaagtt gcatcatttt gtctgactag gtgtccttct   7500
ataatattat ggggtggagg ggggtggtat ggagcaaggg gcaagttggg aagcaaacct   7560
gtagggcctg cggggtctat tgggaaccaa gctggagtgc agtggcacaa tcttggctca   7620
ctgcaatctc cgcctcctgg gttcaagcga ttctcctgcc tcagcctccc gagttgttgg   7680
```

```
gattccaggc atgcatgacc aggctcagct aattttttgtt tttttggtag agacggggtt   7740
tcaccatatt ggccaggctg gtctccaact cctaatctca ggtgatctac ccaccttggc   7800
ctcccaaatt gctgggatta caggcgtgaa ccactgctcc cttccctgtc cttctgattt   7860
taaaataact ataccagcag gaggacgtcc agacacagca taggctacct ggccatgccc   7920
aaccggtggg acatttgagt tgcttgcttg gcactgtcct ctcatgcgtt gggtccactc   7980
agtagatgcc tgttgaattc tgatttaaat cggtccgcgt acggcgtggt aggtccgaac   8040
gaatccatgg attaccctgt tatccctact caaggacatc atccctttag tgagggttaa   8100
ttcacgcagt gggtacggaa ctaaaggcag cacacatcgt gtaatcatgg tcatagctgt   8160
ttcctgtgtg aaattgttat ccgctacgtc tctcccccgc agtaagggct agattaactc   8220
gtctcgtgaa tatccggaac tcccttagt gagggttaat tgcgttgcgc tcactgcccg   8280
ctttccagtc gggaaacctg tcgtgccagc ttaatcatgg tcatagctgt ttcctgtgtg   8340
aaattgttat ccgctaccgg aaacgcttcc ttcatgtgag caaaaggcca gcaaaaggcc   8400
aggaaccgta aaaaggccgc gttgctggcg ttttttccata ggctccgccc cctgacgag   8460 catcacaaaa atcgacgctc aagtcagagg tggcgaaacc cgacaggact ataaagatac   8520
caggcgtttc ccctggaag ctccctcgtg cgctctcctg ttccgaccct gccgcttacc   8580
ggatacctgt ccgcctttct cccttcggga agcgtggcgc tttctcatag ctcacgctgt   8640
aggtatctca gttcggtgta ggtcgttcgc tccaagctgg gctgtgtgca cgaaccccc   8700 gttcagcccg accgctgcgc cttatccggt aactatcgtc ttgagtccaa cccggtaaga   8760
cacgacttat cgccactggc agcagccact ggtaacagga ttagcagagc gaggtatgta   8820
ggcggtgcta cagagttctt gaagtggtgg cctaactacg gctacactag aagaacagta   8880
tttggtatct gcgctctgct gaagccagtt accttcggaa aaagagttgg tagctcttga   8940
tccggcaaac aaaccaccgc tggtagcggt ggtttttttg tttgcaagca gcagattacg   9000
cgcagaaaaa aaggatctca agaagatcct ttgatctttt ctacggggtc tgacgctcag   9060
tggaacgaaa actcacgtta agggattttg gtcatgatct atgtcgggtg cggagaaaga   9120
ggtaatgaaa tggcatacga gtaaacttgg tctgacaccg ctgcatgaga ttatcaaaaa   9180
ggatcttcac ctagatcctt ttaaattaaa aatgaagttt taaatcaatc taaagtatat   9240
atgagtaaac ttggtctgac agttaccaat gcttaatcag tgaggcacct atctcagcga   9300
tctgtctatt tcgttcatcc atagttgcct gactccccgt cgtgtagata actacgatac   9360
gggagggctt accatctggc cccagtgctg caatgatacc gcgagaccca cgctcaccgg   9420
ctccagattt atcagcaata aaccagccag ccggaagcgc cgagcgcaga agtggtcctg   9480
caactttatc cgcctccatc cagtctatta actgttgccg ggaagctaga gtaagtagtt   9540
cgccagttaa tagtttgcgg agcgttgttg ccattgctac aggcatcgtg gtgtcacgct   9600
cgtcgtttgg tatggcttca ttcagctccg gttcccaacg atcaaggcga gttacatgat   9660
cccccatgtt gtgcaaaaaa gcggttagct ccttcggtcc tccgatggtt gtcagaagta   9720
agttggccgc agtgttatca ctcatggtta tggcagcact gcataattct cttactgtca   9780
tgccatccgt aagatgcttt tctgtgactg gtgagtattc aaccaagtca ttctgagaat   9840
agtgtatgcg gcgaccgagt tgctcttgcc cggcgtcaat acgggataat accgcgccac   9900
atagcagaac tttaaaagtg ctcatcattg gaaagcgttc ttcggggcga aaactctcaa   9960
ggatcttacc gctgttgaga tccagttcga tgtaacccac acgagcaccc aactgatctt  10020
```

-continued

```
cagcatcttt tactttcacc agcgtttctg ggtgagcaaa acaggaagg caaaatgccg    10080 caaaaagggg aataagggcg acacggaaat gttgaatact catacgcttc ctttttcaat    10140
agtattgaag catttatcag ggttattgtc tcgggagcga atacatattt gaatgtattt    10200
agaaaaa                                                               10207
```

<210> SEQ ID NO 13
<211> LENGTH: 16979
<212> TYPE: DNA
<213> ORGANISM: Artificial Sequence
<220> FEATURE:
<223> OTHER INFORMATION: Synthetic ubiquitous+ hPlexin D1 + hypoxia
       inducible gene switch construct expressing relaxin and HGF

<400> SEQUENCE: 13

```
taaacaaata ggggttccgc gcacatttcc ccgaaaagtg ccacctgacg tactgaggac     60
gccagggttt tcccagtcac gacgttgtaa acgacggcc agtagcagac aagcccgtca    120
gggcgcgtca gcgggtgttg gcgggtgtcg gggatttagg tgacactata ggctgagcgc    180
cgcacaggca tctagaggct atggcagggc ctgccgcccc gacgttggct gcgagccctg    240
ggccttcacc cgaacttggg gggtggggtg ggaaaagga agaaacgcgg gcgtattggc    300
cccaatgggg tctcggtggg gtatcgacag agtgccagcc ctgggaccga accccgcgtt    360
tatgaacaaa cgacccaaca ccgtgcgttt tattctgtct ttttattgcc gtcatagcgc    420
gggttccttc cggtattgtc tccttccgtg tttcaatcga tttagaagaa ctcgtcaaga    480
aggcgataga aggcgatgcg ctgcgaatcg ggggcggcga taccgtaaag gacgaggaag    540
cggtcagccc attcgccgcc aagttcttca gcaatatcac gggtagccaa cgctatgtcc    600
tgatagcggt cggccacacc cagccgtcca cagtcgatga atccagaaaa gcggccattt    660
tccaccatga tattcggcaa gcaggcatcg ccgtgggtca cgacgagatc ctcgccgtcg    720
ggcatcctcg ccttgagcct ggcgaacagt tcggctggcg cgagccctg atgctcctcg    780 tccagatcat cctgatcgac aagaccggct tccatccgag tacgtgctcg ctcgatgcga    840
tgtttcgctt ggtggtcgaa tgggcatgta gccggatcaa gcgtatgcag ccgccgcatt    900
gcatcagcca tgatggatac tttctcggca ggagcaaggt gagatgacag agatcctgc    960 cccggcactt cgcccaatag cagccagtcc cttcccgctt cagtgacaac gtcgagcacg    1020
gctgcgcaag gaacgcccgt cgtggccagc cacgatagcc gcgctgcctc gtcctggagt    1080
tcattcaggg caccggacag gtcggtcttg acaaaaagaa ccgggcgccc ctgcgctgac    1140
agccggaaca cggcggcatc agagcagccg attgtctgtt gtgcccagtc atagccgaat    1200
agcctctcca cccaagcggc cggagaacca gcgtgcaatc catcttgttc aatggccgat    1260
cccatggtgg ccaattgggt gtctgagcga tgtggctcgg ctggcgacgc aaaagaagat    1320
gcggctgact gtcgaacagg aggagcagag agcgaagcgg gaggctgcgg gctcaatttg    1380
catgcggaat agctctgagg ccgaggcagc ttcggcctct gcataaataa aaaaaattag    1440
tcagccatgg ggcggagaat gggcggaact gggcggagtt aggggcggga tgggcggagt    1500
taggggcggg actatggttg ctgactaatt gagatgcttg ctttgcatac ttctgcctgc    1560
tggggagcct ggggactttc cacacctggt tgctgactaa ttgagatgct tgctttgcat    1620
acttctgcct gctggggagc ctggggactt tccacaccct aacctcgagg ccatcgtggc    1680
acgccagggt tttcccagtc acgacgttgt aaaacgacgg ccagtgctct tctccccgc    1740 gggaggtttt ataaatccga ctgtctagat tgttgttaaa tcacacaaaa aaccaacaca    1800
```

-continued

```
cagatgtaat gaaaataaag atattttatt atcgattcag ctgtcgctgg ggctctccag    1860
catctccatc aggaaggtgt cgatgggcac gtcgccgatc agcctgaaga agaacaggtg    1920
ctccaggcac ttcaggccga tgctcctcag gctgggcagc tcagcagca gcttggcgaa     1980
tctgccgggc tcgtcggggt gggtggtcct ggtgtactcc tccagggcgg cgtacacctt    2040
ctccctcagc agctccacct cctgggcgct tttcaggccc ctcacctcgg ggttgaacag    2100
gatgatggcc ctcaggcagc ccagctcggt cttgtccatc ctcatgtccc tcatcttgct    2160
caccagctcg gtcagcaccc tgtcgaagat ggcgcccact ccggcgctgt gggcgctgtt    2220
cctatggacg tgcaggccgg tggccagcag gatgccgtcc ctcacgtcga tgctcctgtg    2280
gctgaagctg gcgatcagca gctcgttcca tccggccctc agcaggatca cctggtcgtc    2340
caggggcagg ctgctgaagt ggggaatcct cttggcccac tccaccaggg tgaacagctg    2400
cttgtcggcg gcctggcaga tgttggtcac ggggtcgttg ggctgctgc cgctgccgcc     2460
ggttccgccg ggccctcca cgccctggtc gcttttctgc tccacggcga gttcggcctc     2520
cagaatcctg tccacgggca tctccatatg gccgccgtac tcgtcgatgc ccagggcgtc    2580
ggtgaacatc tgctcgaact cgaagtcggc catgtccagg gcgccgtagg gggcgctgtc    2640
gtgggggtg aagccggggc cggggctgtc gccgtcgccc agcatgtcca ggtcgaagtc     2700
gtccagggcg tcggcgtggg ccatggccac gtcctcgccg tccaggtgca gctcgtcgcc    2760
caggctcacg tcggtggggg gggccacctt ccttttcttc ttggggccca tggtggccaa    2820
ttgcccccc cccccccgc atgccgtcta caaaaaagc caaaacggc cagaatttag         2880
cggacaattt actagtctaa cactgaaaat tacatattga cccaaatgat tacatttcaa    2940
aaggtgccta aaaaacttca caaaacacac tcgccaaccc cgagcgcacg tacccagccc    3000
agcagcccgc tactcaccaa gtgacgatca cagcgatcca caaacaagaa ccgcgaccca    3060
aatcccggct gcgacggaac tagctgtgcc acacccggcg cgtccttata taatcatcgg    3120
cgttcaccgc cccacggaga tccctccgca gaatcgccga aagggacta cttttcctcg     3180
cctgttccgc tctctggaaa gaaaaccagt gccctagagt cacccaagtc ccgtcctaaa    3240
atgtccttct gctgatactg gggttctaag gccgagtctt atgagcagcg ggccgctgtc    3300
ctgagcgtcc gggcggaagg atcaggacgc tcgctgcgcc cttcgtctga cgtggcagcg    3360
ctcgccgtga ggaggggggc gcccgcggga ggcgccaaaa cccggcgcgg aggccctcga    3420
gtaggcgaga ccaatgggtg cgccatgggc tcttccaaaa atttaggtga cactataggg    3480
caccgctcgc acctgcgcac aggcccgcgg ctacaaacta cgaacgatca ttctagatac    3540
cacatttgta gaggttttac ttgctttaaa aaacctccca catctccccc tgaacctgaa    3600
acataaaatg aatgcaaatg ttttattaac ttgtttattg cagcttataa tggttacaaa    3660
ttaagcaata gcatcacaaa tttcacaaat taagcatttt tttcactgca ttctagttgt    3720
ggtttgtcca aactcatcaa tgtatcttat catgtctaat cgattcacag ttggtgggg     3780
ctctccagga tgggggggg ctgggtgtgg ctcatgtcgg ccacgtccca aatctcctcc     3840
aggaaggggg gcagcttcct gttcttcagc ttcaggctga tacacatatt gctgttctgc    3900
attcccaggg tcctcagctc gctcaggatg ctcaggatct tgccgtagat cacgctgctc    3960
ctggcgctgc cgctcagctg gttcaggatg tagatcctca gggtgttcag gtagtacctc    4020
tggatctcct ccaccagctg gggctgctcc aggccgggcc tgtcgctgaa gatcaccacg    4080
gcggtcagca gggcgtagtg gatgttgtcc agggccatgc tgtacataca tctgcagaag    4140
tgcaggaggt cctcgatcac ctcggccatg ccagccttcc tgtagttgtc cctggtgtaa    4200
```

```
gcctggttgt tggcgaacag gatgctgtcg ctggcggcgt cgtacctcct ggccaccctc   4260
agcatcatca cctcgctgct gcaagccttc agcagggtga tctggtcggg ctggctgatc   4320
ttggcgaatc cgggcaggcc cttggcgaac tccacgatca gctgcacggt caggatggtc   4380
atctcggtga tctgcctgaa gggggtgtcg ctctcctcgt tctcgtcgtc ggcctgctgc   4440
caggtctggg tgatccttt caggtcctcg tcgctgggct gctcgtagcc gtcctgatac    4500
cagatcagcc tggcgatcag gaactgctgg ttggcggtca gctgggggat gttcttctgc   4560
ctgttggtca ccagcagctt gtcgctcagg aacctgggca cgacctcgtg aatcctggcg   4620
gcctcggggg ggggggctc gcactgcatg atggggggca tgtggtcatc gacggtggtg    4680
gtgctcacgg gcagcttgtc cttctccttc tgggccttct tctccttcct tttcatggcg   4740
cactgggtct cgggcaccac gcactcgggc ctgatcccgg aaactcgggg ctcacggtc    4800 agctgcctct ggcccttgtt gctgctctcc tcgctgctgc tggtggcgct gatcctgtgc   4860
tgcctcaggg tcaggggcat gtcggtctcc acgctggcca gctgtcggt cacggcgtcc    4920 ttgttcacgt tgtcctgcac gaacaggccg gtcagcaggg ccttgatgtc ttgcaggctg   4980
tccatcttca ggatcatgtc caggtcctcc ctggggaaga tcagcaggaa cagctgctcc   5040
agcctctcca gcctgctctc cacctcggtc aggtgggccc tggtcagggg gctcctcttg   5100
gtcttggggc tgtatctgca ctcccagttg ttcttcaggc acttgcgca cttgggcttc    5160 tccttgctgc acttcagctt cttcagcctg cagatgtcgc aagcctgctc gatgctgctc   5220
agcagcttca tggtggccaa ttgcccccc cccccccgc atgccccgga ggcggcggga    5280 ggcgggggc gggtccgggc cacgatgcgc ttcctgcccg cgccagccgc ccccgacccc    5340
ggcgtccggg cccggatcag cctcgccgcg cagtccgggg gcggggcggg ggcggctccg   5400
ctgcggacac gccctcactc cccgcccgg ccccgcccgc ccccggaacc cccgcctgcc    5460
cctggccgcc ctgggccacg ccccgccgtc cgcgggtccc gccgcccgcg ccctccagga   5520
cccgcccgcg gccccagggt ccctccccgt agccgccgcc gccgtcgctc gctctcctcg   5580
ctctttcctc ccacttggcc gcttggcctg cctcgctcgc gcctgttttc tcttttccgc   5640
cctctccccc accccgcctc tccctctctc tgtgtctctc ggtctctgcg cctctccgcc   5700
tctgtcccca ccccaaaactc cgcgcgtgtg gcgcttctcc gggttctgcc tctgcttctc   5760
cttctccctc cgactccgct tcgctctcca gtccctggca gccccgcccc ggccctttc    5820 tagtctcctt ctctctcctg ctccgttttt ccgtccctga cgctcgctcc ctctctccgt   5880
ggctccctct gcctcccct cggacccctcc gtccctctct cggtccctct gagctcccct   5940
ttccttctcc ctctgccttc ccgaaccctg tgtctcccct ccacactcag cctccctcca   6000
ccacctttct caggcactgt ccaggccttc gctcctcgag tggtaataca atggccggtt   6060
cccatggacc tgcatcgtgg tgatctatgt cgggtgcgga gaagaggta atgaaatggc    6120 agaaatggca ccacctaagg tagcgaccgc ggagactagg tgtatttatc taagcgatcg   6180
cttaattaag gccggccgcc gcaataaaat atctttattt tcattacatc tgtgtgttgg   6240
ttttttgtgt gaatccatag tactaacata cgctctccat caaaacaaaa cgaaacaaaa   6300
caaactagca aaataggctg tccccagtgc aagtccaggt gccagaacat ttctctatcc   6360
ataatgcagg ggtaccgggt gatgacggtg aaaacctcca attgcggagt actgtcctcc   6420
gagcggagta ctgtcctccg agcggagtac tgtcctccga gcggagtact gtcctccgag   6480
cggagtactg tcctccgagc ggagtactgt cctccgagcg gagtccccc ggggacctag    6540
```

```
agggtatata atgggtgcct tagctggtgt gtgacctcat cttcctgtac gcccctgcag   6600
gggcgcgcca cgcgtcgaag aaggtgagta atcttaacat gctcttttt ttttttttg    6660
ctaatccctt ttgtgtgctg atgttaggat gacatttaca acaaatgttt gttcctgaca   6720
ggaaaaacct tgctgggtac cttcgttgcc ggacacttct tgtcctctac tttggaaaaa   6780
aggaattgag agccgctagc gccaccatgc ctcgcctgtt ttttttccac ctgttgggag   6840
tctgtttact actgaaccaa ttttccagag cagtcgcgga ctcatggatg gaggaagtta   6900
tcaagttatg cggcagagaa ttagttcgcg cgcagattgc catttgcggc atgagcacct   6960
ggagcaaaag gtctctgagc caggaagatg ctcctcagac acctagacca gtggcagaaa   7020
ttgtgccatc cttcatcaac aaagatacag aaaccataaa tatgatgtca gaatttgttg   7080
ctaatttgcc acaggagctg aagctgaccc tgtctgagat gcagccagca ttaccacagc   7140
tacaacagca cgtccctgtg ctgaaggatt ccagcctgct gtttgaagaa tttaagaaac   7200
ttattcgcaa tagacaaagt gaagccgcag acagcagtcc ttcagagctg aagtacctgg   7260
gcttggatac tcattctcga aaaaagagac aactctacag tgcattggct aacaagtgtt   7320
gccatgttgg ttgtaccaaa agaagccttg ctagattttg ctgaatcgat gcgcaaagc    7380
tttcgcgata ggcgagacca atgggtgtgt acgtagcggc cgcgtcgacg atagcttgat   7440
gggtggcatc cctgtgaccc ctccccagtg cctctcctgg ccctggaagt tgccactcca   7500
gtgcccacca gccttgtcct aataaaatta agttgcatca ttttgtctga ctaggtgtcc   7560
ttctataata ttatggggtg agggggggtg gtatggagca aggggcaagt tgggaagaca   7620
acctgtaggg cctgcgggt ctattgggaa ccaagctgga gtgcagtggc acaatcttgg    7680
ctcactgcaa tctccgcctc ctgggttcaa gcgattctcc tgcctcagcc tcccgagttg   7740
ttgggattcc aggcatgcat gaccaggctc agctaatttt tgtttttttg gtagagacgg   7800
ggtttcacca tattggccag gctggtctcc aactcctaat ctcaggtgat ctacccacct   7860
tggcctccca aattgctggg attacaggcg tgaaccactg ctcccttccc tgtccttctg   7920
attttaaaat aactatacca gcaggaggac gtccagacac agcataggct acctggccat   7980
gcccaaccgg tgggacattt gagttgcttg cttggcactg tcctctcatg cgttgggtcc   8040
actcagtaga tgcctgttga attctgattt aaatcggtcc gcgtacggcg tggtaggtcc   8100
gaacgaatcc atggattacc ctgttatgtg gtcctccagg gttgccgttc cttaactata   8160
acggtcctaa ggtagcgacc gcggagacta ggtgtattta tctaagcgat cgcttaatta   8220
aggccggccg ccgcaataaa atatctttat tttcattaca tctgtgtgtt ggttttttgt   8280
gtgaatccat agtactaaca tacgctctcc atcaaacaa aacgaaacaa acaaactag     8340
caaaataggc tgtccccagt gcaagtccag gtgccagaac atttctctat ccataatgca   8400
ggggtaccgg gtgatgacgg tgaaaacctc caattgtgct gtatataaaa ccagtggtta   8460
tatgtacagt actgctgtat ataaaaccag tggtttatatg tacagtacgt cgactgctgt   8520
atataaaacc agtggttata tgtacagtac tgctgtatat aaaaccagtg gttatatgta   8580
cagtaccccg ggacctaga gggtatataa tgggtgcctt agctggtgtg tgacctcatc   8640
ttcctgtacg cccctgcagg ggcgcgccac gcgtcgaaga aggtgagtaa tcttaacatg   8700
ctctttttt ttttttttgc taatcccttt tgtgtgctga tgttaggatg acatttacaa    8760
caaatgtttg ttcctgacag gaaaaacctt gctgggtacc ttcgttgccg gacacttctt   8820
gtcctctact ttgaaaaaaa ggaattgaga gccgctagcg ccaccatgtg ggtgaccaaa   8880
ctcctgccag ccctgctgct ccagcacgtc ctcctgcatc tcctcctgct ccccatcgcc   8940
```

-continued

| | |
|---|---|
| atcccctatg cagagggaca aaggaaaaga agaaatacaa ttcatgagtt caaaaaatca | 9000 |
| gcaaagacta ccctaatcaa aatagatcca gcactgaaga taaaaaccaa aaaagtgaat | 9060 |
| accgccgacc aatgtgctaa tagatgtact aggaacaaag gacttccatt cacttgcaag | 9120 |
| gcttttgttt ttgataaagc aagaaaacaa tgcctctggt tccccttcaa tagcatgtca | 9180 |
| agtggagtga aaaagaatt tggccatgaa tttgacctct atgaaaacaa agactacatt | 9240 |
| agaaactgca tcattggtaa aggacgcagc tacaagggaa cagtatctat cactaagagt | 9300 |
| ggcatcaaat gtcagccctg gagttccatg ataccacacg aacacagctt tttgccttcg | 9360 |
| agctatcggg gtaaagacct acaggaaaac tactgtcgaa atcccagagg cgaagaaggg | 9420 |
| ggaccctggt gtttcacaag caatccagag gtacgctacg aagtctgtga cattcctcag | 9480 |
| tgttcagaag ttgagtgcat gacctgtaat ggggagagtt atcgaggtct catggatcat | 9540 |
| acagaatcag gcaagatttg tcagcgctgg gatcatcaga caccacaccg gcacaaattc | 9600 |
| ttgcctgaaa gataccccga caagggcttt gatgataatt attgccgcaa tcccgatggc | 9660 |
| cagccgaggc cctggtgcta tactcttgac cctcacaccc gctgggagta ttgcgcaatc | 9720 |
| aagacatgcg ctgacaatac tatgaatgac actgatgttc ctttggaaac aactgagtgc | 9780 |
| atccaaggtc aaggagaagg ctacagggga ctgtcaata ccatttggaa tggcatcccc | 9840 |
| tgtcagcgtt gggattctca gtatcctcac gagcatgaca tgactcctga aaatttcaag | 9900 |
| tgcaaggacc tacgagaaaa ttactgccga aatccagatg ggtctgaatc accctggtgt | 9960 |
| tttaccactg atccaaacat ccgagttggc tactgctccc aaattccaaa ctgtgatatg | 10020 |
| tcacatggac aagattgtta tcgtgggaat ggcaaaaatt atatgggcaa cttatcccaa | 10080 |
| acaagaagcg gactaacctg ttcaatgtgg gacaagaaca tggaggactt acatcgtcat | 10140 |
| atcttctggg aaccagatgc aagtaagctg aatgagaatt actgccgaaa tccagatgat | 10200 |
| gatgctcatg gaccctggtg ctacacggga aatccactca ttccttggga ttattgccct | 10260 |
| atttctcgtt gtgaaggtga taccacacct acaatagtca atttagacca tcccgtaata | 10320 |
| tcttgtgcca aaacgaaaca gctgcgagtt gtaaatggga ttccaacacg aacaaacata | 10380 |
| ggatggatgg ttagtttgag atacagaaac aagcatatct gcggaggatc attgataaag | 10440 |
| gagagttggg ttcttactgc acgacagtgt ttccctagca gagacttgaa agattatgag | 10500 |
| gcttggcttg gcatccacga tgtccacggc agaggcgatg agaaatgcaa acaggttctc | 10560 |
| aatgtttccc agctggtata tggccctgaa ggaagcgacc tggtgctgat gaagctggcc | 10620 |
| agacccgctg tcctggatga ttttgttagt acgattgatt tacctaatta tggatgcaca | 10680 |
| attcctgaaa agaccagttg cagtgtttat ggctggggct acactggact gattaactat | 10740 |
| gatggcctat tacgagtggc acatctctat ataatgggaa atgagaaatg cagccagcat | 10800 |
| catcgaggga aggtgactct gaatgagtct gaaatatgtg ctggggctga aaagattgga | 10860 |
| tcaggaccat gtgaggggga ttatggtggc ccacttgttt gtgagcaaca taaaatgaga | 10920 |
| atggttcttg gtgtcattgt tcctggtcgt ggatgtgcca ttccaaatcg tcctggtatt | 10980 |
| tttgtccgag tagcctacta cgccaaatgg atacacaaaa ttattttaac atataaggtg | 11040 |
| ccccagtcat agatcgattg cgcaaagctt tcgcgatagg cgagaccaat gggtgtgtac | 11100 |
| gtagcggccg ctcgagaact tgtttattgc agcttataat ggttacaaat aaagcaatag | 11160 |
| catcacaaat ttcacaaata aagcattttt ttcactgcat tctagttgtg gtttgtccaa | 11220 |
| actcatcaat gtatcttatc atgtctcgta cggcgtggta ggtccgaacg aatccatgga | 11280 |

```
ttaccctgtt atccctactc atcttcgtcg gacgcgccgt taatatttga tcagccattc   11340
tctgtatgag tactaacgaa cgtgacgcgg tgttactggt aactatgact ctcttaaggt   11400
agccaaatac atcatcccct tagtgagggt taattcacgc agtgccgcgg cgtgtagaaa   11460
atacctatca gctcgaggac gtgacaaacg aagccgcacg tcaggccgg acgtgggggcc    11520 ccagagcgac gctgagtgcg tgcgggactc ggagtacgtg acggagcccc cacgtgggtt   11580
cccgcacgtc cgcgacgtga caaacgaagc cgcacgtcag gccggacgt gggccccag     11640 agcgacgctg agtgcgtgcg ggactcggag tacgtgacgg agccccacg tgggttcccg    11700 cacgtccgcg acgtgacaaa cgaagccgca cgtcagggcc ggacgtgggg ccccagagcg   11760
acgctgagtg cgtgcgggac tcggagtacg tgacggagcc cccacgtggg ttcccgcacg   11820
tccgcgacgt gacaaacgaa gccgcacgtc agggccggac gtggggcccc agagcgacgc   11880
tgagtgcgtg cgggactcgg agtacgtgac ggagccccca cgtgggttcc cgcacgtccg   11940
cgacgtgaca aacgaagccg cacgtcaggg ccggacgtgg ggcccagag cgacgctgag    12000 tgcgtgcggg actcggagta cgtgacggag ccccacgtg gttcccgca cgtccgcgac     12060 gtgacaaacg aagccgcacg tcagggccgg acgtggggcc ccagagcgac gctgagtgcg   12120
tgcgggactc ggagtacgtg acggagcccc cacgtgggtt cccgcacgtc cgcgacgtga   12180
caaacgaagc cgcacgtcag gccggacgt ggggcccag agcgacgctg agtgcgtgcg     12240
ggactcggag tacgtgacgg agccccacg tgggttcccg cacgtccgcg aagacctaga    12300
gggtatataa tgggtgcctt agctggtgtg tgagctcatc ttcctgtgca tgcggggggg   12360
ggggggggca attggccacc atgaaagccc tcaccgctag acaacaggaa gtgtttgacc   12420
tcatcaggga ccatatctcc cagacaggaa tgccccctac cagggccgaa atcgctcaga   12480
ggctgggatt caggagccct aacgctgccg aagaacatct gaaagccctc gccaggaagg   12540
gagtgattga gattgtgtcc ggcgcttcca ggggcattag actcctgcaa gaggaggaag   12600
aaggactccc cctcgtggga agggtcgccg ctggcgaacc cctcctggct caacaacaca   12660
ttgagggaca ctatcaggtc gatcctagcc tctttaaacc caatgccgat ttcctcctga   12720
gggtgtccgg catgagcatg aaggatattg gaatcatgga cggagacctc ctggctgtgc   12780
ataagacaca ggatgtgagg aacggacagg tcgtggtcgc caggatcgac gacgaagtga   12840
cagtgaaaag actcaagaaa cagggaaaca aagtggaact gctccccgaa aactccgagt   12900
ttaagcctat cgtcgtggat ctgaggcagc aatcctttac cattgaggga ctggctgtgg   12960
gagtgattag aaatggcgat tggctcgaat ttcccgggat tagacctgag tgtgtggtcc   13020
ccgaaaccca atgcgctatg aaaagaaaag agaaaaaggc tcagaaagag aaagacaaac   13080
tgcctgtgtc caccacaacc gtcgatgatc acatgccccc tatcatgcag tgtgagcctc   13140
cccctcccga agccgctaga atccacgaag tcgtccccag gttcctctcc gataagctcc   13200
tggaaaccaa tagacaaaag aatatccctc aactcaccgc taaccaacag tttctgattg   13260
ccaggctgat ttggtatcag gatggctatg agcaaccctc cgacgaagac ctcaaggaga   13320
tcacacagac atggcaacag gctgacgatg agaatgagga aagcgatacc cctttcaggc   13380
agattaccga aatgacaatc ctcaccgtcc agctcatcgt cgagtttgcc aaaggactcc   13440
ccggattcgc taagattagc caacccgatc agattaccct cctgaaagcc tgtagctccg   13500
aggtcatgat gctgagagtg gctagaaggt acgatgccgc ttccgatagc gtcctgtttg   13560
ccaataacca agcctatacc agggacaatt acaggaaggc tggcatggcc tatgtgattg   13620
aggatgtgct ccacttttgc agatgtatgt actccatggc tctcgataac attcactatg   13680
```

```
ccctcctgac agccgtcgtg attttctccg acaggcccgg actggaacag cctcaactcg   13740
tggaagaaat tcagaggtac tatctgaata ccctcagaat ttacattctg aatcagctct   13800
ccggcagcgc tagatccagc gtcatctatg gcaaaatcct ctccattctg tccgagctga   13860
gaacactggg aatgcaaaac tccaatatgt gcattagcct caagctcaag aatagaaaac   13920
tgcctccctt tctggaagaa atttgggatg tggctgacat gagccatacc caacccctc    13980
ccattctgga aagccctacc aatctgtaaa tcgatagccg cctggctgag atggggtggg   14040
cagggcagag ctgatcaggg ccgagcagaa ccgcactctt cccaaataaa gcttcctcct   14100
tgaaacacaa atgtttctta cttacacccc atcctgattt cttttcttga gaccagagag   14160
tgggaaagct ctctcttgac ctgaggatgg atctgaaaat tatgagcccc ttgaggacag   14220
ggaatgttat tcatctttga attccgcagc atctagcacc aggtcttgta cagagcaggt   14280
gcccaataaa tggttgaatg aatatatgaa aagtagaggc agagggctgg gcacagtggc   14340
tcacgcctgt aatcctagca ctttgggagg ctgaggtggg tggatcactt gaggtcagga   14400
gttcgagacc agcttggcca acatggctaa acctcatctc tattaaaaat acaaaaatta   14460
gctgggctgg tgcctgtaat cccagctact caggaggctg aggcaggaga atcacttgaa   14520
cccaggagga ggagtttgca gtgagccgag atcgcaccat tgcactccag cctgggcgat   14580
aggagcaaaa ctccatctca aaacaaaaa acaaaacaaa acaaaagaa aaagaaaag      14640
taggggcaga gatgtggggc aggagaggtg actcgggctc agctgcatgg tcctgctctg   14700
cttctttttt cttggagttt gtccgttgga tgacaatgat agtggtgaac aggtatggag   14760
ggcttactaa gtaccaggtg tctagacgag gacgctcggg cttggaccca tggcacatcg   14820
tgtaatcatg gtcatagctg tttcctgtgt gaaattgtta tccgctacgt ctctcccccg   14880
cagtaagggc tagattaact cgtctcgtga atatccggaa ctcccttag tgagggttaa    14940
ttgcgttgcg ctcactgccc gctttccagt cgggaaacct gtcgtgccag cttaatcatg   15000
gtcatagctg tttcctgtgt gaaattgtta tccgctaccg gaaacgcttc cttcatgtga   15060
gcaaaaggcc agcaaaggc caggaaccgt aaaaaggccg cgttgctggc gttttttccat   15120
aggctccgcc cccctgacga gcatcacaaa aatcgacgct caagtcagag gtggcgaaac   15180
ccgacaggac tataaagata ccaggcgttt ccccctggaa gctccctcgt gcgctctcct   15240
gttccgaccc tgccgcttac cggatacctg tccgcctttc tcccttcggg aagcgtggcg   15300
ctttctcata gctcacgctg taggtatctc agttcggtgt aggtcgttcg ctccaagctg   15360
ggctgtgtgc acgaaccccc cgttcagccc gaccgctgcg ccttatccgg taactatcgt   15420
cttgagtcca acccggtaag acacgactta tcgccactgg cagcagccac tggtaacagg   15480
attagcagag cgaggtatgt aggcggtgct acagagttct tgaagtggtg cctaactac     15540
ggctacacta gaagaacagt atttggtatc tgcgctctgc tgaagccagt taccttcgga   15600
aaaagagttg gtagctcttg atccggcaaa caaaccaccg ctggtagcgg tggtttttt    15660
gtttgcaagc agcagattac gcgcagaaaa aaaggatctc aagaagatcc tttgatcttt   15720
tctacgggt ctgacgctca gtggaacgaa aactcacgtt aagggatttt ggtcatgcct     15780
aggacgaaag gaggtcgtga atggataaa aaatacagc gtttttcatg tacaactata      15840
ctagttgtag tgcctaaata atgcttttaa aacttaaaaa tacgtttaaa ccctcagcga   15900
aatggcatac gagtaaactt ggtctgacac cgctgcatga gattatcaaa aaggatcttc   15960
acctagatcc tttaaattaa aaatgaagt tttaaatcaa tctaaagtat atatgagtaa      16020
```

```
acttggtctg acagttacca atgcttaatc agtgaggcac ctatctcagc gatctgtcta    16080
tttcgttcat ccatagttgc ctgactcccc gtcgtgtaga taactacgat acgggagggc    16140
ttaccatctg gccccagtgc tgcaatgata ccgcgagacc cacgctcacc ggctccagat    16200
ttatcagcaa taaaccagcc agccggaagc gccgagcgca gaagtggtcc tgcaacttta    16260
tccgcctcca tccagtctat taactgttgc cgggaagcta gagtaagtag ttcgccagtt    16320
aatagtttgc ggagcgttgt tgccattgct acaggcatcg tggtgtcacg ctcgtcgttt    16380
ggtatggctt cattcagctc cggttcccaa cgatcaaggc gagttacatg atcccccatg    16440
ttgtgcaaaa aagcggttag ctccttcggt cctccgatgg ttgtcagaag taagttggcc    16500
gcagtgttat cactcatggt tatggcagca ctgcataatt ctcttactgt catgccatcc    16560
gtaagatgct tttctgtgac tggtgagtat tcaaccaagt cattctgaga atagtgtatg    16620
cggcgaccga gttgctcttg cccggcgtca atacgggata ataccgcgcc acatagcaga    16680
actttaaaag tgctcatcat tggaagcgt tcttcggggc gaaaactctc aaggatctta    16740
ccgctgttga gatccagttc gatgtaaccc acacgagcac ccaactgatc ttcagcatct    16800
tttactttca ccagcgtttc tgggtgagca aaaacaggaa ggcaaaatgc cgcaaaaaag    16860
ggaataaggg cgacacggaa atgttgaata ctcatacgct ccttttttca atagtattga    16920
agcatttatc agggttattg tctcgggagc gaatacatat ttgaatgtat ttagaaaaa    16979
```

<210> SEQ ID NO 14
<211> LENGTH: 13188
<212> TYPE: DNA
<213> ORGANISM: Artificial Sequence
<220> FEATURE:
<223> OTHER INFORMATION: Synthetic cardiomycyte + hypoxia inducible + hPlexin DI inducible gene switch constant encoding IGF-1

<400> SEQUENCE: 14

```
taaacaaata gggggttccgc gcacatttcc ccgaaaagtg ccacctgacg tactgaggac      60
gccagggttt tcccagtcac gacgttgtaa aacgacggcc agtagcagac aagcccgtca     120
gggcgcgtca gcgggtgttg gcccctaggac gaaaggaggt cgtgaaatgg ataaaaaaat     180
acagcgtttt tcatgtacaa ctatactagt tgtagtgcct aaataatgct tttaaaactt     240
aaaaataatc aatgtcctca gcggggtgtc ggggatttag gtgacactat aggctgagcg     300
ccgcacaggc atctagaggc tatggcaggg cctgccgccc cgacgttggc tgcgagccct     360
gggccttcac ccgaacttgg ggggtggggt ggggaaaagg aagaaacgcg ggcgtattgg     420
ccccaatggg gtctcggtgg ggtatcgaca gagtgccagc cctgggaccg aaccccgcgt     480
ttatgaacaa cgacccaac accgtgcgtt ttattctgtc tttttattgc cgtcatagcg     540
cgggttcctt ccgtattgt ctccttccgt gtttcaatcg attcaaaaga actcgtccag     600
cagacggtaa aaagcaatgc gttgagaatc cggtgcagca atgccataca gcaccagaaa     660
gcgatcagcc cattcaccgc ccagttcttc agcaatgtca cggttgcca gtgcgatgtc     720 ctgatagcga tcagccacgc caggcgacc gcagtcgata aagccggaga acggccgtt     780 ttccaccata atgtttggca gacaagcatc gccgtgggtc acaaccaggt cctcgccatc     840
tggcatacgt gctttcaggc gtgcgaacag ttctgccgt gccagaccct gatgttcctc     900
gtccaggtca tcctgatcaa ccaggccagc ttccatgcga gtgcgtgcgc gctcgatacg     960
gtgtttagct tggtgatcga atgggcaagt agctgggtcc agggtatgca gacggcgcat    1020
agcatcagcc atgatggaaa cctttcctgc cggtgccaga tgagaggaca gcagatcctg    1080
```

```
gcctggaacc tcgcccagca gcagccagtc gcggccagcc tcggtcacaa catccagcac    1140
agctgcgcat ggaacgccgg tagtagccag ccaggacaga cgagctgctt catcttgcag    1200
ttcgttcagt gcgccggaca gatcggtctt aacaaacagc accggacggc cttgagcgga    1260
cagacggaac acagctgcgt cggagcaacc gatagtctgt tgagcccagt catagccaaa    1320
cagacgttcc acccaagcag ccggagaacc agcgtgcaga ccgtcttgtt caatcatggt    1380
ggcaattggg tgtctgagcg atgtggctcg gctggcgacg caaaagaaga tgcggctgac    1440
tgtcgaacag gaggagcaga gagcgaagcg ggaggctgcg ggctcaattt gcatgcttta    1500
gttcctcacc ttgtcgtatt atactatgcc gatatactat gccgatgatt aattgtcaac    1560
gtatacggaa tagctctgag gccgaggcag cttcggcctc tgcataaata aaaaaaatta    1620
gtcagccatg gggcggagaa tgggcggaac tgggcggagt taggggcggg atgggcggag    1680 ttagggggcgg gactatggtt gctgactaat tgagatgctt gctttgcata cttctgcctg    1740
ctggggagcc tggggacttt ccacacctgg ttgctgacta attgagatgc ttgctttgca    1800
tacttctgcc tgctggggag cctggggact ttccacaccc taacctcgag gccatcgtgg    1860
cacgccaggg ttttcccagt cacgacgttg taaaacgacg gccagtgctc ttctcccccg    1920
cgggaggttt tataaatccg actgtctaga ttgttgttaa atcacacaaa aaaccaacac    1980
acagatgtaa tgaaaataaa gatattttat tatcgattca gctgtcgctg gggctctcca    2040
gcatctccat caggaaggtg tcgatgggca cgtcgccgat cagcctgaag aagaacaggt    2100
gctccaggca cttcaggccg atgctcctca ggctgggcag cctcagcagc agcttggcga    2160
atctgccggg ctcgtcgggg tgggtggtcc tggtgtactc ctccagggcg cgtacacct    2220 tctccctcag cagctccacc tcctgggcgc ttttcaggcc cctcacctcg gggttgaaca    2280
ggatgatggc cctcaggcag cccagctcgg tcttgtccat cctcatgtcc ctcatcttgc    2340
tcaccagctc ggtcagcacc ctgtcgaaga tggcgcccac tccggcgctg tgggcgctgt    2400
tcctatggac gtgcaggccg gtggccagca ggatgccgtc cctcacgtcg atgctcctgt    2460
ggctgaagct ggcgatcagc agctcgttcc atccggccct cagcaggatc acctggtcgt    2520
ccaggggcag gctgctgaag tggggaatcc tcttggccca ctccaccagg gtgaacagct    2580
gcttgtcggc ggcctggcag atgttggtca cggggtcgtt ggggctgctg ccgctgccgc    2640
cggttccgcc ggggccctcc acgcctggt cgcttttctg ctccacgcg agttcggcct    2700 ccagaatcct gtccacgggc atctccatat ggccgccgta ctcgtcgatg cccagggcgt    2760
cggtgaacat ctgctcgaac tcgaagtcgg ccatgtccag ggcgccgtag ggggcgctgt    2820 cgtgggggt gaagccgggg ccggggctgt cgccgtcgcc cagcatgtcc aggtcgaagt    2880
cgtccagggc gtcggcgtgg gccatggcca cgtcctcgcc gtccaggtgc agctcgtcgc    2940
ccaggctcac gtcggtgggg ggggccacct tccttttctt cttggggccc atggtggcca    3000
attgcccccc cccccccccg catgcccag tatgatgcct tctctaaatt taccagaaag    3060
aaaggacctg ggatgcttgt cctttaagtg tctctaaaca tggtttgcat agctggatct    3120
cagcttatct gtgcctttcg gctttcgctt ccatacatgg atctgttccc aacagtaact    3180
ccaagctgtc gaaagaagc tatctggcag ctctctgctt catccaacac atggatgata    3240
aaaatacaca tatagcgatt cttccctcga gtaggcgaga ccaatgggtg cgccatgggc    3300
tcttccaaaa atttaggtga cactataggg caccgctcgc acctgcgcac aggcccgcgg    3360 ctacaaaacta cgaacgatca ttctagatac cacatttgta gaggttttac ttgctttaaa    3420
aaacctccca catctccccc tgaacctgaa acataaaatg aatgcaaatg ttttattaac    3480
```

```
ttgtttattg cagcttataa tggttacaaa ttaagcaata gcatcacaaa tttcacaaat    3540
taagcatttt tttcactgca ttctagttgt ggtttgtcca aactcatcaa tgtatcttat    3600
catgtctaat cgattcacag gttggtgggg ctctccagga tggggggggg ctgggtgtgg    3660
ctcatgtcgg ccacgtccca aatctcctcc aggaaggggg gcagcttcct gttcttcagc    3720
ttcaggctga tacacatatt gctgttctgc attcccaggg tcctcagctc gctcaggatg    3780
ctcaggatct tgccgtagat cacgctgctc tggcgctgc cgctcagctg gttcaggatg    3840
tagatcctca gggtgttcag gtagtacctc tggatctcct ccaccagctg ggctgctcc    3900 aggccgggcc tgtcgctgaa gatcaccacg gcggtcagca gggcgtagtg gatgttgtcc    3960
agggccatgc tgtacataca tctgcagaag tgcaggaggt cctcgatcac ctcggccatg    4020
ccagccttcc tgtagttgtc cctggtgtaa gcctggttgt tggcgaacag gatgctgtcg    4080
ctggcggcgt cgtacctcct ggccaccctc agcatcatca cctcgctgct gcaagccttc    4140
agcagggtga tctggtcggg ctggctgatc ttggcgaatc cgggcaggcc cttggcgaac    4200
tccacgatca gctgcacggt caggatggtc atctcggtga tctgcctgaa gggggtgtcg    4260
ctctcctcgt tctcgtcgtc ggcctgctgc caggtctggg tgatccttt caggtcctcg    4320 tcgctgggct gctcgtagcc gtcctgatac cagatcagcc tggcgatcag gaactgctgg    4380
ttggcggtca gctgggggat gttcttctgc ctgttggtca ccagcagctt gtcgctcagg    4440
aacctgggca cgacctcgtg aatcctggcg gcctcggggg gggggggctc gcactgcatg    4500
atggggggca tgtggtcatc gacggtggtg gtgctcacgg gcagcttgtc cttctccttc    4560
tgggccttct tctccttcct tttcatggcg cactgggtct cgggcaccac gcactcgggc    4620
ctgatcccgg gaaactcggg gctcacggtc agctgcctct ggcccttgtt gctgctctcc    4680
tcgctgctgc tggtggcgct gatcctgtgc tgcctcaggg tcagggcat gtcggtctcc    4740 acgctggcca gcctgtcggt cacgcgtcc ttgttcacgt tgtcctgcac gaacaggccg    4800
gtcagcaggg ccttgatgtc ttgcaggctg tccatcttca ggatcatgtc caggtcctcc    4860
ctggggaaga tcagcaggaa cagctgctcc agcctctcca gcctgctctc cacctcggtc    4920
aggtgggccc tggtcagggg gctcctcttg gtcttggggc tgtatctgca ctcccagttg    4980
ttcttcaggc acttggcgca cttgggcttc tccttgctgc acttcagctt cttcagcctg    5040
cagatgtcgc aagcctgctc gatgctgctc agcagcttca tggtggccaa ttgccccccc    5100
ccccccccgc atgcacagga agatgagctc acacaccagc taaggcaccc attatatacc    5160
ctctaggtct tcgcggacgt gcgggaaccc acgtgggggc tccgtcacgt actccgagtc    5220
ccgcacgcac tcagcgtcgc tctggggccc cacgtccggc cctgacgtgc ggcttcgttt    5280
gtcacgtcgc ggacgtgcgg aacccacgt gggggctccg tcacgtactc cgagtcccgc    5340
acgcactcag cgtcgctctg ggccccacg tccgccctg acgtgcggct cgtttgtca    5400 cgtcgcggac gtgcgggaac ccacgtgggg ctccgtcac gtactccgag tcccgcacgc    5460
actcagcgtc gctctgggc cccacgtccg gccctgacgt gcggcttcgt tgtcacgtc    5520 gcggacgtgc gggaacccac gtgggggctc cgtcacgtac tccgagtccc gcacgcactc    5580
agcgtcgctc tggggcccca cgtccggccc tgacgtgcgg cttcgtttgt cacgtcgcgg    5640
acgtgcggga acccacgtgg gggctccgtc acgtactccg agtcccgcac gcactcagcg    5700
tcgctctggg gccccacgtc cggccctgac gtgcggcttc gtttgtcacg tcgcggacgt    5760
gcgggaaccc acgtgggggc tccgtcacgt actccgagtc ccgcacgcac tcagcgtcgc    5820
```

| | |
|---|---|
| tctgggcccc cacgtccggc cctgacgtgc ggcttcgttt gtcacgtcgc ggacgtgcgg | 5880 |
| gaacccacgt gggggctccg tcacgtactc cgagtcccgc acgcactcag cgtcgctctg | 5940 |
| gggccccacg tccggccctg acgtgcggct tcgtttgtca cgtcctcgag tggtaataca | 6000 |
| atggccggtt cccatggacc tgcatcgtgg tgtaactata acggtcctaa ggtagcgacc | 6060 |
| gcggagacta ggtgtattta tctaagcgat cgcttaatta aggccggccg ccgcaataaa | 6120 |
| atatctttat tttcattaca tctgtgtgtt ggttttttgt gtgaatccat agtactaaca | 6180 |
| tacgctctcc atcaaaacaa aacgaaacaa aacaaactag caaaataggc tgtccccagt | 6240 |
| gcaagtccag gtgccagaac atttctctat ccataatgca ggggtaccgg gtgatgacgg | 6300 |
| tgaaaacctc caattgcgga gtactgtcct ccgagcggag tactgtcctc cgagcggagt | 6360 |
| actgtcctcc gagcggagta ctgtcctccg agcggagtac tgtcctccga gcggagtact | 6420 |
| gtcctccgag cggagagtcc ccggggacct agagggtata taatgggtgc cttagctggt | 6480 |
| gtgtgacctc atcttcctgt acgcccctgc aggggcgcgc cacgcgtcga agaaggtgag | 6540 |
| taatcttaac atgctctttt tttttttttt tgctaatccc ttttgtgtgc tgatgttagg | 6600 |
| atgacattta caacaaatgt tgttcctga caggaaaaac cttgctgggt accttcgttg | 6660 |
| ccggacactt cttgtcctct actttggaaa aaggaattg agagccgcta cgccaccat | 6720 |
| gggaaaaatc agcagcctgc ccacccaatt atttaagtgc tgcttttgtg atttcttgaa | 6780 |
| ggtgaagatg cacaccatgt cctcctcgca tctgttctac ctggcgctgt gcctgctgac | 6840 |
| cttcaccagc tctgccacgg ctggaccgga gaccctctgc ggggccgagc tggtggatgc | 6900 |
| cctgcaattc gtgtgtggag acaggggctt ctacttcaac aagcccacag gtatggctc | 6960 |
| cagcagtcgg agagcccccc agacaggcat cgtggatgag tgctgcttca gaagctgtga | 7020 |
| tctaaggagg ctggagatgt attgcgcacc cctcaagcct gccaagtcag ctcgctctgt | 7080 |
| ccgtgcccag cgccacaccg acatgcccaa gacccagaag tatcagcccc catctaccaa | 7140 |
| caagaacacg aagtctcaga gaaggaaagg aagtacattt gaagaacgca agtagatcga | 7200 |
| ttgcgcaaag cttcgcgat aggcgagacc aatgggtgtg tacgtagcgg ccgcgtcgac | 7260 |
| gatagcttga tgggtggcat ccctgtgacc cctccccagt gcctctcctg gccctggaag | 7320 |
| ttgccactcc agtgcccacc agccttgtcc taataaaatt aagttgcatc attttgtctg | 7380 |
| actaggtgtc cttctataat attatggggt ggaggggggt ggtatggagc aaggggcaag | 7440 |
| ttgggaagac aacctgtagg gcctgcgggg tctattggga accaagctgg agtgcagtgg | 7500 |
| cacaatcttg gctcactgca atctccgcct cctgggttca agcgattctc ctgcctcagc | 7560 |
| ctcccgagtt gttgggattc caggcatgca tgaccaggct cagctaattt ttgttttttt | 7620 |
| ggtagagacg gggtttcacc atattggcca ggctggtctc caactcctaa tctcaggtga | 7680 |
| tctacccacc ttggcctccc aaattgctgg gattacaggc gtgaaccact gctcccttcc | 7740 |
| ctgtccttct gattttaaaa taactatacc agcaggagga cgtccagaca cagcataggc | 7800 |
| tacctggcca tgcccaaccg gtgggacatt tgagttgctt gcttggcact gtcctctcat | 7860 |
| gcgttgggtc cactcagtag atgcctgttg aattctgatt taaatcggtc cgcgtacggc | 7920 |
| gtggtaggtc cgaacgaatc catgattac cctgttatcc ctactcaagg acatcatccc | 7980 |
| tttagtgagg gttaattcac gcagtgccgc ggcgtgtaga aaatacctat cagctcgagg | 8040 |
| agcgaaggcc tggacagtgc ctgagaaagg tggtggaggg aggctgagtg tggaggggag | 8100 |
| acacagggtt cgggaaggca gagggagaag gaaaggggag ctcagaggga ccgagagagg | 8160 |
| gacggagggt ccgaggggga ggcagaggga gccacggaga gagggagcga gcgtcaggga | 8220 |

```
cggaaaaacg gagcaggaga gagaaggaga ctagaaaggg ccgggggcgg ggctgccagg    8280
gactggagag cgaagcggag tcggagggag aaggagaagc agaggcagaa cccggagaag    8340
cgccacacgc gcggagtttg gggtggggac agaggcggag aggcgcagag accgagagac    8400
acagagagag ggagaggcgg ggtggggag agggcggaaa agaaaaaca ggcgcgagcg      8460
aggcaggcca agcggccaag tgggaggaaa gagcgaggag agcgagcgac ggcggcggcg    8520
gctacgggga gggaccctgg ggccgcgggc gggtcctgga gggcgcgggc ggcgggaccc    8580
gcggacggcg gggcgtggcc cagggcggcc aggggcaggc gggggttccg ggggcgggcg    8640
gggccggggc ggggagtgag ggcgtgtccg cagcggagcc gccccgccc cgccccgga     8700
ctgcgcggcg aggctgatcc gggcccggac gccggggtcg gggcggctg cgcgggcag     8760
gaagcgcatc gtggcccgga cccgccccc gcctccgcc gcctccgggg catgcggggg    8820
gggggggggg caattggcca ccatgaagct cctgtccagc attgagcaag cctgtgacat    8880
ttgcaggctg aaaaagctca agtgtagcaa agagaaaccc aaatgcgcta agtgtctgaa    8940
aaacaactgg gaatgcagat actcccccaa aaccaaaaga tccccctca ccagggccca    9000
tctgacagag gtcgagtcca gactcgaaag gctggaacag ctcttttctcc tgattttccc    9060
tagagaagac ctcgacatga tcctcaagat ggactccctg caagacatta aggctctgct    9120
caccggactg tttgtgcaag acaatgtgaa taaggatgcc gtcaccgata gactcgcctc    9180
cgtggaaacc gatatgcctc tgacactgag gcagcataga attagcgcta cctccagctc    9240
cgaggaaagc tccaacaaag gccaaagaca actgacagtg tccccgagt tccccgggat    9300
tagacctgag tgtgtggtcc ccgaaaccca atgcgctatg aaaagaaaag agaaaaggc    9360
tcagaaagag aaagacaaac tgcctgtgtc caccacaacc gtcgatgatc acatgccccc    9420
tatcatgcag tgtgagcctc cccctcccga agccgctaga atccacgaag tcgtccccag    9480
gttcctctcc gataagctcc tggaaaccaa tagacaaaag aatatccctc aactcaccgc    9540
taaccaacag tttctgattg ccaggctgat ttggtatcag gatggctatg agcaaccctc    9600
cgacgaagac ctcaagagga tcacacagac atggcaacag gctgacgatg agaatgagga    9660
aagcgatacc cctttcaggc agattaccga aatgacaatc ctcaccgtcc agctcatcgt    9720
cgagtttgcc aaaggactcc ccggattcgc taagattagc caacccgatc agattaccct    9780
cctgaaagcc tgtagctccg aggtcatgat gctgagagtg gctagaaggt acgatgccgc    9840
ttccgatagc gtcctgtttt ccaataacca agcctatacc agggacaatt acaggaaggc    9900
tggcatggcc tatgtgattg aggatgtgct ccacttttgc agatgtatgt actccatggc    9960
tctcgataac attcactatg ccctcctgac agccgtcgtg attttctccg acaggcccgg   10020
actgaacag cctcaactcg tggaagaaat tcagaggtac tatctgaata ccctcagaat   10080
ttacattctg aatcagctct ccggcagcgc tagatccagc gtcatctatg caaaatcct   10140
ctccattctg tccgagctga aacactggg aatgcaaaac tccaatatgt gcattagcct   10200
caagctcaag aatagaaaac tgcctcccctt tctggaagaa atttgggatg tggctgacat   10260
gagcctatac caaccccctc ccattctgga aagccctacc aatctgtaaa tcgatagccg   10320
cctggctgag atggggtggg cagggcagag ctgatcaggg ccgagcagaa ccgcactctt   10380
cccaaataaa gcttcctcct tgaaacacaa atgtttctta cttacacccc atcctgattt   10440
cttttcttga gaccagagag tgggaaagct ctctcttgac ctgaggatgg atctgaaaat   10500
tatgagcccc ttgaggacag ggaatgttat tcatctttga attccgcagc atctagcacc   10560
```

```
aggtcttgta cagagcaggt gcccaataaa tggttgaatg aatatatgaa aagtagaggc    10620
agagggctgg gcacagtggc tcacgcctgt aatcctagca ctttgggagg ctgaggtggg    10680
tggatcactt gaggtcagga gttcgagacc agcttggcca acatggctaa acctcatctc    10740
tattaaaaat acaaaaatta gctgggctgg tgcctgtaat cccagctact caggaggctg    10800
aggcaggaga atcacttgaa cccaggagga ggagtttgca gtgagccgag atcgcaccat    10860
tgcactccag cctgggcgat aggagcaaaa ctccatctca aaaacaaaaa acaaaacaaa    10920
acaaaaagaa aaagaaaag taggggcaga gatgtggggc aggagaggtg actcgggctc    10980
agctgcatgg tcctgctctg cttctttttt cttggagttt gtccgttgga tgacaatgat    11040
agtggtgaac aggtatggag ggcttactaa gtaccaggtg tctagacgag gacgctcggg    11100
cttggaccca tggcacatcg tgtaatcatg gtcatagctg tttcctgtgt gaaattgtta    11160
tccgctacgt ctctcccccg cagtaagggc tagattaact cgtctcgtga atatccggaa    11220
ctccctttag tgagggttaa ttgcgttgcg ctcactgccc gctttccagt cgggaaacct    11280
gtcgtgccag cttaatcatg gtcatagctg tttcctgtgt gaaattgtta tccgctaccg    11340
gaaacgcttc cttcatgtga gcaaaaggcc agcaaaaggc caggaaccgt aaaaaggccg    11400
cgttgctggc gttttccat aggctccgcc cccctgacga gcatcacaaa aatcgacgct    11460
caagtcagag gtggcgaaac ccgacaggac tataaagata ccaggcgttt ccccctggaa    11520
gctccctcgt gcgctctcct gttccgaccc tgccgcttac cggatacctg tccgcctttc    11580
tcccttcggg aagcgtggcg ctttctcata gctcacgctg taggtatctc agttcggtgt    11640
aggtcgttcg ctccaagctg ggctgtgtgc acgaaccccc cgttcagccc gaccgctgcg    11700
ccttatccgg taactatcgt cttgagtcca acccggtaag acacgactta tcgccactgg    11760
cagcagccac tggtaacagg attagcagag cgaggtatgt aggcggtgct acagagttct    11820
tgaagtggtg gcctaactac ggctacacta gaagaacagt atttggtatc tgcgctctgc    11880
tgaagccagt taccttcgga aaaagagttg gtagctcttg atccggcaaa caaaccaccg    11940
ctggtagcgg tggtttttt gtttgcaagc agcagattac gcgcagaaaa aaaggatctc    12000
aagaagatcc tttgatcttt tctacggggt ctgacgctca gtggaacgaa aactcacgtt    12060
aagggatttt ggtcatgatc tatgtcgggt gcggagaaag aggtaatgaa atggcatacg    12120
agtaaacttg gtctgacacc gctgcatgag attatcaaaa aggatcttca cctagatcct    12180
tttaaattaa aaatgaagtt ttaaatcaat ctaaagtata tatgagtaaa cttggtctga    12240
cagttaccaa tgcttaatca gtgaggcacc tatctcagcg atctgtctat ttcgttcatc    12300
catagttgcc tgactccccg tcgtgtagat aactacgata cgggagggct taccatctgg    12360
ccccagtgct gcaatgatac cgcgagaccc acgctcaccg gctccagatt tatcagcaat    12420
aaaccagcca gccggaagcg ccgagcgcag aagtggtcct gcaactttat ccgcctccat    12480
ccagtctatt aactgttgcc gggaagctag agtaagtagt tcgccagtta atagtttgcg    12540
gagcgttgtt gccattgcta caggcatcgt ggtgtcacgc tcgtcgtttg gtatggcttc    12600
attcagctcc ggttcccaac gatcaaggcg agttacatga tcccccatgt tgtgcaaaaa    12660
agcggttagc tccttcggtc ctccgatggt tgtcagaagt aagttggccg cagtgttatc    12720
actcatggtt atggcagcac tgcataattc tcttactgtc atgccatccg taagatgctt    12780
ttctgtgact ggtgagtatt caaccaagtc attctgagaa tagtgtatgc ggcgaccgag    12840
ttgctcttgc ccggcgtcaa tacgggataa taccgcgcca catagcagaa ctttaaaagt    12900
gctcatcatt gggaagcgtt cttcggggcg aaaactctca aggatcttac cgctgttgag    12960
```

```
atccagttcg atgtaaccca cacgagcacc caactgatct tcagcatctt ttactttcac    13020
cagcgtttct gggtgagcaa aaacaggaag gcaaaatgcc gcaaaaaagg gaataagggc    13080
gacacggaaa tgttgaatac tcatacgctt ccttttcaa tagtattgaa gcatttatca    13140
gggttattgt ctcgggagcg aatacatatt tgaatgtatt tagaaaaa                 13188
```

<210> SEQ ID NO 15
<211> LENGTH: 13314
<212> TYPE: DNA
<213> ORGANISM: Artificial Sequence
<220> FEATURE:
<223> OTHER INFORMATION: Synthetic constitutive + TNF + inducible
      promoter gene switch encoding etanercept

<400> SEQUENCE: 15

```
taaacaaata gggttccgc gcacatttcc ccgaaaagtg ccacctgacg tactgaggac      60
gccagggttt tcccagtcac gacgttgtaa aacgacggcc agtagcagac aagcccgtca    120
gggcgcgtca gcgggtgttg gccctaggac gaaaggaggg cgtgaaatgg ataaaaaaat    180
acagcgtttt tcatgtacaa ctatactagt tgtagtgcct aaataatgct tttaaaactt    240
aaaaataatc aatgtcctca gcgggtgtc ggggatttag gtgacactat aggctgagcg    300
ccgcacaggc atctagaggc tatggcaggg cctgccgccc cgacgttggc tgcgagccct    360
gggccttcac ccgaacttgg ggggtggggt ggggaaaagg aagaaacgcg ggcgtattgg    420
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccggtattgt ctccttccgt gtttcaatcg attcaaaaga actcgtccag    600
cagacggtaa aaagcaatgc gttgagaatc cggtgcagca atgccataca gcaccagaaa    660
gcgatcagcc cattcaccgc ccagttcttc agcaatgtca cgggttgcca gtgcgatgtc    720
ctgatagcga tcagccacgc ccaggcgacc gcagtcgata aagccggaga aacggccgtt    780
ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgatacg    960
gtgtttagct tggtgatcga atgggcaagt agctgggtcc agggtatgca gacggcgcat   1020
agcatcagcc atgatggaaa cctttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtcagaa ccgtcttgtt caatcatggt   1380
ggcaattggg tgtctgagcg atgtggctcg gctggcgacg caaaagaaga tgcggctgac   1440
tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt tagggcgggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
```

```
tacttctgcc tgctggggag cctggggact ttccacaccc taacctcgag gccatcgtgg    1860
cacgccaggg ttttcccagt cacgacgttg taaaacgacg gccagtgctc ttctccccccg   1920
cgggaggttt tataaatccg actgtctaga ttgttgttaa atcacacaaa aaaccaacac    1980
acagatgtaa tgaaaataaa gatattttat tatcgattca gctgtcgctg gggctctcca   2040
gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg gcgtacacct   2220
tctccctcag cagctccacc tcctgggcgc ttttcaggcc cctcacctcg gggttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccagggggcag gctgctgaag tgggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag ggggcgctgt   2820
cgtgggggt gaagccgggg ccggggctgt cgccgtcgcc cagcatgtcc aggtcgaagt   2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc ccccccccccg catgccgtct aacaaaaaag ccaaaacgg ccagaattta    3060
gcggacaatt tactagtcta acactgaaaa ttacatattg acccaaatga ttacatttca    3120
aaaggtgcct aaaaaacttc acaaaacaca ctcgccaacc ccgagcgcac gtacccagcc    3180
cagcagcccg ctactcacca agtgacgatc acagcgatcc acaaacaaga accgcgaccc   3240
aaatcccggc tgcgacggaa ctagctgtgc cacacccggc gcgtccttat ataatcatcg   3300
gcgttcaccg ccccacggag atccctccgc agaatcgccg agaagggact acttttcctc   3360
gcctgttccg ctctctggaa agaaaaccag tgccctagag tcacccaagt cccgtcctaa    3420
aatgtccttc tgctgatact ggggttctaa ggccgagtct tatgagcagc gggccgctgt   3480
cctgagcgtc cgggcggaag gatcaggacg ctcgctgcgc ccttcgtctg acgtggcagc    3540
gctcgccgtg aggaggggg cgccgcggg aggcgccaaa acccggcgcg gaggccctcg     3600
agtaggcgag accaatgggt gcgccatggg ctcttccaaa aatttaggtg acactatagg   3660
gcaccgctcg cacctgcgca caggcccgcg gctacaaact acgaacgatc attctagata   3720
ccacatttgt agaggtttta cttgctttaa aaaacctccc acatctcccc ctgaacctga   3780
aacataaaat gaatgcaaat gttttattaa cttgtttatt gcagcttata atggttacaa   3840
attaagcaat agcatcacaa atttcacaaa ttaagcattt ttttcactgc attctagttg   3900
tggtttgtcc aaactcatca atgtatctta tcatgtctaa tcgattcaca ggttggtggg   3960
gctctccagg atggggggg gctgggtgtg gctcatgtcg gccacgtccc aaatctcctc   4020
caggaagggg ggcagcttcc tgttcttcag cttcaggctg atacacatat tgctgttctg   4080
cattcccagg gtcctcagct cgctcaggat gctcaggatc ttgccgtaga tcacgctgct   4140
```

```
cctggcgctg ccgctcagct ggttcaggat gtagatcctc agggtgttca ggtagtacct    4200
ctggatctcc tccaccagct ggggctgctc caggccgggc ctgtcgctga agatcaccac    4260
ggcggtcagc agggcgtagt ggatgttgtc cagggccatg ctgtacatac atctgcagaa    4320
gtgcaggagg tcctcgatca cctcggccat gccagccttc ctgtagttgt ccctggtgta    4380
agcctggttg ttggcgaaca ggatgctgtc gctggcggcg tcgtacctcc tggccaccct    4440
cagcatcatc acctcgctgc tgcaagcctt cagcagggtg atctggtcgg gctggctgat    4500
cttggcgaat ccgggcaggc ccttggcgaa ctccacgatc agctgcacgg tcaggatggt    4560
catctcggtg atctgcctga aggggtgtc gctctcctcg ttctcgtcgt cggcctgctg    4620
ccaggtctgg gtgatccttt tcaggtcctc gtcgctgggc tgctcgtagc cgtcctgata    4680
ccagatcagc ctggcgatca ggaactgctg gttggcggtc agctggggga tgttcttctg    4740
cctgttggtc accagcagct tgtcgctcag gaacctgggc acgacctcgt gaatcctggc    4800
ggcctcgggg ggggggggct cgcactgcat gatgggggc atgtggtcat cgacggtggt    4860
ggtgctcacg ggcagcttgt ccttctcctt ctgggccttc ttctccttcc ttttcatggc    4920
gcactgggtc tcgggcacca cgcactcggg cctgatcccg ggaaactcgg ggctcacggt    4980
cagctgcctc tggcccttgt tgctgctctc ctcgctgctg ctggtggcgc tgatcctgtg    5040
ctgcctcagg gtcaggggca tgtcggtctc cacgctggcc agcctgtcgg tcacggcgtc    5100
cttgttcacg ttgtcctgca cgaacaggcc ggtcagcagg gccttgatgt cttgcaggct    5160
gtccatcttc aggatcatgt ccaggtcctc cctggggaag atcagcagga acagctgctc    5220
cagcctctcc agcctgctct ccacctcggt caggtgggcc ctggtcaggg ggctcctctt    5280
ggtcttgggg ctgtatctgc actcccagtt gttcttcagg cacttggcgc acttgggctt    5340
ctccttgctg cacttcagct tcttcagcct gcagatgtcg caagcctgct cgatgctgct    5400
cagcagcttc atggtggcca attgccccccc ccccccccg catgcctgtc tgacgggcaa    5460
tgctcctctg agagttgtta cagttcagac atggtaatga ctggttttat acagctttgc    5520
ccctcccaca tggcattttt ttttctccct ctgtcttttg atctgtgtcc tttgagtgat    5580
tcaacatttt actcaggaag acatcattag aatagaaata cttgtttgta aaggcatggt    5640
ttaagaaatt ttgggggagg atgaggtcac tctgaaactt aagaatttgt caatatcctc    5700
gagtggtaat acaatggccg gttcccatgg acctgcatcg tggtgtaact ataacggtcc    5760
taaggtagcg accgcggaga ctaggtgtat ttatctaagc gatcgcttaa ttaaggccgg    5820
ccgccgcaat aaaatatctt tattttcatt acatctgtgt gttggttttt tgtgtgaatc    5880
catagtacta acatacgctc tccatcaaaa caaaacgaaa caaaacaaac tagcaaaata    5940
ggctgtcccc agtgcaagtc caggtgccag aacatttctc tatccataat gcaggggtac    6000
cgggtgatga cggtgaaaac ctccaattgc ggagtactgt cctccgagcg gagtactgtc    6060
ctccgagcgg agtactgtcc tccgagcgga gtactgtcct ccgagcggag tactgtcctc    6120
cgagcggagt actgtcctcc gagcggagag tccccggga cctagagggt atataatggg    6180
tgccttagct ggtgtgtgac ctcatcttcc tgtacgcccc tgcaggggcg cgccacgcgt    6240
cgaagaaggt gagtaatctt aacatgctct ttttttttt ttttgctaat ccctttttgtg    6300
tgctgatgtt aggatgacat ttacaacaaa tgtttgttcc tgacaggaaa aaccttgctg    6360
ggtaccttcg ttgccggaca cttcttgtcc tctactttgg aaaaaaggaa ttgagagccg    6420
ctagcgccac catgctgccc gcccaggtcg ccttcacccc ctacgccccc gagcccggca    6480
gcacctgtag actgagagag tattacgacc agaccgccca gatgtgctgc tccaagtgca    6540
```

```
gccccggcca gcacgccaag gtgttctgca ccaagaccag cgacaccgtc tgcgacagct    6600
gcgaggacag cacctacacc cagctgtgga actgggtgcc cgagtgcctg agctgcggca    6660
gcagatgtag cagcgaccag gtggagaccc aggcttgcac cagagagcag aacagaatct    6720
gcacctgtag acccggctgg tactgcgccc tgagcaagca ggagggctgc cgcctgtgcg    6780 ccccccctgag aaagtgcaga cccggcttcg gcgtggccag acccggcacc gagaccagcg    6840
acgttgtgtg caagccctgt gccccggca ccttcagcaa caccaccagc agcaccgaca    6900
tctgccgccc ccaccagatt tgcaacgtgg tggccatccc cggcaacgcc agcatggacg    6960
ccgtgtgtac cagcaccagc cccacccgca gcatggcccc cggcgctgtc cacctccccc    7020
agcccgtgag caccagaagc cagcacaccc agcccacccc cgagcccagc accgcccca    7080 gcaccagctt cctgctgcct atgggaccca gccccccgc cgagggcagc accggcgacg    7140
agcccaagag ctgcgacaag acccacacct gtccccctg ccccgccccc gagctgctgg    7200
gcggccccag cgtgttcctg ttccccccca gcccaagga caccctgatg atctccagaa    7260
cccccgaggt gacatgcgtg gtggtggacg tgagccacga ggaccccag gtgaagttca    7320 actggtacgt ggacggcgtg caagtgcata acgccaagac caagcccaga gagcagcagt    7380
acaacagcac ctacagagtg gtgagcgtgc tgaccgtgct gcaccagaac tggctggacg    7440
gcaaggagta caagtgcaag gtgtccaaca aggccctgcc cgcccccatc gagaaaacca    7500
tcagcaaggc caagggccag cccagagagc cccaggtgta caccctgccc cccagcagag    7560
aggagatgac caagaaccag gtgtccctga cctgtctggt gaaggcttc tacccccagcg    7620 acatcgccgt ggagtgggag agcaacggcc agcccgagaa caactacaag accacccccc    7680
ccgtgctgga cagcgacggc agcttcttcc tgtacagcaa gctgaccgtg gacaagagca    7740
gatggcagca gggcaacgtg ttcagctgct ccgtgatgca cgaggccctg cacaaccact    7800
acacccagaa gtccctgagc ctgagccccg gcaagtgaat cgattgcgca aagctttcgc    7860
gataggcgag accaatgggt gtgtacgtag cggccgcgtc gacgatagct tgatgggtgg    7920
catccctgtg acccctcccc agtgcctctc ctggccctgg aagttgccac tccagtgccc    7980
accagccttg tcctaataaa attaagttgc atcattttgt ctgactaggt gtccttctat    8040
aatattatgg ggtggagggg ggtggtatgg agcaaggggc aagttgggaa gacaacctgt    8100
agggcctgcg gggtctattg ggaaccaagc tggagtgcag tggcacaatc ttggctcact    8160
gcaatctccg cctcctgggt tcaagcgatt ctcctgcctc agcctcccga gttgttggga    8220
ttccaggcat gcatgaccag gctcagctaa ttttgtttt tttggtagag acggggtttc    8280
accatattgg ccaggctggt ctccaactcc taatctcagg tgatctaccc accttggcct    8340
cccaaattgc tgggattaca ggcgtgaacc actgctccct tccctgtcct tctgatttta    8400
aaataactat accagcagga ggacgtccag acacagcata ggctacctgg ccatgcccaa    8460
ccggtgggac atttgagttg cttgcttggc actgtcctct catgcgttgg gtccactcag    8520
tagatgcctg ttgaattctg atttaaatcg gtccgcgtac ggcgtggtag gtccgaacga    8580
atccatggat tacccctgtta tccctactca aggacatcat ccctttagtg agggttaatt    8640
cacgcagtgc cgcggcgtgt agaaaatacc tatcagctcg agcacggggc tcccactctc    8700
aactccgcag cctcagcccc ctcaatgctg aggagcagag ctggtctcct gccctgacag    8760
ctgccaggca catcttgttc cctcaggttg cacaactggg ataaatgacc cgggatgaag    8820
aaaccactgg catccaggaa cttgtcttag accgttttgt aggggaaatg acctgcaggg    8880
```

```
actttcccca gggaccacat ccagcttttc ttcgctccca agaaaccagc agggagcatg    8940
cggggggggg gggggcaat tggccaccat gaagctcctg tccagcattg agcaagcctg    9000
tgacatttgc aggctgaaaa agctcaagtg tagcaaagag aaacccaaat gcgctaagtg    9060
tctgaaaaac aactgggaat gcagatactc ccccaaaacc aaaagatccc ccctcaccag    9120
ggcccatctg acagaggtcg agtccagact cgaaaggctg aacagctct ttctcctgat    9180
tttccctaga gaagacctcg acatgatcct caagatggac tccctgcaag acattaaggc    9240
tctgctcacc ggactgtttg tgcaagacaa tgtgaataag gatgccgtca ccgatagact    9300
cgcctccgtg gaaaccgata tgcctctgac actgaggcag catagaatta gcgctacctc    9360
cagctccgag gaaagctcca acaaaggcca aagacaactg acagtgtccc ccgagttccc    9420
cgggattaga cctgagtgtg tggtccccga acccaatgc gctatgaaaa gaaaagagaa    9480
aaaggctcag aaagagaaag acaaactgcc tgtgtccacc acaaccgtcg atgatcacat    9540
gccccctatc atgcagtgtg agcctccccc tcccgaagcc gctagaatcc acgaagtcgt    9600
ccccaggttc ctctccgata agctcctgga aaccaataga caaaagaata tccctcaact    9660
caccgctaac caacagtttc tgattgccag gctgatttgg tatcaggatg ctatgagca    9720
accctccgac gaagacctca agaggatcac acagacatgg caacaggctg acgatgaaa    9780
tgaggaaagc gataccccctt tcaggcagat taccgaaatg acaatcctca ccgtccagct    9840
catcgtcgag tttgccaaag gactcccccgg attcgctaag attagccaac ccgatcagat    9900
tacccctcctg aaagcctgta gctccgaggt catgatgctg agagtggcta aaggtacga    9960
tgccgcttcc gatagcgtcc tgtttgccaa taaccaagcc tataccaggg acaattcag    10020
gaaggctggc atggcctatg tgattgagga tgtgctccac ttttgcagat gtatgtactc    10080
catggctctc gataacattc actatgccct cctgacagcc gtcgtgattt tctccgacag    10140
gccccggactg aacagcctc aactcgtgga agaaattcag aggtactatc tgaatacccct    10200
cagaatttac attctgaatc agctctccgg cagcgctaga tccagcgtca tctatggcaa    10260
aatcctctcc attctgtccg agctgagaac actgggaatg caaaactcca atatgtgcat    10320
tagcctcaag ctcaagaata gaaaactgcc tcccttctg gaagaaattt gggatgtggc    10380
tgacatgagc catacccaac ccctcccat tctggaaagc cctaccaatc tgtaaatcga    10440
tagccgcctg gctgagatgg ggtgggcagg gcagagctga tcaggccga gcagaaccgc    10500
actcttccca aataaagctt cctccttgaa acacaaatgt ttcttactta caccccatcc    10560
tgattttttt tcttgagacc agagagtggg aaagctctct cttgacctga ggatggatct    10620
gaaaattatg agcccctttga ggacagggaa tgttattcat ctttgaattc cgcagcatct    10680
agcaccaggt cttgtacaga gcaggtgccc aataaaatggt tgaatgaata tatgaaaagt    10740
agaggcagag ggctgggcac agtggctcac gcctgtaatc ctagcacttt gggaggctga    10800
ggtgggtgga tcacttgagg tcaggagttc gagaccagct tggccaacat ggctaaacct    10860
catctctatt aaaaatacaa aaattagctg gctgtggcc tgtaatccca gctactcagg    10920
aggctgaggc aggagaatca cttgaaccca ggaggaggag tttgcagtga gccgagatcg    10980
caccattgca ctccagcctg ggcgatagga gcaaaactcc atctcaaaaa caaaaaacaa    11040
aacaaaacaa aaagaaaaaa gaaaagtagg ggcagagatg tgggcagga gaggtgactc    11100
gggctcagct gcatggtcct gctctgcttc ttttttcttg gagtttgtcc gttggatgac    11160
aatgatagtg gtgaacaggt atggagggct tactaagtac caggtgtcta gacgaggacg    11220
ctcgggcttg gacccatggc acatcgtgta atcatggtca tagctgtttc ctgtgtgaaa    11280
```

```
ttgttatccg ctacgtctct cccccgcagt aagggctaga ttaactcgtc tcgtgaatat    11340
ccggaactcc ctttagtgag ggttaattgc gttgcgctca ctgcccgctt tccagtcggg    11400
aaacctgtcg tgccagctta atcatggtca tagctgtttc ctgtgtgaaa ttgttatccg    11460
ctaccggaaa cgcttccttc atgtgagcaa aaggccagca aaaggccagg aaccgtaaaa    11520
aggccgcgtt gctggcgttt ttccataggc tccgcccccc tgacgagcat cacaaaaatc    11580
gacgctcaag tcagaggtgg cgaaacccga caggactata agataccagg cgtttccccc    11640
ctggaagctc cctcgtgcgc tctcctgttc cgaccctgcc gcttaccgga tacctgtccg    11700
cctttctccc ttcgggaagc gtggcgcttt ctcatagctc acgctgtagg tatctcagtt    11760
cggtgtaggt cgttcgctcc aagctgggct gtgtgcacga accccccgtt cagcccgacc    11820
gctgcgcctt atccggtaac tatcgtcttg agtccaaccc ggtaagacac gacttatcgc    11880
cactggcagc agccactggt aacaggatta gcagagcgag gtatgtaggc ggtgctacag    11940
agttcttgaa gtggtggcct aactacggct acactagaag aacagtattt ggtatctgcg    12000
ctctgctgaa gccagttacc ttcggaaaaa gagttggtag ctcttgatcc ggcaaacaaa    12060
ccaccgctgg tagcggtggt ttttttgttt gcaagcagca gattacgcgc agaaaaaaag    12120
gatctcaaga agatcctttg atcttttcta cggggtctga cgctcagtgg aacgaaaact    12180
cacgttaagg gattttggtc atgatctatg tcgggtgcgg agaaagaggt aatgaaatgg    12240
catacgagta aacttggtct gacaccgctg catgagatta tcaaaaagga tcttcaccta    12300 gatccttttaa aattaaaaat gaagttttaa atcaatctaa agtatatatg agtaaacttg    12360
gtctgacagt taccaatgct taatcagtga ggcacctatc tcagcgatct gtctatttcg    12420
ttcatccata gttgcctgac tccccgtcgt gtagataact acgatacggg agggcttacc    12480
atctggcccc agtgctgcaa tgataccgcg agacccacgc tcaccggctc cagatttatc    12540
agcaataaac cagccagccg gaagcgccga gcgcagaagt ggtcctgcaa ctttatccgc    12600
ctccatccag tctattaact gttgccggga agctagagta agtagttcgc cagttaatag    12660
tttgcggagc gttgttgcca ttgctacagg catcgtggtg tcacgctcgt cgtttggtat    12720
ggcttcattc agctccggtt cccaacgatc aaggcgagtt acatgatccc ccatgttgtg    12780
caaaaaagcg gttagctcct tcggtcctcc gatggttgtc agaagtaagt tggccgcagt    12840
gttatcactc atggttatgg cagcactgca taattctctt actgtcatgc catccgtaag    12900
atgcttttct gtgactggtg agtattcaac caagtcattc tgagaatagt gtatgcggcg    12960
accgagttgc tcttgcccgg cgtcaatacg ggataatacc gcgccacata gcagaacttt    13020
aaaagtgctc atcattggga agcgttcttc gggcgaaaa ctctcaagga tcttaccgct    13080
gttgagatcc agttcgatgt aacccacacg agcacccaac tgatcttcag catcttttac    13140
tttcaccagc gtttctgggt gagcaaaaac aggaaggcaa aatgccgcaa aaagggaat    13200 aagggcgaca cggaaatgtt gaatactcat acgcttcctt tttcaatagt attgaagcat    13260
ttatcagggt tattgtctcg ggagcgaata catatttgaa tgtatttaga aaaa          13314
```

<210> SEQ ID NO 16
<211> LENGTH: 11013
<212> TYPE: DNA
<213> ORGANISM: Artificial Sequence
<220> FEATURE:
<223> OTHER INFORMATION: Synthetic TNF inducible promoter gene switch
      construct expressing etanercept

<400> SEQUENCE: 16

-continued

```
taaacaaata gggttccgc gcacatttcc ccgaaaagtg ccacctgacg tactgaggac       60
gccagggttt tcccagtcac gacgttgtaa aacgacggcc agtagcagac aagcccgtca     120
gggcgcgtca gcgggtgttg gcgggtgtcg gggatttagg tgacactata ggctgagcgc     180
cgcacaggca tctagaggct atggcagggc ctgccgcccc gacgttggct gcgagccctg     240
ggccttcacc cgaacttggg gggtggggtg gggaaaagga agaaacgcgg gcgtattggc     300
cccaatgggg tctcggtggg gtatcgacag agtgccagcc ctgggaccga accccgcgtt     360
tatgaacaaa cgacccaaca ccgtgcgttt tattctgtct ttttattgcc gtcatagcgc     420
gggttccttc cggtattgtc tccttccgtg tttcaatcga ttcaaaagaa ctcgtccagc     480
agacggtaaa aagcaatgcg ttgagaatcc ggtgcagcaa tgccatacag caccagaaag     540
cgatcagccc attcaccgcc cagttcttca gcaatgtcac gggttgccag tgcgatgtcc     600
tgatagcgat cagccacgcc caggcgaccg cagtcgataa agccggagaa acggccgttt     660
tccaccataa tgtttggcag acaagcatcc ccgtgggtca caaccaggtc ctcgccatct     720
ggcatacgtg ctttcaggcg tgcgaacagt tctgccggtg ccagaccctg atgttcctcg     780
tccaggtcat cctgatcaac caggccagct tccatgcgag tgcgtgcgcg ctcgatacgg     840
tgtttagctt ggtgatcgaa tgggcaagta gctgggtcca gggtatgcag acggcgcata     900
gcatcagcca tgatggaaac cttttctgcc ggtgccagat gagaggacag cagatcctgg     960
cctggaacct cgcccagcag cagccagtcg cggccagcct cggtcacaac atccagcaca    1020
gctgcgcatg gaacgccggt agtagccagc caggacagac gagctgcttc atcttgcagt    1080
tcgttcagtg cgccggacag atcggtctta acaaacagca ccggacggcc ttgagcggac    1140
agacggaaca cagctgcgtc ggagcaaccg atagtctgtt gagcccagtc atagccaaac    1200
agacgttcca cccaagcagc cggagaacca gcgtgcagac cgtcttgttc aatcatggtg    1260
gcaattgggt gtctgagcga tgtggctcgg ctggcgacgc aaaagaagat gcggctgact    1320
gtcgaacagg aggagcagag agcgaagcgg gaggctgcgg gctcaatttg catgctttag    1380
ttcctcacct tgtcgtatta tactatgccg atatactatg ccgatgatta attgtcaacg    1440
tatacggaat agctctgagg ccgaggcagc ttcggcctct gcataaataa aaaaaattag    1500
tcagccatgg ggcggagaat gggcggaact gggcggagtt aggggcggga tgggcggagt    1560 tagggggcggg actatggttg ctgactaatt gagatgcttg cttgcatac ttctgcctgc    1620 tggggagcct ggggactttc cacacctggt tgctgactaa ttgagatgct tgctttgcat    1680
acttctgcct gctggggagc tggggacttt ccacaccct aacctcgagg ccatcgtggc    1740
acgccagggt tttcccagtc acgacgttgt aaaacgacgg ccagtgctct tctccccgc     1800 gggaggtttt ataaatccga ctgtctagat accacatttg tagaggtttt acttgcttta    1860
aaaaacctcc cacatctccc cctgaacctg aaacataaaa tgaatgcaaa tgttttatta    1920
acttgtttat tgcagcttat aatggttaca aattaagcaa tagcatcaca aatttcacaa    1980
attaagcatt tttttcactg cattctagtt gtggtttgtc caaactcatc aatgtatctt    2040
atcatgtcta atcgattcac aggttggtgg ggctctccag gatggggggg ggctgggtgt    2100
ggctcatgtc ggccacgtcc caaatctcct ccaggaaggg gggcagcttc ctgttcttca    2160
gcttcaggct gatacacata ttgctgttct gcattcccag ggtcctcagc tcgctcagga    2220
tgctcaggat cttgccgtag atcacgctgc tcctggcgct gccgctcagc tggttcagga    2280
tgtagatcct cagggtgttc aggtagtacc tctggatctc ctccaccagc tgggctgct    2340
```

```
ccaggccggg cctgtcgctg aagatcacca cggcggtcag cagggcgtag tggatgttgt    2400
ccagggccat gctgtacata catctgcaga agtgcaggag gtcctcgatc acctcggcca    2460
tgccagcctt cctgtagttg tccctggtgt aagcctggtt gttggcgaac aggatgctgt    2520
cgctggcggc gtcgtacctc ctggccaccc tcagcatcat cacctcgctg ctgcaagcct    2580
tcagcagggt gatctggtcg ggctggctga tcttggcgaa tccgggcagg cccttggcga    2640
actccacgat cagctgcacg gtcaggatgg tcatctcggt gatctgcctg aaggggtgt    2700 cgctctcctc gttctcgtcg tcggcctgct gccaggtctg ggtgatcctt ttcaggtcct    2760
cgtcgctggg ctgctcgtag ccgtcctgat accagatcag cctggcgatc aggaactgct    2820
ggttggcggt cagctggggg atgttcttct gcctgttggt caccagcagc ttgtcgctca    2880
ggaacctggg cacgacctcg tgaatcctgg cggcctcggg ggggggggc tcgcactgca    2940 tgatgggggg catgtggtca tcgacggtgg tggtgctcac gggcagcttg tccttctcct    3000
tctgggcctt cttctccttc cttttcatgg cgcactgggt ctcgggcacc acgcactcgg    3060
gcctgatccc gggaaactcg gggctcacgg tcagctgcct ctggcccttg ttgctgctct    3120
cctcgctgct gctggtggcg ctgatcctgt gctgcctcag ggtcaggggc atgtcggtct    3180
ccacgctggc cagcctgtcg gtcacggcgt ccttgttcac gttgtcctgc acgaacaggc    3240
cggtcagcag ggccttgatg tcttgcaggc tgtccatctt caggatcatg tccaggtcct    3300
ccctggggaa gatcagcagg aacagctgct ccagcctctc cagcctgctc tccacctcgg    3360
tcaggtgggc cctggtcagg gggctcctct tggtcttggg gctgtatctg cactcccagt    3420
tgttcttcag gcacttggcg cacttgggct tctccttgct gcacttcagc ttcttcagcc    3480
tgcagatgtc gcaagcctgc tcgatgctgc tcagcagctt catggtggca gatctggtcg    3540
cgggaggctg ctggttttcc actcccgaa aaaaatccag cgtctaagca gctgcaagga    3600
gagcctttca gagaagcggg tcctggcagc ggcggggaag tgtccccaaa tgggcagaat    3660
agcctccccg cgtcgggaga gtcgcgtcct tgctcgggtg ttgtaagttc cagtgcaaag    3720
tgcccgcccg ctgctatggg caaagtttcg tggatgcggc tagggttgcg caccgctggc    3780
tgggggatca gcgggagggc tgggccagag gcgaagcccc ctattcgctc cggatctccc    3840
ttcccaggac gcccgcagcg cagctctgct cgccgggctc ctccacccta gcccgccgcc    3900
cgctcgctcc ctctgcctct cgctggaatt actacagcga gttgccggct cagctgtcgc    3960
tggggctctc cagcatctcc atcaggaagg tgtcgatggg cacgtcgccg atcagcctga    4020
agaagaacag gtgctccagg cacttcaggc cgatgctcct caggctgggc agcctcagca    4080
gcagcttggc gaatctgccg ggctcgtcgg ggtgggtggt cctggtgtac tcctccaggg    4140
cggcgtacac cttctccctc agcagctcca cctcctgggc gcttttcagg cccctcacct    4200
cggggttgaa caggatgatg gccctcaggc agcccagctc ggtcttgtcc atcctcatgt    4260
ccctcatctt gctcaccagc tcggtcagca cctgtcgaa gatggcgccc actccggcgc    4320
tgtgggcgct gttcctatgg acgtgcaggc cggtggccag caggatgccg tccctcacgt    4380
cgatgctcct gtggctgaag ctggcgatca gcagctcgtt ccatccggcc ctcagcagga    4440
tcacctggtc gtccagggc aggctgctga agtggggaat cctcttggcc cactccacca    4500
gggtgaacag ctgcttgtcg gcggcctggc agatgttggt cacggggtcg ttggggctgc    4560
tgccgctgcc gccggttccg ccggggccct ccacgccctg gtcgcttttc tgctccacgg    4620
cgagttcggc ctccagaatc ctgtccacgg gcatctccat atggccgccg tactcgtcga    4680
tgcccagggc gtcggtgaac atctgctcga actcgaagtc ggccatgtcc agggcgccgt    4740
```

```
aggggggcgct gtcgtggggg gtgaagccgg ggccggggct gtcgccgtcg cccagcatgt    4800
ccaggtcgaa gtcgtccagg gcgtcggcgt gggccatggc cacgtcctcg ccgtccaggt    4860
gcagctcgtc gcccaggctc acgtcggtgg gggggccac cttccttttc ttcttggggc     4920
ccatggtggc caattgcccc ccccccccc cgcatgcagc tcctgaagcc agtgaggccc     4980
gatgcagata ccgcggagtg aaatagaaag tctgtgcttt ataaagggtc ttgttgcaga    5040
ggcggaggga aatcccttca aggggaaacc cagggcagag ccaggaaaaa agtttaaca     5100
gacacccagc caagttccac tattaacccc ttcagttgct ctcactgctg aagctcctct    5160
ctctgtcctg gcaaagaag acacttccaa gactataaaa tacaggcttt tcctcatctt     5220
cgactccaaa aggctatctt tactggaaag ataaggaca atgctgattg cagaatgaag     5280
ctttctgaat ccaatgtggg ttaagggggt ggggagagaa aaaatggaga cagagtagta    5340
aattctactc tggttttga actggataaa taacgactat gccatgtgaa ttgattttct     5400
ccatcaagga aatatgtttg caattctaaa agagattaat ttttttctct tacaagagaa    5460
aggaaaaagt tatttctttt gatgagtcat tttttaaaaa agggacacca taacttctta    5520
gttttatatt tattcataaa aatagttctt ttagcaacaa acatcaactt tttgaaacta    5580
ttttcttgag tagaaagtaa aggactgtaa ctgaaattgc tgccaaaaca agggaaacaa    5640
ttttttttg ttttagaaaa gttaccaata atttggttaa attgctggat aattggaatt     5700
tttttgcata cttaaatgca agtgtatgga atccatctga agtggcaaat ctcttggctc    5760
gagtaggcga gaccaatggg tgcgccatgg gctcttccaa aaatttaggt gacactatag    5820
ggcaccgctc gcacctgcgc acaggcataa gccaaatgga actacgagac ctgcatcgtg    5880
gtgtaactat aacggtccta aggtagcgac cgcggagact aggtgtattt atctaagcga    5940
tcgcttaatt aaggccggcc gccgcaataa aatatcttta ttttcattac atctgtgtgt    6000
tggttttttg tgtgaatcca tagtactaac atacgctctc catcaaaaca aaacgaaaca    6060
aaacaaacta gcaaaatagg ctgtccccag tgcaagtcca ggtgccagaa catttctcta    6120
tccataatgc aggggtaccg ggtgatgacg gtgaaaacct ccaattgcgg agtactgtcc    6180
tccgagcgga gtactgtcct ccgagcggag tactgtcctc cgagcggagt actgtcctcc    6240
gagcggagta ctgtcctccg agcggagtac tgtcctccga gcggagagtc ccgggggacc    6300
tagagggtat ataatgggtg ccttagctgg tgtgtgacct catcttcctg tacgcccctg    6360
caggggcgcg ccacgcgtcg aagaaggtga gtaatcttaa catgctcttt ttttttttt     6420
ttgctaatcc cttttgtgtg ctgatgttag gatgacattt acaacaaatg tttgttcctg    6480
acaggaaaaa ccttgctggg taccttcgtt gccggacact tcttgtcctc tactttggaa    6540
aaaaggaatt gagagccgct agcgccacca tgctgcccgc ccaggtcgcc ttcacccct    6600
acgcccccga gcccggcagc acctgtagac tgagagagta ttacgaccag accgcccaga    6660
tgtgctgctc caagtgcagc cccggccagc acgccaaggt gttctgcacc aagaccagcg    6720
acaccgtctg cgacagctgc gaggacagca cctacaccca gctgtggaac tgggtgcccg    6780
agtgcctgag ctgcggcagc agatgtagca gcgaccaggt ggagacccag gcttgccaca    6840
gagagcagaa cagaatctgc acctgtagac ccggctggta ctgcgccctg agcaagcagg    6900
agggctgccg cctgtgcgcc cccctgagaa agtgcagacc cggcttcggc gtggccagac    6960
ccggcaccga gaccagcgac gttgtgtgca agccctgtgc ccccggcacc ttcagcaaca    7020
ccaccagcag caccgacatc tgccgccccc accagatttg caacgtggtg gccatccccg    7080
```

```
gcaacgccag catggacgcc gtgtgtacca gcaccagccc cacccgcagc atggcccccg    7140
gcgctgtcca cctcccccag cccgtgagca ccagaagcca gcacacccag cccacccccg    7200
agcccagcac cgcccccagc accagcttcc tgctgcctat gggacccagc cccccgccg    7260 agggcagcac cggcgacgag cccaagagct gcgacaagac ccacacctgt cccccctgcc    7320
ccgcccccga gctgctgggc ggcccagcg tgttcctgtt cccccccaag cccaaggaca    7380
ccctgatgat ctccagaacc cccgaggtga catgcgtggt ggtggacgtg agccacgagg    7440 accccccaggt gaagttcaac tggtacgtgg acggcgtgca agtgcataac gccaagacca    7500
agcccagaga gcagcagtac aacagcacct acagagtggt gagcgtgctg accgtgctgc    7560
accagaactg gctggacggc aaggagtaca agtgcaaggt gtccaacaag gccctgcccg    7620
cccccatcga gaaaaccatc agcaaggcca agggccagcc cagagagccc caggtgtaca    7680
ccctgccccc cagcagagag gagatgacca agaaccaggt gtccctgacc tgtctggtga    7740
agggcttcta ccccagcgac atcgccgtgg agtgggagag caacggccag cccgagaaca    7800
actacaagac caccccccc gtgctggaca gcgacggcag cttcttcctg tacagcaagc    7860
tgaccgtgga caagagcaga tggcagcagg gcaacgtgtt cagctgctcc gtgatgcacg    7920
aggccctgca caaccactac acccagaagt ccctgagcct gagccccggc aagtgaatcg    7980
attgcgcaaa gctttcgcga taggcgagac caatgggtgt gtacgtagcg gccgcgtcga    8040
cgatagcttg atgggtggca tccctgtgac ccctccccag tgcctctcct ggccctggaa    8100
gttgccactc cagtgcccac cagccttgtc ctaataaaat taagttgcat cattttgtct    8160
gactaggtgt ccttctataa tattatgggg tggaggggg tggtatggag caaggggcaa    8220
gttgggaaga caacctgtag ggcctgcggg gtctattggg aaccaagctg gagtgcagtg    8280
gcacaatctt ggctcactgc aatctccgcc tcctgggttc aagcgattct cctgcctcag    8340
cctcccgagt tgttgggatt ccaggcatgc atgaccaggc tcagctaatt tttgtttttt    8400
tggtagagac ggggtttcac catattggcc aggctggtct ccaactccta atctcaggtg    8460
atctacccac cttggcctcc caaattgctg ggattacagg cgtgaaccac tgctcccttc    8520
cctgtccttc tgattttaaa ataactatac cagcaggagg acgtccagac acagcatagg    8580
ctacctggcc atgcccaacc ggtgggacat ttgagttgct tgcttggcac tgtcctctca    8640
tgcgttgggt ccactcagta gatgcctgtt gaattctgat ttaaatcggt ccgcgtacgg    8700
cgtggtaggt ccgaacgaat ccatggatta ccctgttatc cctactcaag gacatcatcc    8760
ctttagtgag ggttaattca cgcagtgggt acggaactaa aggcagcaca catcgtgtaa    8820
tcatggtcat agctgtttcc tgtgtgaaat tgttatccgc tacgtctctc ccccgcagta    8880
agggctagat taactcgtct cgtgaatatc cggaactccc tttagtgagg gttaattgcg    8940
ttgcgctcac tgcccgcttt ccagtcggga aacctgtcgt gccagcttaa tcatggtcat    9000
agctgtttcc tgtgtgaaat tgttatccgc taccggaaac gcttccttca tgtgagcaaa    9060
aggccagcaa aaggccagga accgtaaaaa ggccgcgttg ctggcgtttt tccataggct    9120
ccgcccccct gacgagcatc acaaaaatcg acgctcaagt cagaggtggc gaaacccgac    9180
aggactataa agataccagg cgtttccccc tggaagctcc ctcgtgcgct ctcctgttcc    9240
gaccctgccg cttaccggat acctgtccgc ctttctccct tcgggaagcg tggcgctttc    9300
tcatagctca cgctgtaggt atctcagttc ggtgtaggtc gttcgctcca agctgggctg    9360
tgtgcacgaa ccccccgttc agcccgaccg ctgcgcctta tccggtaact atcgtcttga    9420
gtccaacccg gtaagacacg acttatcgcc actggcagca gccactggta acaggattag    9480
```

| | |
|---|---|
| cagagcgagg tatgtaggcg gtgctacaga gttcttgaag tggtggccta actacggcta | 9540 |
| cactagaaga acagtatttg gtatctgcgc tctgctgaag ccagttacct tcggaaaaag | 9600 |
| agttggtagc tcttgatccg gcaaacaaac caccgctggt agcggtggtt tttttgtttg | 9660 |
| caagcagcag attacgcgca gaaaaaaagg atctcaagaa gatcctttga tcttttctac | 9720 |
| ggggtctgac gctcagtgga acgaaaactc acgttaaggg attttggtca tgcctaggac | 9780 |
| gaaaggaggt cgtgaaatgg ataaaaaaat acagcgtttt tcatgtacaa ctatactagt | 9840 |
| tgtagtgcct aaataatgct tttaaaactt aaaaataatc tatgtcgggt gcggagaaag | 9900 |
| aggtaatgaa atggcaaatc aatgtcctca gcgaaatggc atacgagtaa acttggtctg | 9960 |
| acaccgctgc atgagattat caaaaaggat cttcacctag atcctttaa attaaaaatg | 10020 |
| aagttttaaa tcaatctaaa gtatatatga gtaaacttgg tctgacagtt accaatgctt | 10080 |
| aatcagtgag gcacctatct cagcgatctg tctatttcgt tcatccatag ttgcctgact | 10140 |
| ccccgtcgtg tagataacta cgatacggga gggcttacca tctggcccca gtgctgcaat | 10200 |
| gataccgcga gacccacgct caccggctcc agatttatca gcaataaacc agccagccgg | 10260 |
| aagcgccgag cgcagaagtg gtcctgcaac tttatccgcc tccatccagt ctattaactg | 10320 |
| ttgccgggaa gctagagtaa gtagttcgcc agttaatagt ttgcgagcg ttgttgccat | 10380 |
| tgctacaggc atcgtggtgt cacgctcgtc gtttggtatg gcttcattca gctccggttc | 10440 |
| ccaacgatca aggcgagtta catgatcccc catgttgtgc aaaaaagcgg ttagctcctt | 10500 |
| cggtcctccg atcgttgtca gaagtaagtt ggccgcagtg ttatcactca tggttatggc | 10560 |
| agcactgcat aattctctta ctgtcatgcc atccgtaaga tgcttttctg tgactggtga | 10620 |
| gtattcaacc aagtcattct gagaatagtg tatgcggcga ccgagttgct cttgcccggc | 10680 |
| gtcaatacgg gataataccg cgccacatag cagaacttta aaagtgctca tcattgggaa | 10740 |
| gcgttcttcg gggcgaaaac tctcaaggat cttaccgctg ttgagatcca gttcgatgta | 10800 |
| acccacacga gcacccaact gatcttcagc atctttact ttcaccagcg tttctgggtg | 10860 |
| agcaaaaaca ggaaggcaaa atgccgcaaa aaagggaata agggcgacac ggaaatgttg | 10920 |
| aatactcata cgcttccttt ttcaatagta ttgaagcatt tatcagggtt attgtctcgg | 10980 |
| gagcgaatac atatttgaat gtatttagaa aaa | 11013 |

<210> SEQ ID NO 17
<211> LENGTH: 15706
<212> TYPE: DNA
<213> ORGANISM: Artificial Sequence
<220> FEATURE:
<223> OTHER INFORMATION: Synthetic dual promoter inflammation + hypoxia
      inducible gene switch construct encoding etanercept and EPO

<400> SEQUENCE: 17

| | |
|---|---|
| taaacaaata gggggttccgc gcacatttcc ccgaaaagtg ccacctgacg tactgaggac | 60 |
| gccagggttt tcccagtcac gacgttgtaa aacgacggcc agtagcagac aagcccgtca | 120 |
| gggcgcgtca gcgggtgttg gcgggtgtcg gggatttagg tgacactata ggctgagcgc | 180 |
| cgcacaggca tctagaggct atggcagggc ctgccgcccc gacgttggct gcgagccctg | 240 |
| ggccttcacc cgaacttggg gggtggggtg gggaaaagga agaaacgcgg gcgtattggc | 300 |
| cccaatgggg tctcggtggg gtatcgacag agtgccagcc ctgggaccga accccgcgtt | 360 |
| tatgaacaaa cgacccaaca ccgtgcgttt tattctgtct ttttattgcc gtcatagcgc | 420 |
| gggttccttc cggtattgtc tccttccgtg tttcaatcga tttagaagaa ctcgtcaaga | 480 |

```
aggcgataga aggcgatgcg ctgcgaatcg ggggcggcga taccgtaaag gacgaggaag    540
cggtcagccc attcgccgcc aagttcttca gcaatatcac gggtagccaa cgctatgtcc    600
tgatagcggt cggccacacc cagccgtcca cagtcgatga atccagaaaa gcggccattt    660
tccaccatga tattcggcaa gcaggcatcg ccgtgggtca cgacgagatc ctcgccgtcg    720
ggcatcctcg ccttgagcct ggcgaacagt tcggctggcg cgagcccctg atgctcctcg    780
tccagatcat cctgatcgac aagaccggct tccatccgag tacgtgctcg ctcgatgcga    840
tgtttcgctt ggtggtcgaa tgggcatgta gccggatcaa gcgtatgcag ccgccgcatt    900
gcatcagcca tgatggatac tttctcggca ggagcaaggt gagatgacag gagatcctgc    960
cccggcactt cgcccaatag cagccagtcc cttcccgctt cagtgacaac gtcgagcacg   1020
gctgcgcaag gaacgcccgt cgtggccagc acgatagcc cgcgctgcctc gtcctggagt   1080 tcattcaggg caccggacag gtcggtcttg acaaaaagaa ccgggcgccc ctgcgctgac   1140
agccggaaca cggcggcatc agagcagccg attgtctgtt gtgcccagtc atagccgaat   1200
agcctctcca cccaagcggc cggagaacca gcgtgcaatc catcttgttc aatggccgat   1260
cccatggtgg ccaattgggt gtctgagcga tgtggctcgg ctggcgacgc aaaagaagat   1320
gcggctgact gtcgaacagg aggagcagag agcgaagcgg gaggctgcgg gctcaatttg   1380
catgcggaat agctctgagg ccgaggcagc ttcggcctct gcataaataa aaaaaattag   1440
tcagccatgg ggcggagaat gggcggaact gggcggagtt aggggcggga tgggcggagt   1500
taggggcggg actatggttg ctgactaatt gagatgcttg cttttgcatac ttctgcctgc   1560 tggggagcct ggggactttc cacacctggt tgctgactaa ttgagatgct tgctttgcat   1620
acttctgcct gctggggagc ctggggactt ccacaccct aacctcgagg ccatcgtggc   1680
acgccagggt tttcccagtc acgacgttgt aaaacgacgg ccagtgctct tctcccccgc   1740
gggaggtttt ataaatccga ctgtctagat tgttgttaaa tcacacaaaa aaccaacaca   1800
cagatgtaat gaaaataaag atattttatt atcgattcag ctgtcgctgg ggctctccag   1860
catctccatc aggaaggtgt cgatgggcac gtcgccgatc agcctgaaga agaacaggtg   1920
ctccaggcac ttcaggccga tgctcctcag gctgggcagc ctcagcagca gcttggcgaa   1980
tctgccgggc tcgtcggggt gggtggtcct ggtgtactcc tccagggcgg cgtacacctt   2040
ctccctcagc agctccacct cctgggcgct tttcaggccc ctcacctcgg ggttgaacag   2100
gatgatggcc ctcaggcagc ccagctcggt cttgtccatc ctcatgtccc tcatcttgct   2160
caccagctcg gtcagcaccc tgtcgaagat ggcgcccact ccggcgctgt gggcgctgtt   2220
cctatggacg tgcaggccgg tggccagcag gatgccgtcc ctcacgtcga tgctcctgtg   2280
gctgaagctg gcgatcagca gctcgttcca tccggccctc agcaggatca cctggtcgtc   2340
caggggcagg ctgctgaagt ggggaatcct cttgcccac tccaccaggg tgaacagctg   2400
cttgtcggcg gcctggcaga tgttggtcac ggggtcgttg ggctgctgc cgctgccgcc   2460 ggttccgccg gggccctcca cgccctggtc gcttttctgc tccacggcga gttcggcctc   2520
cagaatcctg tccacgggca tctccatatg gccgccgtac tcgtcgatgc ccagggcgtc   2580
ggtgaacatc tgctcgaact cgaagtcggc catgtccagg gcgccgtagg gggcgctgtc   2640 gtgggggtg aagccggggc cggggctgtc gccgtcgccc agcatgtcca ggtcgaagtc   2700
gtccagggcg tcggcgtggg ccatggccac gtcctcgccg tccaggtgca gctcgtcgcc   2760
caggctcacg tcggtgggg gggccacctt ccttttcttc ttggggccca tggtggccaa   2820
```

```
ttgcccccccc cccccccccgc atgccgtcta caaaaaaagc caaaaacggc cagaatttag    2880
cggacaattt actagtctaa cactgaaaat tacatattga cccaaatgat tacatttcaa    2940
aaggtgccta aaaaacttca caaaacacac tcgccaaccc cgagcgcacg tacccagccc    3000
agcagcccgc tactcaccaa gtgacgatca cagcgatcca caaacaagaa ccgcgaccca    3060
aatcccggct gcgacggaac tagctgtgcc acacccggcg cgtccttata taatcatcgg    3120
cgttcaccgc cccacggaga tccctccgca gaatcgccga gaagggacta cttttcctcg    3180
cctgttccgc tctctggaaa gaaaaccagt gccctagagt cacccaagtc ccgtcctaaa    3240
atgtccttct gctgatactg gggttctaag gccgagtctt atgagcagcg ggccgctgtc    3300
ctgagcgtcc gggcggaagg atcaggacgc tcgctgcgcc cttcgtctga cgtggcagcg    3360
ctcgccgtga ggaggggggc gcccgcggga ggcgccaaaa cccggcgcgg aggccctcga    3420
gtaggcgaga ccaatgggtg cgccatgggc tcttccaaaa atttaggtga cactataggg    3480
caccgctcgc acctgcgcac aggcccgcgc ctacaaacta cgaacgatca ttctagatac    3540
cacatttgta gaggttttac ttgcttttaaa aaacctccca catctccccc tgaacctgaa    3600
acataaaatg aatgcaaatg ttttattaac ttgtttattg cagcttataa tggttacaaa    3660
ttaagcaata gcatcacaaa tttcacaaat taagcatttt tttcactgca ttctagttgt    3720
ggtttgtcca aactcatcaa tgtatcttat catgtctaat cgattcacag gttggtgggg    3780
ctctccagga tggggggggg ctgggtgtgg ctcatgtcgg ccacgtccca aatctcctcc    3840
aggaaggggg gcagcttcct gttcttcagc ttcaggctga tacacatatt gctgttctgc    3900
attcccaggt tcctcagctc gctcaggatg ctcaggatct tgccgtagat cacgctgctc    3960
ctggcgctgc cgctcagctg gttcaggatg tagatcctca gggtgttcag gtagtacctc    4020
tggatctcct ccaccagctg gggctgctcc aggccgggcc tgtcgctgaa gatcaccacg    4080
gcggtcagca gggcgtagtg gatgttgtcc agggccatgc tgtacataca tctgcagaag    4140
tgcaggaggt cctcgatcac ctcggccatg ccagccttcc tgtagttgtc cctggtgtaa    4200
gcctggttgt tggcgaacag gatgctgtcg ctggcggcgt cgtacctcct ggccaccctc    4260
agcatcatca cctcgctgct gcaagccttc agcagggtga tctggtcggg ctggctgatc    4320
ttggcgaatc cgggcaggcc cttggcgaac tccacgatca gctgcacggt caggatggtc    4380
atctcggtga tctgcctgaa gggggtgtcg ctctcctcgt tctcgtcgtc ggcctgctgc    4440
caggtctggg tgatccttt caggtcctcg tcgctgggct gctcgtagcc gtcctgatac    4500
cagatcagcc tggcgatcag gaactgctgg ttggcggtca gctgggggat gttcttctgc    4560
ctgttggtca ccagcagctt gtcgctcagg aacctgggca cgacctcgtg aatcctggcg    4620
gcctcggggg gggggggctc gcactgcatg atgggggca tgtggtcatc gacggtggtg    4680
gtgctcacgg gcagcttgtc cttctccttc tgggccttct tctccttcct tttcatggcg    4740
cactgggtct cgggcaccac gcactcgggc ctgatcccgg gaaactcggg gctcacggtc    4800
agctgcctct ggcccttgtt gctgctctcc tcgctgctgc tggtgcgct gatcctgtgc    4860 tgcctcaggg tcaggggcat gtcggtctcc acgctggcca gcctgtcggt cacggcgtcc    4920
ttgttcacgt tgtcctgcac gaacaggcg gtcagcaggg ccttgatgtc ttgcaggctg    4980
tccatcttca ggatcatgtc caggtcctcc ctggggaaga tcagcaggaa cagctgctcc    5040
agcctctcca gcctgctctc cacctcggtc aggtgggccc tggtcagggg gctcctcttg    5100
gtcttggggc tgtatctgca ctcccagttg ttcttcaggc acttggcgca cttgggcttc    5160
tccttgctgc acttcagctt cttcagcctg cagatgtcgc aagcctgctc gatgctgctc    5220
```

```
agcagcttca tggtggccaa ttgcccccccc ccccccccgc atgctccctg ctggtttctt    5280
gggagcgaag aaaagctgga tgtggtccct ggggaaagtc cctgcaggtc atttccccta    5340
caaaacggtc taagacaagt tcctggatgc cagtggtttc ttcatcccgg gtcatttatc    5400
ccagttgtgc aacctgaggg aacaagatgt gcctggcagc tgtcagggca ggagaccagc    5460
tctgctcctc agcattgagg gggctgaggc tgcggagttg agagtgggag ccccgtgctc    5520
gagtggtaat acaatggccg gttcccatgg acctgcatcg tggtgatcta tgtcgggtgc    5580
ggagaaagag gtaatgaaat ggcagaaatg gcaccaccta aggtagcgac cgcggagact    5640
aggtgtattt atctaagcga tcgcttaatt aaggccggcc gccgcaataa aatatcttta    5700
ttttcattac atctgtgtgt tggttttttg tgtgaatcca tagtactaac atacgctctc    5760
catcaaaaca aaacgaaaca aaacaaacta gcaaaatagg ctgtcccag tgcaagtcca     5820 ggtgccagaa catttctcta tccataatgc aggggtaccg ggtgatgacg tgaaaaacct    5880
ccaattgcgg agtactgtcc tccgagcgga gtactgtcct ccgagcggag tactgtcctc    5940
cgagcggagt actgtcctcc gagcggagta ctgtcctccg agcggagtac tgtcctccga    6000
gcggagagtc cccggggacc tagagggtat ataatgggtg ccttagctgg tgtgtgacct    6060
catcttcctg tacgcccctg caggggcgcg ccacgcgtcg aagaaggtga gtaatcttaa    6120
catgctcttt tttttttttt ttgctaatcc cttttgtgtg ctgatgttag gatgacattt    6180
acaacaaatg tttgttcctg acaggaaaaa ccttgctggg taccttcgtt gccggacact    6240
tcttgtcctc tactttggaa aaaggaatt gagagccgct agcgccacca tgctgcccgc     6300
ccaggtcgcc ttcacccct acgcccccga gcccggcagc acctgtagac tgagagagta     6360
ttacgaccag accgcccaga tgtgctgctc aagtgcagc cccggccagc acgccaaggt     6420
gttctgcacc aagaccagcg acaccgtctg cgacagctgc gaggacagca cctacaccca    6480
gctgtggaac tgggtgcccg agtgcctgag ctgcggcagc agatgtagca gcgaccaggt    6540
ggagacccag gcttgcacca gagagcagaa cagaatctgc acctgtagac ccggctggta    6600
ctgcgccctg agcaagcagg agggctgccg cctgtgcgcc ccctgagaa agtgcagacc     6660 cggcttcggc gtggccagac ccggcaccga gaccagcgac gttgtgtgca agccctgtgc    6720 cccggcacc ttcagcaaca ccaccagcag caccgacatc tgccgccccc accagatttg     6780
caacgtggtg gccatccccg gcaacgccag catggacgcc gtgtgtacca gcaccagccc    6840
cacccgcagc atgggccccg gcgctgtcca cctcccccag cccgtgagca ccagaagcca    6900
gcacacccag cccaccccccg agcccagcac cgcccccagc accagcttcc tgctgcctat    6960
gggacccagc ccccccgccg agggcagcac cggcgacgag cccaagagct gcgacaagac    7020
ccacacctgt ccccccctgcc ccgccccccga gctgctgggc ggcccagcg tgttcctgtt     7080 ccccccccaag cccaaggaca ccctgatgat ctccagaacc cccgaggtga catgcgtggt    7140
ggtggacgtg agccacgagg accccccaggt gaagttcaac tggtacgtgg acggcgtgca    7200
agtgcataac gccaagacca gcccagaga gcagcagtac aacagcacct acagagtggt     7260
gagcgtgctg accgtgctgc accagaactg gctggacggc aaggagtaca gtgcaaggt     7320 gtccaacaag gccctgcccg ccccccatcga gaaaaccatc agcaaggcca gggccagcc    7380 cagagagccc caggtgtaca ccctgccccc cagcagagag gagatgacca agaaccaggt    7440
gtccctgacc tgtctggtga agggcttcta ccccagcgac atcgccgtgg agtgggagag    7500
caacggccag cccgagaaca actacaagac cacccccccc gtgctggaca gcgacggcag    7560
```

```
cttcttcctg tacagcaagc tgaccgtgga caagagcaga tggcagcagg gcaacgtgtt    7620
cagctgctcc gtgatgcacg aggccctgca caaccactac acccagaagt ccctgagcct    7680
gagccccggc aagtgaatcg attgcgcaaa gctttcgcga taggcgagac caatgggtgt    7740
gtacgtagcg gccgcgtcga cgatagcttg atgggtggca tccctgtgac ccctccccag    7800
tgcctctcct ggccctggaa gttgccactc cagtgcccac cagccttgtc ctaataaaat    7860
taagttgcat cattttgtct gactaggtgt ccttctataa tattatgggg tggagggggg    7920
tggtatggag caaggggcaa gttgggaaga caacctgtag ggcctgcggg gtctattggg    7980
aaccaagctg gagtgcagtg gcacaatctt ggctcactgc aatctccgcc tcctgggttc    8040
aagcgattct cctgcctcag cctcccgagt tgttgggatt ccaggcatgc atgaccaggc    8100
tcagctaatt tttgtttttt tggtagagac ggggtttcac catattggcc aggctggtct    8160
ccaactccta atctcaggtg atctacccac cttggcctcc caaattgctg ggattacagg    8220
cgtgaaccac tgctcccttc cctgtccttc tgattttaaa ataactatac cagcaggagg    8280
acgtccagac acagcatagg ctacctggcc atgcccaacc ggtgggacat ttgagttgct    8340
tgcttggcac tgtcctctca tgcgttgggt ccactcagta gatgcctgtt gaattctgat    8400
ttaaatcggt ccgcgtacgg cgtggtaggt ccgaacgaat ccatggatta ccctgttatg    8460
tggtcctcca gggttgccgt tccttaacta taacggtcct aaggtagcga ccgcggagac    8520
taggtgtatt tatctaagcg atcgcttaat taaggccggc cgccgcaata aaatatcttt    8580
attttcatta catctgtgtg ttggtttttt gtgtgaatcc atagtactaa catacgctct    8640
ccatcaaaac aaaacgaaac aaaacaaact agcaaaatag gctgtcccca gtgcaagtcc    8700
aggtgccaga acatttctct atccataatg caggggtacc gggtgatgac ggtgaaaacc    8760
tccaattgtg ctgtatataa aaccagtggt tatatgtaca gtactgctgt atataaaacc    8820
agtggttata tgtacagtac gtcgactgct gtatataaaa ccagtggtta tatgtacagt    8880
actgctgtat ataaaccag tggttatatg tacagtaccc ggggaccta gagggtatat    8940
aatgggtgcc ttagctggtg tgtgacctca tcttcctgta cgcccctgca ggggcgcgcc    9000
acgcgtcgaa gaaggtgagt aatcttaaca tgctcttttt tttttttttt gctaatccct    9060
tttgtgtgct gatgttagga tgacatttac aacaaatgtt tgttcctgac aggaaaaacc    9120
ttgctgggta ccttcgttgc cggacacttc ttgtcctcta ctttggaaaa aaggaattga    9180
gagccgctag cgccaccatg ggcgtccacg aatgccctgc ctggctgtgg ctgctcctgt    9240
ccctgctgtc tctcccctc ggcctcccg tcctgggagc cctcccagg ctgatttgcg    9300
atagcagggt gctggagaga tacctgttgg aagccaagga agccgagaat atcacaaccg    9360
gatgcgccga gcactgctcc ctgaatgaga atatcacagt gcctgacaca aaggtcaact    9420
tttacgcttg gaaagaatg gaggtcggcc aacaggctgt ggaagtgtgg cagggactgg    9480
ctctgctgtc cgaagccgtc ctgagggggcc aagccctcct ggtcaactcc agccaaccct    9540
gggagcctct gcaactgcat gtggataagg ctgtgtccgg cctcagatcc ctgacaaccc    9600
tcctgagagc cctgggcgct cagaaagagg ctatctcccc ccctgacgct gcctccgccg    9660
ctcccctcag aacaatcaca gccgatacct ttagaaaact gtttagagtc tactccaact    9720
ttctgagggg caaactgaaa ctgtataccg agaggcttg caggaccgga gacaggtaaa    9780
tcgattgcgc aaagctttcg cgataggcga ccaatggg tgtgtacgta gcggccgctc    9840
gagaacttgt ttattgcagc ttataatggt tacaaataaa gcaatagcat cacaaatttc    9900
acaaataaag cattttttttc actgcattct agttgtggtt tgtccaaact catcaatgta    9960
```

```
tcttatcatg tctcgtacgg cgtggtaggt ccgaacgaat ccatggatta ccctgttatc    10020
cctactcatc ttcgtcggac gcgccgttaa tatttgatca gccattctct gtatgagtac    10080
taacgaacgt gacgcggtgt tactggtaac tatgactctc ttaaggtagc caaatacatc    10140 atcccttag tgagggttaa ttcacgcagt gccgcggcgt gtagaaaata cctatcagct    10200
cgaggacgtg acaaacgaag ccgcacgtca gggccggacg tggggcccca gagcgacgct    10260
gagtgcgtgc gggactcgga gtacgtgacg gagcccccac gtgggttccc gcacgtccgc    10320
gacgtgacaa cgaagccgc acgtcagggc cggacgtggg gccccagagc gacgctgagt    10380
gcgtgcggga ctcggagtac gtgacggagc cccacgtgg gttcccgcac gtccgcgacg    10440
tgacaaacga agccgcacgt cagggccgga cgtggggccc cagagcgacg ctgagtgcgt    10500
gcgggactcg gagtacgtga cggagccccc acgtgggttc ccgcacgtcc gcacgtgac    10560 aaacgaagcc gcacgtcagg gccggacgtg ggccccaga gcgacgctga gtgcgtgcgg    10620
gactcggagt acgtgacgga gccccacgt gggttcccgc acgtccgcga cgtgacaaac    10680
gaagccgcac gtcagggccg gacgtggggc ccagagcga cgctgagtgc gtgcgggact    10740
cggagtacgt gacggagccc ccacgtgggt tcccgcacgt ccgcgacgtg acaaacgaag    10800
ccgcacgtca gggccggacg tggggcccca gagcgacgct gagtgcgtgc gggactcgga    10860
gtacgtgacg gagcccccac gtgggttccc gcacgtccgc gacgtgacaa cgaagccgc    10920 acgtcagggc cggacgtggg gccccagagc gacgctgagt gcgtgcggga ctcggagtac    10980
gtgacggagc cccacgtgg gttcccgcac gtccgcgaag acctagaggg tatataatgg    11040
gtgccttagc tggtgtgtga gctcatcttc ctgtgcatgc gggggggggg ggggcaatt    11100 ggccaccatg aaagccctca ccgctagaca acaggaagtg tttgacctca tcagggacca    11160
tatctcccag acaggaatgc cccctaccag ggccgaaatc gctcagaggc tgggattcag    11220
gagccctaac gctgccgaag aacatctgaa agccctcgcc aggaagggag tgattgagat    11280
tgtgtccggc gcttccaggg gcattagact cctgcaagag gaggaagaag gactccccct    11340
cgtgggaagg gtcgccgctg gcgaacccct cctggctcaa caacacattg agggacacta    11400
tcaggtcgat cctagcctct ttaaacccaa tgccgatttc ctcctgaggg tgtccggcat    11460
gagcatgaag gatattggaa tcatggacgg agacctcctg gctgtgcata agacacagga    11520
tgtgaggaac ggacaggtcg tggtcgccag gatcgacgac gaagtgacag tgaaaagact    11580
caagaaacag ggaaacaaag tggaactgct ccccgaaaac tccgagttta gcctatcgt    11640 cgtggatctg aggcagcaat cctttaccat tgagggactg gctgtgggag tgattagaaa    11700
tggcgattgg ctcgaatttc ccgggattag acctgagtgt gtggtccccg aaacccaatg    11760
cgctatgaaa agaaagaga aaaggctca gaaagagaaa gacaaactgc ctgtgtccac    11820
cacaaccgtc gatgatcaca tgccccctat catgcagtgt gagcctcccc ctcccgaagc    11880
cgctagaatc cacgaagtcg tccccaggtt cctctccgat aagctcctgg aaaccaatag    11940
acaaaagaat atccctcaac tcaccgctaa ccaacagttt ctgattgcca ggctgatttg    12000
gtatcaggat ggctatgagc aaccctccga cgaagacctc aagaggatca cacagacatg    12060
gcaacaggct gacgatgaga atgaggaaag cgataccccct tcaggcaga ttaccgaaat    12120 gacaatcctc accgtccagc tcatcgtcga gtttgccaaa ggactccccg gattcgctaa    12180
gattagccaa cccgatcaga ttaccctcct gaaagcctgt agctccgagg tcatgatgct    12240
gagagtggct agaaggtacg atgccgcttc cgatagcgtc ctgtttgcca ataaccaagc    12300
```

```
ctataccagg gacaattaca ggaaggctgg catggcctat gtgattgagg atgtgctcca   12360
cttttgcaga tgtatgtact ccatggctct cgataacatt cactatgccc tcctgacagc   12420
cgtcgtgatt ttctccgaca ggcccggact ggaacagcct caactcgtgg aagaaattca   12480
gaggtactat ctgaataccc tcagaattta cattctgaat cagctctccg gcagcgctag   12540
atccagcgtc atctatggca aaatcctctc cattctgtcc gagctgagaa cactgggaat   12600
gcaaaactcc aatatgtgca ttagcctcaa gctcaagaat agaaaactgc ctcccttttct   12660
ggaagaaatt tgggatgtgg ctgacatgag ccatacccaa ccccctccca ttctggaaag   12720
ccctaccaat ctgtaaatcg atagccgcct ggctgagatg gggtgggcag ggcagagctg   12780
atcagggccg agcagaaccg cactcttccc aaataaagct tcctccttga aacacaaatg   12840
tttcttactt acaccccatc ctgatttctt ttcttgagac cagagagtgg gaaagctctc   12900
tcttgacctg aggatggatc tgaaaattat gagccccttg aggacaggga atgttattca   12960
tctttgaatt ccgcagcatc tagcaccagg tcttgtacag agcaggtgcc caataaatgg   13020
ttgaatgaat atatgaaaag tagaggcaga gggctgggca cagtggctca cgcctgtaat   13080
cctagcactt tgggaggctg aggtgggtgg atcacttgag gtcaggagtt cgagaccagc   13140
ttggccaaca tggctaaacc tcatctctat taaaaataca aaaattagct gggctggtgc   13200
ctgtaatccc agctactcag gaggctgagg caggagaatc acttgaaccc aggaggagga   13260
gtttgcagtg agccgagatc gcaccattgc actccagcct gggcgatagg agcaaaactc   13320
catctcaaaa acaaaaaaca aacaaaaca aaagaaaaa agaaaagtag gggcagagat   13380
gtggggcagg agaggtgact cgggctcagc tgcatggtcc tgctctgctt ctttttttctt   13440
ggagtttgtc cgttggatga caatgatagt ggtgaacagg tatggagggc ttactaagta   13500
ccaggtgtct agacgaggac gctcgggctt ggacccatgg cacatcgtgt aatcatggtc   13560
atagctgttt cctgtgtgaa attgttatcc gctacgtctc tcccccgcag taagggctag   13620
attaactcgt ctcgtgaata tccggaactc ccttttagtga gggttaattg cgttgcgctc   13680
actgcccgct ttccagtcgg gaaacctgtc gtgccagctt aatcatggtc atagctgttt   13740
cctgtgtgaa attgttatcc gctaccggaa acgcttcctt catgtgagca aaaggccagc   13800
aaaaggccag gaaccgtaaa aaggccgcgt tgctggcgtt tttccatagg ctccgccccc   13860
ctgacgagca tcacaaaaat cgacgctcaa gtcagaggtg gcgaaacccg acaggactat   13920
aaagatacca ggcgtttccc cctggaagct ccctcgtgcg ctctcctgtt ccgaccctgc   13980
cgcttaccgg atacctgtcc gcctttctcc cttcgggaag cgtggcgctt tctcatagct   14040
cacgctgtag gtatctcagt tcggtgtagg tcgttcgctc caagctgggc tgtgtgcacg   14100
aaccccccgt tcagcccgac cgctgcgcct tatccggtaa ctatcgtctt gagtccaacc   14160
cggtaagaca cgacttatcg ccactggcag cagccactgg taacaggatt agcagagcga   14220
ggtatgtagg cggtgctaca gagttcttga agtggtggcc taactacggc tacactagaa   14280
gaacagtatt tggtatctgc gctctgctga agccagttac cttcggaaaa agagttggta   14340
gctcttgatc cggcaaacaa accaccgctg gtagcggtgg tttttttgtt tgcaagcagc   14400
agattacgcg cagaaaaaaa ggatctcaag aagatccttt gatcttttct acggggtctg   14460
acgctcagtg gaacgaaaac tcacgttaag ggattttggt catgcctagg acgaaaggag   14520
gtcgtgaaat ggataaaaaa atacagcgtt tttcatgtac aactatacta gttgtagtgc   14580
ctaaataatg cttttaaaac ttaaaaatac gtttaaaccc tcagcgaaat ggcatacgag   14640
taaacttggt ctgacaccgc tgcatgagat tatcaaaaag gatcttcacc tagatccttt   14700
```

```
taaattaaaa atgaagtttt aaatcaatct aaagtatata tgagtaaact tggtctgaca    14760
gttaccaatg cttaatcagt gaggcaccta tctcagcgat ctgtctattt cgttcatcca    14820
tagttgcctg actcccgtc gtgtagataa ctacgatacg ggagggctta ccatctggcc    14880
ccagtgctgc aatgataccg cgagaccac gctcaccggc tccagattta tcagcaataa    14940
accagccagc cggaagcgcc gagcgcagaa gtggtcctgc aactttatcc gcctccatcc    15000
agtctattaa ctgttgccgg gaagctagag taagtagttc gccagttaat agttgcgga     15060 gcgttgttgc cattgctaca ggcatcgtgg tgtcacgctc gtcgtttggt atggcttcat    15120
tcagctccgt tcccaacga tcaaggcgag ttacatgatc ccccatgttg tgcaaaaaag    15180
cggttagctc cttcggtcct ccgatggttg tcagaagtaa gttggccgca gtgttatcac    15240
tcatggttat ggcagcactg cataattctc ttactgtcat gccatccgta agatgctttt    15300
ctgtgactgg tgagtattca accaagtcat tctgagaata gtgtatgcgg cgaccgagtt    15360
gctcttgccc ggcgtcaata cgggataata ccgcgccaca tagcagaact ttaaaagtgc    15420
tcatcattgg gaagcgttct cggggcgaa aactctcaag gatcttaccg ctgttgagat     15480
ccagttcgat gtaacccaca cgagcaccca actgatcttc agcatctttt actttcacca    15540
gcgtttctgg gtgagcaaaa acaggaaggc aaaatgccgc aaaaaaggga ataagggcga    15600
cacggaaatg ttgaatactc atacgcttcc ttttcaata gtattgaagc atttatcagg     15660
gttattgtct cgggagcgaa tacatatttg aatgtattta gaaaaa                   15706

<210> SEQ ID NO 18
<211> LENGTH: 17505
<212> TYPE: DNA
<213> ORGANISM: Artificial Sequence
<220> FEATURE:
<223> OTHER INFORMATION: Synthetic dual promoter gene switch construct
      encoding human Factor VIII:C

<400> SEQUENCE: 18
taaacaaata ggggttccgc gcacatttcc ccgaaaagtg ccacctgacg tactgaggac       60
gccagggttt tcccagtcac gacgttgtaa aacgacggcc agtagcagac aagcccgtca     120
gggcgcgtca gcgggtgttg gccctaggac gaaaggaggt cgtgaaatgg ataaaaaaat    180
acagcgtttt tcatgtacaa ctatactagt tgtagtgcct aaataatgct tttaaaactt    240
aaaaataatc aatgtcctca gcggggtgtc ggggatttag gtgacactat aggctgagcg    300
ccgcacaggc atctagaggc tatggcaggg cctgccgccc cgacgttggc tgcgagccct    360
gggccttcac ccgaacttgg ggggtggggt ggggaaaagg aagaaacgcg ggcgtattgg    420
ccccaatggg gtctcggtgg ggtatcgaca gagtgccagc cctgggaccg aaccccgcgt    480
ttatgaacaa acgacccaac accgtgcgtt ttattctgtc tttttattgc cgtcatagcg    540
cgggttcctt ccgtattgt ctccttccgt gtttcaatcg attcaaaaga actcgtccag     600
cagacggtaa aaagcaatgc gttgagaatc cggtgcagca atgccataca gcaccagaaa    660
gcgatcagcc cattcaccgc ccagttcttc agcaatgtca cggggttgcca gtgcgatgtc    720 ctgatagcga tcagccacgc ccaggcgacc gcagtcgata aagccggaga aacgccgtt     780 ttccaccata atgtttggca gacaagcatc gccgtgggtc acaaccaggt cctcgccatc    840
tggcatacgt gctttcaggc gtgcgaacag ttctgccggt gccagaccct gatgttcctc    900
gtccaggtca tcctgatcaa ccaggccagc ttccatgcga gtgcgtgcgc gctcgataacg    960 gtgtttagct tggtgatcga atgggcaagt agctgggtcc agggtatgca gacggcgcat   1020
```

```
agcatcagcc atgatggaaa ccttttctgc cggtgccaga tgagaggaca gcagatcctg   1080
gcctggaacc tcgcccagca gcagccagtc gcggccagcc tcggtcacaa catccagcac   1140
agctgcgcat ggaacgccgg tagtagccag ccaggacaga cgagctgctt catcttgcag   1200
ttcgttcagt gcgccggaca gatcggtctt aacaaacagc accggacggc cttgagcgga   1260
cagacggaac acagctgcgt cggagcaacc gatagtctgt tgagcccagt catagccaaa   1320
cagacgttcc acccaagcag ccggagaacc agcgtcaga ccgtcttgtt caatcatggt    1380
ggcaattggg tgtctgagcg atgtggctcg gctggcgacg caaagaaga tgcggctgac    1440 tgtcgaacag gaggagcaga gagcgaagcg ggaggctgcg ggctcaattt gcatgcttta   1500
gttcctcacc ttgtcgtatt atactatgcc gatatactat gccgatgatt aattgtcaac   1560
gtatacggaa tagctctgag gccgaggcag cttcggcctc tgcataaata aaaaaaatta   1620
gtcagccatg gggcggagaa tgggcggaac tgggcggagt taggggcggg atgggcggag   1680
ttaggggcgg gactatggtt gctgactaat tgagatgctt gctttgcata cttctgcctg   1740
ctggggagcc tggggacttt ccacacctgg ttgctgacta attgagatgc ttgctttgca   1800
tacttctgcc tgctggggag cctggggact ttccacaccc taacctcgag gccatcgtgg   1860
cacgccaggg ttttcccagt cacgacgttg taaaacgacg ccagtgctc ttctcccccg     1920 cgggaggttt tataaatccg actgtctaga ttgttgttaa atcacacaaa aaaccaacac   1980
acagatgtaa tgaaaataaa gatattttat tatcgattca gctgtcgctg ggctctcca    2040 gcatctccat caggaaggtg tcgatgggca cgtcgccgat cagcctgaag aagaacaggt   2100
gctccaggca cttcaggccg atgctcctca ggctgggcag cctcagcagc agcttggcga   2160
atctgccggg ctcgtcgggg tgggtggtcc tggtgtactc ctccagggcg cgtacacct    2220 tctccctcag cagctccacc tcctgggcgc ttttcaggcc cctcacctcg gggttgaaca   2280
ggatgatggc cctcaggcag cccagctcgg tcttgtccat cctcatgtcc ctcatcttgc   2340
tcaccagctc ggtcagcacc ctgtcgaaga tggcgcccac tccggcgctg tgggcgctgt   2400
tcctatggac gtgcaggccg gtggccagca ggatgccgtc cctcacgtcg atgctcctgt   2460
ggctgaagct ggcgatcagc agctcgttcc atccggccct cagcaggatc acctggtcgt   2520
ccaggggcag gctgctgaag tggggaatcc tcttggccca ctccaccagg gtgaacagct   2580
gcttgtcggc ggcctggcag atgttggtca cggggtcgtt ggggctgctg ccgctgccgc   2640
cggttccgcc ggggccctcc acgccctggt cgcttttctg ctccacggcg agttcggcct   2700
ccagaatcct gtccacgggc atctccatat ggccgccgta ctcgtcgatg cccagggcgt   2760
cggtgaacat ctgctcgaac tcgaagtcgg ccatgtccag ggcgccgtag ggggcgctgt   2820 cgtgggggt gaagccgggg ccgggctgt cgccgtcgcc cagcatgtcc aggtcgaagt      2880
cgtccagggc gtcggcgtgg gccatggcca cgtcctcgcc gtccaggtgc agctcgtcgc   2940
ccaggctcac gtcggtgggg ggggccacct tccttttctt cttggggccc atggtggcca   3000
attgcccccc ccccccccg catgccgtct aacaaaaaag ccaaaacgg ccagaattta      3060 gcggacaatt tactagtcta acactgaaaa ttacatattg acccaaatga ttacatttca   3120
aaaggtgcct aaaaaacttc acaaaacaca ctcgccaacc ccgagcgcac gtacccagcc   3180
cagcagcccg ctactcacca agtgacgatc acagcgatcc acaaacaaga accgcgaccc   3240
aaatcccggc tgcgacggaa ctagctgtgc cacacccggc gcgtccttat ataatcatcg   3300
gcgttcaccg ccccacggag atccctccgc agaatcgccg agaagggact acttttcctc   3360
```

```
gcctgttccg ctctctggaa agaaaaccag tgccctagag tcacccaagt cccgtcctaa    3420
aatgtccttc tgctgatact ggggttctaa ggccgagtct tatgagcagc gggccgctgt    3480
cctgagcgtc cgggcggaag gatcaggacg ctcgctgcgc ccttcgtctg acgtggcagc    3540
gctcgccgtg aggaggggg cgcccgcggg aggcgccaaa accggcgcg gaggccctcg      3600 agtaggcgag accaatgggt gcgccatggg ctcttccaaa aatttaggtg acactatagg    3660
gcaccgctcg cacctgcgca caggcccgcg gctacaaact acgaacgatc attctagata    3720
ccacatttgt agaggtttta cttgctttaa aaaacctccc acatctcccc ctgaacctga    3780
aacataaaat gaatgcaaat gttttattaa cttgtttatt gcagcttata atggttacaa    3840
attaagcaat agcatcacaa atttcacaaa ttaagcattt ttttcactgc attctagttg    3900
tggtttgtcc aaactcatca atgtatctta tcatgtctaa tcgattcaca ggttggtggg    3960
gctctccagg atggggggg gctgggtgtg gctcatgtcg gccacgtccc aaatctcctc     4020
caggaagggg ggcagcttcc tgttcttcag cttcaggctg atacacatat tgctgttctg    4080
cattcccagg gtcctcagct cgctcaggat gctcaggatc ttgccgtaga tcacgctgct    4140
cctggcgctg ccgctcagct ggttcaggat gtagatcctc agggtgttca ggtagtacct    4200
ctggatctcc tccaccagct ggggctgctc caggccgggc ctgtcgctga agatcaccac    4260
ggcggtcagc agggcgtagt ggatgttgtc cagggccatg ctgtacatac atctgcagaa    4320
gtgcaggagg tcctcgatca cctcggccat gccagccttc ctgtagttgt ccctggtgta    4380
agcctggttg ttggcgaaca ggatgctgtc gctggcggcg tcgtacctcc tggccaccct    4440
cagcatcatc acctcgctgc tgcaagcctt cagcagggtg atctggtcgg gctggctgat    4500
cttggcgaat ccgggcaggc ccttggcgaa ctccacgatc agctgcacgg tcaggatggt    4560
catctcggta atctgcctga agggggtgtc gctctcctcg ttctcgtcgt cggcctgctg    4620
ccaggtctgg gtgatccttt tcaggtcctc gtcgctgggc tgctcgtagc cgtcctgata    4680
ccagatcagc ctggcgatca ggaactgctg gttggcggtc agctggggga tgttcttctg    4740
cctgttggtc accagcagct tgtcgctcag gaacctgggc acgacctcgt gaatcctggc    4800
ggcctcgggg gggggggct cgcactgcat gatggggggc atgtggtcat cgacggtggt     4860
ggtgctcacg ggcagcttgt ccttctcctt ctgggccttc ttctccttcc ttttcatggc    4920
gcactgggtc tcgggcacca cgcactcggg cctgatcccg ggaaactcgg ggctcacggt    4980
cagctgcctc tggcccttgt tgctgctctc ctcgctgctg ctggtggcgc tgatcctgtg    5040
ctgcctcagg gtcaggggca tgtcggtctc cacgctggcc agcctgtcgg tcacggcgtc    5100
cttgttcacg ttgtcctgca cgaacaggcc ggtcagcagg gccttgatgt cttgcaggct    5160
gtccatcttc aggatcatgt ccaggtcctc cctggggaag atcagcagga acagctgctc    5220
cagcctctcc agcctgctct ccacctcggt caggtgggcc ctggtcaggg ggctcctctt    5280
ggtcttgggg ctgtatctgc actcccagtt gttcttcagg cacttggcgc acttgggctt    5340
ctccttgctg cacttcagct tcttcagcct gcagatgtcg caagcctgct cgatgctgct    5400
cagcagcttc atggtggcca attgccccccc cccccccccg catgccacta agatctgcat   5460
tttgacctag tttaaaagta aaacataagc gtgtcacctc aggatcattg tatttcttgc    5520
ttttacacct aatattcttc aaaattagca actattcctt caaaatgcct taaatacgtt    5580
aatattccgc aagcctcccc tcaattttac aaggctaagt cacttaatac gaaattcgtc    5640
attcaaggtt tcaacgtcaa cagcggaaaa tccagagcgc tctcttacca agcgtccaca    5700
gctttcccca ctaactgttc cggatattca aactccccg accgaactcc aatctgcctc     5760
```

```
aaacctaagc acggtgttag gcaaactgaa acaaaacca aacccacaag actcgcgaaa    5820
taaaaatccc attgaaacac aagaagggc acctttctca cactgggatt ccaaagtaaa    5880
ggcttccaga aaccacacaa actacctctt ttccgccttc cccgcgaagt aaactcgaca    5940
gaatcgccga tcggttaggc gtccgttagt ttccgtcaac ccgcgcgcgc caaccgccct    6000 cgccccctc aggtcaacaa ggcccactgt cccggaaagg cccagcgccg cgtcacctcg    6060
ccctcccctc ccccacgccc tccctcagc ggcccaccca accccaagaa gcctccacct    6120
tgacctcacc cattcccccc tctcacaccc cccaaggtc gttacggctg cgggccagta    6180
cctgttagcg gataccagga tcctgccaat caccaaccac gtccaccac agggacacaa    6240 acaagctcac ccaacaaagc caaccgcccc taaatgctcc gggctggcgg aggcaaattt    6300
atgcaacgag tgttgcgtca cttatcaccc ctcacgtaga cgccgtctcc gtgcgccgct    6360
gaaagtagtt cgccgcgccc aacctcccga gaggcagttt aggcttttca actgagcccc    6420
aaattcctca tagccgtaag aaaggctcct aaaaaattat ttcccttctc ctctatgcgc    6480
ttctcttcct tctttaggaa aatataagaa aattatcagg cggatgaatt tgagttgaag    6540
aaaccttcct cgaaagctct ggaaacttcc ttgcagcgcc ggcactgatt ggttaggcct    6600
gcgaaggcga ggtcggcgct gattggtggg ggacgcggtg gctctgttgt tgctgggctc    6660
cacctggggg ggcttagcgc cgaggttgct aagtaactga gcgcgcgtcg ccgcacaggt    6720 cttcctttt ttttcttgag acggatttcg ctcttgtttc ccaggctgga gtgcaatggc    6780
gcgatctcgg ctcatcgcaa cctccgcctc ccgggttcaa gcgattctcc tgcctcagcc    6840
tcccaagtag ctgggattac agctcgagtg gtaatacaat ggccggttcc catggacctg    6900
catcgtggtg taactataac ggtcctaagg tagcgaccgc ggagactagg tgtatttatc    6960
taagcgatcg cttaattaag gccggccgcc gcaataaaat atctttattt tcattacatc    7020
tgtgtgttgg ttttttgtgt gaatccatag tactaacata cgctctccat caaaacaaaa    7080
cgaaacaaaa caaactagca aaataggctg tccccagtgc aagtccaggt gccagaacat    7140
ttctctatcc ataatgcagg ggtaccgggt gatgacggtg aaaacctcca attgcggagt    7200
actgtcctcc gagcggagta ctgtcctccg agcggagtac tgtcctccga gcggagtact    7260
gtcctccgag cggagtactg tcctccgagc ggagtactgt cctccgagcg gagagtcccc    7320
ggggacctag agggtatata atgggtgcct tagctggtgt gtgacctcat cttcctgtac    7380
gcccctgcag gggcgcgcca cgcgtcgaag aaggtgagta atcttaacat gctctttttt    7440 ttttttttg ctaatccctt ttgtgtgctg atgttaggat gacatttaca acaaatgttt    7500
gttcctgaca ggaaaaacct tgctgggtac cttcgttgcc ggacacttct tgtcctctac    7560 tttgaaaaa aggaattgag agccgctagc gccaccatgg ctaccaggag atattacctc    7620
ggcgctgtgg aactgtcctg ggattacatg cagtccgacc tcggcgaact gcctgtggat    7680
gccaggttcc ctcccagggt gcctaagtcc ttccctttca atacctccgt ggtctacaaa    7740
aagacactgt ttgtggaatt tacagaccat ctgtttaaca ttgccaaacc caggcccct    7800 tggatgggcc tcctgggacc cacaatccaa gccgaagtgt atgacacagt ggtcatcaca    7860
ctgaaaaaca tggcctccca ccccgttagc ctgcacgctg tcggcgtcag ctattggaaa    7920
gcctccgagg gagccgaata cgatgaccaa acctcccaga gggagaaaga ggatgacaaa    7980
gtgtttcccg gaggctccca cacatacgtc tggcaagtgc tcaaggaaaa cggacctatg    8040
gcctccgacc ctctgtgtct gacatactcc tacctgagcc atgtggatct ggtcaaggat    8100
```

```
ctgaatagcg gactgattgg cgctctgctc gtgtgtagag aaggctccct ggctaaggaa    8160
aagacacaga cactgcataa gtttatcctc ctgtttgccg ttttgatga gggaaagtcc     8220
tggcatagcg aaaccaaaaa ctccctgatg caggatagag atgccgccag tgctagagct    8280
tggcctaaga tgcacaccgt caatggctat gtgaatagat ccctgcctgg cctcatcgga    8340
tgccatagaa aaagcgtcta ctggcacgtc atcggaatgg gaaccacacc cgaagtgcat    8400
agcatttttcc ttgaaggaca cacattcctc gtgaggaacc atagacaagc ctccctggaa   8460
atctccccca ttacctttct gacagcccaa accctcctga tggacctcgg ccaattcctc    8520
ctgttttgcc atatctccag ccatcagcat gacggaatgg aagcctatgt gaaagtggat    8580
agctgtcccg aggagcccca gctcagaatg aagaataacg aagaagccga ggactacgat    8640
gacgatctga cagactccga gatggatgtc gtgaggttcg atgacgataa ctccccctcc    8700
ttcattcaga ttagatccgt ggctaagaaa caccctaaga catgggtcca ctatatcgct    8760
gccgaggaag aagattggga ctatgcccct ctggtcctgg ctcccgatga caggagctat    8820
aagtcccagt atctgaataa cggaccccag agaatcggca ggaagtataa gaaagtgagg    8880
ttcatggcct ataccgatga gacattcaaa accagggagg ctatccaaca cgaaagcgga    8940
atcctcggcc ctctgctcta cggagaggtc ggcgataccc tcctgattat ctttaagaat    9000
caggccagta ggccctataa catttaccct cacggaatca cagatgtgag acctctgtat    9060
agcaggagac tccccaaagg cgtcaagcat ctgaaagact ttcccattct gcctggcgaa    9120
atctttaagt ataagtggac cgtcaccgtc gaggatggcc ctaccaaaag cgatcccagg    9180
tgcctcacca ggtactatag ctccttcgtc aacatggaga gggacctcgc ctccggcctc    9240
atcggacccc tcctgatttg ctataaggaa agcgtcgatc aaagaggaaa ccaaatcatg    9300
agcgataaga ggaacgtcat cttgttctcc gtgtttgacg aaaacaggag ctggtacttg    9360
accgaaaaca ttcagaggtt cctccccaat cccgctggcg tccagcttga ggaccctgag    9420
tttcaagcct ccaacattat gcacagcatt aacggatacg ttttcgatag cctccagctg    9480
tccgtctgcc tccacgaggt cgcttactgg tacattctgt ccatcggagc caaaccgat    9540
ttcctgagcg tctttttag cggatacaca ttcaaacaca aaatggtcta cgaggataca    9600
ctgacactgt ttcccttag cggagagaca gtgtttatga gcatggagaa ccctggcctc    9660
tggattctgg gatgccataa ctccgacttt agaaatagag gaatgacagc cctcctgaaa    9720
gtgtccagct gtgacaaaaa cacaggcgat tactatgagg atagctatga ggacatttcc    9780
gcctatctgc tgtcaaaaaa caatgccatt gagcctagat ccttctccca gaatagcagg    9840
caccctagca caagacaaaa gcaattcaat gccacaacca ttcccgaaaa cgacatcgaa    9900
aagacagacc cttggtttgc ccatagaaca cccatgccca aaatccaaaa cgtcagctcc    9960
agcgatctgc tcatgctcct gaggcagtcc cccacacccc acggcctgag cctgtccgat   10020
ctgcaagagg ctaagtatga cacattctcc gacgatccct ccccggagc cattgactcc    10080
aacaatagcc tgagcgaaat gacacacttt agacccagc tgcaccatag cggagacatg    10140
gtgtttaccc ctgagtccgg cctccagctc agactcaacg aaaagctcgg cacaaccgct   10200
gccacagagc tgaagaaact ggatttcaaa gtgtccagca aagcaataa cctcatctcc    10260
accattccct ccgacaatct ggctgccgga accgataaca caagctccct gggacccct    10320
tccatgcccg tccactatga ctcccagctc gacacaaccc ttttggaaa gaaaagctcc    10380
cccctcaccg aaagcggagg ccctctgtcc gtgtccgagg aaaacaatga cagcaagctg   10440
ctggagagcg gactgatgaa ctcccaggaa agctcctggg gaaagaatgt gtccagcaca   10500
```

```
gagtccggca ggctgtttaa gggaaagaga gcccacggcc ctgccctcct gacaaaggat    10560
aacgctctgt ttaaggtcag cattagcctc ctgaaaacca ataagacaag caataactcc    10620
gccacaaaca gaaagaccca cattgacgga ccctccctgc tcatcgaaaa ctccccctcc    10680
gtgtggcaga atatcctcga atccgacaca gagtttaaga aagtgacacc cctcatccat    10740
gacaggatgc tcatggataa gaatgccaca gccctcagac tcaaccacat gagcaacaaa    10800
accacaagca gcaagaacat ggagatggtc cagcaaaaga agagggacc cattcccct     10860 gacgctcaga atcccgatat gtccttcttt aagatgctgt ttctgcctga gtccgccagg    10920
tggattcaga ggacccacgg caaaaactcc ctgaatagcg gacagggacc ctcccccaaa    10980
cagctcgtgt ccctgggacc cgaaaagtcc gtggaaggcc aaaactttct gtccgagaaa    11040
aacaaagtgg tcgtgggaaa gggagagttt accaaggacg ttggcctgaa ggaaatggtg    11100
tttcctagct ccagaaatct gtttctgaca aacctcgaca atctgcatga gaataacaca    11160
cacaatcagg aaaagaaaat ccaagaggaa atcgaaaaga agagacact gattcaggaa      11220 aacgtcgtgc tcccccaaat ccataccgtc accggaacca aaaactttat gaaaaacctt     11280
ttcctcctgt ccaccaggca gaatgtgaaa ggctcctacg atggcgctta cgctcccgtc    11340
ctgcaagact ttagatccct gaatgactcc accaatagaa caaagaaaca cacagcccat    11400
ttctccaaga aggcgagga ggaaaacctg gaaggactgg gaaaccaaac caaacagatt     11460
gtggaaaagt atgcctgtac cacaagaatt agccctaaca caagccaaca gaattcgtc    11520 acccaaagat ccaagagagc cctgaagcaa ttcaggctgc ctctggaaga acagagctg    11580 gagaaaagaa ttatcgtgga tgatacctcc acccaatggt ccaagaatat gaaacacctc    11640 accctagca cactgacaca gattgactat aacgaaaagg aaaagggagc cattacccaa    11700
agccctctgt ccgactgtct gacaagatcc cactccatcc ctcaggctaa caggagccct    11760
ctgcctatcg ctaaggtcag ctccttccct agcattagac ctatctatct gacaagagtc    11820
ctgtttcagg ataactccag ccatctgcct gccgcctctt atagaaaaaa ggatagcgga    11880
gtgcaagagt ccagccattt cctccaggga gccaaaaaga ataacctgag cctcgccatt    11940
ctgacactgg aaatgacagg cgatcagagg gaggtcggct ccctgggaac ctccgccaca    12000
aactccgtga catacaaaaa ggtcgagaat accgtcctgc ctaagcctga cctccccaaa    12060
acctccggca aagtggaact gctccccaaa gtgcatatct atcagaaaga cctctttcct    12120
accgaaacct ccaacggaag cccccggcca ctggatctgg tcgagggaag cctcctgcaa    12180
ggcacagagg gagccattaa gtggaacgaa gccaatagac ctggcaaagt gcctttcctc    12240
agagtcgcca cagagtccag cgctaagaca cccagcaagc tgctggaccc cctcgcctgg    12300
gacaatcact atggcacaca gattcccaaa gaggaatgga aaagccaaga gaaaagccct    12360
gagaaaaccg ctttcaaaaa gaaagacaca atcctgagcc tcaacgcttg cgaaagcaat    12420
cacgctatcg ctgccattaa cgaaggccaa aacaaaccg aaatcgaagt gacatgggcc    12480
aagcagggca ggaccgaaag actctgctcc cagaatcccc ctgtgctcaa gaggcaccaa    12540
agagaaatca caagaacaac cctccagtcc gaccaagagg aaatcgacta cgatgacaca    12600
atctccgtgg aaatgaaaaa ggaggacttt gacatttacg atgaggatga gaatcagtcc    12660
cccaggagct ttcagaaaaa gacaagacat tactttatcg ctgccgtcga gaggctgtgg    12720
gactatggca tgagcagcag ccctcacgtc ctgaggaaca gagcccagag cggaagcgtc    12780 cccccaattca aaaaggtcgt gtttcaggag ttcacagacg gcagcttcac ccaacccctc    12840
```

```
tacaggggcg aactgaatga gcatctggga ctgctcggcc cttacattag agccgaggtg    12900
gaggataaca ttatggtcac ctttagaaat caggccagca ggccctatag cttttactcc    12960
agcctcatct cctacgagga agatcagagg cagggagccg aacccaggaa gaatttcgtc    13020
aagcctaacg aaaccaaaac ctatttctgg aaggtccagc atcacatggc ccctaccaaa    13080
gacgaatttg attgcaaagc ctgggcctat ttctccgacg ttgacctgga gaaagacgtg    13140
cattccggcc tcatcggacc cctcctggtc tgccatacca ataccctcaa ccctgcccac    13200
ggcagacagg tgaccgtcca ggagtttgct ctgttttca caatctttga cgaaaccaaa    13260
agctggtact ttaccgaaaa catggagagg aactgtagag cccctgtaa cattcagatg    13320 gaggacccca cattcaaaga gaattacagg ttccatgcca ttaacggata cattatggat    13380
accctccccg gactggtcat ggctcaggat cagaggatca ggtggtatct gctgtctatg    13440
ggctccaacg aaaacattca ctccatccat ttctccggcc atgtgtttac cgtcagaaaa    13500
aaggaggagt ataagatggc cctctacaat ctgtatcccg gagtgtttga cacagtggaa    13560
atgctcccct ccaaggctgg catttggagg gtggaatgcc tcatcggaga gcatctgcac    13620
gccggaatgt ccaccctgtt tctcgtgtat agcaataagt gtcagacacc cctcggcatg    13680
gcctccggcc atatcaggga cttcagatt accgccagcg acagtatgg ccaatgggct    13740 cccaaactgg ctagactcca ctatagcgga agcattaacg cttggtccac caaagagcct    13800
ttctcctgga ttaaggtgga cctcctggct cccatgatta ccacggaat caaaacccaa    13860 ggcgctagac aaaagtttag ctccctgtat atctcccagt ttatcattat gtatagcctc    13920 gacgaaaga aatggcaaac ctatagagga aactccaccg gaaccctcat ggtgttcttt    13980
ggcaatgtgg atagctccgg cattaagcat aacattttca atcccctat cattgccagg    14040 tacattagac tccaccctac ccattactcc atcaggagca cactgaggat ggaactgatg    14100
ggctgtgacc tcaactcctg ctccatgccc ctcggcatgg aaagcaaagc cattagcgat    14160
gcccaaatca cagcctccag ctatttcaca aatatgttcg ctacctggag ccctagcaaa    14220
gccaggctgc atctgcaagg caggagcaat gcctggagac ctcaggtcaa caatcccaaa    14280
gagtggctgc aagtggattt ccaaaagaca atgaaagtga caggcgtcac cacacaggga    14340
gtgaaaagcc tcctgacaag catgtacgtc aaggagttcc tcatctccag ctcccaggat    14400
ggccatcagt ggaccctgtt cttcagaat ggcaaagtga agtgttca gggaaaccaa    14460 gactccttca cacccgtcgt gaatagcctc gaccctcccc tcctgacaag atacctgaga    14520 atccacccc aaagctgggt gcatcagatt gccctcagaa tggaggtcct gggatgcgaa    14580
gcccaagacc tctactaaat cgattgcgca agctttcgc gataggcgag accaatgggt    14640
gtgtacgtag cggccgcgtc gacgatagct tgatgggtgg catccctgtg accctcccc    14700 agtgcctctc ctggccctgg aagttgccac tccagtgccc accagccttg tcctaataaa    14760
attaagttgc atcatttgt ctgactaggt gtccttctat aatattatgg ggtgaggggg    14820
ggtggtatgg agcaagggc aagttgggaa gacaacctgt agggcctgcg gggtctattg    14880
ggaaccaagc tggagtgcag tggcacaatc ttggctcact gcaatctccg cctcctgggt    14940
tcaagcgatt ctcctgcctc agcctcccga gttgttggga ttccaggcat gcatgaccag    15000
gctcagctaa ttttgtttt tttggtagag acggggtttc accatattgg ccaggctggt    15060
ctccaactcc taatctcagg tgatctaccc accttggcct cccaaattgc tgggattaca    15120
ggcgtgaacc actgctccct tccctgtcct tctgatttta aaataactat accagcagga    15180
ggacgtccag acacagcata ggctacctgg ccatgcccaa ccggtgggac atttgagttg    15240
```

```
cttgcttggc actgtcctct catgcgttgg gtccactcag tagatgcctg ttgaattctg   15300
atttaaatcg gtccgcgtac ggcgtggtag gtccgaacga atccatggat taccctgtta   15360
tccctactca aggacatcat cccctttagtg agggttaatt cacgcagtgg gtacggaact   15420
aaaggcagca cacatcgtgt aatcatggtc atagctgttt cctgtgtgaa attgttatcc   15480
gctacgtctc tcccccgcag taagggctag attaactcgt ctcgtgaata tccggaactc   15540
cctttagtga gggttaattg cgttgcgctc actgcccgct ttccagtcgg gaaacctgtc   15600
gtgccagctt aatcatggtc atagctgttt cctgtgtgaa attgttatcc gctaccggaa   15660
acgcttcctt catgtgagca aaaggccagc aaaaggccag gaaccgtaaa aaggccgcgt   15720
tgctggcgtt tttccatagg ctccgccccc ctgacgagca tcacaaaaat cgacgctcaa   15780
gtcagaggtg gcgaaacccg acaggactat aaagatacca ggcgtttccc cctggaagct   15840
ccctcgtgcg ctctcctgtt ccgaccctgc cgcttaccgg atacctgtcc gcctttctcc   15900
cttcgggaag cgtggcgctt tctcatagct cacgctgtag gtatctcagt tcggtgtagg   15960
tcgttcgctc caagctgggc tgtgtgcacg aaccccccgt tcagcccgac cgctgcgcct   16020
tatccggtaa ctatcgtctt gagtccaacc cggtaagaca cgacttatcg ccactggcag   16080
cagccactgg taacaggatt agcagagcga ggtatgtagg cggtgctaca gagttcttga   16140
agtggtggcc taactacggc tacactagaa gaacagtatt tggtatctgc gctctgctga   16200
agccagttac cttcggaaaa agagttggta gctcttgatc cggcaaacaa accaccgctg   16260
gtagcggtgg tttttttgtt tgcaagcagc agattacgcg cagaaaaaaa ggatctcaag   16320
aagatccttt gatcttttct acggggtctg acgctcagtg gaacgaaaac tcacgttaag   16380
ggattttggt catgatctat gtcgggtgcg gagaaagagg taatgaaatg gcatacgagt   16440
aaacttggtc tgacaccgct gcatgagatt atcaaaaagg atcttcacct agatcctttt   16500
aaattaaaaa tgaagtttta aatcaatcta agtatatat gagtaaactt ggtctgacag   16560
ttaccaatgc ttaatcagtg aggcacctat ctcagcgatc tgtctatttc gttcatccat   16620
agttgcctga ctccccgtcg tgtagataac tacgatacgg gagggcttac catctggccc   16680
cagtgctgca atgataccgc gagacccacg ctcaccggct ccagatttat cagcaataaa   16740
ccagccagcc ggaagcgccc agcgcagaag tggtcctgca actttatccg cctccatcca   16800
gtctattaac tgttgccggg aagctagagt aagtagttcg ccagttaata gtttgcggag   16860
cgttgttgcc attgctacag gcatcgtggt gtcacgctcg tcgtttggta tggcttcatt   16920
cagctccggt tcccaacgat caaggcgagt tacatgatcc cccatgttgt gcaaaaaagc   16980
ggttagctcc ttcggtcctc cgatggttgt cagaagtaag ttggccgcag tgttatcact   17040
catggttatg gcagcactgc ataattctct tactgtcatg ccatccgtaa gatgcttttc   17100
tgtgactggt gagtattcaa ccaagtcatt ctgagaatag tgtatgcggc gaccgagttg   17160
ctcttgcccg gcgtcaatac gggataatac cgcgccacat agcagaactt taaaagtgct   17220
catcattggg aagcgttctt cggggcgaaa actctcaagg atcttaccgc tgttgagatc   17280
cagttcgatg taacccacac gagcacccaa ctgatcttca gcatctttta ctttcaccag   17340
cgtttctggg tgagcaaaaa caggaaggca aaatgccgca aaaaagggaa taagggcgac   17400
acggaaatgt tgaatactca tacgcttcct ttttcaatag tattgaagca tttatcaggg   17460
ttattgtctc gggagcgaat acatatttga atgtatttag aaaaa              17505
```

<210> SEQ ID NO 19

<211> LENGTH: 16379
<212> TYPE: DNA
<213> ORGANISM: Artificial Sequence
<220> FEATURE:
<223> OTHER INFORMATION: Synthetic single promoter gene switch construct encoding human factor VIII:C

<400> SEQUENCE: 19

| | | | | | |
|---|---|---|---|---|---|
| taaacaaata | gggttccgc | gcacatttcc | ccgaaaagtg | ccacctgacg | tactgaggac | 60 |
| gccagggttt | tcccagtcac | gacgttgtaa | aacgacggcc | agtagcagac | aagcccgtca | 120 |
| gggcgcgtca | gcgggtgttg | gcgggtgtcg | gggatttagg | tgacactata | ggctgagcgc | 180 |
| cgcacaggca | tctagaggct | atggcagggc | ctgccgcccc | gacgttggct | gcgagccctg | 240 |
| ggccttcacc | cgaacttggg | gggtggggtg | gggaaaagga | agaaacgcgg | gcgtattggc | 300 |
| cccaatgggg | tctcggtggg | gtatcgacag | agtgccagcc | ctgggaccga | accccgcgtt | 360 |
| tatgaacaaa | cgacccaaca | ccgtgcgttt | tattctgtct | ttttattgcc | gtcatagcgc | 420 |
| gggttccttc | cggtattgtc | tccttccgtg | tttcaatcga | ttcaaaagaa | ctcgtccagc | 480 |
| agacggtaaa | aagcaatgcg | ttgagaatcc | ggtgcagcaa | tgccatacag | caccagaaag | 540 |
| cgatcagccc | attcaccgcc | cagttcttca | gcaatgtcac | gggttgccag | tgcgatgtcc | 600 |
| tgatagcgat | cagccacgcc | caggcgaccg | cagtcgataa | agccggagaa | acggccgttt | 660 |
| tccaccataa | tgtttggcag | acaagcatcc | cgtgggtca | caaccaggtc | ctcgccatct | 720 |
| ggcatacgtg | ctttcaggcg | tgcgaacagt | tctgccggtg | ccagaccctg | atgttcctcg | 780 |
| tccaggtcat | cctgatcaac | caggccagct | tccatgcgag | tgcgtgcgcg | ctcgatacgg | 840 |
| tgtttagctt | ggtgatcgaa | tgggcaagta | gctgggtcca | gggtatgcag | acggcgcata | 900 |
| gcatcagcca | tgatggaaac | cttttctgcc | ggtgccagat | gagaggacag | cagatcctgg | 960 |
| cctggaacct | cgcccagcag | cagccagtcg | cggccagcct | cggtcacaac | atccagcaca | 1020 |
| gctgcgcatg | gaacgccggt | agtagccagc | caggacagac | gagctgcttc | atcttgcagt | 1080 |
| tcgttcagtg | cgccggacag | atcggtctta | acaaacagca | ccggacggcc | ttgagcggac | 1140 |
| agacggaaca | cagctgcgtc | ggagcaaccg | atagtctgtt | gagcccagtc | atagccaaac | 1200 |
| agacgttcca | cccaagcagc | cggagaacca | gcgtgcagac | cgtcttgttc | aatcatggtg | 1260 |
| gcaattgggt | gtctgagcga | tgtggctcgg | ctggcgacgc | aaaagaagat | gcggctgact | 1320 |
| gtcgaacagg | aggagcagag | agcgaagcgg | gaggctgcgg | gctcaatttg | catgctttag | 1380 |
| ttcctcacct | tgtcgtatta | tactatgccg | atatactatg | ccgatgatta | attgtcaacg | 1440 |
| tatacggaat | agctctgagg | ccgaggcagc | ttcggcctct | gcataaataa | aaaaaattag | 1500 |
| tcagccatgg | ggcggagaat | gggcggaact | gggcggagtt | aggggcggga | tgggcggagt | 1560 |
| taggggcggg | actatggttg | ctgactaatt | gagatgcttg | ctttgcatac | ttctgcctgc | 1620 |
| tggggagcct | ggggactttc | cacacctggt | tgctgactaa | ttgagatgct | gctttgcat | 1680 |
| acttctgcct | gctggggagc | ctggggactt | tccacaccct | aacctcgagg | ccatcgtggc | 1740 |
| acgccagggt | tttcccagtc | acgacgttgt | aaaacgacgg | ccagtgctct | tctcccccgc | 1800 |
| gggaggtttt | ataaatccga | ctgtctagat | accacatttg | tagaggtttt | acttgcttta | 1860 |
| aaaaacctcc | cacatctccc | cctgaacctg | aaacataaaa | tgaatgcaaa | tgttttatta | 1920 |
| acttgtttat | tgcagcttat | aatggttaca | aattaagcaa | tagcatcaca | aatttcacaa | 1980 |
| attaagcatt | ttttcactg | cattctagtt | gtggtttgtc | caaactcatc | aatgtatctt | 2040 |
| atcatgtcta | atcgattcac | aggttggtgg | ggctctccag | gatgggggg | ggctgggtgt | 2100 |

```
ggctcatgtc ggccacgtcc caaatctcct ccaggaaggg gggcagcttc ctgttcttca    2160
gcttcaggct gatacacata ttgctgttct gcattcccag ggtcctcagc tcgctcagga    2220
tgctcaggat cttgccgtag atcacgctgc tcctggcgct gccgctcagc tggttcagga    2280
tgtagatcct cagggtgttc aggtagtacc tctggatctc ctccaccagc tggggctgct    2340
ccaggccggg cctgtcgctg aagatcacca cggcggtcag cagggcgtag tggatgttgt    2400
ccagggccat gctgtacata catctgcaga agtgcaggag gtcctcgatc acctcggcca    2460
tgccagcctt cctgtagttg tccctggtgt aagcctggtt gttggcgaac aggatgctgt    2520
cgctggcggc gtcgtacctc ctggccaccc tcagcatcat cacctcgctg ctgcaagcct    2580
tcagcagggt gatctggtcg ggctggctga tcttggcgaa tccgggcagg cccttggcga    2640
actccacgat cagctgcacg gtcaggatgg tcatctcggt gatctgcctg aaggggtgt    2700
cgctctcctc gttctcgtcg tcggcctgct gccaggtctg ggtgatcctt ttcaggtcct    2760
cgtcgctggg ctgctcgtag ccgtcctgat accagatcag cctggcgatc aggaactgct    2820
ggttggcggt cagctggggg atgttcttct gcctgttggt caccagcagc ttgtcgctca    2880
ggaacctggg cacgacctcg tgaatcctgg cggcctcggg ggggggggc tcgcactgca    2940
tgatgggggg catgtggtca tcgacggtgg tggtgctcac gggcagcttg tccttctcct    3000
tctgggcctt cttctccttc cttttcatgg cgcactgggt ctcgggcacc acgcactcgg    3060
gcctgatccc gggaaactcg ggctcacgg tcagctgcct ctggcccttg ttgctgctct    3120
cctcgctgct gctggtggcg ctgatcctgt gctgcctcag ggtcaggggc atgtcggtct    3180
ccacgctggc cagcctgtcg gtcacggcgt ccttgttcac gttgtcctgc acgaacaggc    3240
cggtcagcag ggccttgatg tcttgcaggc tgtccatctt caggatcatg tccaggtcct    3300
ccctggggaa gatcagcagg aacagctgct ccagcctctc cagcctgctc tccacctcgg    3360
tcaggtgggc cctggtcagg gggctcctct tggtcttggg gctgtatctg cactcccagt    3420
tgttcttcag gcacttggcg cacttgggct tctccttgct gcacttcagc ttcttcagcc    3480
tgcagatgtc gcaagcctgc tcgatgctgc tcagcagctt catggtggca gatctggtcg    3540
cgggaggctg ctggttttcc actacccgaa aaaaatccag cgtctaagca gctgcaagga    3600
gagcctttca gagaagcggg tcctggcagc ggcggggaag tgtccccaaa tgggcagaat    3660
agcctccccg cgtcgggaga gtcgcgtcct tgctcgggtg ttgtaagttc cagtgcaaag    3720
tgcccgcccg ctgctatggg caaagtttcg tggatgcggc tagggttgcg caccgctggc    3780
tgggggatca gcgggagggc tgggccagag gcgaagcccc ctattcgctc cggatctccc    3840
ttcccaggac gcccgcagcg cagctctgct cgccgggctc ctccacccta gcccgccgcc    3900
cgctcgctcc ctctgcctct cgctggaatt actacagcga gttgccggct cagctgtcgc    3960
tggggctctc cagcatctcc atcaggaagg tgtcgatggg cacgtcgccg atcagcctga    4020
agaagaacag gtgctccagg cacttcaggc cgatgctcct caggctgggc agcctcagca    4080
gcagcttggc gaatctgccg ggctcgtcgg ggtgggtggt cctggtgtac tcctccaggg    4140
cggcgtacac cttctcccctc agcagctcca cctcctgggc gcttttcagg cccctcacct    4200
cggggttgaa caggatgatg gccctcaggc agcccagctc ggtcttgtcc atcctcatgt    4260
ccctcatctt gctcaccagc tcggtcagca ccctgtcgaa gatggcgccc actccggcgc    4320
tgtgggcgct gttcctatgg acgtgcaggc cggtggccag caggatgccg tccctcacgt    4380
cgatgctcct gtggctgaag ctggcgatca gcagctcgtt ccatccgccc tcagcagga    4440
tcacctggtc gtccaggggc aggctgctga agtggggaat cctcttggcc cactccacca    4500
```

```
gggtgaacag ctgcttgtcg gcggcctggc agatgttggt cacggggtcg ttggggctgc    4560
tgccgctgcc gccggttccg ccggggccct ccacgccctg gtcgcttttc tgctccacgg    4620
cgagttcggc ctccagaatc ctgtccacgg gcatctccat atggccgccg tactcgtcga    4680
tgcccagggc gtcggtgaac atctgctcga actcgaagtc ggccatgtcc agggcgccgt    4740 aggggggcgct gtcgtggggg gtgaagccgg gccggggct gtcgccgtcg cccagcatgt    4800
ccaggtcgaa gtcgtccagg gcgtcggcgt gggccatggc cacgtcctcg ccgtccaggt    4860
gcagctcgtc gcccaggctc acgtcggtgg gggggccac cttccttttc ttcttggggc    4920
ccatggtggc caattgcccc ccccccccc cgcatgccgc ctaacaaaaa agccaaaaac    4980
ggccagaatt tagcggacaa tttactagtc taacactgaa aattacatat tgacccaaat    5040
gattacattt caaaaggtgc ctaaaaaact tcacaaaaca cactcgccaa ccccgagcgc    5100
acgtacccag cccagcagcc cgctactcac caagtgacga tcacagcgat ccacaaacaa    5160
gaaccgcgac ccaaatcccg gctgcgacgg aactagctgt gccacacccg gcgcgtcctt    5220
atataatcat cggcgttcac cgccccacgg agatccctcc gcagaatcgc cgagaaggga    5280 ctactttttcc tcgcctgttc cgctctctgg aaagaaaacc agtgccctag agtcacccaa    5340
gtcccgtcct aaaatgtcct tctgctgata ctggggttct aaggccgagt cttatgagca    5400
gcgggccgct gtcctgagcg tccggcggga aggatcagga cgctcgctgc gcccttcgtc    5460
tgacgtggca gcgctcgccg tgaggagggg ggcgcccgcg ggaggcgcca aaacccggcg    5520
cggaggccct cgagtaggcg agaccaatgg gtgcgccatg ggctcttcca aaaatttagg    5580
tgacactata gggcaccgct cgcacctgcg cacaggcata agccaaatgg aactacgaga    5640
cctgcatcgt ggtgtaacta taacggtcct aaggtagcga ccgcggagac taggtgtatt    5700
tatctaagcg atcgcttaat taaggccggc cgccgcaata aaatatcttt attttcatta    5760
catctgtgtg ttggtttttt gtgtgaatcc atagtactaa catacgctct ccatcaaaac    5820
aaaacgaaac aaaacaaact agcaaaatag gctgtcccca gtgcaagtcc aggtgccaga    5880
acatttctct atccataatg cagggtacc gggtgatgac ggtgaaaacc tccaattgcg    5940
gagtactgtc ctccgagcgg agtactgtcc tccgagcgga gtactgtcct ccgagcggag    6000
tactgtcctc cgagcggagt actgtcctcc gagcggagta ctgtcctccg agcggagagt    6060 cccggggac ctagagggta tataatgggt gccttagctg gtgtgtgacc tcatcttcct    6120
gtacgcccct gcagggcgc gccacgcgtc gaagaaggtg agtaatctta acatgctctt    6180
tttttttttt tttgctaatc cctttttgtgt gctgatgtta ggatgacatt tacaacaaat    6240
gtttgttcct gacaggaaaa accttgctgg gtaccttcgt tgccggacac ttcttgtcct    6300
ctactttgga aaaaggaat tgagagccgc tagcgccacc atggctacca ggagatatta    6360
cctcggcgct gtggaactgt cctgggatta catgcagtcc gacctcggcg aactgcctgt    6420
ggatgccagg ttccctccca gggtgcctaa gtccttccct ttcaatacct ccgtggtcta    6480
caaaaagaca ctgtttgtgg aatttacaga ccatctgttt aacattgcca acccaggcc    6540 cccttggatg ggcctcctgg acccacaat ccaagccgaa gtgtatgaca cagtggtcat    6600
cacactgaaa aacatggcct cccaccccgt tagcctgcac gctgtcggcg tcagctattg    6660
gaaagcctcc gagggagccg aatacgatga ccaaacctcc cagagggaga aagaggatga    6720
caaagtgttt cccggaggct cccacacata cgtctgcaa gtgctcaagg aaaacggacc    6780
tatggcctcc gaccctctgt gtctgacata ctcctacctg agccatgtgg atctggtcaa    6840
```

```
ggatctgaat agcggactga ttggcgctct gctcgtgtgt agagaaggct ccctggctaa    6900
ggaaaagaca cagacactgc ataagtttat cctcctgttt gccgttttg atgagggaaa     6960
gtcctggcat agcgaaacca aaaactccct gatgcaggat agagatgccg ccagtgctag    7020
agcttggcct aagatgcaca ccgtcaatgg ctatgtgaat agatccctgc ctggcctcat    7080
cggatgccat agaaaaagcg tctactggca cgtcatcgga atgggaacca cacccgaagt    7140
gcatagcatt ttccttgaag acacacatt cctcgtgagg aaccatagac aagcctccct     7200
ggaaatctcc cccattacct ttctgacagc ccaaaccctc ctgatggacc tcggccaatt    7260
cctcctgttt tgccatatct ccagccatca gcatgacgga atggaagcct atgtgaaagt    7320
ggatagctgt cccgaggagc cccagctcag aatgaagaat aacgaagaag ccgaggacta    7380
cgatgacgat ctgacagact ccgagatgga tgtcgtgagg ttcgatgacg ataactcccc    7440
ctccttcatt cagattagat ccgtggctaa gaaacaccct aagacatggg tccactatat    7500
cgctgccgag gaagaagatt gggactatgc ccctctggtc ctggctcccg atgacaggag    7560
ctataagtcc cagtatctga ataacggacc ccagagaatc ggcaggaagt ataagaaagt    7620
gaggttcatg gcctataccg atgagacatt caaaaccagg gaggctatcc aacacgaaag    7680
cggaatcctc ggccctctgc tctacggaga ggtcggcgat accctcctga ttatcttaa     7740
gaatcaggcc agtaggccct ataacattta ccctcacgga atcacagatg tgagacctct    7800
gtatagcagg agactcccca aaggcgtcaa gcatctgaaa gactttccca ttctgcctgg    7860
cgaaatcttt aagtataagt ggaccgtcac cgtcgaggat ggccctacca aaagcgatcc    7920
caggtgcctc accaggtact atagctcctt cgtcaacatg gagagggacc tcgcctccgg    7980
cctcatcgga cccctcctga tttgctataa ggaaagcgtc gatcaaagag gaaaccaaat    8040
catgagcgat aagaggaacg tcatcttgtt ctccgtgttt gacgaaaaca ggagctggta    8100
cttgaccgaa acattcaga ggttcctccc caatcccgct ggcgtccagc ttgaggaccc     8160
tgagtttcaa gcctccaaca ttatgcacag cattaacgga tacgttttcg atagcctcca    8220
gctgtccgtc tgcctccacg aggtcgctta ctggtacatt ctgtccatcg agcccaaac     8280
cgatttcctg agcgtctttt ttagcggata cacattcaaa cacaaaatgg tctacgagga    8340
tacactgaca ctgtttccct ttagcggaga gacagtgttt atgagcatgg agaaccctgg    8400
cctctggatt ctgggatgcc ataactccga ctttagaaat agaggaatga cagccctcct    8460
gaaagtgtcc agctgtgaca aaaacacagg cgattactat gaggatagct atgaggacat    8520
ttccgcctat ctgctgtcaa aaacaatgc cattgagcct agatccttct cccagaatag    8580
caggcaccct agcacaagac aaaagcaatt caatgccaca accattcccg aaaacgacat    8640
cgaaaagaca gacccttggt ttgcccatag aacacccatg cccaaaatcc aaaacgtcag    8700
ctccagcgat ctgctcatgc tcctgaggca gtcccccaca cccacggcc tgagcctgtc     8760
cgatctgcaa gaggctaagt atgagacatt ctccgacgat ccctcccccg gagccattga    8820
ctccaacaat agcctgagcg aaatgacaca ctttagaccc cagctgcacc atagcggaga    8880
catggtgttt accctgagt ccggcctcca gctcagactc aacgaaaagc tcggcacaac     8940
cgctgccaca gagctgaaga aactggattt caaagtgtcc agcacaagca ataacctcat    9000
ctccaccatt ccctccgaca atctggctgc cggaaccgat aacacaagct ccctgggacc    9060
cccttccatg cccgtccact atgactccca gctcgacaca accctttttg gaaagaaaag    9120
ctccccccctc accgaaagcg gaggccctct gtccctgtcc gaggaaaaca atgacagcaa    9180
gctgctggag agcggactga tgaactccca ggaaagctcc tggggaaaga atgtgtccag    9240
```

```
cacagagtcc ggcaggctgt taagggaaa gagagcccac ggccctgccc tcctgacaaa    9300
ggataacgct ctgtttaagg tcagcattag cctcctgaaa accaataaga caagcaataa    9360
ctccgccaca aacagaaaga cccacattga cggaccctcc ctgctcatcg aaaactcccc    9420
ctccgtgtgg cagaatatcc tcgaatccga cacagagttt aagaaagtga caccctcat    9480 ccatgacagg atgctcatgg ataagaatgc cacagccctc agactcaacc acatgagcaa    9540
caaaaccaca agcagcaaga acatggagat ggtccagcaa aagaaagagg gacccattcc    9600
ccctgacgct cagaatcccg atatgtcctt ctttaagatg ctgtttctgc ctgagtccgc    9660
caggtggatt cagaggaccc acggcaaaaa ctccctgaat agcggacagg gaccctcccc    9720
caaacagctc gtgtccctgg gacccgaaaa gtccgtggaa ggccaaaact ttctgtccga    9780
gaaaacaaaa gtggtcgtgg aaagggaga gtttaccaag gacgttggcc tgaaggaaat    9840
ggtgtttcct agctccagaa atctgtttct gacaaacctc gacaatctgc atgagaataa    9900
cacacacaat caggaaaaga aaatccaaga ggaaatcgaa aagaaagaga cactgattca    9960
ggaaaacgtc gtgctccccc aaatccatac cgtcaccgga accaaaaact ttatgaaaaa    10020
ccttttcctc ctgtccacca ggcagaatgt ggaaggctcc tacgatggcg cttacgctcc    10080
cgtcctgcaa gactttagat ccctgaatga ctccaccaat agaacaaaga aacacacagc    10140
ccatttctcc aagaaaggcg aggaggaaaa cctggaagga ctgggaaacc aaaccaaaca    10200
gattgtggaa aagtatgcct gtaccacaag aattagccct aacacaagcc aacagaattt    10260
cgtcacccaa agatccaaga gagccctgaa gcaattcagg ctgcctctgg aagaaacaga    10320
gctggagaaa agaattatcg tggatgatac ctccacccaa tggtccaaga atatgaaaca    10380 cctcaccccct agcacactga cacagattga ctataacgaa aaggaaaagg gagccattac    10440
ccaaagccct ctgtccgact gtctgacaag atcccactcc atccctcagg ctaacaggag    10500
ccctctgcct atcgctaagg tcagctcctt ccctagcatt agacctatct atctgacaag    10560
agtcctgttt caggataact ccagccatct gcctgccgcc tcttatagaa aaaggatag    10620 cggagtgcaa gagtccagcc atttcctcca gggagccaaa aagaataacc tgagcctcgc    10680
cattctgaca ctggaaatga caggcgatca gagggaggtc ggctccctgg aacctccgc    10740 cacaaactcc gtgacataca aaaggtcga gaataccgtc ctgcctaagc ctgacctccc    10800 caaaaacctcc ggcaaagtgg aactgctccc caaagtgcat atctatcaga aagacctctt    10860
tcctaccgaa acctccaacg gaagccccgg ccacctggat ctggtcgagg aagcctcct    10920 gcaaggcaca gagggagcca ttaagtgaa cgaagccaat agacctggca aagtgccttt    10980
cctcagagtc gccacagagt ccagcgctaa gacacccagc aagctgctgg acccctcgc    11040 ctgggacaat cactatggca cacagattcc caaagaggaa tggaaaagcc aagagaaag    11100 ccctgagaaa accgctttca aaagaaaga cacaatcctg agcctcaacg cttgcgaaag    11160
caatcacgct atcgctgcca ttaacgaagg ccaaaacaaa cccgaaatcg aagtgacatg    11220
ggccaagcag ggcaggaccg aaagactctg ctcccagaat cccctgtgc tcaagaggca    11280 ccaaagagaa atcacaagaa caaccctcca gtccgaccaa gaggaaatcg actacgatga    11340
cacaatctcc gtggaaatga aaaggagga ctttgacatt tacgatgagg atgagaatca    11400 gtccccccagg agctttcaga aaagacaag acattacttt atcgctgccg tcgagaggct    11460
gtgggactat ggcatgagca gcagccctca cgtcctgagg aacagagccc agagcggaag    11520
cgtcccccaa ttcaaaaagg tcgtgtttca ggagttcaca gacggcagct tcacccaacc    11580
```

```
cctctacagg ggcgaactga atgagcatct gggactgctc ggcccttaca ttagagccga    11640
ggtggaggat aacattatgg tcacctttag aaatcaggcc agcaggccct atagctttta    11700
ctccagcctc atctcctacg aggaagatca gaggcaggga gccgaaccca ggaagaattt    11760
cgtcaagcct aacgaaacca aaacctattt ctggaaggtc cagcatcaca tggcccctac    11820
caaagacgaa tttgattgca aagcctgggc ctatttctcc gacgttgacc tggagaaaga    11880
cgtgcattcc ggcctcatcg gacccctcct ggtctgccat accaataccc tcaaccctgc    11940
ccacggcaga caggtgaccg tccaggagtt tgctctgttt ttcacaatct tgacgaaac     12000 caaaagctgg tactttaccg aaaacatgga gaggaactgt agagcccct gtaacattca     12060 gatggaggac cccacattca aagagaatta caggttccat gccattaacg atacattat     12120 ggataccctc cccggactgg tcatggctca ggatcagagg atcaggtggt atctgctgtc    12180
tatgggctcc aacgaaaaca ttcactccat ccatttctcc ggccatgtgt ttaccgtcag    12240
aaaaaaggag gagtataaga tggccctcta caatctgtat cccggagtgt ttgagacagt    12300
ggaaatgctc ccctccaagg ctggcatttg gagggtggaa tgcctcatcg gagagcatct    12360
gcacgccgga atgtccaccc tgtttctcgt gtatagcaat aagtgtcaga caccctcgg    12420 catggcctcc ggccatatca gggactttca gattaccgcc agcggacagt atggccaatg    12480
ggctcccaaa ctggctagac tccactatag cggaagcatt aacgcttggt ccaccaaaga    12540
gcctttctcc tggattaagg tggacctcct ggctcccatg attatccacg aatcaaaac     12600 ccaaggcgct agacaaaagt ttagctccct gtatatctcc cagtttatca ttatgtatag    12660
cctcgacgga aagaaatggc aaacctatag aggaaactcc accggaaccc tcatggtgtt    12720
ctttggcaat gtggatagct ccggcattaa gcataacatt ttcaatcccc ctatcattgc    12780
caggtacatt agactccacc ctacccatta ctccatcagg agcacactga ggatggaact    12840
gatgggctgt gacctcaact cctgctccat gccctcggc atggaaagca agccattag      12900 cgatgcccaa atcacagcct ccagctattt cacaaatatg ttcgctacct ggagccctag    12960
caaagccagg ctgcatctgc aaggcaggag caatgcctgg agacctcagg tcaacaatcc    13020
caaagagtgg ctgcaagtgg atttccaaaa gacaatgaaa gtgacaggcg tcaccacaca    13080
gggagtgaaa agcctcctga caagcatgta cgtcaaggag ttcctcatct ccagctccca    13140
ggatggccat cagtggaccc tgttctttca gaatggcaaa gtgaaagtgt tcagggaaa     13200 ccaagactcc ttcacacccg tcgtgaatag cctcgaccct cccctcctga caagatacct    13260
gagaatccac ccccaaagct gggtgcatca gattgccctc agaatggagg tcctgggatg    13320
cgaagcccaa gacctctact aaatcgattg cgcaaagctt tcgcgatagg cgagaccaat    13380
gggtgtgtac gtagcggccg cgtcgacgat agcttgatgg gtgcatccc tgtgacccct    13440 ccccagtgcc tctcctggcc ctggaagttg ccactccagt gcccaccagc cttgtcctaa    13500
taaaattaag ttgcatcatt ttgtctgact aggtgtcctt ctataatatt atggggtgga    13560
ggggggtggt atggagcaag gggcaagttg gaagacaac ctgtagggcc tgcgggtct      13620 attgggaacc aagctggagt gcagtggcac aatcttggct cactgcaatc tccgcctcct    13680
gggttcaagc gattcctg cctcagcctc ccgagttgtt gggattccag gcatgcatga      13740
ccaggctcag ctaattttg ttttttggt agagacgggg tttcaccata ttggccaggc      13800
tggtctccaa ctcctaatct caggtgatct acccaccttg gcctcccaaa ttgctgggat    13860
tacaggcgtg aaccactgct cccttccctg tccttctgat tttaaaataa ctataccagc    13920
aggaggacgt ccagacacag cataggctac ctggccatgc ccaaccggtg ggacatttga    13980
```

-continued

```
gttgcttgct tggcactgtc ctctcatgcg ttgggtccac tcagtagatg cctgttgaat    14040
tctgatttaa atcggtccgc gtacggcgtg gtaggtccga acgaatccat ggattaccct    14100
gttatcccta ctcaaggaca tcatcccttt agtgagggtt aattcacgca gtgggtacgg    14160
aactaaaggc agcacacatc gtgtaatcat ggtcatagct gtttcctgtg tgaaattgtt    14220
atccgctacg tctctccccc gcagtaaggg ctagattaac tcgtctcgtg aatatccgga    14280
actcccttta gtgagggtta attgcgttgc gctcactgcc cgctttccag tcgggaaacc    14340
tgtcgtgcca gcttaatcat ggtcatagct gtttcctgtg tgaaattgtt atccgctacc    14400
ggaaacgctt ccttcatgtg agcaaaaggc cagcaaaagg ccaggaaccg taaaaaggcc    14460
gcgttgctgg cgttttttcca taggctccgc ccccctgacg agcatcacaa aaatcgacgc    14520
tcaagtcaga ggtggcgaaa cccgacagga ctataaagat accaggcgtt ccccctgga    14580
agctccctcg tgcgctctcc tgttccgacc ctgccgctta ccggatacct gtccgccttt    14640
ctcccttcgg gaagcgtggc gctttctcat agctcacgct gtaggtatct cagttcggtg    14700
taggtcgttc gctccaagct gggctgtgtg cacgaacccc ccgttcagcc cgaccgctgc    14760
gccttatccg gtaactatcg tcttgagtcc aacccggtaa gacacgactt atcgccactg    14820
gcagcagcca ctggtaacag gattagcaga gcgaggtatg taggcggtgc tacagagttc    14880
ttgaagtggt ggcctaacta cggctacact agaagaacag tatttggtat ctgcgctctg    14940
ctgaagccag ttaccttcgg aaaaagagtt ggtagctctt gatccggcaa acaaaccacc    15000
gctggtagcg gtggttttttt tgtttgcaag cagcagatta cgcgcagaaa aaaggatct    15060
caagaagatc ctttgatctt ttctacgggg tctgacgctc agtggaacga aaactcacgt    15120
taagggattt tggtcatgcc taggacgaaa ggaggtcgtg aaatggataa aaaaatacag    15180
cgtttttcat gtacaactat actagttgta gtgcctaaat aatgctttta aaacttaaaa    15240
ataatctatg tcgggtgcgg agaaagaggt aatgaaatgg caaatcaatg tcctcagcga    15300
aatggcatac gagtaaactt ggtctgacac cgctgcatga gattatcaaa aaggatcttc    15360
acctagatcc tttttaaatta aaaatgaagt tttaaatcaa tctaaagtat atatgagtaa    15420
acttggtctg acagttacca atgcttaatc agtgaggcac ctatctcagc gatctgtcta    15480
tttcgttcat ccatagttgc ctgactcccc gtcgtgtaga taactacgat acgggagggc    15540
ttaccatctg gccccagtgc tgcaatgata ccgcgagacc cacgctcacc ggctccagat    15600
ttatcagcaa taaaccagcc agccggaagc gccgagcgca gaagtggtcc tgcaacttta    15660
tccgcctcca tccagtctat taactgttgc cgggaagcta gagtaagtag ttcgccagtt    15720
aatagtttgc ggagcgttgt tgccattgct acaggcatcg tggtgtcacg ctcgtcgttt    15780
ggtatggctt cattcagctc cggttcccaa cgatcaaggc gagttacatg atcccccatg    15840
ttgtgcaaaa aagcggttag ctccttcggt cctccgatgg ttgtcagaag taagttggcc    15900
gcagtgttat cactcatggt tatggcagca ctgcataatt ctcttactgt catgccatcc    15960
gtaagatgct tttctgtgac tggtgagtat tcaaccaagt cattctgaga atagtgtatg    16020
cggcgaccga gttgctcttg cccggcgtca atacgggata ataccgcgcc acatagcaga    16080
actttaaaag tgctcatcat tggaagcgt tcttcggggc gaaaactctc aaggatctta    16140
ccgctgttga gatccagttc gatgtaaccc acacgagcac ccaactgatc ttcagcatct    16200
tttactttca ccagcgtttc tgggtgagca aaaacaggaa ggcaaaatgc cgcaaaaaag    16260
ggaataaggg cgacacggaa atgttgaata ctcatacgct tccttttttca atagtattga    16320
```
agcatttatc agggttattg tctcgggagc gaatacatat ttgaatgtat ttagaaaaa    16379

<210> SEQ ID NO 20
<211> LENGTH: 158
<212> TYPE: PRT
<213> ORGANISM: Homo sapiens
<220> FEATURE:
<223> OTHER INFORMATION: Human Insulin like growth factor (IGF-1)

<400> SEQUENCE: 20

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Tyr Gln Pro Pro Ser Thr Asn Lys Asn Thr
    130                 135                 140

Lys Ser Gln Arg Arg Lys Gly Ser Thr Phe Glu Glu Arg Lys
145                 150                 155
```

<210> SEQ ID NO 21
<211> LENGTH: 288
<212> TYPE: PRT
<213> ORGANISM: Homo sapiens
<220> FEATURE:
<223> OTHER INFORMATION: Human basic fibroblast growth factor (bFGF)

<400> SEQUENCE: 21

```
Met Val Gly Val Gly Gly Gly Asp Val Glu Asp Val Thr Pro Arg Pro
1               5                   10                  15

Gly Gly Cys Gln Ile Ser Gly Arg Gly Ala Arg Gly Cys Asn Gly Ile
            20                  25                  30

Pro Gly Ala Ala Ala Trp Glu Ala Ala Leu Pro Arg Arg Arg Pro Arg
        35                  40                  45

Arg His Pro Ser Val Asn Pro Arg Ser Arg Ala Ala Gly Ser Pro Arg
    50                  55                  60

Thr Arg Gly Arg Arg Thr Glu Glu Arg Pro Ser Gly Ser Arg Leu Gly
65                  70                  75                  80

Asp Arg Gly Arg Gly Arg Ala Leu Pro Gly Gly Arg Leu Gly Gly Arg
                85                  90                  95

Gly Arg Gly Arg Ala Pro Glu Arg Val Gly Gly Arg Gly Arg Gly Arg
            100                 105                 110

Gly Thr Ala Ala Pro Arg Ala Ala Pro Ala Ala Arg Gly Ser Arg Pro
        115                 120                 125

Gly Pro Ala Gly Thr Met Ala Ala Gly Ser Ile Thr Thr Leu Pro Ala
    130                 135                 140
```

```
Leu Pro Glu Asp Gly Gly Ser Gly Ala Phe Pro Pro Gly His Phe Lys
145                 150                 155                 160

Asp Pro Lys Arg Leu Tyr Cys Lys Asn Gly Gly Phe Phe Leu Arg Ile
            165                 170                 175

His Pro Asp Gly Arg Val Asp Gly Val Arg Glu Lys Ser Asp Pro His
            180                 185                 190

Ile Lys Leu Gln Leu Gln Ala Glu Glu Arg Gly Val Val Ser Ile Lys
            195                 200                 205

Gly Val Cys Ala Asn Arg Tyr Leu Ala Met Lys Glu Asp Gly Arg Leu
            210                 215                 220

Leu Ala Ser Lys Cys Val Thr Asp Glu Cys Phe Phe Phe Glu Arg Leu
225                 230                 235                 240

Glu Ser Asn Asn Tyr Asn Thr Tyr Arg Ser Arg Lys Tyr Thr Ser Trp
                245                 250                 255

Tyr Val Ala Leu Lys Arg Thr Gly Gln Tyr Lys Leu Gly Ser Lys Thr
            260                 265                 270

Gly Pro Gly Gln Lys Ala Ile Leu Phe Leu Pro Met Ser Ala Lys Ser
            275                 280                 285

<210> SEQ ID NO 22
<211> LENGTH: 193
<212> TYPE: PRT
<213> ORGANISM: Homo sapiens
<220> FEATURE:
<223> OTHER INFORMATION: Human erythropoietin

<400> SEQUENCE: 22

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Gln Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 23
<211> LENGTH: 134
<212> TYPE: PRT
```

```
<213> ORGANISM: Homo sapiens
<220> FEATURE:
<223> OTHER INFORMATION: Human BNP

<400> SEQUENCE: 23

Met Asp Pro Gln Thr Ala Pro Ser Arg Ala Leu Leu Leu Leu Phe
1               5                   10                  15

Leu His Leu Ala Phe Leu Gly Gly Arg Ser His Pro Leu Gly Ser Pro
            20                  25                  30

Gly Ser Ala Ser Asp Leu Glu Thr Ser Gly Leu Gln Glu Gln Arg Asn
            35                  40                  45

His Leu Gln Gly Lys Leu Ser Glu Leu Gln Val Glu Gln Thr Ser Leu
50                  55                  60

Glu Pro Leu Gln Glu Ser Pro Arg Pro Thr Gly Val Trp Lys Ser Arg
65                  70                  75                  80

Glu Val Ala Thr Glu Gly Ile Arg Gly His Arg Lys Met Val Leu Tyr
                85                  90                  95

Thr Leu Arg Ala Pro Arg Ser Pro Lys Met Val Gln Gly Ser Gly Cys
                100                 105                 110

Phe Gly Arg Lys Met Asp Arg Ile Ser Ser Ser Ser Gly Leu Gly Cys
            115                 120                 125

Lys Val Leu Arg Arg His
            130

<210> SEQ ID NO 24
<211> LENGTH: 562
<212> TYPE: PRT
<213> ORGANISM: Homo sapiens
<220> FEATURE:
<223> OTHER INFORMATION: Human tPA

<400> SEQUENCE: 24

Met Asp Ala Met Lys Arg Gly Leu Cys Cys Val Leu Leu Cys Gly
1               5                   10                  15

Ala Val Phe Val Ser Pro Ser Gln Glu Ile His Ala Arg Phe Arg Arg
            20                  25                  30

Gly Ala Arg Ser Tyr Gln Val Ile Cys Arg Asp Glu Lys Thr Gln Met
            35                  40                  45

Ile Tyr Gln Gln His Gln Ser Trp Leu Arg Pro Val Leu Arg Ser Asn
50                  55                  60

Arg Val Glu Tyr Cys Trp Cys Asn Ser Gly Arg Ala Gln Cys His Ser
65                  70                  75                  80

Val Pro Val Lys Ser Cys Ser Glu Pro Arg Cys Phe Asn Gly Gly Thr
                85                  90                  95

Cys Gln Gln Ala Leu Tyr Phe Ser Asp Phe Val Cys Gln Cys Pro Glu
                100                 105                 110

Gly Phe Ala Gly Lys Cys Cys Glu Ile Asp Thr Arg Ala Thr Cys Tyr
            115                 120                 125

Glu Asp Gln Gly Ile Ser Tyr Arg Gly Thr Trp Ser Thr Ala Glu Ser
            130                 135                 140

Gly Ala Glu Cys Thr Asn Trp Asn Ser Ser Ala Leu Ala Gln Lys Pro
145                 150                 155                 160

Tyr Ser Gly Arg Arg Pro Asp Ala Ile Arg Leu Gly Leu Gly Asn His
                165                 170                 175

Asn Tyr Cys Arg Asn Pro Asp Arg Asp Ser Lys Pro Trp Cys Tyr Val
                180                 185                 190
```

```
Phe Lys Ala Gly Lys Tyr Ser Ser Glu Phe Cys Ser Thr Pro Ala Cys
        195                 200                 205

Ser Glu Gly Asn Ser Asp Cys Tyr Phe Gly Asn Gly Ser Ala Tyr Arg
210                 215                 220

Gly Thr His Ser Leu Thr Glu Ser Gly Ala Ser Cys Leu Pro Trp Asn
225                 230                 235                 240

Ser Met Ile Leu Ile Gly Asn Val Tyr Thr Ala Gln Asn Pro Ser Ala
            245                 250                 255

Gln Ala Leu Gly Leu Gly Lys His Asn Tyr Cys Arg Asn Pro Asp Gly
        260                 265                 270

Asp Ala Lys Pro Trp Cys His Val Leu Lys Asn Arg Arg Leu Thr Trp
    275                 280                 285

Glu Tyr Cys Asp Val Pro Ser Cys Ser Thr Cys Gly Leu Arg Gln Tyr
290                 295                 300

Ser Gln Pro Gln Phe Arg Ile Lys Gly Gly Leu Phe Ala Asp Ile Ala
305                 310                 315                 320

Ser His Pro Trp Gln Ala Ala Ile Phe Ala Lys His Arg Arg Ser Pro
            325                 330                 335

Gly Glu Arg Phe Leu Cys Gly Gly Ile Leu Ile Ser Ser Cys Trp Ile
        340                 345                 350

Leu Ser Ala Ala His Cys Phe Gln Glu Arg Phe Pro Pro His His Leu
    355                 360                 365

Thr Val Ile Leu Gly Arg Thr Tyr Arg Val Val Pro Gly Glu Glu Glu
370                 375                 380

Gln Lys Phe Glu Val Glu Lys Tyr Ile Val His Lys Glu Phe Asp Asp
385                 390                 395                 400

Asp Thr Tyr Asp Asn Asp Ile Ala Leu Leu Gln Leu Lys Ser Asp Ser
            405                 410                 415

Ser Arg Cys Ala Gln Glu Ser Ser Val Val Arg Thr Val Cys Leu Pro
        420                 425                 430

Pro Ala Asp Leu Gln Leu Pro Asp Trp Thr Glu Cys Glu Leu Ser Gly
    435                 440                 445

Tyr Gly Lys His Glu Ala Leu Ser Pro Phe Tyr Ser Glu Arg Leu Lys
450                 455                 460

Glu Ala His Val Arg Leu Tyr Pro Ser Ser Arg Cys Thr Ser Gln His
465                 470                 475                 480

Leu Leu Asn Arg Thr Val Thr Asp Asn Met Leu Cys Ala Gly Asp Thr
            485                 490                 495

Arg Ser Gly Gly Pro Gln Ala Asn Leu His Asp Ala Cys Gln Gly Asp
        500                 505                 510

Ser Gly Gly Pro Leu Val Cys Leu Asn Asp Gly Arg Met Thr Leu Val
    515                 520                 525

Gly Ile Ile Ser Trp Gly Leu Gly Cys Gly Gln Lys Asp Val Pro Gly
530                 535                 540

Val Tyr Thr Lys Val Thr Asn Tyr Leu Asp Trp Ile Arg Asp Asn Met
545                 550                 555                 560

Arg Pro

<210> SEQ ID NO 25
<211> LENGTH: 185
<212> TYPE: PRT
<213> ORGANISM: Homo sapiens
<220> FEATURE:
<223> OTHER INFORMATION: Human relaxin
```

```
<400> SEQUENCE: 25

Met Pro Arg Leu Phe Phe Phe His Leu Leu Gly Val Cys Leu Leu Leu
1               5                   10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
50                  55                  60

Thr Pro Arg Pro Val Ala Glu Ile Val Pro Ser Phe Ile Asn Lys Asp
65                  70                  75                  80

Thr Glu Thr Ile Asn Met Met Ser Glu Phe Val Ala Asn Leu Pro Gln
                85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
                165                 170                 175

Thr Lys Arg Ser Leu Ala Arg Phe Cys
            180                 185

<210> SEQ ID NO 26
<211> LENGTH: 728
<212> TYPE: PRT
<213> ORGANISM: Homo sapiens
<220> FEATURE:
<223> OTHER INFORMATION: Human hepatocyte growth factor (HGF)

<400> SEQUENCE: 26

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
```

```
              165                 170                 175
Cys Arg Asn Pro Arg Gly Glu Glu Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590
```

-continued

```
Phe Val Ser Thr Ile Asp Leu Pro Asn Tyr Gly Cys Thr Ile Pro Glu
        595                 600             605

Lys Thr Ser Cys Ser Val Tyr Gly Trp Gly Tyr Thr Gly Leu Ile Asn
    610             615                 620

Tyr Asp Gly Leu Leu Arg Val Ala His Leu Tyr Ile Met Gly Asn Glu
625             630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660             665             670

Tyr Gly Gly Pro Leu Val Cys Glu Gln His Lys Met Arg Met Val Leu
        675             680                 685

Gly Val Ile Val Pro Gly Arg Gly Cys Ala Ile Pro Asn Arg Pro Gly
    690             695             700

Ile Phe Val Arg Val Ala Tyr Tyr Ala Lys Trp Ile His Lys Ile Ile
705             710             715                 720

Leu Thr Tyr Lys Val Pro Gln Ser
                725
```